United States Patent
Beattie et al.

(10) Patent No.: US 9,598,470 B2
(45) Date of Patent: Mar. 21, 2017

(54) COMPOSITIONS AND METHODS TO PREVENT CANCER BY STABILIZING P53 THROUGH NON MDM2-MEDIATED PATHWAYS

(76) Inventors: Craig W. Beattie, Chicago, IL (US); Tohru Yamada, Lombard, IL (US); Tapas K. Das Gupta, River Forest, IL (US)

( * ) Notice: Subject to any disclaimer, the term of this patent is extended or adjusted under 35 U.S.C. 154(b) by 411 days.

(21) Appl. No.: 12/467,799

(22) Filed: May 18, 2009

(65) Prior Publication Data

US 2010/0093057 A1 Apr. 15, 2010

Related U.S. Application Data

(63) Continuation-in-part of application No. 12/389,120, filed on Feb. 19, 2009, now Pat. No. 9,434,770, which is a continuation-in-part of application No. 12/314,703, filed on Dec. 15, 2008, now abandoned, application No. 12/467,799, which is a continuation-in-part of application No. 12/337,167, filed on Dec. 17, 2008, now Pat. No. 8,158,574, which is a continuation-in-part of application No. 11/854,654, filed on Sep. 13, 2007, now Pat. No.
(Continued)

(51) Int. Cl.
| | | |
|---|---|---|
| *A61K 39/00* | (2006.01) | |
| *A61K 38/00* | (2006.01) | |
| *C07K 14/195* | (2006.01) | |
| *C07K 14/21* | (2006.01) | |

(52) U.S. Cl.
CPC ............ *C07K 14/195* (2013.01); *C07K 14/21* (2013.01); *A61K 38/00* (2013.01); *G01N 2333/16* (2013.01)

(58) Field of Classification Search
None
See application file for complete search history.

(56) References Cited

U.S. PATENT DOCUMENTS

| | | |
|---|---|---|
| 2002/0164703 A1 | 11/2002 | Pawlowski et al. |
| 2006/0149037 A1 | 7/2006 | Chakrabarty et al. |

(Continued)

FOREIGN PATENT DOCUMENTS

| | | |
|---|---|---|
| WO | 0044888 | 8/2000 |
| WO | 03097085 A1 | 11/2003 |

(Continued)

OTHER PUBLICATIONS

Iwabuchi et al., PNAS, 1994, 91:6098-6102.*

(Continued)

*Primary Examiner* — Janet L Andres
*Assistant Examiner* — M. Franco Salvoza
(74) *Attorney, Agent, or Firm* — Don J. Pelto, Esq.; Sheppard, Mullin, Richter & Hampton LLP

(57) ABSTRACT

The present invention relates to compositions and methods comprising chemopreventive agents that may be cupredoxin(s) or variants, derivatives and structural equivalents of cupredoxins, and at least one other chemopreventive agent. Specifically, these compositions may comprise azurin from *Pseudomonas aeruginosa*, and/or the 50-77 residue region of azurin (p28). The compositions of the invention may be used to prevent or inhibit the development of premalignant lesions in mammalian cells, tissues and animals, and thus prevent cancer.

3 Claims, 48 Drawing Sheets

Related U.S. Application Data 7,618,939, application No. 12/467,799, which is a continuation-in-part of application No. 11/244,105, filed on Oct. 6, 2005, now Pat. No. 7,691,383.

(60) Provisional application No. 61/013,709, filed on Dec. 14, 2007, provisional application No. 60/844,358, filed on Sep. 14, 2006, provisional application No. 60/700,297, filed on Jul. 19, 2005, provisional application No. 60/680,500, filed on May 13, 2005, provisional application No. 60/616,782, filed on Oct. 7, 2004.

(56) References Cited

U.S. PATENT DOCUMENTS

| | | | |
|---|---|---|---|
| 2008/0103087 A1* | 5/2008 | Mehta et al. | 514/2 |
| 2008/0226560 A1 | 9/2008 | Das Gupta et al. | |
| 2009/0202441 A1* | 8/2009 | Taylor et al. | 424/9.4 |
| 2010/0267608 A1* | 10/2010 | Das Gupta | C07K 14/21 514/1.1 |

FOREIGN PATENT DOCUMENTS

| | | | | |
|---|---|---|---|---|
| WO | 2008033820 A2 | 3/2008 | | |
| WO | 2008033987 A2 | 3/2008 | | |
| WO | WO 2008070672 A2 * | 6/2008 | | C07K 14/195 |
| WO | 2008098216 A2 | 8/2008 | | |
| WO | 2009078977 A2 | 6/2009 | | |

OTHER PUBLICATIONS

Yolcu et al., Oncogene, 2001, 20:1398-1401.*
Yamada et al., Infection and Immunity, 2002, 70(12):7054-7062.*
De Grandis et al., Journal of Molecular Recognition, 2007, 20:215-226.*
Canters, FEBS Letters, 1987, 212(1):168-172 with sequence alignments.*
Punj et al., Cancer Biology & Therapy, 2004, 3(8):708-714.*
Murphy et al., "Structural comparison of cupredoxin domains: domain recycling to construct proteins with novel functions," Protein Science 6:761-770 (1997).*
Rudikoff et al., "Single amino acid substitution altering antigen-binding specificity," PNAS vol. 79: pp. 1979-1983 (1982).*
Manfredi et al., "p53 and Apoptosis: It's Not Just in the Nucleus Anymore," vol. 11, Issue 3: 552-554 (2003).*
Konduri et al., "Estrogen receptor abrogates transcriptional repression of p53 tumor suppressor protein," Proc. Amer. Assoc. Cancer Res. vol. 46, Abstract 3654, 2005.
Yamada et al., "Apoptosis or growth arrest: Modulation of tumor suppressor p52's specificity by bacterial redox protein azurin," PNAS, 101(14):4770-4775, Apr. 6, 2004.
Ye et al., "The construction of the eukaryotic expression plasmid pcDNA3.1/azurin and the increased apoptosis of U2OS cells transfected with it," Cell. Mol. Biol. Letters, 12(3):407-421, Abstract, 2007.
Ayed et al., Nature Structural Biology 8(9):756-760 (2001).
Leng et al., Cell 112(6):779-791 (2003).
Punj et al., Biochemical and Biophysical Research Communications 312(1):109-114 (2003).
Yamada et al., European Symposium on Environmental Biotehcnology, ESEB 2004, Edited by W. Verstraete. New York: A.A. Balkema Publishers, 2004, pp. 15-19.
Yamada et al., Mol. Cancer Ther. 8(10):2947-2958 (2009), (Abstract only).
Yamada et al., Chemistry Today 28(1):30-32 (2010).
Yamada et al., Cell Cycle 3:6 pp. 752-755 (2004).
Ni et al., Cancer Letters 261:1-11 (2008).
Yamada et al., Natl. Acadamy of Sciences 99:22 14098-14103 (2002).
Chaudhari et al., Biochemistry, American Chemical Society 46:7 1799-1810 (2007).
Punj, V. et al., Oncogene 23:13 2367-2378 (2004).
Yamada, T. et al., Proc. Natl. Acad. Sci. 99:22 14098-14103 (2002).
Office Action, dated Feb. 19, 2014, in European Patent Application No. 09 837 921.7.
Yamada T. et al.: "Internalization of bacterial redox protein azurin in mammalian cells: entry domain and specificity," Cellular Microbiology, vol. 7, No. 10, pp. 1418-1431 (Jul. 5, 2005).
Uchida, C. et al., Medical*Online, vol. 22, No. 13, pp. 1800-1807 (2004).
Taranta, M. et al.: "Probing the interaction between p53 and the bacterial protein azurin by single molecule force spectroscopy," Journal of Molecular Recognition, vol. 21, No. 1, Jan. 1, 2008, pp. 63-70.
Taranta, M. et al.: "Modeling the interaction between the N-terminal domain of the tumor suppressor p53 and azurin," Journal of Molecular Recognition, vol. 22, No. 3, May 1, 2009, pp. 215-222.
Taylor, B. et al.: "Noncationic Peptides Obtained From Azurin Preferentially Enter Cancer Cells," Cancer Res 2009, 69: (2) pp. 537-546.

* cited by examiner

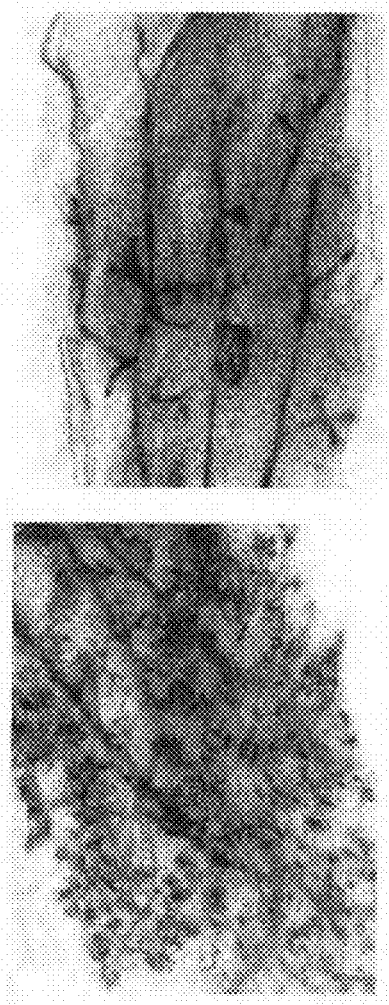

THE EFFICACY OF PEPTIDE P28 IN COMBINATION WITH FENTRETINIDE (4-HPR) ON THE DEVELOPMENT OF DMBA-INDUCED ALVEOLAR LESIONS IN MOUSE MAMMARY GLAND ORGAN CULTURE

Group 1: DMBA (2 µg/ml)
9/15
60% incidence

Group 2: 4-HPR (1 µM)
3/15
20% incidence

Group 3: p28 (1.25 µg/ml)

4/15
26.7% incidence

Group 4: p28 (1.25 µg/ml) + 4-HPR (1 µM)

2/15
13.3% incidence

Group 5: p28 (25 µg/ml)

3/15
20% incidence

Group 6: p28 (25 µg/ml) + 4-HPR (1 µM)

2/15
13.3% incidence

AZURIN TRUNCATION WITH ALPHA-HELICAL STRUCTURE

RESULT OF 70 ns SIMULATION

MEASUREMENT OF THIOETHER BRIDGE POSITIONS BASED ON DISTANCES BETWEEN Cα ATOMS IN A SIMULATED STRUCTURE

SEQUENCE LISTING

<160> NUMBER OF SEQ ID NOS: 90

<210> SEQ ID NO 1
<211> LENGTH: 128
<212> TYPE: PRT

<213> ORGANISM: Pseudomonas aeruginosa

<400> SEQUENCE: 1

```
Ala Glu Cys Ser Val Asp Ile Gln Gly Asn Asp Gln Met Gln Phe Asn
1               5                   10                  15

Thr Asn Ala Ile Thr Val Asp Lys Ser Cys Lys Gln Phe Thr Val Asn
            20                  25                  30

Leu Ser His Pro Gly Asn Leu Pro Lys Asn Val Met Gly His Asn Trp
        35                  40                  45

Val Leu Ser Thr Ala Ala Asp Met Gln Gly Val Val Thr Asp Gly Met
    50                  55                  60

Ala Ser Gly Leu Asp Lys Asp Tyr Leu Lys Pro Asp Asp Ser Arg Val
65                  70                  75                  80

Ile Ala His Thr Lys Leu Ile Gly Ser Gly Glu Lys Asp Ser Val Thr
                85                  90                  95

Phe Asp Val Ser Lys Leu Lys Glu Gly Glu Gln Tyr Met Phe Phe Cys
            100                 105                 110

Thr Phe Pro Gly His Ser Ala Leu Met Lys Gly Thr Leu Thr Leu Lys
        115                 120                 125
```

<210> SEQ ID NO 2
<211> LENGTH: 28
<212> TYPE: PRT
<213> ORGANISM: Pseudomonas aeruginosa

<400> SEQUENCE: 2

```
Leu Ser Thr Ala Ala Asp Met Gln Gly Val Val Thr Asp Gly Met Ala
1               5                   10                  15

Ser Gly Leu Asp Lys Asp Tyr Leu Lys Pro Asp Asp
            20                  25
```

<210> SEQ ID NO 3
<211> LENGTH: 105
<212> TYPE: PRT
<213> ORGANISM: Phormidium laminosum

<400> SEQUENCE: 3

```
Glu Thr Phe Thr Val Lys Met Gly Ala Asp Ser Gly Leu Leu Gln Phe
1               5                   10                  15

Glu Pro Ala Asn Val Thr Val His Pro Gly Asp Thr Val Lys Trp Val
            20                  25                  30

Asn Asn Lys Leu Pro Pro His Asn Ile Leu Phe Asp Asp Lys Gln Val
        35                  40                  45

Pro Gly Ala Ser Lys Glu Leu Ala Asp Lys Leu Ser His Ser Gln Leu
    50                  55                  60

Met Phe Ser Pro Gly Glu Ser Tyr Glu Ile Thr Phe Ser Ser Asp Phe
65                  70                  75                  80

Pro Ala Gly Thr Tyr Thr Tyr Tyr Cys Ala Pro His Arg Gly Ala Gly
                85                  90                  95

Met Val Gly Lys Ile Thr Val Glu Gly
            100                 105
```

<210> SEQ ID NO 4
<211> LENGTH: 155
<212> TYPE: PRT
<213> ORGANISM: Thiobacillus ferrooxidans

<400> SEQUENCE: 4

```
Gly Thr Leu Asp Thr Thr Trp Lys Glu Ala Thr Leu Pro Gln Val Lys
1               5                   10                  15

Ala Met Leu Glu Lys Asp Thr Gly Lys Val Ser Gly Asp Thr Val Thr
            20                  25                  30

Tyr Ser Gly Lys Thr Val His Val Ala Ala Val Leu Pro Gly
        35                  40                  45

Phe Pro Phe Pro Ser Phe Glu Val His Asp Lys Lys Asn Pro Thr Leu
        50                  55                  60

Glu Ile Pro Ala Gly Ala Thr Val Asp Val Thr Phe Ile Asn Thr Asn
65                  70                  75                  80

Lys Gly Phe Gly His Ser Phe Asp Ile Thr Lys Lys Gly Pro Pro Tyr
                85                  90                  95

Ala Val Met Pro Val Ile Asp Pro Ile Val Ala Gly Thr Gly Phe Ser
                100                 105                 110

Pro Val Pro Lys Asp Gly Lys Phe Gly Tyr Thr Asp Phe Thr Trp His
            115                 120                 125

Pro Thr Ala Gly Thr Tyr Tyr Tyr Val Cys Gln Ile Pro Gly His Ala
        130                 135                 140

Ala Thr Gly Met Phe Gly Lys Ile Val Val Lys
145                 150                 155
```

<210> SEQ ID NO 5
<211> LENGTH: 124
<212> TYPE: PRT
<213> ORGANISM: Achromobacter cycloclastes

<400> SEQUENCE: 5

```
Ala Asp Phe Glu Val His Met Leu Asn Lys Gly Lys Asp Gly Ala Met
1               5                   10                  15

Val Phe Glu Pro Ala Ser Leu Lys Val Ala Pro Gly Asp Thr Val Thr
            20                  25                  30

Phe Ile Pro Thr Asp Lys Gly His Asn Val Glu Thr Ile Lys Gly Met
        35                  40                  45

Ile Pro Asp Gly Ala Glu Ala Phe Lys Ser Lys Ile Asn Glu Asn Tyr
    50                  55                  60

Lys Val Thr Phe Thr Ala Pro Gly Val Tyr Gly Val Lys Cys Thr Pro
65                  70                  75                  80

His Tyr Gly Met Gly Met Val Gly Val Val Gln Val Gly Asp Ala Pro
                85                  90                  95

Ala Asn Leu Glu Ala Val Lys Gly Ala Lys Asn Pro Lys Lys Ala Gln
                100                 105                 110

Glu Arg Leu Asp Ala Ala Leu Ala Ala Leu Gly Asn
            115                 120
```

<210> SEQ ID NO 6
<211> LENGTH: 128
<212> TYPE: PRT
<213> ORGANISM: Alcaligenes faecalis

<400> SEQUENCE: 6

```
Ala Cys Asp Val Ser Ile Glu Gly Asn Asp Ser Met Gln Phe Asn Thr
1               5                   10                  15

Lys Ser Ile Val Val Asp Lys Thr Cys Lys Glu Phe Thr Ile Asn Leu
            20                  25                  30

Lys His Thr Gly Lys Leu Pro Lys Ala Ala Met Gly His Asn Val Val
        35                  40                  45
```

Val Ser Lys Lys Ser Asp Glu Ser Ala Val Ala Thr Asp Gly Met Lys
50                  55                  60

Ala Gly Leu Asn Asn Asp Tyr Val Lys Ala Gly Asp Glu Arg Val Ile
65                  70                  75                  80

Ala His Thr Ser Val Ile Gly Gly Glu Thr Asp Ser Val Thr Phe
            85                  90                  95

Asp Val Ser Lys Leu Lys Glu Gly Glu Asp Tyr Ala Phe Phe Cys Ser
                100                 105                 110

Phe Pro Gly His Trp Ser Ile Met Lys Gly Thr Ile Glu Leu Gly Ser
            115                 120                 125

<210> SEQ ID NO 7
<211> LENGTH: 129
<212> TYPE: PRT
<213> ORGANISM: Achromobacter xylosoxidans

<400> SEQUENCE: 7

Ala Gln Cys Glu Ala Thr Ile Glu Ser Asn Asp Ala Met Gln Tyr Asn
1               5                   10                  15

Leu Lys Glu Met Val Val Asp Lys Ser Cys Lys Gln Phe Thr Val His
                20                  25                  30

Leu Lys His Val Gly Lys Met Ala Lys Val Ala Met Gly His Asn Trp
            35                  40                  45

Val Leu Thr Lys Glu Ala Asp Lys Gln Gly Val Ala Thr Asp Gly Met
50                  55                  60

Asn Ala Gly Leu Ala Gln Asp Tyr Val Lys Ala Gly Asp Thr Arg Val
65                  70                  75                  80

Ile Ala His Thr Lys Val Ile Gly Gly Gly Glu Ser Asp Ser Val Thr
            85                  90                  95

Phe Asp Val Ser Lys Leu Thr Pro Gly Glu Ala Tyr Ala Tyr Phe Cys
                100                 105                 110

Ser Phe Pro Gly His Trp Ala Met Met Lys Gly Thr Leu Lys Leu Ser
            115                 120                 125

Asn

<210> SEQ ID NO 8
<211> LENGTH: 129
<212> TYPE: PRT
<213> ORGANISM: Bordetella bronchiseptica

<400> SEQUENCE: 8

Ala Glu Cys Ser Val Asp Ile Ala Gly Thr Asp Gln Met Gln Phe Asp
1               5                   10                  15

Lys Lys Ala Ile Glu Val Ser Lys Ser Cys Lys Gln Phe Thr Val Asn
                20                  25                  30

Leu Lys His Thr Gly Lys Leu Pro Arg Asn Val Met Gly His Asn Trp
            35                  40                  45

Val Leu Thr Lys Thr Ala Asp Met Gln Ala Val Glu Lys Asp Gly Ile
50                  55                  60

Ala Ala Gly Leu Asp Asn Gln Tyr Leu Lys Ala Gly Asp Thr Arg Val
65                  70                  75                  80

Leu Ala His Thr Lys Val Leu Gly Gly Gly Glu Ser Asp Ser Val Thr
            85                  90                  95

Phe Asp Val Ala Lys Leu Ala Ala Gly Asp Asp Tyr Thr Phe Phe Cys
                100                 105                 110

Ser Phe Pro Gly His Gly Ala Leu Met Lys Gly Thr Leu Lys Leu Val

<210> SEQ ID NO 9
<211> LENGTH: 129
<212> TYPE: PRT
<213> ORGANISM: Methylomonas sp.

<400> SEQUENCE: 9

```
Ala Ser Cys Glu Thr Thr Val Thr Ser Gly Asp Thr Met Thr Tyr Ser
1               5                   10                  15
Thr Arg Ser Ile Ser Val Pro Ala Ser Cys Ala Glu Phe Thr Val Asn
            20                  25                  30
Phe Glu His Lys Gly His Met Pro Lys Thr Gly Met Gly His Asn Trp
        35                  40                  45
Val Leu Ala Lys Ser Ala Asp Val Gly Asp Val Ala Lys Glu Gly Ala
    50                  55                  60
His Ala Gly Ala Asp Asn Asn Phe Val Thr Pro Gly Asp Lys Arg Val
65                  70                  75                  80
Ile Ala Phe Thr Pro Ile Ile Gly Gly Gly Glu Lys Thr Ser Val Lys
                85                  90                  95
Phe Lys Val Ser Ala Leu Ser Lys Asp Glu Ala Tyr Thr Tyr Phe Cys
            100                 105                 110
Ser Tyr Pro Gly His Phe Ser Met Met Arg Gly Thr Leu Lys Leu Glu
        115                 120                 125
Glu
```

<210> SEQ ID NO 10
<211> LENGTH: 166
<212> TYPE: PRT
<213> ORGANISM: Neisseria meningitidis

<400> SEQUENCE: 10

```
Cys Ser Gln Glu Pro Ala Ala Pro Ala Ala Glu Ala Thr Pro Ala Ala
1               5                   10                  15
Glu Ala Pro Ala Ser Glu Ala Pro Ala Ala Glu Ala Ala Pro Ala Asp
            20                  25                  30
Ala Ala Glu Ala Pro Ala Ala Gly Asn Cys Ala Ala Thr Val Glu Ser
        35                  40                  45
Asn Asp Asn Met Gln Phe Asn Thr Lys Asp Ile Gln Val Ser Lys Ala
    50                  55                  60
Cys Lys Glu Phe Thr Ile Thr Leu Lys His Thr Gly Thr Gln Pro Lys
65                  70                  75                  80
Thr Ser Met Gly His Asn Ile Val Ile Gly Lys Thr Glu Asp Met Asp
                85                  90                  95
Gly Ile Phe Lys Asp Gly Val Gly Ala Ala Asp Thr Asp Tyr Val Lys
            100                 105                 110
Pro Asp Asp Ala Arg Val Val Ala His Thr Lys Leu Ile Gly Gly Gly
        115                 120                 125
Glu Glu Ser Ser Leu Thr Leu Asp Pro Ala Lys Leu Ala Asp Gly Glu
    130                 135                 140
Tyr Lys Phe Ala Cys Thr Phe Pro Gly His Gly Ala Leu Met Asn Gly
145                 150                 155                 160
Lys Val Thr Leu Val Asp
                165
```

-continued

<210> SEQ ID NO 11
<211> LENGTH: 128
<212> TYPE: PRT
<213> ORGANISM: Pseudomonas fluorescen

<400> SEQUENCE: 11

Ala Glu Cys Lys Thr Thr Ile Asp Ser Thr Asp Gln Met Ser Phe Asn
1               5                   10                  15

Thr Lys Ala Ile Glu Ile Asp Lys Ala Cys Lys Thr Phe Thr Val Glu
            20                  25                  30

Leu Thr His Ser Gly Ser Leu Pro Lys Asn Val Met Gly His Asn Leu
        35                  40                  45

Val Ile Ser Lys Gln Ala Asp Met Gln Pro Ile Ala Thr Asp Gly Leu
    50                  55                  60

Ser Ala Gly Ile Asp Lys Asn Tyr Leu Lys Glu Gly Asp Thr Arg Val
65                  70                  75                  80

Ile Ala His Thr Lys Val Ile Gly Ala Gly Glu Lys Asp Ser Leu Thr
                85                  90                  95

Ile Asp Val Ser Lys Leu Asn Ala Ala Glu Lys Tyr Gly Phe Phe Cys
            100                 105                 110

Ser Phe Pro Gly His Ile Ser Met Met Lys Gly Thr Val Thr Leu Lys
        115                 120                 125

<210> SEQ ID NO 12
<211> LENGTH: 128
<212> TYPE: PRT
<213> ORGANISM: Pseudomonas chlororaphis

<400> SEQUENCE: 12

Ala Glu Cys Lys Val Asp Val Asp Ser Thr Asp Gln Met Ser Phe Asn
1               5                   10                  15

Thr Lys Glu Ile Thr Ile Asp Lys Ser Cys Lys Thr Phe Thr Val Asn
            20                  25                  30

Leu Thr His Ser Gly Ser Leu Pro Lys Asn Val Met Gly His Asn Trp
        35                  40                  45

Val Leu Ser Lys Ser Ala Asp Met Ala Gly Ile Ala Thr Asp Gly Met
    50                  55                  60

Ala Ala Gly Ile Asp Lys Asp Tyr Leu Lys Pro Gly Asp Ser Arg Val
65                  70                  75                  80

Ile Ala His Thr Lys Ile Ile Gly Ser Gly Glu Lys Asp Ser Val Thr
                85                  90                  95

Phe Asp Val Ser Lys Leu Thr Ala Gly Glu Ser Tyr Glu Phe Phe Cys
            100                 105                 110

Ser Phe Pro Gly His Asn Ser Met Met Lys Gly Ala Val Val Leu Lys
        115                 120                 125

<210> SEQ ID NO 13
<211> LENGTH: 129
<212> TYPE: PRT
<213> ORGANISM: Xylella fastidiosa

<400> SEQUENCE: 13

Lys Thr Cys Ala Val Thr Ile Ser Ala Asn Asp Gln Met Lys Phe Asp
1               5                   10                  15

Gln Asn Thr Ile Lys Ile Ala Ala Glu Cys Thr His Val Asn Leu Thr
            20                  25                  30

Leu Thr His Thr Gly Lys Lys Ser Ala Arg Val Met Gly His Asn Trp

```
                 35                  40                  45

Val Leu Thr Lys Thr Thr Asp Met Gln Ala Val Ala Leu Ala Gly Leu
     50                  55                  60

His Ala Thr Leu Ala Asp Asn Tyr Val Pro Lys Ala Asp Pro Arg Val
 65                  70                  75                  80

Ile Ala His Thr Ala Ile Ile Gly Gly Gly Glu Arg Thr Ser Ile Thr
                 85                  90                  95

Phe Pro Thr Asn Thr Leu Ser Lys Asn Val Ser Tyr Thr Phe Phe Cys
                100                 105                 110

Ser Phe Pro Gly His Trp Ala Leu Met Lys Gly Thr Leu Asn Phe Gly
                115                 120                 125

Gly

<210> SEQ ID NO 14
<211> LENGTH: 138
<212> TYPE: PRT
<213> ORGANISM: Cucumis sativus

<400> SEQUENCE: 14

Met Gln Ser Thr Val His Ile Val Gly Asp Asn Thr Gly Trp Ser Val
  1               5                  10                  15

Pro Ser Ser Pro Asn Phe Tyr Ser Gln Trp Ala Ala Gly Lys Thr Phe
                 20                  25                  30

Arg Val Gly Asp Ser Leu Gln Phe Asn Phe Pro Ala Asn Ala His Asn
                 35                  40                  45

Val His Glu Met Glu Thr Lys Gln Ser Phe Asp Ala Cys Asn Phe Val
     50                  55                  60

Asn Ser Asp Asn Asp Val Glu Arg Thr Ser Pro Val Ile Glu Arg Leu
 65                  70                  75                  80

Asp Glu Leu Gly Met His Tyr Phe Val Cys Thr Val Gly Thr His Cys
                 85                  90                  95

Ser Asn Gly Gln Lys Leu Ser Ile Asn Val Val Ala Ala Asn Ala Thr
                100                 105                 110

Val Ser Met Pro Pro Ser Ser Ser Pro Ser Ser Val Met Pro
                115                 120                 125

Pro Pro Val Met Pro Pro Ser Pro Ser
                130                 135

<210> SEQ ID NO 15
<211> LENGTH: 162
<212> TYPE: PRT
<213> ORGANISM: Chloroflexus aurantiacus

<400> SEQUENCE: 15

Met Lys Ile Thr Leu Arg Met Met Val Leu Ala Val Leu Thr Ala Met
  1               5                  10                  15

Ala Met Val Leu Ala Ala Cys Gly Gly Gly Ser Ser Gly Gly Ser
                 20                  25                  30

Thr Gly Gly Gly Ser Gly Ser Gly Pro Val Thr Ile Glu Ile Gly Ser
                 35                  40                  45

Lys Gly Glu Glu Leu Ala Phe Asp Lys Thr Gly Leu Thr Val Ser Ala
     50                  55                  60

Gly Gln Thr Val Thr Ile Arg Phe Lys Asn Asn Ser Ala Val Gln Gln
 65                  70                  75                  80

His Asn Trp Ile Leu Val Lys Gly Gly Glu Ala Glu Ala Ala Asn Ile
                 85                  90                  95
```

```
Ala Asn Ala Gly Leu Ser Ala Gly Pro Ala Ala Asn Tyr Leu Pro Ala
            100                 105                 110

Asp Lys Ser Asn Ile Ile Ala Glu Ser Pro Leu Ala Asn Gly Asn Glu
        115                 120                 125

Thr Val Glu Val Thr Phe Thr Ala Pro Ala Ala Gly Thr Tyr Leu Tyr
    130                 135                 140

Ile Cys Thr Val Pro Gly His Tyr Pro Leu Met Gln Gly Lys Leu Val
145                 150                 155                 160

Val Asn

<210> SEQ ID NO 16
<211> LENGTH: 140
<212> TYPE: PRT
<213> ORGANISM: Chloroflexus aurantiacus

<400> SEQUENCE: 16

Ala Ala Asn Ala Pro Gly Gly Ser Asn Val Val Asn Glu Thr Pro Ala
1               5                   10                  15

Gln Thr Val Glu Val Arg Ala Ala Pro Asp Ala Leu Ala Phe Ala Gln
            20                  25                  30

Thr Ser Leu Ser Leu Pro Ala Asn Thr Val Val Arg Leu Asp Phe Val
        35                  40                  45

Asn Gln Asn Asn Leu Gly Val Gln His Asn Trp Val Leu Val Asn Gly
    50                  55                  60

Gly Asp Asp Val Ala Ala Val Asn Thr Ala Ala Gln Asn Asn Ala
65                  70                  75                  80

Asp Ala Leu Phe Val Pro Pro Asp Thr Pro Asn Ala Leu Ala Trp
                85                  90                  95

Thr Ala Met Leu Asn Ala Gly Glu Ser Gly Ser Val Thr Phe Arg Thr
            100                 105                 110

Pro Ala Pro Gly Thr Tyr Leu Tyr Ile Cys Thr Phe Pro Gly His Tyr
        115                 120                 125

Leu Ala Gly Met Lys Gly Thr Leu Thr Val Thr Pro
    130                 135                 140

<210> SEQ ID NO 17
<211> LENGTH: 96
<212> TYPE: PRT
<213> ORGANISM: Cucumis sativus

<400> SEQUENCE: 17

Ala Val Tyr Val Val Gly Gly Ser Gly Gly Trp Thr Phe Asn Thr Glu
1               5                   10                  15

Ser Trp Pro Lys Gly Lys Arg Phe Arg Ala Gly Asp Ile Leu Leu Phe
            20                  25                  30

Asn Tyr Asn Pro Ser Met His Asn Val Val Val Asn Gln Gly Gly
    35                  40                  45

Phe Ser Thr Cys Asn Thr Pro Ala Gly Ala Lys Val Tyr Thr Ser Gly
    50                  55                  60

Arg Asp Gln Ile Lys Leu Pro Lys Gly Gln Ser Tyr Phe Ile Cys Asn
65                  70                  75                  80

Phe Pro Gly His Cys Gln Ser Gly Met Lys Ile Ala Val Asn Ala Leu
                85                  90                  95

<210> SEQ ID NO 18
<211> LENGTH: 166
```

<212> TYPE: PRT
<213> ORGANISM: Neisseria gonorrhoeae

<400> SEQUENCE: 18

Cys Ser Gln Glu Pro Ala Ala Pro Ala Glu Ala Thr Pro Ala Gly
1               5                   10                  15

Glu Ala Pro Ala Ser Glu Ala Pro Ala Glu Ala Ala Pro Ala Asp
                20                  25                  30

Ala Ala Glu Ala Pro Ala Ala Gly Asn Cys Ala Ala Thr Val Glu Ser
                35                  40                  45

Asn Asp Asn Met Gln Phe Asn Thr Lys Asp Ile Gln Val Ser Lys Ala
                50                  55                  60

Cys Lys Glu Phe Thr Ile Thr Leu Lys His Thr Gly Thr Gln Pro Lys
65                  70                  75                  80

Ala Ser Met Gly His Asn Leu Val Ile Ala Lys Ala Glu Asp Met Asp
                85                  90                  95

Gly Val Phe Lys Asp Gly Val Gly Ala Ala Asp Thr Asp Tyr Val Lys
                100                 105                 110

Pro Asp Asp Ala Arg Val Val Ala His Thr Lys Leu Ile Gly Gly Gly
                115                 120                 125

Glu Glu Ser Ser Leu Thr Leu Asp Pro Ala Lys Leu Ala Asp Gly Asp
                130                 135                 140

Tyr Lys Phe Ala Cys Thr Phe Pro Gly His Gly Ala Leu Met Asn Gly
145                 150                 155                 160

Lys Val Thr Leu Val Asp
                165

<210> SEQ ID NO 19
<211> LENGTH: 150
<212> TYPE: PRT
<213> ORGANISM: Vibrio parahaemolyticus

<400> SEQUENCE: 19

Met Ser Leu Arg Ile Leu Ala Ala Thr Leu Ala Leu Ala Gly Leu Ser
1               5                   10                  15

Phe Gly Ala Gln Ala Ser Ala Glu Cys Glu Val Ser Ile Asp Ala Asn
                20                  25                  30

Asp Met Met Gln Phe Ser Thr Lys Thr Leu Ser Val Pro Ala Thr Cys
                35                  40                  45

Lys Glu Val Thr Leu Thr Leu Asn His Thr Gly Lys Met Pro Ala Gln
                50                  55                  60

Ser Met Gly His Asn Val Val Ile Ala Asp Thr Ala Asn Ile Gln Ala
65                  70                  75                  80

Val Gly Thr Asp Gly Met Ser Gly Ala Asp Asn Ser Tyr Val Lys
                85                  90                  95

Pro Asp Asp Glu Arg Val Tyr Ala His Thr Lys Val Val Gly Gly Gly
                100                 105                 110

Glu Ser Thr Ser Ile Thr Phe Ser Thr Glu Lys Met Thr Ala Gly Gly
                115                 120                 125

Asp Tyr Ser Phe Phe Cys Ser Phe Pro Gly His Trp Ala Ile Met Gln
                130                 135                 140

Gly Lys Phe Glu Phe Lys
145                 150

<210> SEQ ID NO 20
<211> LENGTH: 33

```
<212> TYPE: PRT
<213> ORGANISM: Chloroflexus aurantiacus

<400> SEQUENCE: 20

His Asn Trp Val Leu Val Asn Gly Gly Asp Asp Val Ala Ala Val
1               5                   10                  15

Asn Thr Ala Ala Gln Asn Asn Ala Asp Ala Leu Phe Val Pro Pro Pro
                20                  25                  30

Asp

<210> SEQ ID NO 21
<211> LENGTH: 27
<212> TYPE: PRT
<213> ORGANISM: Pseudomonas syringae

<400> SEQUENCE: 21

Ser Lys Lys Ala Asp Ala Ser Ala Ile Thr Thr Asp Gly Met Ser Val
1               5                   10                  15

Gly Ile Asp Lys Asp Tyr Val Lys Pro Asp Asp
                20                  25

<210> SEQ ID NO 22
<211> LENGTH: 27
<212> TYPE: PRT
<213> ORGANISM: Neisseria meningitidis

<400> SEQUENCE: 22

Ile Gly Lys Thr Glu Asp Met Asp Gly Ile Phe Lys Asp Gly Val Gly
1               5                   10                  15

Ala Ala Asp Thr Asp Tyr Val Lys Pro Asp Asp
                20                  25

<210> SEQ ID NO 23
<211> LENGTH: 27
<212> TYPE: PRT
<213> ORGANISM: Vibrio parahaemolyticus

<400> SEQUENCE: 23

Ala Asp Thr Ala Asn Ile Gln Ala Val Gly Thr Asp Gly Met Ser Ala
1               5                   10                  15

Gly Ala Asp Asn Ser Tyr Val Lys Pro Asp Asp
                20                  25

<210> SEQ ID NO 24
<211> LENGTH: 27
<212> TYPE: PRT
<213> ORGANISM: Bordetella bronchiseptica

<400> SEQUENCE: 24

Thr Lys Thr Ala Asp Met Gln Ala Val Glu Lys Asp Gly Ile Ala Ala
1               5                   10                  15

Gly Leu Asp Asn Gln Tyr Leu Lys Ala Gly Asp
                20                  25

<210> SEQ ID NO 25
<211> LENGTH: 18
<212> TYPE: PRT
<213> ORGANISM: Pseudomonas aeruginosa

<400> SEQUENCE: 25

Leu Ser Thr Ala Ala Asp Met Gln Gly Val Val Thr Asp Gly Met Ala
1               5                   10                  15
```

Ser Gly

<210> SEQ ID NO 26
<211> LENGTH: 19
<212> TYPE: PRT
<213> ORGANISM: Pseudomonas aeruginosa

<400> SEQUENCE: 26

Leu Ser Thr Ala Ala Asp Met Gln Gly Val Val Thr Asp Gly Met Ala
1               5                   10                  15

Ser Gly Leu

<210> SEQ ID NO 27
<211> LENGTH: 20
<212> TYPE: PRT
<213> ORGANISM: Pseudomonas aeruginosa

<400> SEQUENCE: 27

Leu Ser Thr Ala Ala Asp Met Gln Gly Val Val Thr Asp Gly Met Ala
1               5                   10                  15

Ser Gly Leu Asp
            20

<210> SEQ ID NO 28
<211> LENGTH: 21
<212> TYPE: PRT
<213> ORGANISM: Pseudomonas aeruginosa

<400> SEQUENCE: 28

Leu Ser Thr Ala Ala Asp Met Gln Gly Val Val Thr Asp Gly Met Ala
1               5                   10                  15

Ser Gly Leu Asp Lys
            20

<210> SEQ ID NO 29
<211> LENGTH: 22
<212> TYPE: PRT
<213> ORGANISM: Pseudomonas aeruginosa

<400> SEQUENCE: 29

Leu Ser Thr Ala Ala Asp Met Gln Gly Val Val Thr Asp Gly Met Ala
1               5                   10                  15

Ser Gly Leu Asp Lys Asp
            20

<210> SEQ ID NO 30
<211> LENGTH: 23
<212> TYPE: PRT
<213> ORGANISM: Pseudomonas aeruginosa

<400> SEQUENCE: 30

Leu Ser Thr Ala Ala Asp Met Gln Gly Val Val Thr Asp Gly Met Ala
1               5                   10                  15

Ser Gly Leu Asp Lys Asp Tyr
            20

<210> SEQ ID NO 31
<211> LENGTH: 24
<212> TYPE: PRT
<213> ORGANISM: Pseudomonas aeruginosa

<400> SEQUENCE: 31

-continued

```
Leu Ser Thr Ala Ala Asp Met Gln Gly Val Val Thr Asp Gly Met Ala
1               5                   10                  15

Ser Gly Leu Asp Lys Asp Tyr Leu
            20

<210> SEQ ID NO 32
<211> LENGTH: 25
<212> TYPE: PRT
<213> ORGANISM: Pseudomonas aeruginosa

<400> SEQUENCE: 32

Leu Ser Thr Ala Ala Asp Met Gln Gly Val Val Thr Asp Gly Met Ala
1               5                   10                  15

Ser Gly Leu Asp Lys Asp Tyr Leu Lys
            20                  25

<210> SEQ ID NO 33
<211> LENGTH: 26
<212> TYPE: PRT
<213> ORGANISM: Pseudomonas aeruginosa

<400> SEQUENCE: 33

Leu Ser Thr Ala Ala Asp Met Gln Gly Val Val Thr Asp Gly Met Ala
1               5                   10                  15

Ser Gly Leu Asp Lys Asp Tyr Leu Lys Pro
            20                  25

<210> SEQ ID NO 34
<211> LENGTH: 27
<212> TYPE: PRT
<213> ORGANISM: Pseudomonas aeruginosa

<400> SEQUENCE: 34

Leu Ser Thr Ala Ala Asp Met Gln Gly Val Val Thr Asp Gly Met Ala
1               5                   10                  15

Ser Gly Leu Asp Lys Asp Tyr Leu Lys Pro Asp
            20                  25

<210> SEQ ID NO 35
<211> LENGTH: 53
<212> TYPE: PRT
<213> ORGANISM: Pseudomonas aeruginosa

<400> SEQUENCE: 35

Pro Gly Asn Leu Pro Lys Asn Val Met Gly His Asn Trp Val Leu Ser
1               5                   10                  15

Thr Ala Ala Asp Met Gln Gly Val Val Thr Asp Gly Met Ala Ser Gly
            20                  25                  30

Leu Asp Lys Asp Tyr Leu Lys Pro Asp Asp Ser Arg Val Ile Ala His
        35                  40                  45

Thr Lys Leu Ile Gly
    50

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
```

```
gatgactgcc atggaggag                                                19
```

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

```
catgcccgtt cttagttggt                                               20
```

<210> SEQ ID NO 38
<211> LENGTH: 18
<212> TYPE: PRT
<213> ORGANISM: Pseudomonas aeruginosa

<400> SEQUENCE: 38

Val Thr Asp Gly Met Ala Ser Gly Leu Asp Lys Asp Tyr Leu Lys Pro
1               5                   10                  15

Asp Asp

<210> SEQ ID NO 39
<211> LENGTH: 12
<212> TYPE: PRT
<213> ORGANISM: Pseudomonas aeruginosa

<400> SEQUENCE: 39

Ser Gly Leu Asp Lys Asp Tyr Leu Lys Pro Asp Asp
1               5                   10

<210> SEQ ID NO 40
<211> LENGTH: 10
<212> TYPE: PRT
<213> ORGANISM: Pseudomonas aeruginosa

<400> SEQUENCE: 40

Leu Asp Lys Asp Tyr Leu Lys Pro Asp Asp
1               5                   10

<210> SEQ ID NO 41
<211> LENGTH: 11
<212> TYPE: PRT
<213> ORGANISM: Pseudomonas aeruginosa

<400> SEQUENCE: 41

Gly Leu Asp Lys Asp Tyr Leu Lys Pro Asp Asp
1               5                   10

<210> SEQ ID NO 42
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Ser Thr Ala Ala Asp Met Gln Ala Val Thr Asp Thr Met Ala
1               5                   10                  15

Ser Gly Leu Asp Lys Asp Tyr Leu Lys Pro Asp Asp
            20                  25

-continued

<210> SEQ ID NO 43
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Ser Thr Ala Ala Asp Leu Gln Gly Val Val Thr Asp Gly Leu Ala
1               5                   10                  15

Ser Gly Leu Asp Lys Asp Tyr Leu Lys Pro Asp Asp
            20                  25

<210> SEQ ID NO 44
<211> LENGTH: 28
<212> TYPE: PRT
<213> ORGANISM: Artificial Sequence
<220> FEATURE:
<223> OTHER INFORMATION: Description of artificial sequence: Synthetic
      peptide

<400> SEQUENCE: 44

Leu Ser Thr Ala Ala Asp Val Gln Gly Val Val Thr Asp Gly Val Ala
1               5                   10                  15

Ser Gly Leu Asp Lys Asp Tyr Leu Lys Pro Asp Asp
            20                  25

<210> SEQ ID NO 45
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Asp Pro Lys Leu Tyr Asp Lys Asp Leu Gly Ser Ala Met Gly Asp
1               5                   10                  15

Thr Val Val Gly Gln Met Asp Ala Ala Thr Ser Leu
            20                  25

<210> SEQ ID NO 46
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<223> OTHER INFORMATION: C-term amidated

<400> SEQUENCE: 46

Leu Ser Thr Ala Ala Asp Met Gln Gly Val Val Thr Asp Gly Met Ala
1               5                   10                  15

Ser Gly Leu Asp Lys Asp Tyr Leu Lys Pro Asp Asp
            20                  25

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Val Ser Pro Pro Ala Arg
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Tyr Thr Pro Pro Ala Leu
1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Phe Ser Phe Phe Ala Phe
1               5

<210> SEQ ID NO 50
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Ser Thr Ala Ala Asp Met Gln Gly Val Val Thr Asp Gly Met Ala
1               5                   10                  15

Ser Gly Leu Asp Lys Asp Tyr Leu Thr Pro Gly Cys
            20                  25

<210> SEQ ID NO 51
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Ser Thr Ala Ala Asp Cys Gln Gly Val Val Thr Asp Gly Met Ala
1               5                   10                  15

Ser Gly Leu Asp Lys Asp Tyr Leu Lys Pro Asp Asp
            20                  25

<210> SEQ ID NO 52
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Ser Thr Ala Ala Cys Met Gln Gly Val Val Thr Asp Gly Met Ala
1               5                   10                  15

Ser Gly Leu Asp Lys Asp Tyr Leu Lys Pro Asp Asp
            20                  25

<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Ser Thr Ala Cys Asp Met Gln Gly Val Val Thr Asp Gly Met Ala
1               5                   10                  15

Ser Gly Leu Asp Lys Asp Tyr Leu Lys Pro Asp Asp
            20                  25

<210> SEQ ID NO 54
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Ser Thr Ala Ala Thr Met Gln Cys Val Val Thr Asp Gly Met Ala
1               5                   10                  15

Ser Gly Leu Asp Lys Asp Tyr Leu Lys Pro Asp Asp
            20                  25

<210> SEQ ID NO 55
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Ser Thr Ala Ala Thr Met Gln Gly Cys Val Thr Asp Gly Met Ala
1               5                   10                  15

Ser Gly Leu Asp Lys Asp Tyr Leu Lys Pro Asp Asp
            20                  25

<210> SEQ ID NO 56
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Ser Thr Ala Ala Asn Thr Gln Gly Cys Val Thr Asp Gly Met Ala
1               5                   10                  15

Ser Gly Leu Asp Lys Asp Tyr Leu Lys Pro Asp Asp
            20                  25

<210> SEQ ID NO 57
<211> LENGTH: 28
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 57

Leu Ser Thr Ala Ala Asn Thr Gln Gly Val Cys Thr Asp Gly Met Ala
1               5                   10                  15

Ser Gly Leu Asp Lys Asp Tyr Leu Lys Pro Asp Asp
            20                  25

<210> SEQ ID NO 58
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Ser Thr Ala Ala Asp Met Thr Ala Val Cys Thr Asp Gly Met Ala
1               5                   10                  15

Ser Gly Leu Asp Lys Asp Tyr Leu Lys Pro Asp Asp
            20                  25

<210> SEQ ID NO 59
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Ser Thr Ala Ala Asp Met Thr Ala Val Val Cys Asp Gly Met Ala
1               5                   10                  15

Ser Gly Leu Asp Lys Asp Tyr Leu Lys Pro Asp Asp
            20                  25

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Ser Thr Ala Ala Asp Met Gln Thr Val Val Cys Asp Gly Met Ala
1               5                   10                  15

Ser Gly Leu Asp Lys Asp Tyr Leu Lys Pro Asp Asp
            20                  25

<210> SEQ ID NO 61
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Leu Ser Thr Ala Ala Asp Met Gln Thr Val Val Thr Cys Gly Met Ala
1               5                   10                  15

Ser Gly Leu Asp Lys Asp Tyr Leu Lys Pro Asp Asp
```

```
            20                  25

<210> SEQ ID NO 62
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Leu Ser Thr Ala Ala Asp Met Gln Ala Thr Val Thr Cys Gly Met Ala
1               5                   10                  15

Ser Gly Leu Asp Lys Asp Tyr Leu Lys Pro Asp Asp
            20                  25

<210> SEQ ID NO 63
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Ser Thr Ala Ala Asp Met Gln Ala Thr Val Thr Asp Cys Met Ala
1               5                   10                  15

Ser Gly Leu Asp Lys Asp Tyr Leu Lys Pro Asp Asp
            20                  25

<210> SEQ ID NO 64
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Ser Thr Ala Ala Asp Met Gln Gly Val Thr Ala Asp Cys Met Ala
1               5                   10                  15

Ser Gly Leu Asp Lys Asp Tyr Leu Lys Pro Asp Asp
            20                  25

<210> SEQ ID NO 65
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Ser Thr Ala Ala Asp Met Gln Gly Val Thr Ala Asp Gly Cys Ala
1               5                   10                  15

Ser Gly Leu Asp Lys Asp Tyr Leu Lys Pro Asp Asp
            20                  25

<210> SEQ ID NO 66
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 66

Leu Ser Thr Ala Ala Asp Met Gln Gly Val Val Thr Asn Gly Cys Ala
1               5                   10                  15

Ser Gly Leu Asp Lys Asp Tyr Leu Lys Pro Asp Asp
            20                  25

<210> SEQ ID NO 67
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Leu Ser Thr Ala Ala Asp Met Gln Gly Val Val Thr Ala Thr Met Gly
1               5                   10                  15

Ser Gly Leu Cys Lys Asp Tyr Leu Lys Pro Asp Asp
            20                  25

<210> SEQ ID NO 68
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Leu Ser Thr Ala Ala Asp Met Gln Gly Val Val Thr Asp Leu Thr Ala
1               5                   10                  15

Ser Gly Leu Cys Lys Asp Tyr Leu Lys Pro Asp Asp
            20                  25

<210> SEQ ID NO 69
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Leu Ser Trp Ala Ala Asp Met Gln Gly Val Val Thr Asp Gly Met Ala
1               5                   10                  15

Ser Gly Leu Asp Lys Asp Tyr Leu Lys Pro Asp Asp
            20                  25

<210> SEQ ID NO 70
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Leu Ser Thr Ala Ala Asp Met Trp Gly Val Val Thr Asp Gly Met Ala
1               5                   10                  15

Ser Gly Leu Asp Lys Asp Tyr Leu Lys Pro Asp Asp
            20                  25

<210> SEQ ID NO 71
<211> LENGTH: 28

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Leu Ser Thr Ala Ala Asp Met Gln Gly Val Val Trp Asp Gly Met Ala
1               5                   10                  15

Ser Gly Leu Asp Lys Asp Tyr Leu Lys Pro Asp Asp
            20                  25

<210> SEQ ID NO 72
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Ser Thr Ala Ala Asp Met Gln Gly Val Val Thr Asp Trp Met Ala
1               5                   10                  15

Ser Gly Leu Asp Lys Asp Tyr Leu Lys Pro Asp Asp
            20                  25

<210> SEQ ID NO 73
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Ser Trp Ala Ala Asp Met Trp Gly Val Val Thr Asp Gly Met Ala
1               5                   10                  15

Ser Gly Leu Asp Lys Asp Tyr Leu Lys Pro Asp Asp
            20                  25

<210> SEQ ID NO 74
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Leu Ser Trp Ala Ala Asp Met Gln Gly Val Val Trp Asp Gly Met Ala
1               5                   10                  15

Ser Gly Leu Asp Lys Asp Tyr Leu Lys Pro Asp Asp
            20                  25

<210> SEQ ID NO 75
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Ser Trp Ala Ala Asp Met Gln Gly Val Val Thr Asp Trp Met Ala
1               5                   10                  15

Ser Gly Leu Asp Lys Asp Tyr Leu Lys Pro Asp Asp
            20                  25

<210> SEQ ID NO 76
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Ser Thr Ala Ala Asp Met Trp Gly Val Val Trp Asp Gly Met Ala
1               5                   10                  15

Ser Gly Leu Asp Lys Asp Tyr Leu Lys Pro Asp Asp
            20                  25

<210> SEQ ID NO 77
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Ser Thr Ala Ala Asp Met Trp Gly Val Val Thr Asp Trp Met Ala
1               5                   10                  15

Ser Gly Leu Asp Lys Asp Tyr Leu Lys Pro Asp Asp
            20                  25

<210> SEQ ID NO 78
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Ser Thr Ala Ala Asp Met Gln Gly Val Val Trp Asp Trp Met Ala
1               5                   10                  15

Ser Gly Leu Asp Lys Asp Tyr Leu Lys Pro Asp Asp
            20                  25

<210> SEQ ID NO 79
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Ser Trp Ala Ala Asp Met Trp Gly Val Val Trp Asp Trp Met Ala
1               5                   10                  15

Ser Gly Leu Asp Lys Asp Tyr Leu Lys Pro Asp Asp
            20                  25

<210> SEQ ID NO 80
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (1)..(1)
<223> OTHER INFORMATION: Leu or Acetylated-Leu
<220> FEATURE:
<221> NAME/KEY: MOD_RES
<222> LOCATION: (3)..(3)
<223> OTHER INFORMATION: Thr or Trp
<220> FEATURE:
<221> NAME/KEY: MOD_RES
<222> LOCATION: (7)..(7)
<223> OTHER INFORMATION: Met, Leu or Val
<220> FEATURE:
<221> NAME/KEY: MOD_RES
<222> LOCATION: (8)..(8)
<223> OTHER INFORMATION: Gln or Trp
<220> FEATURE:
<221> NAME/KEY: MOD_RES
<222> LOCATION: (9)..(9)
<223> OTHER INFORMATION: Gly or Ala
<220> FEATURE:
<221> NAME/KEY: MOD_RES
<222> LOCATION: (12)..(12)
<223> OTHER INFORMATION: Thr or Trp
<220> FEATURE:
<221> NAME/KEY: MOD_RES
<222> LOCATION: (14)..(14)
<223> OTHER INFORMATION: Gly, Thr or Trp
<220> FEATURE:
<221> NAME/KEY: MOD_RES
<222> LOCATION: (15)..(15)
<223> OTHER INFORMATION: Met, Leu or Val
<220> FEATURE:
<221> NAME/KEY: MOD_RES
<222> LOCATION: (28)..(28)
<223> OTHER INFORMATION: Asp or Amidated-Asp

<400> SEQUENCE: 80

Xaa Ser Xaa Ala Ala Asp Xaa Xaa Xaa Val Val Xaa Asp Xaa Xaa Ala
1               5                   10                  15

Ser Gly Leu Asp Lys Asp Tyr Leu Lys Pro Asp Xaa
            20                  25

<210> SEQ ID NO 81
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp or Acetylated-Asp
<220> FEATURE:
<221> NAME/KEY: MOD_RES
<222> LOCATION: (14)..(14)
<223> OTHER INFORMATION: Met, Leu or Val
<220> FEATURE:
<221> NAME/KEY: MOD_RES
<222> LOCATION: (15)..(15)
<223> OTHER INFORMATION: Gly, Thr or Trp
<220> FEATURE:
<221> NAME/KEY: MOD_RES
<222> LOCATION: (17)..(17)
<223> OTHER INFORMATION: Thr or Trp
<220> FEATURE:
<221> NAME/KEY: MOD_RES
<222> LOCATION: (20)..(20)
<223> OTHER INFORMATION: Gly or Ala
<220> FEATURE:
<221> NAME/KEY: MOD_RES
<222> LOCATION: (21)..(21)
<223> OTHER INFORMATION: Gln or Trp
<220> FEATURE:
<221> NAME/KEY: MOD_RES
```

```
<222> LOCATION: (22)..(22)
<223> OTHER INFORMATION: Met, Leu or Val
<220> FEATURE:
<221> NAME/KEY: MOD_RES
<222> LOCATION: (26)..(26)
<223> OTHER INFORMATION: Thr or Trp
<220> FEATURE:
<221> NAME/KEY: MOD_RES
<222> LOCATION: (28)..(28)
<223> OTHER INFORMATION: Leu or Amidated-Leu

<400> SEQUENCE: 81

Xaa Asp Pro Lys Leu Tyr Asp Lys Asp Leu Gly Ser Ala Xaa Xaa Asp
1               5                   10                  15

Xaa Val Val Xaa Xaa Xaa Asp Ala Ala Xaa Ser Xaa
            20                  25

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Arg Arg Arg Arg Arg Arg Arg
1               5

<210> SEQ ID NO 83
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gtccatgcaa ggtgatg                                                  17

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gaacgccact tgtccctcta                                               20

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ser Gly Leu Asp Lys Asp
1               5

<210> SEQ ID NO 86
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 86

Val Thr Asp Gly Met Ala Ser Gly
1               5

<210> SEQ ID NO 87
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
cagccaagtc tgtgacttgc acgtac                                          26

<210> SEQ ID NO 88
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ctatgtcgaa aagtgtttct gtcatc                                          26

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
acctgacctg ccgtctagaa                                                 20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
tccaccaccc tgttgctgta                                                 20
```

COMPOSITIONS AND METHODS TO PREVENT CANCER BY STABILIZING P53 THROUGH NON MDM2-MEDIATED PATHWAYS

CROSS REFERENCE TO RELATED APPLICATIONS

This application claims priority under 35 U.S.C. §§119 and 120 to, and is a continuation-in-part of, U.S. patent application Ser. No. 12/389,120, filed Feb. 19, 2009, which is a continuation-in-part of U.S. patent application Ser. No. 12/314,703, filed on Dec. 15, 2008, now abandoned, and which claims priority to U.S. Provisional Patent Application Ser. No. 61/013,709, filed on Dec. 14, 2007. This application is also a continuation-in-part of Ser. No. 12/337,167, filed on Dec. 17, 2008, issued as U.S. Pat. No. 8,158,574 on Apr. 17, 2012, which is a continuation-in-part of U.S. patent application Ser. No. 11/854,654, filed on Sep. 13, 2007, issued as U.S. Pat. No. 7,618,939 on Nov. 17, 2009, which claims priority to U.S. Provisional Application Ser. No. 60/844,358, filed Sep. 14, 2006, and which is a continuation-in-part of U.S. patent application Ser. No. 11/244,105, filed Oct. 6, 2005, issued as U.S. Pat. No. 7,691,383 on Apr. 6, 2010, which claims priority to U.S. Provisional Patent Application Ser. No. 60/700,297, filed Jul. 19, 2005, U.S. Provisional Patent Application Ser. No. 60/680,500, filed May 13, 2005 and U.S. Provisional Patent Application Ser. No. 60/616,782, filed Oct. 7, 2004. The entire content of these prior applications is fully incorporated herein by reference.

FIELD OF THE INVENTION

The present invention relates to compositions comprising variants, derivatives and structural equivalents of cupredoxins and at least one other chemopreventive agent for chemopreventive therapy which are used for cancer-related therapy, and specifically for inhibiting the development of premalignant lesions in mammalian cells, tissues and animals. The invention also relates to the use and/or administration of cupredoxins, and variants, derivatives and structural equivalents of cupredoxins, and at least one other chemopreventive agent in chemopreventive therapy and/or as chemopreventive agents in mammals to inhibit the development of premalignant lesions, and ultimately cancer.

BACKGROUND

Cancer chemoprevention is the use of natural, synthetic or biologic chemical agents to reverse, suppress, or prevent carcinogenic progression to invasive cancer. Recent clinical trials in preventing cancer in high-risk populations suggest that chemopreventive therapy is a realistic treatment for high-risk patients. Chemopreventive therapy is based on the concepts of multifocal field carcinogenesis and multistep carcinogenesis. In field carcinogenesis, generalized carcinogen exposure throughout the tissue field results in diffuse epithelial injury in tissue and clonal proliferation of the mutated cells. These genetic mutations throughout the field increase the likelihood that one or more premalignant or malignant lesions may develop in the field. Multistep carcinogenesis in the stepwise accumulation of these genetic and phenotypic alterations. Arresting one or more steps in the multistep carcinogenesis may impede or prevent the development of cancer. See generally Tsao et al., CA Cancer J Clin 54:150-180 (2004).

Azurin, and other cupredoxins, are cytotoxic specifically towards cancer cells. Azurin induces apoptosis in J774 lung cancer cells. Yamada et al., PNAS 99(22):14098-14103 (2002). On entry into J774 lung cancer cells, azurin localizes in the cytosol and nuclear fractions, and forms a complex with tumor suppressor protein p53, thereby stabilizing it and enhancing its intracellular level. Id. The induction of azurin-mediated apoptosis is not limited to J774 cells. Azurin can also enter cancer cells such as human melanoma UISO-Mel-2, human breast cancer MCF-7 cells, and osteosarcoma. Yamada et al., Infect Immun. 70:7054-7062 (2002); Punj et al., Oncogene. 23:2367-2378 (2004). Azurin allowed the elevation of the intracellular p53 levels, leading to enhanced Bax formation and induction of apoptosis in such cells. Most interestingly, intraperitoneal injection of azurin in nude mice harboring xenografted Mel-2 or MCF-7 human cancers led to statistically significant regression of such cancers. Id.

The mouse mammary gland organ culture (MMOC) model has been fairly well established to study effects of hormonal regulation of mammary gland development and epithelial cell transformation. The MMOC assay may be used to evaluate the inhibitory effects of potential chemopreventive agents on both hormone-induced structural differentiation of mammary glands and on the development of DMBA-induced preneoplastic hyperplastic alveolar nodule-like lesions in the gland. Mammary glands respond to hormones in organ cultures to differentiate into alveolar structures or for inducing expression of casein and a-lactalbumin. Mammary glands from young, virgin animals, when incubated for 6 days in the presence of insulin (I)+prolactin (P)+aldosterone (A), can differentiate into fully-grown glands. These glands morphologically resemble the glands obtained from pregnant mice. Aldosterone can be replaced by estrogen (E)+progesterone (Pg). Inclusion of hydrocortisone (H) to the medium stimulates the functional differentiation of the mammary glands. Mehta and Banerjee, Acta Endocrinol. 80:501 (1975); Mehta and Moon, *Breast Cancer: Treatment and Prognosis* 300, 300 (Basil A Stoll ed., Blackwell Press 1986). Thus, the hormone-induced structural and functional differentiation, observed in this culture system, mimics the responses to hormones observed during various physiological stages of the animal.

Mice exhibit a distinct preneoplastic stage prior to cancer formation in MMOC. Such preneoplastic lesions in C3H mice are induced by murine mammary tumor virus or in BALB/c mice by DMBA. Exposure of the glands to 2 μg/ml DMBA between days 3 and 4 of growth phases followed by regression of the glands for 2-3 weeks in the medium containing only insulin, results in the formation of mammary alveolar lesions (MAL). Hawthorne et al., Pharmaceutical Biology 40:70-74 (2002); Mehta et al., Methods in Cell Science 19:19-24 (1997). Furthermore, transplantation of epithelial cells, prepared from glands containing the DMBA-induced mammary lesions, into syngeneic host resulted in the development of mammary adenocarcinoma. Telang et al., PNAS 76:5886-5890 (1979). Pathologically, these tumors were similar to those observed in vivo when mice of the same strain are administered DMBA. Id.

DMBA-induced mammary lesion formation in MMOC can be inhibited by a variety of classes of chemopreventive agents such as retinoids. These agents include chemopreventive agents derived from the natural products such as brassinin and resveretrol, thiols, antioxidants, inhibitors of ornithine decarboxylase such as OFMO and deguelin, inhibitors of prostaglandin synthesis, Ca regulators, etc. Jang et al., Science 275:218-220 (1997); Mehta, Eur. J. Cancer 36:1275-1282 (2000); Metha et al., J. Natl. Cancer Inst. 89:212-219 (1997). These studies clearly demonstrate that this organ culture system offers a unique model to determine the effectiveness of compounds against mammary carcinogenesis. The results can be expected to closely correlate to the inhibition obtained by in vivo administration of such compounds.

In the presence of aldosterone and hydrocortisone, and in the absence of estrogen and progesterone, the MMOC can be induced to develop estrogen independent MAL. The MMOC may also be induced to form mammary ductal lesions (MDL). The MDL can be induced if estrogen and progesterone instead of aldosterone and hydrocortisone are included in the medium. The alveolar structures in the presence of ovarian steroids are very small but the intraductal lesions are observed in histopathological sections. Mehta et al., J. Natl. Cancer Inst. 93:1103-1106 (2001). The anti-estrogens, which selectively work on ovarian hormone dependent ER+ breast cancers such as Tamoxifen, inhibited MDL formation and not MAL. Thus, this modified culture model in addition to conventional MAL induction protocol now can be used to evaluate effects of chemopreventive agents on both MAL and MDL.

In chemically transformed experimental MMOC models, p53 is rarely mutated or altered, but inactivation of p53 leads to increased aneuploidy in tumors. Further studies in mice bearing C3(1)-Tag transgene suggested that abrogation of p53 function can be a critical event in tumor formation even in the presence of oncogenes. Studies have shown that p53 is inactivated or suppressed by estrogen. Thus, this model can be used to evaluate the effects of azurin on the development of premalignant lesions and the ability of azurin to modulate p53 expression in mammary epithelial cells. This model can also be used to evaluate the effect of estrogen receptor (ER) inhibiting compounds in combination with azurin.

SUMMARY OF THE EMBODIMENTS

The present invention relates to methods comprising administration or other use of compounds and/or peptides that may be cupredoxin(s), or variants, derivatives, truncations, or structural equivalents of cupredoxins, that have chemopreventive effects on premalignant lesions and/or cancer.

In some embodiments of the present invention, the cupredoxin is selected from the group consisting of azurin, pseudoazurin, plastocyanin, rusticyanin, Laz, auracyanin, stellacyanin and cucumber basic protein. In further embodiments, the cupredoxin is azurin. In other embodiments, the cupredoxin is from an organism selected from the group consisting of *Pseudomonas aeruginosa, Alcaligenes faecalis, Achromobacter xylosoxidan, Bordetella bronchiseptica, Methylomonas* sp., *Neisseria meningitidis, Neisseria gonorrhea, Pseudomonas fluorescens, Pseudomonas chlororaphis, Xylella fastidiosa* and *Vibrio parahaemolyticus*. In certain embodiments, the cupredoxin is from *Pseudomonas aeruginosa*. In other embodiments, the cupredoxin is azurin from *Pseudomonas aeruginosa*. In other embodiments, the cupredoxin has been modified using one or more of the methods and/or techniques disclosed herein. In other embodiments, the peptide is a truncation of a cupredoxin contemplated herein. In other embodiments, the peptides may comprise azurin from *Pseudomonas aeruginosa*, and/or the 50-77 residue region of azurin (p28, SEQ ID NO: 2), and/or the 50-67 residue region of azurin (p18, SEQ ID NO: 25), and/or the 60-77 residue region of azurin (p18b, SEQ ID NO: 38), and/or the 60-67 residue region of azurin (SEQ ID NO: 86)

The present invention also relates to a method, comprising preventing the ubiquitination of p53 in a cell by contacting the cell with a cupredoxin-derived peptide. In further embodiments, the peptide is a truncation of a cupredoxin. In another embodiment, the cupredoxin is azurin. In a further embodiment, the azurin is from *Pseudomonas aeruginosa*. In another embodiment, the peptide comprises SEQ ID NO: 2. In a further embodiment, the peptide consists of SEQ ID NO: 2. In other embodiments, the peptide comprises an amino acid sequence selected from the group consisting of SEQ ID NO: 25, SEQ ID NO: 38, SEQ ID NO: 39, and SEQ ID NO: 86.

The present invention also relates to a method, comprising preventing ubiquitination of p53 by contacting the p53 with a compound that binds to p53 within a hydrophobic DNA-binding domain. In a further embodiment, the hydrophobic DNA-binding domain comprises amino acids 80-276. In yet another embodiment, the hydrophobic DNA-binding domain consists of amino acids 80-276. In another embodiment of this method, the compound is a cupredoxin-derived peptide. In a further embodiment, the peptide is a truncation of a cupredoxin. In another embodiment, the cupredoxin is azurin. In another embodiment, the peptide comprises SEQ ID NO: 2. In a further embodiment the peptide consists of SEQ ID NO: 2. In yet another embodiment, wherein the peptide comprises an amino acid sequence selected from the group consisting of SEQ ID NO: 25, SEQ ID NO: 38, and SEQ ID NO: 39.

The present invention also relates to a method, comprising inhibiting the development of cancer by blocking ubiquitination of p53, wherein said blocking is achieved by contacting p53 with a compound that binds to p53 within a hydrophobic DNA-binding domain. In a further embodiment, the hydrophobic DNA-binding domain comprises amino acids 80-276. In yet another embodiment, the hydrophobic DNA-binding domain consists of amino acids 80-276. In another embodiment, the compound is a cupredoxin-derived peptide. In a further embodiment, the peptide is a truncation of a cupredoxin. In another embodiment, the cupredoxin is azurin. In another embodiment, the peptide comprises SEQ ID NO: 2, and in yet another embodiment, the peptide consists of SEQ ID NO: 2. In another embodiment, the peptide comprises an amino acid sequence selected from the group consisting of SEQ ID NO: 25, SEQ ID NO: 38, and SEQ ID NO: 39.

The present invention also relates to a method, comprising preventing proteasomal degradation of p53 by contacting the p53 with a compound that binds to p53 within a hydrophobic DNA binding domain. In one embodiment, the hydrophobic DNA-binding domain comprises amino acids 80-276. In another embodiment, the hydrophobic DNA-binding domain consists of amino acids 80-276. In another embodiment, the compound is a cupredoxin-derived peptide. In a further embodiment, the peptide is a truncation of a cupredoxin. In another embodiment, the cupredoxin is azurin. In yet another embodiment, the peptide comprises SEQ ID NO: 2. In another embodiment, the peptide consists of SEQ ID NO: 2. In one embodiment, the peptide comprises an amino acid sequence selected from the group consisting of SEQ ID NO: 25, SEQ ID NO: 38, and SEQ ID NO: 39.

The present invention also relates to a method, comprising preventing proteasomal degradation of p53 through MDM2-independent and Parc-independent pathways by contacting the p53 with a compound that binds to p53 at a hydrophobic DNA-binding domain. In a further embodiment, the hydrophobic DNA-binding domain comprises amino acids 80-276. In yet another embodiment, the hydrophobic DNA-binding domain consists of amino acids 80-276. In some embodiments, the compound is a cupredoxin-derived peptide. In further embodiments, the peptide is a truncation of a cupredoxin. In another embodiment, the cupredoxin is azurin. In yet another embodiment, the peptide comprises SEQ ID NO: 2. In a further embodiment, the peptide consists of SEQ ID NO: 2. In yet another embodiment, the peptide comprises an amino acid sequence selected from the group consisting of SEQ ID NO: 25, SEQ ID NO: 38, and SEQ ID NO: 39.

These and other aspects, advantages, and features of the invention will become apparent from the following figures and detailed description of the specific embodiments.

DESCRIPTION OF THE SEQUENCES

SEQ ID NO: 1. Amino acid sequence of azurin from *Pseudomonas aeruginosa* (Ala Gin Cys Ser Val Asp Ile Gin Gly Asn Asp Gln Met Gin Phe Asn Thr Asn Ala Ile Thr Val Asp Lys Ser Cys Lys Gln Phe Thr Val Asn Leu Ser His Pro Gly Asn Leu Pro Lys Asn Val Met Gly His Asn Trp Val Leu Ser Thr Ala Ala Asp Met Gin Gly Val Val Thr Asp Gly Met Ala Ser Gly Leu Asp Lys Asp Tyr Leu Lys Pro Asp Asp Ser Arg Val Ile Ala His Thr Lys Leu Ile Gly Ser Gly Glu Lys Asp Ser Val Thr Phe Asp Val Ser Lys Leu Lys Glu Gly Glu Gln Tyr Met Phe Phe Cys Thr Phe Pro Gly His Ser Ala Leu Met Lys Gly Thr Leu Thr Leu Lys).

SEQ ID NO: 2. Amino acid sequence of p28, *Pseudomonas aeruginosa* azurin residues 50-77 (Leu Ser Thr Ala Ala Asp Met Gin Gly Val Val Thr Asp Gly Met Ala Ser Gly Leu Asp Lys Asp Tyr Leu Lys Pro Asp Asp).

SEQ ID NO: 3. Amino acid sequence of plastocyanin from *Phormidium laminosum* (Glu Thr Phe Thr Val Lys Met Gly Ala Asp Ser Gly Leu Leu Gin Phe Glu Pro Ala Asn Val Thr Val His Pro Gly Asp Thr Val Lys Trp Val Asn Asn Lys Leu Pro Pro His Asn Ile Leu Phe Asp Asp Lys Gln Val Pro Gly Ala Ser Lys Glu Leu Ala Asp Lys Leu Ser His Ser Gin Leu Met Phe Ser Pro Gly Glu Ser Tyr Glu Ile Thr Phe Ser Ser Asp Phe Pro Ala Gly Thr Tyr Thr Tyr Tyr Cys Ala Pro His Arg Gly Ala Gly Met Val Gly Lys He Thr Val Glu Gly).

SEQ ID NO: 4. Amino acid sequence of rusticyanin from *Thiobacillus ferrooxidans* (Gly Thr Leu Asp Thr Thr Trp Lys Glu Ala Thr Leu Pro Gin Val Lys Ala Met Leu Glu Lys Asp Thr Gly Lys Val Ser Gly Asp Thr Val Thr Tyr Ser Gly Lys Thr Val His Val Val Ala Ala Ala Val Len Pro Gly Phe Pro Phe Pro Ser Phe Glu Val His Asp Lys Lys Asn Pro Thr Leu Glu Ile Pro Ala Gly Ala Thr Val Asp Val Thr Phe Ile Asn Thr Asn Lys Gly Phe Gly His Ser Phe Asp Ile Thr Lys Lys Gly Pro Pro Tyr Ala Val Met Pro Val Ile Asp Pro Ile Val Ala Gly Thr Gly Phe Ser Pro Val Pro Lys Asp Gly Lys Phe Gly Tyr Thr Asp Phe Thr Trp His Pro Thr Ala Gly Thr Tyr Tyr Tyr Val Cys Gln Ile Pro Gly His Ala Ala Thr Gly Met Phe Gly Lys Ile Val Val Lys).

SEQ ID NO: 5. Amino acid sequence of pseudoazurin from *Achromobacter cycloclastes* (Ala Asp Phe Glu Val His Met Leu Asn Lys Gly Lys Asp Gly Ala Met Val Phe Glu Pro Ala Ser Leu Lys Val Ala Pro Gly Asp Thr Val Thr Phe Ile Pro Thr Asp Lys Gly His Asn Val Glu Thr Ile Lys Gly Met Ile Pro Asp Gly Ala Gin Ala Phe Lys Ser Lys Ile Asn Glu Asn Tyr Lys Val Thr Phe Thr Ala Pro Gly Val Tyr Gly Val Lys Cys Thr Pro His Tyr Gly Met Gly Met Val Gly Val Val Gln Val Gly Asp Ala Pro Ala Asn Leu Asp Ala Val Lys Gly Ala Lys Asn Pro Lys Lys Ala Gin Glu Arg Leu Asp Ala Ala Leu Ala Ala Leu Gly Asn).

SEQ ID NO: 6. Amino acid sequence of azurin from *Alcaligenes faecalis* (Ala Cys Asp Val Ser Ile Glu Gly Asn Asp Ser Met Gln Phe Asn Thr Lys Ser Ile Val Val Asp Lys Thr Cys Lys Glu Phe Thr Ile Asn Leu Lys His Thr Gly Lys Leu Pro Lys Ala Ala Met Gly His Asn Val Val Val Ser Lys Lys Ser Asp Glu Ser Ala Val Ala Thr Asp Gly Met Lys Ala Gly Leu Asn Asn Asp Tyr Val Lys Ala Gly Asp Glu Arg Val Ile Ala His Thr Ser Val Ile Gly Gly Gly Glu Thr Asp Ser Val Thr Phe Asp Val Ser Lys Leu Lys Glu Gly Glu Asp Tyr Ala Phe Phe Cys Ser Phe Pro Gly His Trp Ser Ile Met Lys Gly Thr Ile Glu Leu Gly Ser).

SEQ ID NO: 7. Amino acid sequence of azurin from *Achromobacter xylosoxidans* ssp. *denitrificans* I (Ala Gln Cys Glu Ala Thr Ile Glu Ser Asn Asp Ala Met Gin Tyr Asn Leu Lys Glu Met Val Val Asp Lys Ser Cys Lys Gin Phe Thr Val His Leu Lys His Val Gly Lys Met Ala Lys Val Ala Met Gly His Asn Trp Val Leu Thr Lys Glu Ala Asp Lys Gln Gly Val Ala Thr Asp Gly Met Asn Ala Gly Leu Ala Gln Asp Tyr Val Lys Ala Gly Asp Thr Arg Val Ile Ala His Thr Lys Val Ile Gly Gly Gly Glu Ser Asp Ser Val Thr Phe Asp Val Ser Lys Leu Thr Pro Gly Glu Ala Tyr Ala Tyr Phe Cys Ser Phe Pro Gly His Trp Ala Met Met Lys Gly Thr Leu Lys Leu Ser Asn).

SEQ ID NO: 8. Amino acid sequence of azurin from *Bordetella bronchiseptica* (Ala Glu Cys Ser Val Asp Ile Ala Gly Thr Asp Gin Met Gin Phe Asp Lys Lys Ala Ile Glu Val Ser Lys Ser Cys Lys Gln Phe Thr Val Asn Leu Lys His Thr Gly Lys Leu Pro Arg Asn Val Met Gly His Asn Trp Val Leu Thr Lys Thr Ala Asp Met Gln Ala Val Glu Lys Asp Gly Ile Ala Ala Gly Leu Asp Asn Gln Tyr Leu Lys Ala Gly Asp Thr Arg Val Leu Ala His Thr Lys Val Leu Gly Gly Gly Glu Ser Asp Ser Val Thr Phe Asp Val Ala Lys Leu Ala Ala Gly Asp Asp Tyr Thr Phe Phe Cys Ser Phe Pro Gly His Gly Ala Leu Met Lys Gly Thr Leu Lys Leu Val Asp).

SEQ ID NO: 9. Amino acid sequence of azurin from *Methylomonas* sp. J (Ala Ser Cys Glu Thr Thr Val Thr Ser Gly Asp Thr Met Thr Tyr Ser Thr Arg Ser Ile Ser Val Pro Ala Ser Cys Ala Glu Phe Thr Val Asn Phe Glu His Lys Gly His Met Pro Lys Thr Gly Met Gly His Asn Trp Val Leu Ala Lys Ser Ala Asp Val Gly Asp Val Ala Lys Glu Gly Ala His Ala Gly Ala Asp Asn Asn Phe Val Thr Pro Gly Asp Lys Arg Val Ile Ala Phe Thr Pro Ile Ile Gly Gly Gly Glu Lys Thr Ser Val Lys Phe Lys Val Ser Ala Leu Ser Lys Asp Glu Ala Tyr Thr Tyr Phe Cys Ser Tyr Pro Gly His Phe Ser Met Met Arg Gly Thr Leu Lys Leu Glu Glu).

SEQ ID NO: 10. Amino acid sequence of azurin from *Neisseria meningitidis* Z2491 (Cys Ser Gln Glu Pro Ala Ala Pro Ala Ala Glu Ala Thr Pro Ala Ala Glu Ala Pro Ala Ser Glu Ala Pro Ala Ala Glu Ala Ala Pro Ala Asp Ala Ala Glu Ala Pro Ala Ala Gly Asn Cys Ala Ala Thr Val Glu Ser Asn Asp Asn Met Gin Phe Asn Thr Lys Asp Ile Gln Val Ser Lys Ala Cys Lys Glu Phe Thr Ile Thr Leu Lys His Thr Gly Thr Gin Pro Lys Thr Ser Met Gly His Asn Ile Val Ile Gly Lys Thr Glu Asp Met Asp Gly Ile Phe Lys Asp Gly Val Gly Ala Ala Asp Thr Asp Tyr Val Lys Pro Asp Asp Ala Arg Val Val Ala His Thr Lys Leu Ile Gly Gly Gly Glu Glu Ser Ser Leu Thr Leu Asp Pro Ala Lys Leu Ala Asp Gly Glu Tyr Lys Phe Ala Cys Thr Phe Pro Gly His Gly Ala Leu Met Asn Gly Lys Val Thr Leu Val Asp).

SEQ ID NO: 11. Amino acid sequence of azurin from *Pseudomonas fluorescen* (Ala Glu Cys Lys Thr Thr Ile Asp Ser Thr Asp Gln Met Ser Phe Asn Thr Lys Ala Ile Glu Ile Asp Lys Ala Cys Lys Thr Phe Thr Val Glu Leu Thr His Ser Gly Ser Leu Pro Lys Asn Val Met Gly His Asn Leu Val Ile Ser Lys Gln Ala Ala Asp Met Gin Pro Ile Ala Thr Asp Gly Leu Ser Ala Gly Ile Asp Lys Asn Tyr Leu Lys Glu Gly Asp Thr Arg Val Ile Ala His Thr Lys Val Ile Gly Ala Gly Glu Lys Asp Ser Leu Thr Ile Asp Val Ser Lys Leu Asn Ala Ala Glu Lys Tyr Gly Phe Phe Cys Ser Phe Pro Gly His Ile Ser Met Met Lys Gly Thr Val Thr Leu Lys).

SEQ ID NO: 12. Amino acid sequence of azurin from *Pseudomonas chlororaphis* (Ala Glu Cys Lys Val Asp Val Asp Ser Thr Asp Gln Met Ser Phe Asn Thr Lys Glu Ile Thr Ile Asp Lys Ser Cys Lys Thr Phe Thr Val Asn Leu Thr His Ser Gly Ser Leu Pro Lys Asn Val Met Gly His Asn Trp Val Leu Ser Lys Ser Ala Asp Met Ala Gly Ile Ala Thr Asp Gly Met Ala Ala Gly Ile Asp Lys Asp Tyr Leu Lys Pro Gly Asp Ser Arg Val Ile Ala His Thr Lys Ile Ile Gly Ser Gly Glu Lys Asp Ser Val Thr Phe Asp Val Ser Lys Leu Thr Ala Gly Glu Ser Tyr Glu Phe Phe Cys Ser Phe Pro Gly His Asn Ser Met Met Lys Gly Ala Val Val Leu Lys).

SEQ ID NO: 13. Amino acid sequence of azurin from *Xylella fastidiosa* 9a5c (Lys Thr Cys Ala Val Thr Ile Ser Ala Asn Asp Gln Met Lys Phe Asp Gln Asn Thr Ile Lys Ile Ala Ala Glu Cys Thr His Val Asn Leu Thr Leu Thr His Thr Gly Lys Lys Ser Ala Arg Val Met Gly His Asn Trp Val Leu Thr Lys Thr Thr Asp Met Gln Ala Val Ala Leu Ala Gly Leu His Ala Thr Leu Ala Asp Asn Tyr Val Pro Lys Ala Asp Pro Arg Val Ile Ala His Thr Ala Ile Ile Gly Gly Gly Glu Arg Thr Ser Ile Thr Phe Pro Thr Asn Thr Leu Ser Lys Asn Val Ser Tyr Thr Phe Phe Cys Ser Phe Pro Gly His Trp Ala Leu Met Lys Gly Thr Leu Asn Phe Gly Gly).

SEQ ID NO: 14. Amino acid sequence of stellacyanin from *Cucumis sativus* (Met Gln Ser Thr Val His Ile Val Gly Asp Asn Thr Gly Trp Ser Val Pro Ser Ser Pro Asn Phe Tyr Ser Gln Trp Ala Ala Gly Lys Thr Phe Arg Val Gly Asp Ser Leu Gln Phe Asn Phe Pro Ala Asn Ala His Asn Val His Glu Met Glu Thr Lys Gln Ser Phe Asp Ala Cys Asn Phe Val Asn Ser Asp Asn Asp Val Glu Arg Thr Ser Pro Val Ile Glu Arg Leu Asp Glu Leu Gly Met His Tyr Phe Val Cys Thr Val Gly Thr His Cys Ser Asn Gly Gln Lys Leu Ser Ile Asn Val Val Ala Ala Asn Ala Thr Val Ser Met Pro Pro Pro Ser Ser Ser Pro Pro Ser Ser Val Met Pro Pro Pro Val Met Pro Pro Pro Ser Pro Ser).

SEQ ID NO: 15. Amino acid sequence of auracyanin A from *Chloroflexus aurantiacus* (Met Lys Ile Thr Leu Arg Met Met Val Leu Ala Val Leu Thr Ala Met Ala Met Val Leu Ala Ala Cys Gly Gly Gly Gly Ser Ser Gly Gly Ser Thr Gly Gly Gly Ser Gly Ser Gly Pro Val Thr Ile Glu Ile Gly Ser Lys Gly Glu Glu Leu Ala Phe Asp Lys Thr Glu Leu Thr Val Ser Ala Gly Gln Thr Val Thr Ile Arg Phe Lys Asn Asn Ser Ala Val Gln His Asn Trp Ile Leu Val Lys Gly Gly Glu Ala Glu Ala Ala Asn Ile Ala Asn Ala Gly Leu Ser Ala Gly Pro Ala Ala Asn Tyr Leu Pro Ala Asp Lys Ser Asn Ile Ile Ala Glu Ser Pro Leu Ala Asn Gly Asn Glu Thr Val Glu Val Thr Phe Thr Ala Pro Ala Ala Gly Thr Tyr Leu Tyr Ile Cys Thr Val Pro Gly His Tyr Pro Leu Met Gln Gly Lys Leu Val Val Asn).

SEQ ID NO: 16. Amino acid sequence of auracyanin B from *Chloroflexus aurantiacus* (Ala Ala Asn Ala Pro Gly Gly Ser Asn Val Val Asn Glu Thr Pro Ala Gln Thr Val Glu Val Arg Ala Ala Pro Asp Ala Leu Ala Phe Ala Gln Thr Ser Leu Ser Leu Pro Ala Asn Thr Val Val Arg Leu Asp Phe Val Asn Gln Asn Asn Leu Gly Val Gln His Asn Trp Val Leu Val Asn Gly Gly Asp Asp Val Ala Ala Ala Val Asn Thr Ala Ala Gln Asn Asn Ala Asp Ala Leu Phe Val Pro Pro Pro Asp Thr Pro Asn Ala Leu Ala Trp Thr Ala Met Leu Asn Ala Gly Glu Ser Gly Ser Val Thr Phe Arg Thr Pro Ala Pro Gly Thr Tyr Leu Tyr Ile Cys Thr Phe Pro Gly His Tyr Leu Ala Gly Met Lys Gly Thr Leu Thr Val Thr Pro).

SEQ ID NO: 17. Amino acid sequence of cucumber basic protein from *Cucumis sativus* (Ala Val Tyr Val Val Gly Gly Ser Gly Gly Trp Thr Phe Asn Thr Glu Ser Trp Pro Lys Gly Lys Arg Phe Arg Ala Gly Asp Ile Leu Leu Phe Lys Tyr Asn Pro Ser Met His Asn Val Val Val Val Asn Gly Gly Phe Ser Thr Cys Asn Thr Pro Ala Gly Ala Lys Val Tyr Thr Ser Gly Arg Asp Gln Ile Lys Leu Pro Lys Gly Gln Ser Tyr Phe Ile Cys Asn Phe Pro Gly His Cys Gln Ser Gly Met Lys Ile Ala Val Asn Ala Leu).

SEQ ID NO: 18. Amino acid sequence of Laz from *Neisseria gonorrhoeae* F62 (Cys Ser Gln Glu Pro Ala Ala Pro Ala Ala Glu Ala Thr Pro Ala Gly Glu Ala Pro Ala Ser Glu Ala Pro Ala Ala Glu Ala Ala Pro Ala Asp Ala Ala Glu Ala Pro Ala Ala Gly Asn Cys Ala Ala Thr Val Glu Ser Asn Asp Asn Met Gln Phe Asn Thr Lys Asp Ile Gln Val Ser Lys Ala Cys Lys Glu Phe Thr Ile Thr Leu Lys His Thr Gly Thr Gln Pro Lys Ala Ser Met Gly His Asn Leu Val Ile Ala Lys Ala Glu Asp Met Asp Gly Val Phe Lys Asp Gly Val Gly Ala Ala Asp Thr Asp Tyr Val Lys Pro Asp Asp Ala Arg Val Val Ala His Thr Lys Leu Ile Gly Gly Gly Glu Glu Ser Ser Leu Thr Leu Asp Pro Ala Lys Leu Ala Asp Gly Asp Tyr Lys Phe Ala Cys Thr Phe Pro Gly His Gly Ala Leu Met Asn Gly Lys Val Thr Leu Val Asp).

SEQ ID NO: 19. Amino acid sequence of the azurin from *Vibrio parahaemolyticus* (Met Ser Leu Arg Ile Leu Ala Ala Thr Leu Ala Leu Ala Gly Leu Ser Phe Gly Ala Gln Ala Ser Ala Glu Cys Glu Val Ser Ile Asp Ala Asn Asp Met Met Gln Phe Ser Thr Lys Thr Leu Ser Val Pro Ala Thr Cys Lys Glu Val Thr Leu Thr Leu Asn His Thr Gly Lys Met Pro Ala Gln Ser Met Gly His Asn Val Val Ile Ala Asp Thr Ala Asn Ile Gln Ala Val Gly Thr Asp Gly Met Ser Ala Gly Ala Asp Asn Ser Tyr Val Lys Pro Asp Asp Glu Arg Val Tyr Ala His Thr Lys Val Val Gly Gly Gly Glu Ser Thr Ser Ile Thr Phe Ser Thr Glu Lys Met Thr Ala Gly Gly Asp Tyr Ser Phe Phe Cys Ser Phe Pro Gly His Trp Ala Ile Met Gln Gly Lys Phe Glu Phe Lys).

SEQ ID NO: 20. Amino acid sequence of amino acids 57 to 89 of auracyanin B of *Chloroflexus aurantiacus* (His Asn Trp Val Leu Val Asn Gly Gly Asp Asp Val Ala Ala Ala Val Asn Thr Ala Ala Gln Asn Asn Ala Asp Ala Leu Phe Val Pro Pro Pro Asp).

SEQ ID NO: 21. Amino acid sequence of amino acids 51-77 of *Pseudomonas syringae* azurin (Ser Lys Lys Ala Asp Ala Ser Ala Ile Thr Thr Asp Gly Met Ser Val Gly Ile Asp Lys Asp Tyr Val Lys Pro Asp Asp).

SEQ ID NO: 22. Amino acid sequence of amino acids 89-115 of *Neisseria meningitidis* Laz (Ile Gly Lys Thr Glu Asp Met Asp Gly Ile Phe Lys Asp Gly Val Gly Ala Ala Asp Thr Asp Tyr Val Lys Pro Asp Asp).

SEQ ID NO: 23. Amino acid sequence of amino acids 52-78 of *Vibrio parahaemolyticus* azurin (Ala Asp Thr Ala Asn Ile Gln Ala Val Gly Thr Asp Gly Met Ser Ala Gly Ala Asp Asn Ser Tyr Val Lys Pro Asp Asp).

SEQ ID NO: 24. Amino acid sequence of amino acids 51-77 of *Bordetella bronchiseptica* azurin (Thr Lys Thr Ala Asp Met Gln Ala Val Glu Lys Asp Gly Ile Ala Ala Gly Leu Asp Asn Gln Tyr Leu Lys Ala Gly Asp).

SEQ ID NO: 25. Amino acid sequence of p18, *Pseudomonas aeruginosa* azurin residues 50-67 (Leu Ser Thr Ala Ala Asp Met Gln Gly Val Val Thr Asp Gly Met Ala Ser Gly).

SEQ ID NO: 26. Amino acid sequence of *Pseudomonas aeruginosa* azurin residues 50-68 (Leu Ser Thr Ala Ala Asp Met Gln Gly Val Val Thr Asp Gly Met Ala Ser Gly Leu).

SEQ ID NO: 27. Amino acid sequence of *Pseudomonas aeruginosa* azurin residues 50-69 (Leu Ser Thr Ala Ala Asp Met Gln Gly Val Val Thr Asp Gly Met Ala Ser Gly Leu Asp).

SEQ ID NO: 28. Amino acid sequence of *Pseudomonas aeruginosa* azurin residues 50-70 (Leu Ser Thr Ala Ala Asp Met Gln Gly Val Val Thr Asp Gly Met Ala Ser Gly Leu Asp Lys).

SEQ ID NO: 29. Amino acid sequence of *Pseudomonas aeruginosa* azurin residues 50-71 (Leu Ser Thr Ala Ala Asp Met Gln Gly Val Val Thr Asp Gly Met Ala Ser Gly Leu Asp Lys Asp).

SEQ ID NO: 30. Amino acid sequence of *Pseudomonas aeruginosa* azurin residues 50-72 (Leu Ser Thr Ala Ala Asp Met Gln Gly Val Val Thr Asp Gly Met Ala Ser Gly Leu Asp Lys Asp Tyr)

SEQ ID NO: 31. Amino acid sequence of *Pseudomonas aeruginosa* azurin residues 50-73 (Leu Ser Thr Ala Ala Asp Met Gln Gly Val Val Thr Asp Gly Met Ala Ser Gly Leu Asp Lys Asp Tyr Leu).

SEQ ID NO: 32. Amino acid sequence of *Pseudomonas aeruginosa* azurin residues 50-74 (Leu Ser Thr Ala Ala Asp Met Gln Gly Val Val Thr Asp Gly Met Ala Ser Gly Leu Asp Lys Asp Tyr Leu Lys).

SEQ ID NO: 33. Amino acid sequence of *Pseudomonas aeruginosa* azurin residues 50-75 (Leu Ser Thr Ala Ala Asp Met Gln Gly Val Val Thr Asp Gly Met Ala Ser Gly Leu Asp Lys Asp Tyr Leu Lys Pro).

SEQ ID NO: 34 Amino acid sequence of *Pseudomonas aeruginosa* azurin residues 50-76 (Leu Ser Thr Ala Ala Asp Met Gln Gly Val Val Thr Asp Gly Met Ala Ser Gly Leu Asp Lys Asp Tyr Leu Lys Pro Asp).

SEQ ID NO: 35. Amino acid sequence of *Pseudomonas aeruginosa* azurin residues 36-88 (Pro Gly Asn Leu Pro Lys Asn Val Met Gly His Asn Trp Val Leu Ser Thr Ala Ala Asp Met Gln Gly Val Val Thr Asp Gly Met Ala Ser Gly Leu Asp Lys Asp Tyr Leu Lys Pro Asp Asp Ser Arg Val Ile Ala His Thr Lys Leu Ile Gly).

SEQ ID NOS: 36 and 83. Nucleotide sequence of primers for p53 (forward: 5-GATGACTGCCATGGAGGAG-3' reverse: 5'-GTCCATGCAAGGTGATG-3').

SEQ ID NOS: 37 and 84. Nucleotide sequence of primers for 18S (forwards 5'-CATGCCCGTTCTTAGTTGGT-3' reverse: 5'-GAACGCCACTTGTCCCTCTA-3').

SEQ ID NO: 38. Amino acid sequence of p18b, *Pseudomonas aeruginosa* azurin residues 60-77 (Val Thr Asp Gly Met Ala Ser Gly Leu Asp Lys Asp Tyr Leu Lys Pro Asp Asp).

SEQ ID NO: 39. Sequence of C-terminal 12 amino acids of p28, *Pseudomonas aeruginosa* azurin residues 66-77, also referred to as p12 (Ser Gly Leu Asp Lys Asp Tyr Len Lys Pro Asp Asp).

SEQ ID NO: 40. Sequence of C-terminal 10 amino acids of p28, *Pseudomonas aeruginosa* azurin residues 68-77 (Len Asp Lys Asp Tyr Leu Lys Pro Asp Asp).

SEQ ID NO: 41. Sequence of C-terminal 11 amino acids of p28, *Pseudomonas aeruginosa* azurin residues 67-77 (Gly Leu Asp Lys Asp Tyr Leu Lys Pro Asp Asp).

SEQ ID NO: 42 is the amino acid sequence of a variant of the azurin truncation p28 (Leu Ser Thr Ala Ala Asp Met Gln Ala Val Val Thr Asp Thr Met Ala Set Gly Leu Asp Lys Asp Tyr Leu Lys Pro Asp Asp).

SEQ ID NO: 43 is the amino acid sequence of a variant of the azurin truncation p28 (Leu Ser Thr Ala Ala Asp Leu Gln Gly Val Val Thr Asp Gly Leu Ala Set Gly Leu Asp Lys Asp Tyr Leu Lys Pro Asp Asp).

SEQ ID NO: 44 is the amino acid sequence of a variant of the azurin truncation p28 (Leu Ser Thr Ala Ala Asp Val Gln Gly Val Val Thr Asp Gly Val Ala Ser Gly Leu Asp Lys Asp Tyr Leu Lys Pro Asp Asp).

SEQ ID NO: 45 is the amino acid sequence of a modified cupredoxin derived peptide (Asp Asp Pro Lys Len Tyr Asp Lys Asp Leu Gly Ser Ala Met Gly Asp Thr Val Val Gly Gln Met Asp Ala Ala Thr Ser Leu).

SEQ ID NO: 46 is the amino acid sequence of a modified cupredoxin derived peptide (Acetylation-Leu Ser Thr Ala Ala Asp Met Gln Gly Val Val Thr Asp Gly Met Ala Ser Gly Len Asp Lys Asp Tyr Leu Lys Pro Asp Asp-amidation).

SEQ ID NO: 47 is the amino acid sequence of a hexapeptide (Val Ser Pro Pro Ala Arg).

SEQ ID NO: 48 is the amino acid sequence of a hexapeptide (Tyr Thr Pro Pro Ala Leu).

SEQ ID NO: 49 is the amino acid sequence of a hexapeptide (Phe Ser Phe Phe Ala Phe).

SEQ ID NO: 50 is the amino acid sequence of a modified cupredoxin-derived peptide (Leu Ser Thr Ala Ala Asp Met Gln Gly Val Val Thr Asp Gly Met Ala Ser Gly Leu Asp Lys Asp Tyr Leu Thr Pro Gly Cys).

SEQ ID NO: 51 is the amino acid sequence of a modified cupredoxin-derived peptide (Leu Ser Thr Ala Ala Asp Cys Gln Gly Val Val Thr Asp Gly Met Ala Ser Gly Leu Asp Lys Asp Tyr Leu Lys Pro Asp Asp).

SEQ ID NO: 52 is the amino acid sequence of a modified cupredoxin-derived peptide (Leu Ser Thr Ala Ala Cys Met Gln Gly Val Val Thr Asp Gly Met Ala Ser Gly Leu Asp Lys Asp Tyr Leu Lys Pro Asp Asp).

SEQ ID NO: 53 is the amino acid sequence of a modified cupredoxin-derived peptide (Leu Ser Thr Ala Cys Asp Met Gln Gly Val Val Thr Asp Gly Met Ala Ser Gly Leu Asp Lys Asp Tyr Leu Lys Pro Asp Asp).

SEQ ID NO: 54 is the amino acid sequence of a modified cupredoxin-derived peptide (Leu Ser Thr Ala Ala Thr Met Gln Cys Val Val Thr Asp Gly Met Ala Ser Gly Leu Lys Asp Tyr Leu Lys Pro Asp Asp).

SEQ ID NO: 55 is the amino acid sequence of a modified cupredoxin-derived peptide (Leu Ser Thr Ala Ala Thr Met Gln Gly Cys Val Thr Asp Gly Met Ala Ser Gly Leu Asp Lys Asp Tyr Leu Lys Pro Asp Asp).

SEQ ID NO: 56 is the amino acid sequence of a modified cupredoxin-derived peptide (Leu Ser Thr Ala Ala Asn Thr Gln Gly Cys Val Thr Asp Gly Met Ala Ser Gly Leu Asp Lys Asp Tyr Leu Lys Pro Asp Asp).

SEQ ID NO: 57 is the amino acid sequence of a modified cupredoxin-derived peptide (Leu Ser Thr Ala Ala Asn Thr Gln Gly Val Cys Thr Asp Gly Met Ala Ser Gly Leu Asp Lys Asp Tyr Leu Lys Pro Asp Asp).

SEQ ID NO: 58 is the amino acid sequence of a modified cupredoxin-derived peptide (Leu Ser Thr Ala Ala Asp Met Thr Ala Val Cys Thr Asp Gly Met Ala Ser Gly Leu Asp Lys Asp Tyr Leu Lys Pro Asp Asp).

SEQ ID NO: 59 is the amino acid sequence of a modified cupredoxin-derived peptide (Leu Ser Thr Ala Ala Asp Met Thr Ala Val Val Cys Asp Gly Met Ala Ser Gly Leu Asp Lys Asp Tyr Leu Lys Pro Asp Asp).

SEQ ID NO: 60 is the amino acid sequence of a modified cupredoxin-derived peptide (Leu Ser Thr Ala Ala Asp Met Gln Thr Val Val Cys Asp Gly Met Ala Ser Gly Leu Asp Lys Asp Tyr Leu Lys Pro Asp Asp).

SEQ ID NO: 61 is the amino acid sequence of a modified cupredoxin-derived peptide (Leu Ser Thr Ala Ala Asp Met Gln Thr Val Thr Cys Gly Met Ala Ser Gly Leu Asp Lys Asp Tyr Leu Lys Pro Asp Asp).

SEQ ID NO: 62 is the amino acid sequence of a modified cupredoxin-derived peptide (Leu Ser Thr Ala Ala Asp Met Gln Ala Thr Val Thr Cys Gly Met Ala Ser Gly Leu Asp Lys Asp Tyr Leu Lys Pro Asp Asp).

SEQ ID NO: 63 is the amino acid sequence of a modified cupredoxin-derived peptide (Leu Ser Thr Ala Ala Asp Met Gln Ala Thr Val Thr Asp Cys Met Ala Ser Gly Leu Asp Lys Asp Tyr Leu Lys Pro Asp Asp).

SEQ ID NO: 64 is the amino acid sequence of a modified cupredoxin-derived peptide (Leu Ser Thr Ala Ala Asp Met Gln Gly Val Thr Ala Asp Cys Met Ala Ser Gly Leu Asp Lys Asp Tyr Leu Lys Pro Asp Asp).

SEQ ID NO: 65 is the amino acid sequence of a modified cupredoxin-derived peptide (Leu Ser Thr Ala Ala Asp Met Gln Gly Val Thr Ala Asp Gly Cys Ala Ser Gly Leu Asp Lys Asp Tyr Leu Lys Pro Asp Asp).

SEQ ID NO: 66 is the amino acid sequence of a modified cupredoxin-derived peptide (Leu Ser Thr Ala Ala Asp Met Gln Gly Val Val Thr Asn Gly Cys Ala Ser Gly Leu Asp Lys Asp Tyr Leu Lys Pro Asp Asp).

SEQ ID NO: 67 is the amino acid sequence of a modified cupredoxin-derived peptide (Leu Ser Thr Ala Ala Asp Met Gln Gly Val Val Thr Ala Thr Met Gly Ser Gly Leu Cys Lys Asp Tyr Leu Lys Pro Asp Asp).

SEQ ID NO: 68 is the amino acid sequence of a modified cupredoxin-derived peptide (Leu Ser Thr Ala Ala Asp Met Gln Gly Val Val Thr Asp Leu Thr Ala Ser Gly Leu Cys Lys Asp Tyr Leu Lys Pro Asp Asp).

SEQ ID NO: 69 is the amino acid sequence of a modified cupredoxin-derived peptide (Leu Ser Trp Ala Ala Asp Met Gln Gly Val Val Thr Asp Gly Met Ala Ser Gly Leu Asp Lys Asp Tyr Leu Lys Pro Asp Asp).

SEQ ID NO: 70 is the amino acid sequence of a modified cupredoxin-derived peptide (Leu Ser Thr Ala Ala Asp Met Trp Gly Val Val Thr Asp Gly Met Ala Ser Gly Leu Asp Lys Asp Tyr Leu Lys Pro Asp Asp).

SEQ ID NO: 71 is the amino acid sequence of a modified cupredoxin-derived peptide (Leu Ser Thr Ala Ala Asp Met Gln Gly Val Val Trp Asp Gly Met Ala Ser Gly Leu Asp Lys Asp Tyr Leu Lys Pro Asp Asp).

SEQ ID NO: 72 is the amino acid sequence of a modified cupredoxin-derived peptide (Leu Ser Thr Ala Ala Asp Met Gln Gly Val Val Thr Asp Trp Met Ala Ser Gly Leu Asp Lys Asp Tyr Leu Lys Pro Asp Asp).

SEQ ID NO: 73 is the amino acid sequence of a modified cupredoxin-derived peptide (Leu Ser Trp Ala Ala Asp Met Trp Gly Val Val Thr Asp Gly Met Ala Ser Gly Leu Asp Lys Asp Tyr Leu Lys Pro Asp Asp).

SEQ ID NO: 74 is the amino acid sequence of a modified cupredoxin-derived peptide (Leu Ser Trp Ala Ala Asp Met Gln Gly Val Val Trp Asp Gly Met Ala Ser Gly Leu Asp Lys Asp Tyr Leu Lys Pro Asp Asp).

SEQ ID NO: 75 is the amino acid sequence of a modified cupredoxin-derived peptide (Leu Ser Trp Ala Ala Asp Met Gln Gly Val Val Thr Asp Trp Met Ala Ser Gly Leu Asp Lys Asp Tyr Leu Lys Pro Asp Asp).

SEQ ID NO: 76 is the amino acid sequence of a modified cupredoxin-derived peptide (Leu Ser Thr Ala Ala Asp Met Trp Gly Val Val Trp Asp Gly Met Ala Ser Gly Leu Asp Lys Asp Tyr Leu Lys Pro Asp Asp).

SEQ ID NO: 77 is the amino acid sequence of a modified cupredoxin-derived peptide (Leu Ser Thr Ala Ala Asp Met Trp Gly Val Val Thr Asp Trp Met Ala Ser Gly Leu Asp Lys Asp Tyr Leu Lys Pro Asp Asp).

SEQ ID NO: 78 is the amino acid sequence of a modified cupredoxin-derived peptide (Leu Ser Thr Ala Ala Asp Met Gln Gly Val Val Trp Asp Trp Met Ala Ser Gly Leu Asp Lys Asp Tyr Leu Lys Pro Asp Asp).

SEQ ID NO: 79 is the amino acid sequence of a modified cupredoxin-derived peptide (Leu Ser Trp Ala Ala Asp Met Trp Gly Val Val Trp Asp Trp Met Ala Ser Gly Leu Asp Lys Asp Tyr Leu Lys Pro Asp Asp).

SEQ ID NO: 80 is the amino acid sequence of a modified cupredoxin-derived peptide ($X_1$ Ser $X_2$ Ala Ala Asp $X_3$ $X_4$ $X_5$ Val Val $X_6$ Asp $X_7 X_8$ Ala Ser Gly Leu Asp Lys Asp Tyr Leu Lys Pro Asp $X_9$).

SEQ ID NO: 81 is the amino acid sequence of a modified cupredoxin-derived peptide ($X_1$ Asp Pro Lys Leu Tyr Asp Lys Asp Leu Gly Ser Ala $X_2$ $X_3$ Asp $X_4$ Val Val $X_5$ $X_6$ $X_7$ Asp Ala Ala $X_8$ Ser $X_9$).

SEQ ID NO: 82 is the amino acid sequence of cationic peptide $Arg_8$ (Arg Arg Arg Arg Arg Arg Arg Arg).

SEQ ID NO: 85 is a sequence of amino acids in p28 that may interact with p53 (Ser Gly Leu Asp Lys Asp).

SEQ ID NO: 86 is a sequence of amino acids in p28 that may have maximal binding to p53 (Val Thr Asp Gly Met Ala Ser Gly).

SEQ ID NOS: 87 and 88 are nucleotide sequences for primers for p53 (5'-CAG CCA AGT CTG TGA CTT GCA CGT AC-3' and 5'-CTA TGT CGA AAA GTG TTT CTG TCA TC)

SEQ ID NOS: 89 and 90 are nucleotide sequences for primers for GAPDH (5'-ACC TGA CCT GCC GTC TAG AA-3' and 5'-TCC ACC ACC CTG TTG CTG TA-3').

BRIEF DESCRIPTION OF THE FIGURES

FIG. 1 depicts photographs of the glands evaluated for the efficacy of p28 (SEQ ID NO: 2) and azurin. FIG. 1A shows a representative photograph of alveolar lesions in a DMBA-treated gland and its comparison with a gland that was treated with DMBA along with a chemopreventive agent.

FIGS. 11A and 11B are photographs showing penetration of azurin derived peptides into cancer cell lines of diverse histogenesis and their normal counterparts. FIGS. 11A and 11B are photographs showing penetration of Alexafluor 568 labeled p28 (SEQ ID NO: 2) and p18 (SEQ ID NO: 25), respectively, after 2 hrs at 37° C. The cationic $Arg_8$ (SEQ ID NO: 82) was used as a control. FIG. 11C are graphs depicting flow eytometric analysis of the penetration of Alexafluor 568 labeled p28 (SEQ ID NO: 2) or p18 (SEQ ID NO: 25) into the same cell lines after 2 hrs at 37° C. FIG. 11D are graphs depicting fold increase over fluorescence from normal cells. Similar observations of p28 (SEQ ID NO: 2) or p18 (SEQ ID NO: 25) entry into 4 melanoma cell lines show a several fold increase over fluorescence from normal cells.

DETAILED DESCRIPTION OF THE INVENTION

Definitions

Figure 1B:
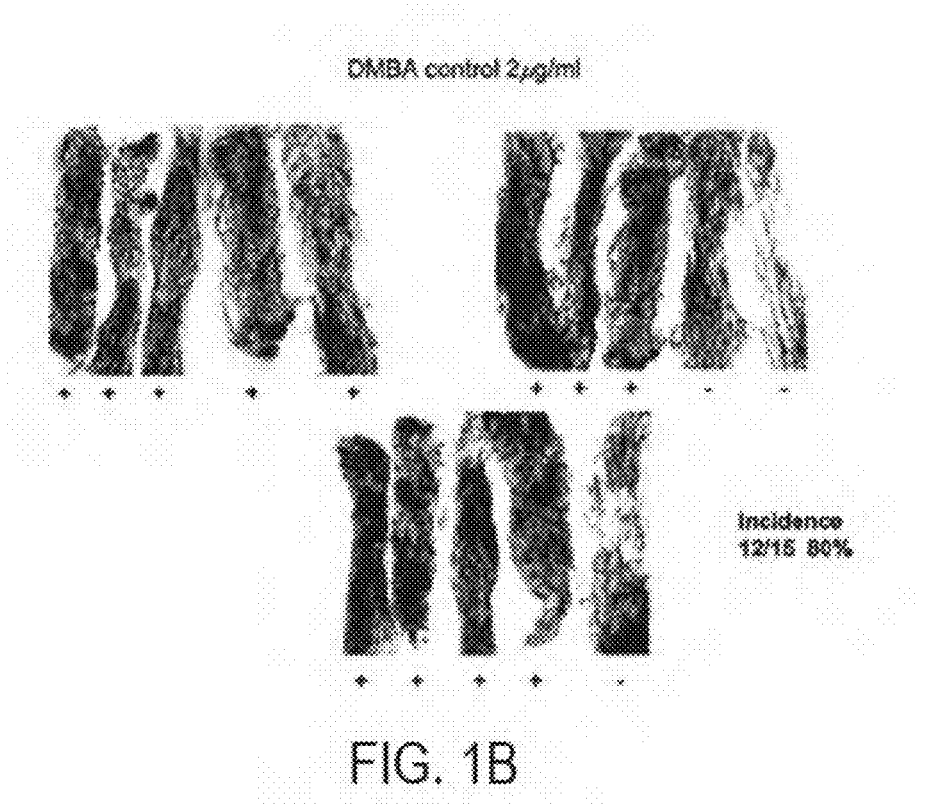
FIGS. 1B-1G show representative photographs of the effects of p28 (SEQ ID NO: 2) on the development of alveolar lesions.
Figure 1C:
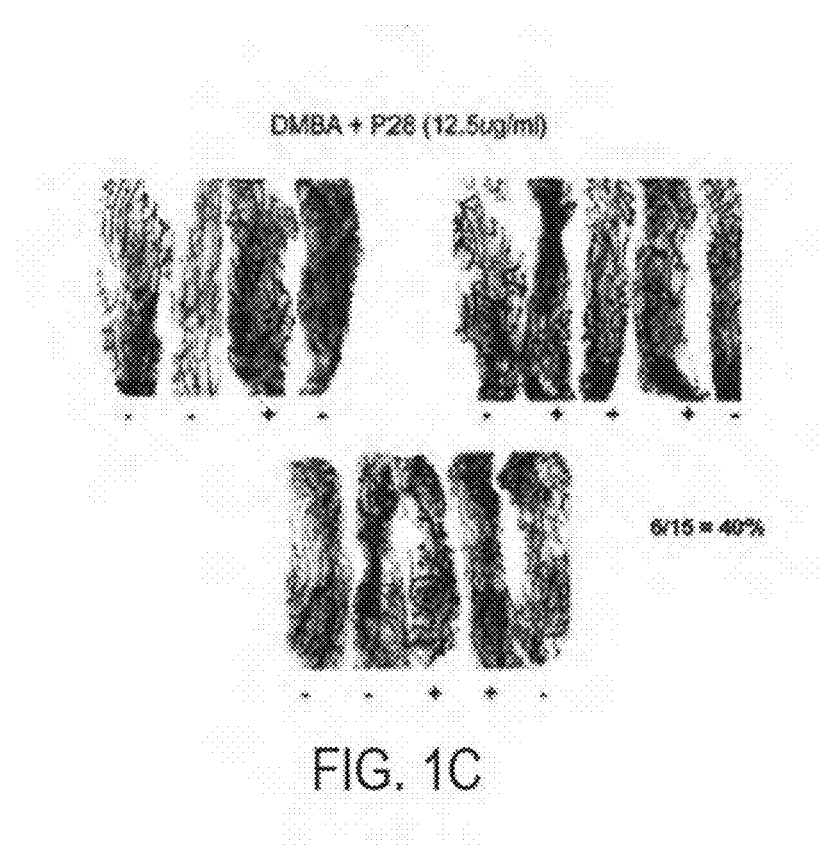
Figure 1D:
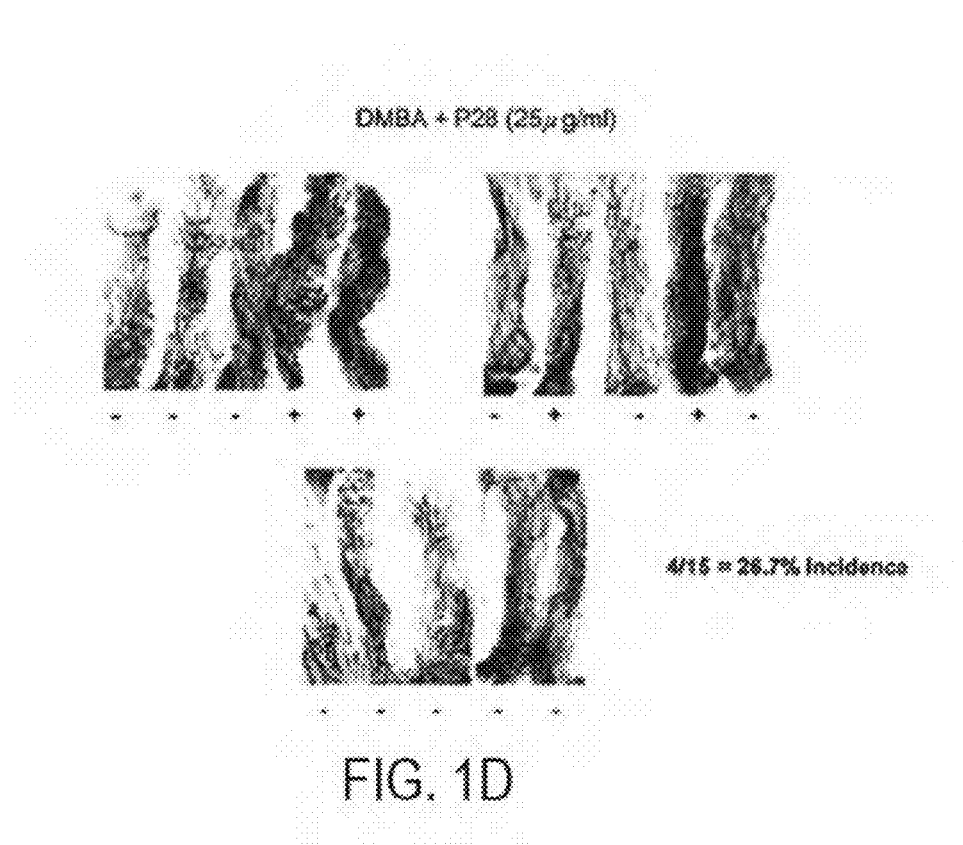
Figure 1E:
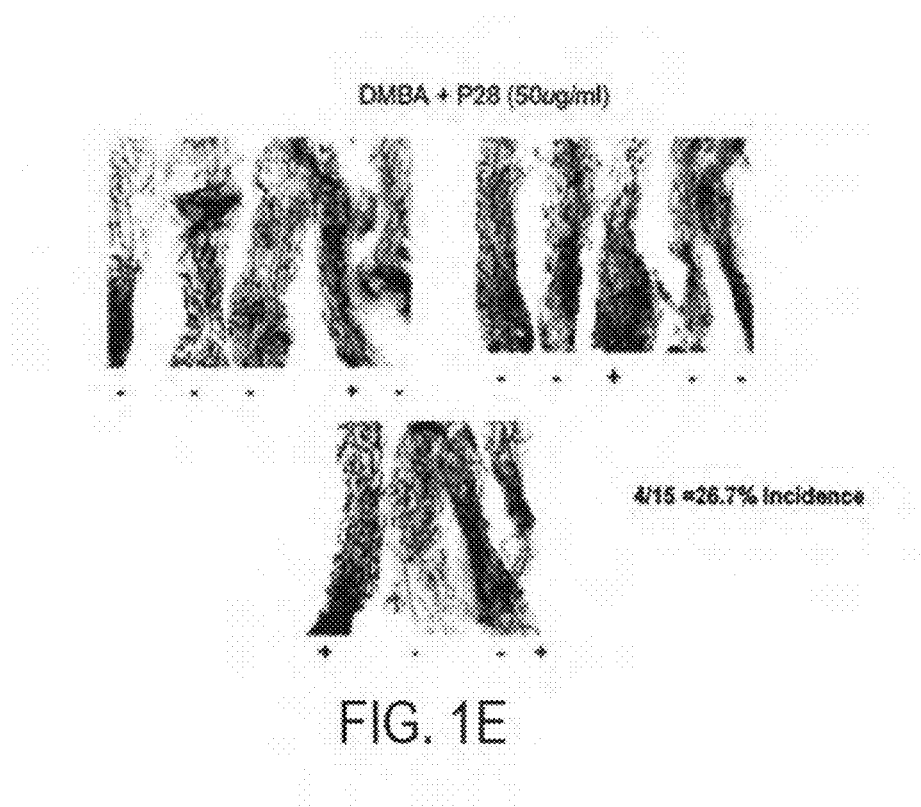
Figure 1F:
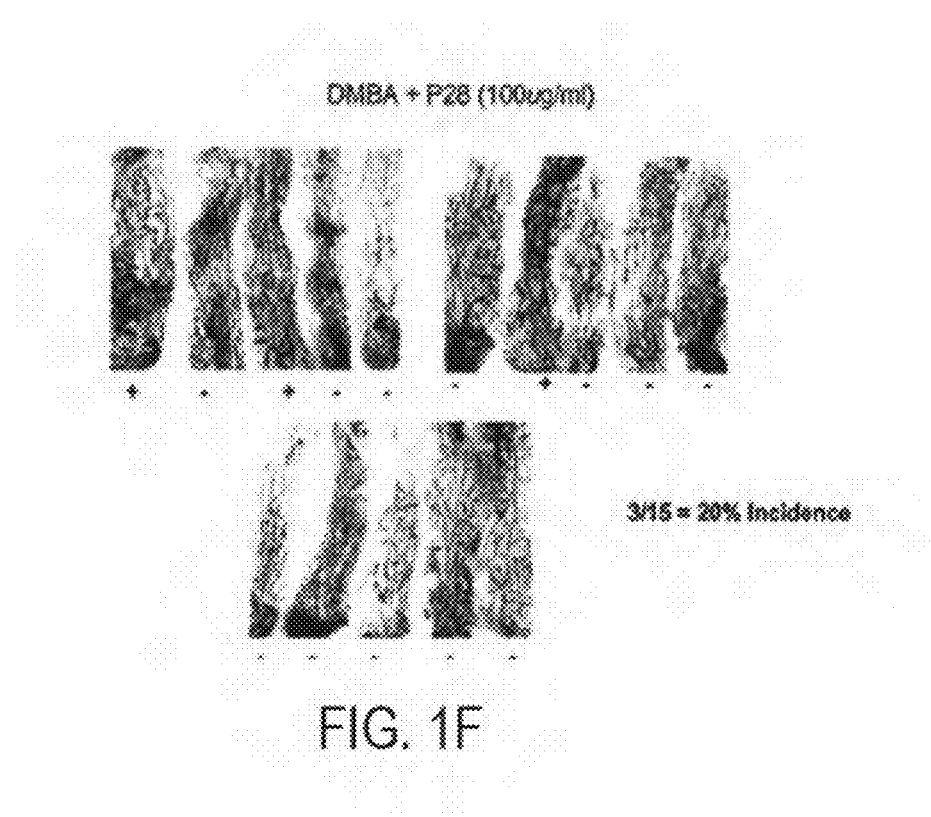
Figure 1G:
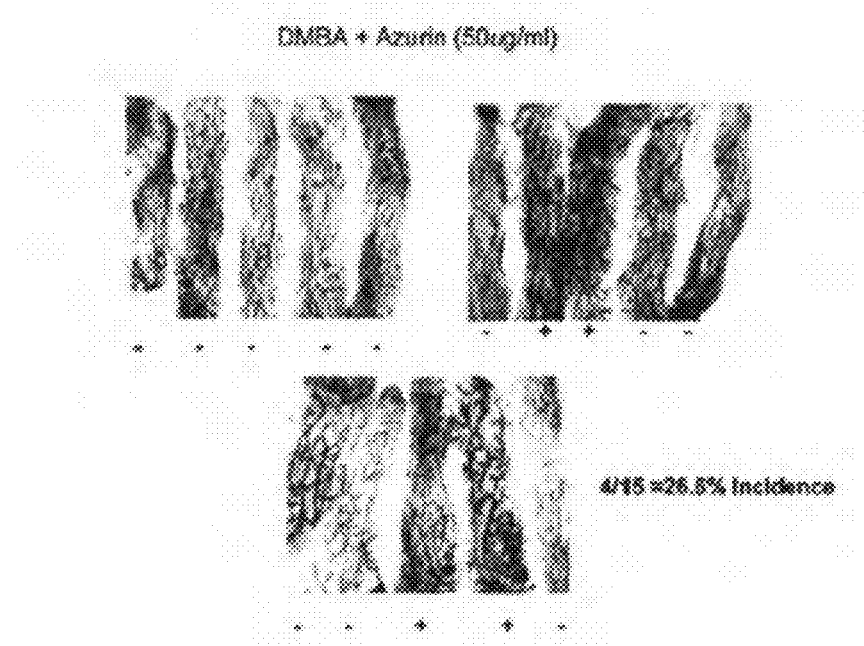

As used herein, the term "cell" includes either the singular or the plural of the term, unless specifically described as a "single cell."

As used herein, the terms "polypeptide," "peptide," and "protein" are used interchangeably to refer to a polymer of amino acid residues. The terms apply to amino acid polymers in which one or more amino acid residue is an artificial chemical analogue of a corresponding naturally occurring amino acid. The terms also apply to naturally occurring amino acid polymers. The terms "polypeptide," "peptide," and "protein" are also inclusive of modifications including, but not limited to, glycosylation, lipid attachment, sulfation, gamma-carboxylation of glutamic acid residues, hydroxylation and ADP-ribosylation. It will be appreciated that polypeptides are not always entirely linear. For instance, polypeptides may be branched as a result of ubiquitination and they may be circular (with or without branching), generally as a result of post-translation events, including natural processing event and events brought about by human manipulation which do not occur naturally. Circular, branched and branched circular polypeptides may be synthesized by non-translation natural process and by entirely synthetic methods as well.

As used herein, the term "pharmacologic activity" means the effect of a drug or other chemical on a biological system. The effect of chemical may be beneficial (therapeutic) or harmful (toxic). The pure chemicals or mixtures may be of natural origin (plant, animal, or mineral) or may be synthetic compounds.

As used herein, the term "premalignant" means precancerous, or before abnormal cells divide without control.

As used herein, the term "antiestrogen" means a substance that blocks the activity of estrogens, or otherwise prevents cells from making or using estrogen.

As used herein, the term "ER" means estrogen receptor.

As used herein, the term "lesion" means an area of abnormal tissue.

As used herein, the term "pathological condition" includes anatomic and physiological deviations from the normal that constitute an impairment of the normal state of the living animal or one of its parts, that interrupts or modifies the performance of the bodily functions, and is a response to various factors (as malnutrition, industrial hazards, or climate), to specific infective agents (as worms, parasitic protozoa, bacteria, or viruses), to inherent defects of the organism (as genetic anomalies), or to combinations of these factors.

As used herein, the term "condition" includes anatomic and physiological deviations from the normal that constitute an impairment of the normal state of the living animal or one of its parts, that interrupts or modifies the performance of the bodily functions.

As used herein, the term "suffering from" includes presently exhibiting the symptoms of a pathological condition, having a pathological condition even without observable symptoms, in recovery from a pathological condition, or recovered from a pathological condition.

As used herein, the term "chemoprevention" is the use of drugs, vitamins, or other natural or synthetic agents, which may be biologic or chemical, to try to reduce the risk of, prevent, suppress, reverse, or delay the development, or recurrence of, premalignant lesions and/or cancer.

As used herein, the term "second chemopreventive agent" refers to drugs, vitamins, or other natural or synthetic agents, which may be biologic or chemical, which reduce the risk of, prevent, suppress, reverse, or delay the development of, or recurrence of, premalignant lesions and/or cancer, other than truncations of azurin.

A used herein, the term "treatment" includes preventing, lowering, stopping, or reversing the progression or severity of the condition or symptoms associated with a condition being treated. As such, the term "treatment" includes medical and/or prophylactic administration, as appropriate. Treatment may also include preventing or lessening the development of a condition, such as premalignant lesions or cancer.

As used herein, the term "inhibit cell growth" means the slowing or ceasing of cell division and/or cell expansion. This term also includes the inhibition of cell development or increases in cell death.

A "therapeutically effective amount" is an amount effective to prevent, lower, stop or reverse the development of, or to partially or totally alleviate the existing symptoms of a particular condition for which the subject being treated. Determination of a therapeutically effective amount is well within the capability of those skilled in the art.

The term "substantially pure," as used herein, when used to modify a protein or other cellular product of the invention, refers to, for example, a protein isolated from the growth medium or cellular contents, in a form substantially free of, or unadulterated by, other proteins and/or other compounds. The term "substantially pure" refers to a factor in an amount of at least about 75%, by dry weight, of isolated fraction, or at least "75% substantially pure." More specifically, the term "substantially pure" refers to a compound of at least about 85%, by dry weight, of isolated fraction, or at least "85% substantially pure." Most specifically, the term "substantially pure" refers to a compound of at least about 95%, by dry weight, of isolated fraction, or at least "95% substantially pure." The term "substantially pure" may also be used to modify a synthetically-made protein or compound of the invention, where, for example, the synthetic protein is isolated from the reagents and by products of the synthesis reaction(s).

The term "pharmaceutical grade," as used herein, when referring to a peptide or compound of the invention, is a peptide or compound that is isolated substantially or essentially from components which normally accompany the material as it is found in its natural state, including synthesis reagents and by-products, and substantially or essentially isolated from components that would impair its use as a pharmaceutical. For example, a "pharmaceutical grade" peptide may be isolated from any carcinogen. In some instances, "pharmaceutical grade" may be modified by the intended method of administration, such as "intravenous pharmaceutical grade," in order to specify a peptide or compound that is substantially or essentially isolated from any substance that would render the composition unsuitable for intravenous administration to a patient. For example, an "intravenous pharmaceutical grade" peptide may be isolated from detergents, such as SDS, and anti-bacterial agents, such as azide.

The terms "isolated," "purified" or "biologically pure" refer to material which is substantially or essentially free from components which normally accompany the material as it is found in its native state. Thus, isolated peptides in accordance with the invention preferably do not contain materials normally associated with the peptides in their in situ environment. An "isolated" region of a polypeptide refers to a region that does not include the whole sequence of the polypeptide from which the region was derived. An "isolated" nucleic acid, protein, or respective fragment thereof has been substantially removed from its in vivo environment so that it may be manipulated by the skilled artisan, such as but not limited to, nucleotide sequencing, restriction digestion, site-directed mutagenesis, and subcloning into expression vectors for a nucleic acid fragment as well as obtaining the protein or protein fragment in substantially pure quantities.

The term "variant" as used herein with respect to a peptide, refers to amino acid sequence variants which may have amino acids replaced, deleted, or inserted as compared to the wild-type polypeptide. Variants may be truncations of the wild-type peptide. A "deletion" is the removal of one or more amino acids from within the polypeptide, which a "truncation" is the removal of one or more amino acids from one or both ends of the polypeptide. Thus, a variant peptide may be made by manipulation of genes encoding the polypeptide. A variant may be made by altering the basic composition or characteristics of the polypeptide, but not at least some of its pharmacologic activities. For example, a "variant" of azurin can be a mutated azurin that retains its ability to inhibit the development of premalignant mammalian cells. In some cases, a variant peptide is synthesized with non-natural amino acids, such as $\epsilon$-(3,5-dinitrobenzoyl)-Lys residues. Ghadiri & Fernholz, J. Am. Chem. Soc., 112:9633-9635 (1990). In some embodiments, the variant has not more than 20 amino acids replaced, deleted or inserted compared to wild-type peptide or part thereof. In some embodiments, the variant has not more than 15 amino acids replaced, deleted or inserted compared to wild-type peptide or part thereof. In some embodiments, the variant has not more than 10 amino acids replaced, deleted or inserted compared to wild-type peptide or part thereof. In some embodiments, the variant has not more than 6 amino acids replaced, deleted or inserted compared to wild-type peptide or part thereof. In some embodiments, the variant has not more than 5 amino acids replaced, deleted or inserted compared to wild-type peptide or part thereof. In some embodiments, the variant has not more than 3 amino acids replaced, deleted or inserted compared to wild-type peptide or part thereof.

The term "amino acid," as used herein, means an amino acid moiety that comprises any naturally-occurring or non-naturally occurring or synthetic amino acid residue, i.e., any moiety comprising at least one carboxyl and at least one amino residue directly linked by one, two three or more carbon atoms, typically one (a) carbon atom.

The term "derivative" as used herein with respect to a peptide refers to a peptide that is derived from the subject peptide. A derivation includes chemical modifications of the peptide such that the peptide still retains some of its fundamental activities. For example, a "derivative" of azurin can, for example, be a chemically modified azurin that retains its ability to inhibit angiogenesis in mammalian cells. Chemical modifications of interest include, but are not limited to, amidation, acetylation, sulfation, polyethylene glycol (PEG) modification, phosphorylation or glycosylation of the peptide. In addition, a derivative peptide may be a fusion of a polypeptide or fragment thereof to a chemical compound, such as but not limited to, another peptide, drug molecule or other therapeutic or pharmaceutical agent or a detectable probe.

The term "percent (%) amino acid sequence identity" is defined as the percentage of amino acid residues in a polypeptide that are identical with amino acid residues in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences. In a specific embodiment, Blastp (available from the National Center for Biotechnology Information, Bethesda Md.) is used using the default parameters of long complexity filter, expect 10, word size 3, existence 11 and extension 1.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

% amino acid sequence identity=$X/Y*100$ where

X is the number of amino acid residues scored as identical matches by the sequence alignment program's or algorithm's alignment of A and B and Y is the total number of amino acid residues in B.

If the length of amino acid sequence A is not equal to the length of amino acid sequence B, the % amino acid sequence identity of A to B will not equal the % amino acid sequence identity of B to A. When comparing longer sequences to shorter sequences, the shorter sequence will be the "B" sequence. For example, when comparing truncated peptides to the corresponding wild-type polypeptide, the truncated peptide will be the "B" sequence.

General

The present invention provides compositions comprising cupredoxin, and variants, derivatives, truncations, and structural equivalents of cupredoxins, and methods to prevent the development of cancer in mammals. The invention also provides compositions comprising chemopreventive cupredoxins or variants, derivatives, truncations, and structural equivalents thereof and other chemopreventive agents.

The present invention also provides methods comprising administration or other use of compounds and/or peptides that may be cupredoxin(s), or variants, derivatives, truncations, or structural equivalents of cupredoxins, that have chemopreventive effects on premalignant lesions and/or cancer.

The invention also provides variants, derivatives, truncations, and structural equivalents of cupredoxin that retain the ability to prevent the development of cancer or the re-occurrence of cancer in mammals. The invention also provides compositions comprising *Pseudomonas aeruginosa* azurin, variants, derivatives, truncations, and structural equivalents of azurin, and their use to treat patients, and particularly patients at a higher risk of developing cancer than the general population.

Finally, the invention provides methods to study the development of cancer in mammalian cells, tissues and animals by contacting the cells with a cupredoxin, or variant, derivative, truncation, or structural equivalent thereof, before or after inducing premalignant lesions, and observing the development of premalignant and/or malignant cells.

For each of these embodiments, the invention provides the combination or co-administration of the cupredoxins or variants, derivatives, truncations, and structural equivalents thereof with another chemopreventive agent.

Preferential Entry into Cells

A redox protein elaborated by *Pseudomonas aerugisnosa*, the cupredoxin azurin, selectively enters J774 lung cancer cells but not normal cells, and induces apoptosis. Zaborina et al., Microbiology 146:2521-2530 (2000). Azurin can also selectively enter and kill human melanoma UISO-Mel-2 or human breast cancer MCF-7 cells. Yamada et al., PNAS 99:14098-14103 (2002); Punj et al., Oncogene 23:2367-2378 (2004). Azurin thus targets cancer cells but not normal cells because of its inability to enter normal cells. Fialho et al, Recent Patents Anticancer Drug Discov. 2: 224-234 (2007).

Azurin from *P. aeruginosa* preferentially enters J774 murine reticulum cell sarcoma cells, forms a complex with and stabilizes the tumor suppressor protein p53, enhances the intracellular concentration of p53, and induces apoptosis. Yamada et al., Infection and Immunity 70:7054-7062 (2002). Detailed studies of various domains of the azurin molecule showed that amino acids 50-77 (p28, SEQ ID NO: 2) represented a protein transduction domain (PTD) critical for internalization and subsequent apoptotic activity. Yamada et al, Cell. Microbiol. 7:1418-1431 (2005).

The temperature dependent entry of cationic cell penetrating peptides ("CPPs"), which supports an endocytotic component to cell penetration, is reflected in the entry of azurin and p28 (SEQ ID NO: 2). Yamada, T., et al., Cell Microbiol 7: 1418-1431 (2005). The entry of 50-67 of azurin (p18, SEQ ID NO: 25) into normal and malignant cells appears accelerated relative to p28 (SEQ ID NO: 2). The lower $K_m$ and higher $V_{max}$ of p18 (SEQ ID NO: 25) suggest that aa 50-67 define an amphipathic structure when associated with phospholipid membranes that more closely represents the actual PTD of azurin. However, an energy dependent endocytotic or pore related process is not the only entry mechanism available to these peptides. For example, the metabolic and membrane potential inhibitors sodium azide and ouabain ($Na^+$ $K^+$ ATPase inhibitor), which inhibit the entry of cationic peptides, did not impair the entry of either p18 (SEQ ID NO: 25) or p28 (SEQ ID NO: 2) into UISO-Mel-2 cells or fibroblasts (FIGS. 15B,C), showing that either peptide may penetrate the cell membrane directly.

p18 (SEQ ID NO: 25), p28 (SEQ ID NO: 2) and azurin penetrate the plasma membrane and reach late endosomes, lysosomes and the golgi associated with caveolae in what has been described as a dynamin-independent clathrinin dependent carrier mediated manner. Kirkham, M. and Parton, R. G., Biochem Biophys Acta 1746: 349-363 (2005). The striking inhibition of penetration by nocodazole and relative lack of inhibition by cytochalasin-D, which disrupts actin filaments, supports caveolae mediated entry. This route of entry has been described for integral cell surface components and seemingly disparate molecules, i.e., dextran, and a broad range of pathogens or their products that also utilize caveolae to bypass classic endocytic pathways. Depletion of cholesterol from the plasma membrane with β-methylcylodextran, filipin or nystatin to disrupt lipid rafts, plasma membrane domains that provide fluid platforms to segregate membrane components and compartmentalize membranes, significantly inhibited the penetration of p18 (SEQ ID NO: 25) (50%) and p28 (SEQ ID NO: 2) (~60%) into UISO-Mel-2 cells and fibroblasts (35% and 42%, respectively) demonstrating that a significant percentage (~60%) of p18 (SEQ ID NO: 25) and p28 (SEQ ID NO: 2) penetrates the plasma membrane via caveolae. Caveolae are a 50- to 100-nm omega-shaped subset of lipid raft invaginations of the plasma membrane defined by the presence of caveolin specific proteins (caveolin-1, -2, or -3) that function as regulators of signal transduction.

Figure 15A:
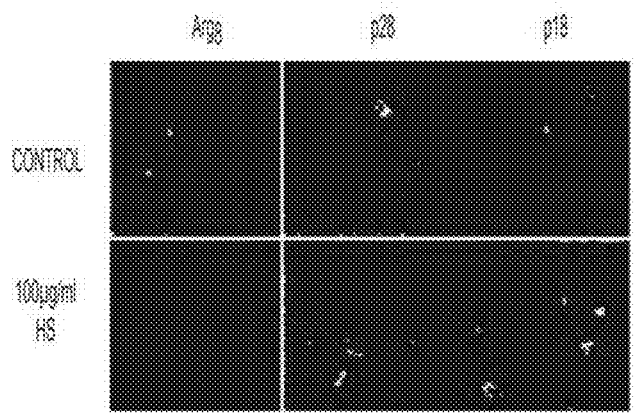
FIGS. 15A-D. (A) Depicts photographs showing confocal analysis of p28 (SEQ ID NO: 2), p18 (SEQ ID NO: 25) (20 µM) and $Arg_8$ (SEQ ID NO: 82) (10 µM) entry into UISO-Mel-2 cells after 1 hr at 37° C. in the presence/absence of heparin sulfate (100 µg/ml). (B) Graphs showing flow cytometric analysis of p28 (SEQ ID NO: 2) or p18 (SEQ ID NO: 25) entry in the presence of inhibitors. Cell fluorescence intensity in the absence of inhibitor (control) was considered as 100%. (C) Graphs depicting FACS analysis of p28 (SEQ ID NO: 2) and p18 (SEQ ID NO: 25) entry into fibroblasts in presence of inhibitors. (D) Depicts photographs showing colocalization of p18 (SEQ ID NO: 25) and p28 (SEQ ID NO: 2) with caveolin I (Panel 1). UISO-Mel-2 cells were incubated with Alexafluor 568 labeled p18 (SEQ ID NO: 25) or p28 (SEQ ID NO: 2) (20 µM) or media for 2 hrs at 37° C. Cells were fixed and processed for anti-caveolin 1 immunostaining. Confocal analysis of entry of Alexafluor 568 labeled p18 (SEQ ID NO: 25) or p28 (SEQ ID NO: 2) (20 µM) into UISO-Mel-2 cells after 2 hrs at 37° C. followed by antigolgin 97 antibodies (Panel 2). Colocalization of Alexafluor 568 labeled azurin, p28 (SEQ ID NO: 2) and p18 (SEQ ID NO: 25) (red) with mitotracker (green) (Panel 3) and Lysotracker (green) (Panel 4) dyes in UISO-Mel-2 cells. Cells were incubated at 37° C. with 20 µM azurin, p28 (SEQ ID NO: 2), p18 (SEQ ID NO: 25) or media only. After 90 min incubation, mitotracker/lysotracker probes were added and cells incubated for 30 min. Cells were counterstained with DAPI (blue). Colocalization of azurin, p28 (SEQ ID NO: 2) or p18 (SEQ ID NO: 25) appears as a yellow florescence.
Figure 15B:
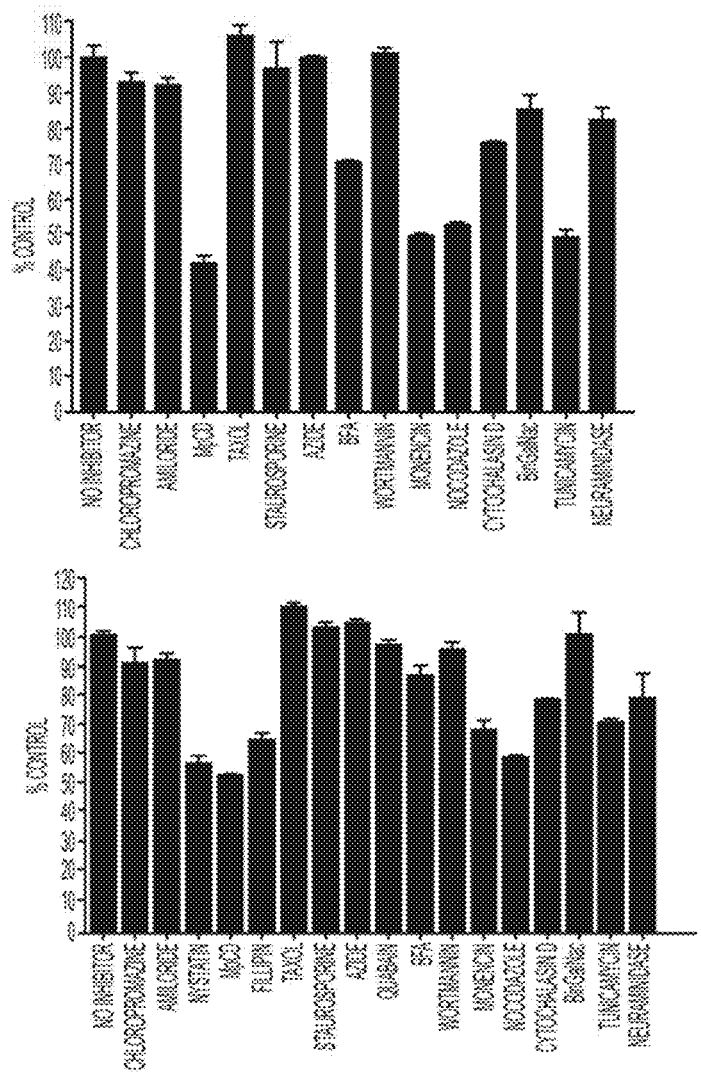

Brefeldin A disrupts the Golgi apparatus and inhibited p18 (SEQ ID NO: 25) accumulation, so it follows that this pathway is also utilized in p18 (SEQ ID NO: 25) and p28 (SEQ ID NO: 2) entry and intracellular transport. Cell penetration of p18 (SEQ ID NO: 25) and p28 (SEQ ID NO: 2) via caveolae comports with the evidence that inhibitors of N-glycosylation reduce cell entry by ~60% in UISO-Mel-2 cells and 25% and 35% respectively in fibroblasts. The percentile differences between p18 (SEQ ID NO: 25) and p28 (SEQ ID NO: 2) entry relate to the numbers of N-glycosylation membrane structures in cancer vs normal cells and the relative route of entry of p28 (SEQ ID NO: 2) and p18 (SEQ ID NO: 25) via this mechanism. FIGS. 15B, C.

Azurin, p28 (SEQ ID NO: 2), and p18 (SEQ ID NO: 25) all bind to cancer cells with high affinity and high capacity relative to many other potential anti-cancer peptides. It is believed that, after binding, this protein/receptor complex localizes in caveolae and is internalized, eventually moving (via caveosomes) to the golgi, ER, and nucleus. In addition to caveolar-mediated entry, kinetic analysis also demonstrates that p28 (SEQ ID NO: 2) and p18 (SEQ ID NO: 25) penetrate the plasma membrane via a non-clathrin caveolae mediated process. A clathrin- and caveolin-independent pathway can exist as a constitutive internalization mechanism, such as for the interleukin 2 receptor and for certain glycosyl-phosphatidylinositol (GPI)-anchored proteins. Lamaze, C., et al., Mol Cell 7: 661-671 (2001); Sabharanjak, S., et al., Dev Cell, 2: 411-423 (2002).

An increase in caveolin-1 expression in cancer cells over normal cells is not likely to be the sole basis for the preferential entry of azurin, p28 (SEQ ID NO: 2) and p18 (SEQ ID NO: 25) into cancer cells. Fibroblasts and a number of other normal cells also have significant numbers of caveolae on their surface. The findings reflected in Examples 6-12 demonstrate that the cellular penetration of aa 50-67 (SEQ ID NO: 25) and 50-77 (SEQ ID NO: 2) of azurin is unique relative to all current CCPs in its preference for cancer cells, and that the C-terminal 10-12 amino acids of p28 (SEQ ID NO: 2) contain the domain responsible for cell cycle inhibition and apoptotic activity.

Chemoprevention

Azurin, and peptides derived from azurin, such as p28 (SEQ ID NO: 2), have chemopreventive properties. Azurin and p28 (SEQ ID NO: 2) prevent the formation of premalignant preneoplastic lesions in mouse mammary gland organ culture. In a mouse mammary gland organ culture model, azurin at 50 µg/ml was found to inhibit the formation of alveolar lesions by 67%. Likewise, p28 (SEQ ID NO: 2) at 25 µg/ml was found to inhibit the formation of alveolar lesions by 67%. See Example 1. Further, azurin at 50 µg/ml was found to inhibit the formation of ductal lesions by 79%, and p28 (SEQ ID NO: 2) at 25 µg/ml inhibited the formation of ductal lesions by 71%. See Example 1. Confocal microscopy and FACS showed that azurin and p28 (SEQ ID NO: 2) entered normal murine mammary epithelial cells (MM3MG) and mammary cancer cells (4T1). p28 (SEQ ID NO: 2) also entered human umbilical vein endothelial cells (HUVEC) in a temperature, time and concentration dependent manner and inhibited capillary tube formation of HUVEC plated on Matrigel® in a dose dependent manner.

Further support for the efficacy of variants, derivatives, and structural equivalents of cupredoxins and specifically azurin and p28 (SEQ ID NO: 2) in preventing the formation of premalignant preneoplastic lesions is found in Examples 2 through 4. Both azurin and p28 (SEQ ID NO: 2) inhibited the development of mammary alveolar lesions as well as in ovarian hormone dependent mammary ductal lesions in MMOC. p28 (SEQ ID NO: 2) inhibited the development and multiplicity of MAL and MDL in dose dependent manner. The inhibition was due to antiproliferative effects, as evident from reduced Ki67 expression in these glands. Estrogen and progesterone treated glands expressed ER and PR, however the glands incubated with aldosterone and hydrocortisone did not stain for steroid receptors when analyzed with immunohistochemistry. Since p28 (SEQ ID NO: 2) and azurin inhibited development of both hormone independent MAL and estrogen progesterone dependent MDL, it can be concluded that azurin and p28 (SEQ ID NO: 2) action are not totally dependent on the estrogen and progesterone receptors and may be efficacious for both hormone independent and dependent lesions.

Interactions Between Cupredoxin-Derived Peptides and p53

The most likely mechanism of azurin and p28 (SEQ ID NO: 2) in inhibiting preneoplastic lesions is disclosed in the Examples below. Using computational procedures of rigid-body protein docking and cluster analyses, the binding of p53 and azurin has been extensively studied and the structural results have been validated using computational mutagenesis approaches. See Apivo et al., Biochem Biophys Res Commun. 332: 965-968 (2005). The later reports strongly suggest that the mechanism of azurin action in suppressing tumor cell growth is mediated by physical interactions with p53, as discussed herein. The status of p53 expression in breast cancer suggests that nearly 50-60% of the breast cancers contain wild type p53. Junk et al., Neoplasia. 10: 450-461 (2008); Gasco et al., Breast Cancer Res. 4(2):70-76 (2002). It has also been reported by several investigators that inactivation of p53 is one of the frequent and significant events in human cancer. Kastan, Cell. 128: 837-840 (2007).

The inactivation of p53 or its suppression of action is observed in estrogen receptor (ER) positive breast cancer cells. In MCF 7 cells, ERα directly binds to p53 and inactivates its function. Sengupta et al., Ann NY Acad Sci. 1024: 54-71 (2004); Konduri et al., Cancer Res. 2007; 67: 7746-7755 (2007). These studies address a clear possibility of a mechanism of ERα-mediated cell proliferation and suppression of p53 mediated apoptosis. This interaction of ERα and p53 has been demonstrated by ChIP assays. Radiation is shown to be effective in restoring the stable p53 and suppresses surviving expression in these cells. The mechanism by which radiation mediates its effects is not well understood, however it is postulated that this may be direct effect of disruption of ERα-p53 association by radiotherapy. Liu et al., J. Biol. Chem. 281: 9837-9340 (2006).

It is now known that p28 (SEQ ID NO: 2) not only increases accumulation of nuclear p53 in mammary cells, but also induces expression of p53 mRNA. The results disclosed in Examples 2-4 herein indicate that the interference by estrogen with p53 may result in decreased p53 expression in mammalian cells. However, inhibition of ductal lesions induced by DMBA in the presence of estradiol and increased nuclear accumulation of p53 following p28 (SEQ ID NO: 2) treatment shows that p53 stabilization by p28 (SEQ ID NO: 2) may be responsible for the suppression of MDL formation in these glands.

It is also now known that p28 (SEQ ID NO: 2) enhances the expression of p53 and thus has an inhibitory effect on the formation of premalignant preneoplastic lesions. See, for example, Examples 13-19. The results discussed in Example 4 show that the presence of estrogen interferes with p28

(SEQ ID NO: 2)-mediated induction of p53 mRNA, but that the p53/p28 (SEQ ID NO: 2) interaction is unaffected likely due to different binding sites on p53 protein for ER and p28. Another interesting observation was the difference in azurin and p28 (SEQ ID NO: 2) action on p53 mRNA expression.

It is therefore now known that cupredoxins and variants, derivatives, truncations, and structural equivalents of cupredoxins and specifically azurin and variants, derivatives, truncations, and structural equivalents of azurin, including p28 (SEQ ID NO: 2), may be used to inhibit, suppress, delay, prevent, and/or reverse the formation of premalignant preneoplastic lesions, and thus the development of cancer, and specifically breast cancer, in mammalian patients.

As shown by Examples 3 and 4, p28 (SEQ ID NO: 2) or azurin, in combination with Tamoxifen, has an unexpected, increased inhibitory effect on the formation of premalignant preneoplastic lesions, and thus the development of cancer. Tamoxifen has been successfully used in the treatment of breast cancer patients that are ER positive. It has also been approved for the use in breast cancer prevention trials. Tamoxifen inhibits development of mammary ductal lesions (MDL). It is established that the action of Tamoxifen is mediated via the estrogen receptor pathway. It was not expected that Tamoxifen, in combination with a cupredoxin and/or variants, derivatives, or structural equivalents of cupredoxins, such as azurin, would have a synergistic effect on the formation of premalignant preneoplastic lesions.

The ER-p53 complex prevents the expression of p53. Tamoxifen treatment prevents ER from binding to p53, so incubation of glands with p28 (SEQ ID NO: 2) in the presence of Tamoxifen enhances or increases the expression of p53 in these glands. As shown in Example 4 and FIG. 7A, incubation of glands with Tamoxifen and p28 (SEQ ID NO: 2) resulted in an unexpected 120 fold increase in p53 mRNA expression as compared to the glands treated with p28 (SEQ ID NO: 2) alone.

Due to the high degree of structural similarity between cupredoxins, it is likely that other cupredoxins and/or variants, derivatives, truncations, or structural equivalents of cupredoxins, will inhibit the formation of premalignant lesions in mammals as well as azurin and p28 (SEQ ID NO: 2), and would, in combination with Tamoxifen, will have synergistic effects on the formation of premalignant lesions and cancer. Such cupredoxins may be found in, for example, bacteria or plants. Several cupredoxins are known to have pharmacokinetic activities similar to those of azurin from *Pseudomonas aeruginosa*. For example, rusticyanin from *Thiobacillus ferrooxidans* can also enter macrophages and induce apoptosis. Yamada et al., Cell Cycle 3:1182-1187 (2004); Yamada et al., Cell. Micro. 7:1418-1431 (2005). Plastocyanin from *Phormidium laminosum* and pseudoazurin form *Achromobacter cycloclastes* also are cytotoxic towards macrophages. U.S. Pat. Pub. No. 20060040269, published Feb. 23, 2006. It is therefore contemplated that other cupredoxins may be used in the compositions and methods of the invention. Further, variants, derivatives, truncations, and structural equivalents of cupredoxins that retain the ability to inhibit the formation of cancer in mammals may also be used in the compositions and methods of the invention. These variants and derivatives may include, but are not limited to, truncations of a cupredoxin, conservative substitutions of amino acids and proteins modifications such as PEGylation and all-hydrocarbon stabling of α-helices.

Inhibition of Cancer Through p53

The interaction of amino acids 50-77 of azurin (p28, SEQ ID NO: 2) and p53 was studied and is described in Examples 13-19 below. As disclosed herein, p28 (SEQ ID NO: 2) exhibits preferential penetration and has an anti-proliferative effect on human breast cancer cells that is mediated by p53, a tumor suppressor protein that becomes functionally active in response to stress and triggers either cell cycle arrest or apoptotic cell death. Experiments using a series of GST-pull down assays, glycerol gradient centrifugation, microcalorimetric experiments, single molecule force spectroscopy, and computer modeling show that azurin binds within either the N-terminal or DNA-binding domains of p53 and increases its intracellular levels.

Suggestions that the azurin binding domain for p53 includes a hydrophobic patch described by azurin Met44 and Met64 are supported by evidence that a disrupted hydrophobic patch mutant (mutant azurin M44KM64E) is less cytotoxic to human melanoma (Mel-2) cells than wt azurin. This shows that the p53 binding domain of the azurin molecule surrounds the hydrophobic patch. A recent docking simulation study demonstrated a significant loss of ~75 kJ/mol in the interaction free energy of the mutant complex with respect to wild type azurin, again indicating that the hydrophobic patch of azurin surrounding residues Met44 and Met64 is important for interaction with p53. As Met64 resides within the p53 binding site of p28 (SEQ ID NO: 2) (aa 15 of p28), competition assays, mutant studies, and docking experiments clearly show that this is the azurin domain that binds to p53. Interestingly, this is also the region identified as the PTD for azurin entry into cells.

The increase in p53 in response to p28 (SEQ ID NO: 2) occurs post-translationally and essentially results from a reduction in proteasome degradation of p53. As p53 stability is predominantly regulated through the ubiquitin-proteasomal pathway, identification of molecules that block ubiquitination of p53 is a promising therapeutic strategy for the treatment of cancers. Small molecules such as the cis-imidazole analog Nutlin and HLI98, which interfere with p53:MDM2 interaction and inhibit the E3 ubiquitin ligase activity of MDM2, respectively, have been screened for potential as cancer therapeutics. Among the known ubiquitin ligases for p53, MDM2, COP1, Pirh2, ARF-BP1 and possibly Parc and TOPORS are expressed in breast cancer cells where they directly interact with p53 and promote ubiquitination and degradation. Interestingly, COP1 is significantly overexpressed in breast (25 out of 32) and ovarian cancers (76 out of 171) and ARF-BP1 is also highly expressed in 80% (16 out of 20) of breast cancer cell lines including MCF-7 and T47D while its expression level in normal breast MCF-10A is very low. Although the binding region(s) of TOPORS and ARF-BP1 on p53 remains undetermined, it has been suggested that COP1 associates within the central to C-terminal domain of p53. Pirh2 has been reported to interact within the region between amino acids 82-292 in the p53 DNA binding domain (DBD). Parc, Parkin-like ubiquitin ligase, appears to bind within the C-terminal region of p53 (aa 290-393).

p28 (SEQ ID NO: 2) does not bind to the N-terminal MDM2 binding region (FIG. 22B) or the C-terminal region of p53 (FIG. 22D), so it follows that p28 (SEQ ID NO: 2) does not inhibit the binding of either MDM2 or Parc to p53. Taken together, the data disclosed herein show that p28 (SEQ ID NO: 2) binds within aa 80-276 of the p53 DBD and interferes with the interaction between p53 and the ubiquitin ligases Pirh2, COP1 and possibly TOPORS and ARF-BP1, thereby leading to a decrease in the ubiquitination and degradation of p53. This suggestion fits well with computer modeling data suggesting azurin binds to the flexible $L_1$ (aa 113-115) and $s_7$-$s_8$ (aa 221 and 224-229) loops of the p53

DBD and stabilizes them through protein-protein tight packing. De Grandis V, et al., J Mol Recognit 2007; 20:215-26. As the $L_1$ and $s_7$-$s_8$ loops are the most unstable regions in the p53 DBD, due to their very loose packing against each other or against the β-sheet core, it results in very high mobility. This conformational flexibility plays a key role in determining macromolecular recognition specificity, allowing for high efficiency and rapid turn-over of protein-protein interactions. De Grandis V, et al., J Mol Recognit 2007; 20:215-26. Although the $L_1$ and $s_7$-$s_8$ regions also associate with the $β_1$-$β_2$ and $β_7$-$β_8$ sheets in azurin, which do not incorporate p28 (SEQ ID NO: 2) region, aa Met64, Leu68 and Tyr72 are included within the p53 DBD-azurin binding region and are within aa 60-77 (p18b, SEQ ID NO: 38) of azurin. De Grandis V, et al., J Mol Recognit 2007; 20:215-26.

Figure 23A:
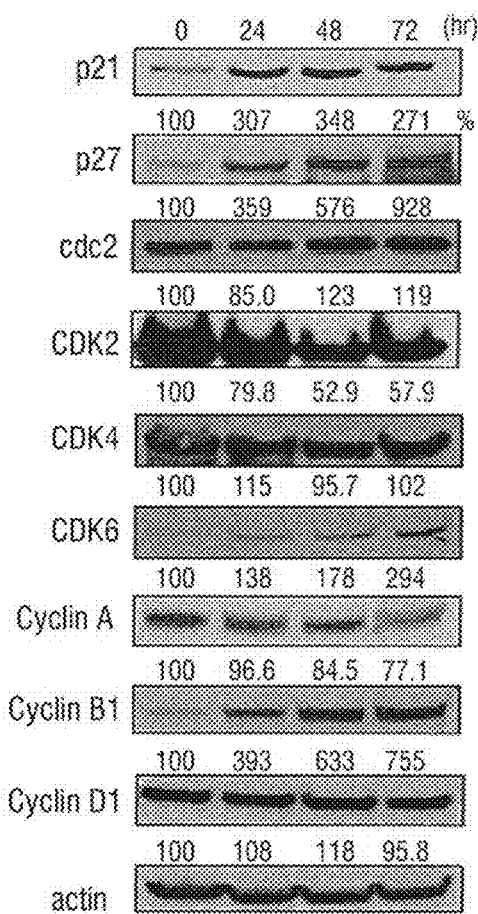
FIG. 23. Photographs depicting induction of the cyclin (CDK and CDKI) cascade by p28 (SEQ ID NO: 2). MCF-7 (A) and MDD2 cells (B) were exposed to p28 (SEQ ID NO: 2) (50 µmol/L) for 24, 48 and 72 hr and protein levels determined by immunoblotting. Intracellular localization and relative level of p21 (C) and cyclin B1 (D) in MCF-7 cells. Cells were cultured on cover slips with p28 (SEQ ID NO: 2) (50 µmol/L) for 72 h. p21 and cyclin B were stained with their corresponding specific antibodies. (E) The level of phosphorylated cdc2 was determined with an anti p-cdc2 antibody (Santa Cruz Biotechnology, CA) in MCF-7 (left panel) and MDD2 (right panel) cells. All results normalized by actin as an internal control (A and E).

The tumor suppressor protein p53 is a predominantly nuclear protein that acts as a transcriptional regulator for many genes, including the 21 kDa protein p21/Waf1/Cip1, an inhibitor of cell cycle progression. Treatment of MCF-7 cells with p28 (SEQ ID NO: 2) increased p53 levels, leading to higher intracellular levels of p21, a strong inhibitor of cyclin dependent kinase (CDK) activity, especially cdc2 and CDK2 that regulate cell cycle progression at $G_1$ and $G_2$/M, respectively. In the progression through the $G_2$/M phase, cdc2 and CDK2 kinases are activated primarily in association with cyclin B and cyclin A. The CDK inhibitor p21 associates efficiently with cyclin A in $G_2$/M arrested cells, although under the same conditions, cyclin B1 does not associate with p21 and the level of cyclin B1 increases continuously. This shows that the p28 (SEQ ID NO: 2)-induced $G_2$/M arrest in MCF-7 cells is associated with inhibition of CDK2 and cyclin A (FIG. 23A).

Figure 20A:
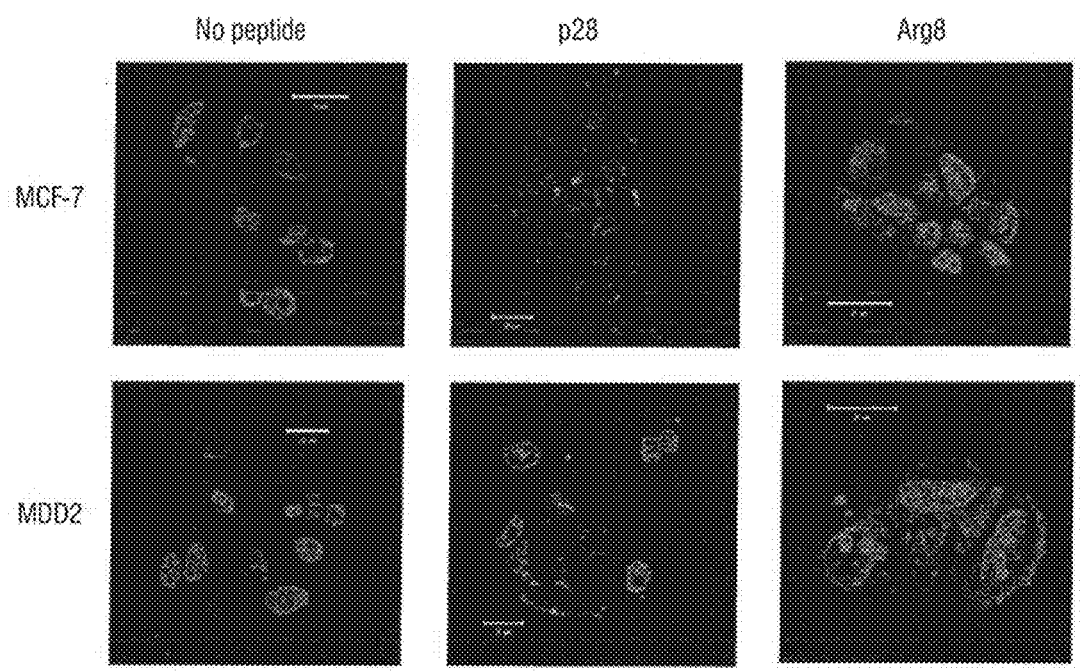
FIG. 20. (A) contains photographs depicting MCF-7 and MDD2 cells cultured on cover slips overnight in phenol-red free MEM, which were treated with 20 µmol/L p28 (SEQ ID NO: 2) or 10 µmol/L of the cationic (positive control) peptide, octaarginine ($Arg_8$, SEQ ID NO: 82), for 2 hr at 37° C. Red-Alexa fluor 568 labeled p28 (SEQ ID NO: 2), Blue-DAPI (nucleus). (B) and (C) are graphs depicting FACS analyses of isogenic breast cancer cells treated with p28 (SEQ ID NO: 2). MCF-7 (B) and MDD2 cells (C) were treated with p28 (SEQ ID NO: 2) (50 µmol/L) for 48 and 72 hr. Cells were stained with propidium iodide and analyzed by flow cytometry as described in Yamada, et al., Proc Natl Acad Sci USA, 101:4770-4775 (2004). The percentage of cells in the $G_1$, S, $G_2$/M and sub-$G_1$ (apoptosis) phases are indicated.

The p28 (SEQ ID NO: 2)-induced increase in p21 in MCF-7 cells was also accompanied by a time-dependent increase in p27, another member of the Cip/Kip CDKI family. Hsu et al., 2008 recently demonstrated that induction of p53 increased both p21 and p27 promoter activity as determined by luciferase assay. Cellular and Molecular Life Sciences (CMLS), 2008. In addition, p53 DNA binding activity of the p21 and p27 promoters is activated by the p53 inducer, progesterone, which means that not only p21, but also p27 is transcriptionally regulated by p53. Collectively, data shows that p28 (SEQ ID NO: 2) enhancement of p53 levels subsequently up-regulates p21 and p27, inducing a significant decrease in intracellular CDK2 and cyclin A levels in MCF-7 cells and inhibition of the cell cycle at $G_2$/M (FIG. 20A). The reported lack of or inefficient association between cyclin B1 and p21, suggests the increase in cyclin B1 activity following exposure to p28 (SEQ ID NO: 2) may reflect a similar pattern following a p28 (SEQ ID NO: 2)-induced increase in p21. An increase in phosphorylated cdc2 (inactive form) following exposure to p28 (SEQ ID NO: 2) accompanied the increased cellular level of cyclin B1, suggesting the increase in the cdc2-cyclin B complex reflects the increase in cdc2 phosphorylation.

Nocodazole, a known distributor of microtubules, and transcriptional and translational activator of p21, also induces a similar $G_2$ arrest in MCF-7 and MDA-MB-468 human breast cancer cells, accompanied by high levels of cytoplasmic cyclin B1. Differentiation agents such as all-trans retinoic acid (ATRA) and sodium butyrate (SB) produce growth inhibition and $G_1$ arrest in oral squamous carcinoma cells that correlates with the induction of $G_1$ phase cell cycle regulatory proteins CDK6, p21 and p27, and the inhibition of the $G_2$ phase cell cycle regulatory protein CDK2. Since p28 (SEQ ID NO: 2) did not enhance p21 in MDD2 cells, and p27 appears absent in these cells, the levels of CDK2 and cyclin A were not significantly altered (FIG. 23B) and no inhibition of cell cycle occurred. Additional evidence for a p28 (SEQ ID NO: 2)-induced decrease in the CDK2 and cyclin A complex, a key regulator of cdc2 activity in human cells, causing a $G_1$ and $G_2$/M arrest is found in the $G_2$ delay that follows cyclin A RNAi introduction to HeLa cells, which inactivates the CDK2-cyclin A complex causing cell cycle arrest in $G_2$/M.

Figure 23B:
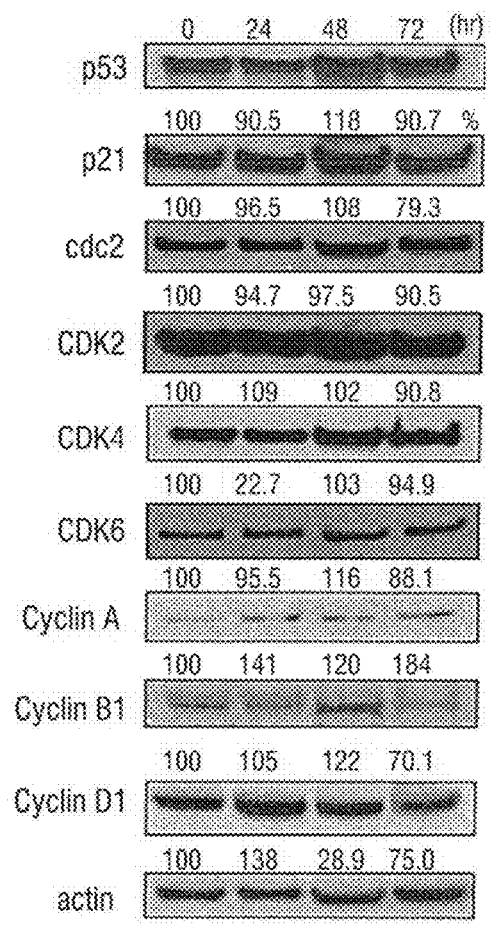

Although Cip/Kip family proteins such as p21 and p27 are potent inhibitors of cyclin A dependent CDK2, they also act as positive regulators of cyclin D-dependent kinases. Cip/Kip family proteins can stabilize CDK4 and CDK6. CDK4 is amplified and overexpressed in wide variety of tumors including breast, gliomas, sarcomas and carcinomas of the uterine cervix, whereas the CDK6 gene is amplified in certain type of malignancies including squamous cell carcinomas, gliomas and lymphoid tumors. Although, the initial or control level of CDK6 is lower than CDK4, CDK6, but not CDK4 levels are continuously elevated in MCF-7 cells exposed to p28 (SEQ ID NO: 2). Again, there was no alteration in CDK4 and CDK6 in MDD2 cells where p53 and p21 did not increase in response to p28 (SEQ ID NO: 2) (FIG. 23B). The Ink4 group, $p16^{Ink4a}$, $p15^{Ink4b}$, $p18^{Ink4c}$ and $p19^{Ink4d}$ of CDKIs specifically associates with and inhibits CDK4 and CDK6 which regulate cell cycle progression at $G_1$. Since the $p16^{Ink4a}$ gene is homozygously deleted in MCF-7 cells, Ink4 CDKI proteins should exhibit less of an inhibitory effect on CDK6 than CDK4, providing a rationale for the increase on CDK6 observed in CDK6 in the presence of essentially stable CDK4 levels.

Collectively, these results demonstrate that p28 (SEQ ID NO: 2) binds to p53 within a hydrophobic DNA-binding domain (aa 80-276), stabilizing the protein and increasing p53 levels by decreasing proteasomal degradation. p28 (SEQ ID NO: 2) subsequently up-regulates p21 and p27 and inactivates the CDK2-cyclin A complex, thereby causing a $G_2$/M cell cycle arrest in MCF-7 breast cancer cells in vitro and inhibition of MCF-7 xenograft growth in athymic mice. Its preferential penetration of human solid tumor cells and prevention of p53 degradation through MDM2 and Parc-independent pathways demonstrate that p28 (SEQ ID NO: 2) and similar peptides provide a novel source of cytotostatic and cytotoxic (apoptotic) agents in the treatment of cancer.

Compositions of the Invention

The invention provides for compounds that can bind p53 and stabilize it, and/or prevent ubiquitination of p53. The invention further provides for chemopreventive agents such as cupredoxins and/or variants, derivatives, truncations, or structural equivalents of cupredoxins, alone or in combination with at least one other chemopreventive agent. In some embodiments, the first chemopreventive agent is a cupredoxin or a truncation thereof. In some such embodiments, the first chemopreventive agent is a truncation of azurin, wherein the truncation comprises one or more of the amino acid sequences selected from the group consisting of SEQ ID NO: 2 and SEQ ID NO: 25. The at least one other chemopreventive agent may be an antiestrogen, including one that blocks the activity of estrogen or progesterone, such as Tamoxifen or fenretinide, or one that prevents the production of estrogen or progesterone, such as aromatase inhibitors like exemestane, anastrozole, and letrozole, or other compounds with similar properties.

The invention further provides for chemopreventive agents that are variants, derivatives, truncations or structural equivalents of cupredoxin. In some embodiments, the chemopreventive agent is isolated. In some embodiments, the chemopreventive agent is substantially pure or pharmaceutical grade. In other embodiments, the chemopreventive agent is in a composition that comprises, or consists essentially of, the chemopreventive agent. In other embodiments, the chemopreventive agent is in a composition that comprises both the chemopreventive agent and at least one other chemopreventive agent. In another specific embodiment, the chemopreventive agent is non-antigenic and does not raise an immune response in a mammal, and more specifically a human. In some embodiments, the chemopreventive agent is less that a full-length cupredoxin, and retains some of the pharmacologic activities of the cupredoxins. Specifically, in some embodiments, the chemopreventive agent may retain the ability to inhibit the development of premalignant lesions in the mouse mammary gland organ culture.

The invention also provides compositions comprising at least one chemopreventive agent that is a cupredoxin, or variant, derivative, truncation, or structural equivalent of a cupredoxin, specifically in a pharmaceutical composition, alone or in combination with at least one other chemopreventive agent. In specific embodiments, the pharmaceutical composition is designed for a particular mode of administration, for example, but not limited to, oral, intraperitoneal, or intravenous. Such compositions may be hydrated in water, or may be dried (such as by lyophilization) for later hydration. Such compositions may be in solvents other than water, such as but not limited to, alcohol.

Because of the high structural homology between the cupredoxins, it is contemplated that cupredoxins will have the same chemopreventive properties as azurin and p28 (SEQ ID NO: 2). In some embodiments, the cupredoxin is, but is not limited to, azurin, pseudoazurin, plastocyanin, rusticyanin, auracyanin, stellacyanin, cucumber basic protein or Laz. In particularly specific embodiments, the azurin is derived from *Pseudomonas aeruginosa, Alcaligenes faecalis, Achromobacter xylosoxidans* ssp. *denitrificans* I, *Bordetella bronchiseptica, Methylomonas* sp., *Neisseria meningitidis, Neisseria gonorrhea, Pseudomonas fluorescens, Pseudomonas chlororaphis, Xylella fastidiosa, Ulva pertussis* or *Vibrio parahaemolyticus*. In a specific embodiment, the azurin is from *Pseudomonas aeruginosa*. In other specific embodiments, the cupredoxin comprises an amino acid sequence that is SEQ ID NOS: 1-19 and 25.

The invention provides chemopreventive agents that are amino acid sequence variants of cupredoxins which have amino acids replaced, deleted, or inserted as compared to the wild-type cupredoxin. Variants of the invention may be truncations of the wild-type cupredoxin. In some embodiments, the chemopreventive agent of the invention comprises a region of a cupredoxin that is less that the full length wild-type polypeptide. In some embodiments, the chemopreventive agent of the invention comprises more than about 10 residues, more than about 15 residues or more than about 20 residues of a truncated cupredoxin. In some embodiments, the chemopreventive agent comprises not more than about 100 residues, not more than about 50 residues, not more than about 40 residues, not more than about 30 residues or not more than about 20 residues of a truncated cupredoxin. In some embodiments, a cupredoxin has to chemopreventive agent, and more specifically SEQ ID NOS: 1-19 and 25 has to the chemopreventive agent of the invention, at least about 70% amino acid sequence identity, at least about 80% amino acid sequence identity, at least about 90% amino acid sequence identity, at least about 95% amino acid sequence identity or at least about 99% amino acid sequence identity.

In specific embodiments, the chemopreventive agent comprises *P. aeruginosa* azurin residues 50-77 (p28, SEQ ID NO: 2), azurin residues 50-67 (p18, SEQ ID NO: 25), azurin residues 50-68 (SEQ ID NO: 26), azurin residues 50-69 (SEQ ID NO: 27), azurin residues 50-70 (SEQ ID NO: 28), azurin residues 50-71 (SEQ ID NO: 29), azurin residues 50-72 (SEQ ID NO: 30), azurin residues 50-73 (SEQ ID NO: 31), azurin residues 50-74 (SEQ ID NO: 32), azurin residues 50-75 (SEQ ID NO: 33), azurin residues 50-76 (SEQ ID NO: 34) or azurin residues 36-88 (SEQ ID NO: 35). In other embodiments, the chemopreventive agent consists of *P. aeruginosa* azurin residues 50-77 (SEQ ID NO: 2), azurin residues 50-67 (SEQ ID NO: 25), azurin residues 50-68 (SEQ ID NO: 26), azurin residues 50-69 (SEQ ID NO: 27), azurin residues 50-70 (SEQ ID NO: 28), azurin residues 50-71 (SEQ ID NO: 29), azurin residues 50-72 (SEQ ID NO: 30), azurin residues 50-73 (SEQ ID NO: 31), azurin residues 50-74 (SEQ ID NO: 32), azurin residues 50-75 (SEQ ID NO: 33), azurin residues 50-76 (SEQ ID NO: 34), azurin residues 36-88 (SEQ ID NO: 35), or azurin residues 60-67 (SEQ ID NO: 86). In other specific embodiments, the chemopreventive agent consists of the equivalent residues of a cupredoxin other that azurin. It is also contemplated that other cupredoxin variants can be designed that have a similar pharmacologic activity to azurin residues 50-77 (p28, SEQ ID NO: 2), or azurin residues 36-88 (SEQ ID NO: 35). To do this, the subject cupredoxin amino acid sequence will be aligned to the *Pseudomonas aeruginosa* azurin sequence using BLAST, BLAST2, ALIGN2 or Megalign (DNASTAR), the relevant residues located on the *P. aeruginosa* azurin amino acid sequence, and the equivalent residues found on the subject cupredoxin sequence, and the equivalent peptide thus designed.

In one embodiment of the invention, the chemopreventive agent contains at least amino acids 57 to 89 of auracyanin B of *Chloroflexus aurantiacus* (SEQ ID NO: 20). In another embodiment of the invention, the chemopreventive agent contains at least amino acids 51-77 of *Pseudomonas syringae* azurin (SEQ ID NO: 21). In another embodiment of the invention, the chemopreventive agent contains at least amino acids 89-115 of *Neisseria meningitidis* Laz (SEQ ID NO: 22). In another embodiment of the invention, the chemopreventive agent contains at least amino acids 52-78 of *Vibrio parahaemolyticus* azurin (SEQ ID NO: 23). In another embodiment of the invention, the chemopreventive agent contains at least amino acids 51-77 of *Bordetella bronchiseptica* azurin (SEQ ID NO: 24).

The chemopreventive agents may also include peptides made with synthetic amino acids not naturally occurring. For example, non-naturally occurring amino acids may be integrated into the chemopreventive agent to extend or optimize the half-life of the composition in the bloodstream. Such chemopreventive agents include, but are not limited to, D,L-peptides (diastereomer), (for example Futaki et al., J. Biol. Chem. 276(8):5836-40 (2001); Papo et al., Cancer Res. 64(16):5779-86 (2004); Miller et al, Biochem. Pharmacol. 36(1):169-76, (1987); peptides containing unusual amino acids (for example Lee et al., J. Pept. Res. 63(2):69-84 (2004)), olefin-containing non-natural amino acid followed by hydrocarbon stapling (for example Schafmeister et al., J. Am. Chem. Soc. 122:5891-5892 (2000); Walenski et al., Science 305:1466-1470 (2004)), and peptides comprising ε-(3,5-dinitrobenzoyl)-Lys residues.

In other embodiments, the chemopreventive agent of the invention is a derivative of a cupredoxin. The derivatives of cupredoxin are chemical modifications of the peptide such that the peptide still retains some of its fundamental activities. For example, a "derivative" of azurin can be a chemically modified azurin that retains its ability to inhibit the development of premalignant lesions in mammalian cells, tissues or animals. Chemical modifications of interest include, but are not limited to, hydrocarbon stabling, amidation, acetylation, sulfation, polyethylene glycol (PEG) modification, phosphorylation and glycosylation of the peptide, and the methods and techniques disclosed herein. In addition, a derivative peptide maybe a fusion of a cupredoxin, or variant, derivative or structural equivalent thereof to a chemical compound, such as but not limited to, another peptide, drug molecule or other therapeutic or pharmaceutical agent or a detectable probe. Derivatives of interest include chemical modifications by which the half-life in the bloodstream of the peptides and compositions of the invention can be extended or optimized, such as by several methods well known to those in the art, including but not limited to, circularized peptides (for example Monk et al., BioDrugs 19(4):261-78, (2005); DeFreest et al., J. Pept. Res. 63(5):409-19 (2004)), N- and C-terminal modifications (for example Labrie et al., Clin. Invest. Med. 13(5):275-8, (1990)), and olefin-containing non-natural amino acid followed by hydrocarbon stapling (for example Schafmeister et al., J. Am. Chem. Soc. 122:5891-5892 (2000); Walenski et al., Science 305:1466-1470 (2004)).

In some embodiments, the cupredoxin may be varied using methods that include, but are not limited to, those which decrease the hydrolysis of the peptide, decrease the deamidation of the peptide, decrease the oxidation, decrease the immunogenicity and/or increase the structural stability of the peptide. It is contemplated that two or more of the modifications described herein may be combined in one modified cupredoxin derived peptide, as well as combinations of one or more modifications described herein with other modification to improve pharmacokinetic properties that are well know to those in the art. Many methods to design such variants and derivatives are well known in the art.

Biotransformation

One approach to improving the pharmacokinetic properties of chemopreventive agents, particularly cupredoxin-derived peptides such as truncations of azurin, is to create variants and derivatives of the cupredoxin derived peptides that are less susceptible to biotransformation. Biotransformation may decrease the pharmacologic activity of the peptide as well as increase the rate at which it is eliminated from the patient's body. One way of achieving this is to determine the amino acids and/or amino acid sequences that are most likely to be biotransformed and to replace these amino acids with ones that are not susceptible to that particular transformative process.

In some embodiments, the cupredoxin derived peptides may include unnatural amino acids or modified amino acids. In some embodiments, the introduction of certain unnatural amino acids enhances the pharmacokinetic properties of the cupredoxin derived peptide. Such introduction may be site-specific and may be done to avoid certain biochemical modifications in vivo. Exemplary unnatural amino acids include b-amino acids (e.g., b3 and b2), homo-amino acids, cyclic amino acids, aromatic amino acids, Pro and Pyr derivatives, 3-substituted Alanine derivatives, Glycine derivatives, Ring-substituted Phe and Tyr Derivatives, Linear Core Amino Acids and Diamino Acids. Such unnatural amino acids may be incorporated into peptides by site directed modification, ribosomal translation, or by chemical synthesis of the peptide. Each of these methods may be applied in synthesizing cupredoxin derived peptides.

For example, modified cupredoxin derived peptides may be synthesized by the use of wild-type Aminoacyl-tRNA synthetases (AARSs) with unnatural amino acids building for the production of unnatural cupredoxin variants. See Hartman, et al., PLoS One, 2(10): e972 (2007); Miranda, et al., J. Am. Chem. Soc. 129: 13153-13159 (2007). The specificity of the ribosomal translation apparatus limits the diversity of unnatural amino acids that may be incorporated into peptides using ribosomal translation. Over ninety unnatural building blocks that are AARS substrates have been uncovered including side chain and backbone analogs. Hartman, et al, PLoS One, 2(10): e972 (2007). Over fifty unnatural amino acids may be incorporated into peptides with high efficiency using an all-enzymatic translation system, with peptides containing up to thirteen different unnatural amino acids. Hartman, et al., PLoS One, 2(10): e972 (2007). In some embodiments, such amino acids may be incorporated in cupredoxin derived peptides.

Other modifications may include the use of optically active α-amino acids. The use of optically active α-amino acids and their derivatives is being expanded for their use in pharmaceuticals, agrochemicals and as chiral ligands. In particular, chiral glycine and alanine equivalents plan an important role. At least one stereoselective strategy for constructing α-amino acids has been proposed, allowing for enantiopure α-amino acids in predetermined stereochemistry. Lu, et al. "Asymmetric Synthesis of α-amino acids: Preparation and alkylation of monocyclic iminolactones derived from α-Methyl trans-cinnamaldehyde" published on Internet on Sept. 11, 2008 (to be published in J. Org. Chem.), the disclosure of which is incorporated by reference herein. The modified cupredoxin derived peptides may be synthesized using the optically active α-amino acids to produce enantiomerically enriched iterations.

Hydrolysis is generally a problem in peptides containing aspartate. Aspartate is susceptible to dehydration to form a cyclic imide intermediate, causing the aspartate to be converted to the potentially inactive iso-aspartate analog, and ultimately cleaving the peptide chain. For example, in the presence of aspartic acid—proline in the peptide sequence, the acid catalyzed formation of cyclic imide intermediate can result to cleavage of the peptide chain. Similarly, in the presence of aspartic acid—glycine in the peptide sequence, the cyclic intermediate can be hydrolyzed either into the original aspartate form (harmless) or into the iso-aspartate analog. Eventually, all of the aspartate form can be completely converted into the iso-aspartate analog. Similarly sequences with serine can also be dehydrated to form a cyclic imide intermediate that can cleave the peptide chain. Cleavage of the peptide may result in reduced plasma half-life as well as reduced specific pharmacologic activity of the peptide.

It is contemplated that substituting other amino acids for asparagine and/or serine in the sequence of the cupredoxin derived peptide may result in a peptide with improved pharmacokinetic properties such as a longer plasma half-life and increased specific activity of a pharmacologic activity of the peptide. In one contemplated variant, at one or more asparagine residues of the cupredoxin derived peptide may be replaced with another amino acid residue, and specifically a glutamic acid residue. In another contemplated variant, one or more serine residues of the cupredoxin derived peptide may be replaced with another amino acid residue, and specifically a threonine residue. In some variants of cupredoxin derived peptide, one or more asparagine residues and one or more serine residues are substituted. In some embodiments, conservative substitutions are made. In other embodiments, non-conservative substitutions are made.

Deamidation of amino acid residues is a particular problem in biotransformation. This base-catalyzed reaction frequently occurs in sequences containing asparagine—glycine or glutamine—glycine and follows a mechanism analogous to the aspartic acid—glycine sequence above. The deamidation of the asparagine—glycine sequence forms a cyclic imide intermediate that is subsequently hydrolyzed to form the aspartate or iso-asparate analog of asparagine. In addition, the cyclic imide intermediate can lead to racemization into D-aspartic acid or D-iso-aspartic acid analogs of asparagine, all of which can potentially lead to inactive forms of the peptide.

It is contemplated that deamidation in the cupredoxin peptides may be prevented by replacing a glycine, asparagine and/or glutamine of the asparagine—glycine or glutamine—glycine sequences of the cupredoxin with another amino acid and may result in a peptide with improved pharmacokinetic properties, such as a longer plasma half-life and increased specific activity of a pharmacologic activity of the peptide. In some embodiments, the one or more glycine residues of the cupredoxin derived peptide are replaced by another amino acid residue. In specific embodiments, one or more glycine residues of the cupredoxin derived peptide are replaced with a threonine or an alanine residue. In some embodiments, the one or more asparagine or glutamine residues of the cupredoxin derived peptide are replaced by another amino acid residue. In specific embodiments, one or more asparagine or glutamine residues of the cupredoxin derived peptide are replaced with an alanine residue. In other specific embodiments, the glycine at residues 58 and/or 63 of *P. aeruginosa* azurin (SEQ ID NO: 1), or equivalent glycines of other cupredoxins, are replaced with an alanine or a threonine. In other specific embodiments, the methionine at residue 59 of *P. aeruginosa azurin* (SEQ ID NO: 1), or an equivalent methionine residue of another cupredoxin derived peptide, is replaced by an alanine residue. In other specific embodiments, the glycine at residue 63 of *P. aeruginosa azurin* (SEQ ID NO: 1), or an equivalent glycine residue of another cupredoxin derived peptide, is replaced by a threonine residue. In some embodiments, conservative substitutions are made. In other embodiments, non-conservative substitutions are made. In specific embodiments, the modified cupredoxin derived peptide of the invention comprises the following sequence, wherein the underlined amino acids are substituted into the wildtype *Pseudomonas aeruginosa* p28 sequence

```
LSTAADMQAVVTDTMASGLDKDYLKPDD.   (SEQ ID NO: 42)
```

Reversible and irreversible oxidation of amino acids are other biotransformative processes that may also pose a problem that may reduce the pharmacologic activity, and/or plasma half-life of cupredoxin derived peptides. The cysteine and methionine residues are the predominant residues that undergo reversible oxidation. Oxidation of cysteine is accelerated at higher pH, where the thiol is more easily deprotonated and readily forms intra-chain or inter-chain disulfide bonds. These disulfide bonds can be readily reversed in vitro by treatment with dithiothreitol (DTT) or tris(2-carboxyethylphosphine) hydrochloride (TCEP). Methionine oxidizes by both chemical and photochemical pathways to form methionine sufoxide and further into methionine sulfone, both of which are almost impossible to reverse.

It is contemplated that oxidation in the cupredoxin derived peptides may be prevented by replacing methionine and/or cysteine residues with other residues. In some embodiments, one or more methionine and/or cysteine residues of the cupredoxin derived peptide are replaced by another amino acid residue. In specific embodiments, the methionine residue is replaced with a leucine or valine residue. In other specific embodiments, one or more of the methionines at residues 56 and 64 of *P. aeruginosa* azurin (SEQ ID NO: 1), or equivalent methionine residues in other cupredoxin derived peptides, are replaced with leucine or valine. In some embodiments, conservative substitutions are made. In other embodiments, non-conservative substitutions are made. In specific embodiments, the cupredoxin peptides of the invention comprise one of the following sequences, wherein the underlined amino acid is substituted into the wildtype *Pseudomonas aeruginosa* p28 sequence:

```
LSTAADLQGVVTDGLASGLDKDYLKPDD    (SEQ ID NO: 43)
or
LSTAADVQGVVTDGVASGLDKDYLKPDD.   (SEQ ID NO: 44)
```

Another biotransformative process that may affect the pharmacologic activity, plasma half-life and/or immunogenicity of the cupredoxin derived peptides is diketopiperazine and pyroglutamic acid formation. Diketopiperazine formation usually occurs when glycine is in the third position from the N-terminus, and more especially if proline or glycine is in position 1 or 2. The reaction involves nucleophilic attack of the N-terminal nitrogen on the amide carbonyl between the second and third amino acid, which leads to the cleavage of the first two amino acids in the form of a diketopiperazine. On the other hand, pyroglutamic acid formation may be almost inevitable if glutamine is in the N-terminus. This is an analogous reaction where the N-terminal nitrogen attacks the side chain carbonyl carbon of glutamine to form a deaminated pyroglutamayl peptide analog. This conversion also occurs in peptide containing asparagine in the N-terminus, but to a much lesser extent.

It is contemplated that diketopiperazine and pyroglutamic acid formation may be decreased in cupredoxin derived peptides by replacing glycine in position 1, 2, or 3 from the N-terminus, proline in position 3 from the N-terminus, or asparagine at the N-terminus of the peptide with another amino acid residue. In some embodiments, a glycine in positions 1, 2, or 3 from the N-terminus of the cupredoxin derived peptide is replaced with another amino acid residue. In specific embodiments, the glycine residue is replaced by a threonine or alanine residue. In another embodiment, a proline at position 3 from the N-terminus of the cupredoxin derived peptide is replaced with another amino acid residue. In specific embodiments, the proline is replaced by an alanine residue. In another embodiment, an asparagine at the N-terminus is replaced with another amino acid residue. In specific embodiments, the asparagine residue is replaced by a glutamine residue. In some embodiments, conservative substitutions are made. In other embodiments, non-conservative substitutions are made.

Another biotransformative process that may affect the pharmacologic activity, plasma half-life and/or immunogenicity of the cupredoxin derived peptide is racemization. This term is loosely used to refer to the overall loss of chiral integrity of the amino acid or peptide. Racemization involves the base-catalyzed conversion of one enantiomer (usually the L-form) of an amino acid into a 1:1 mixture of L- and D-enantiomers. One way to improve stability of the peptide in general is by making a retro-inverso (D-isomer) peptide. The double inversion of peptide structure often leaves the surface topology of the side-chain intact and has been used extensively to stabilize biologically active peptides. Snyder et al., PLoS Biol. 2:0186-0193 (2004). A D-amino acid substituted Tat is internalized into cells as well as the L-amino acid peptide. Futaki et al., J. Biol. Chem. 276:5836-5840 (2001); Huq et al., Biochemistry 38:5172-5177 (1999). In some embodiments, one or more amino acid residues of the cupredoxin derived peptide are replaced by the D-isomer of that amino acid residue. In other embodiments, all of the amino acid residues of the cupredoxin derived peptide are replaced with D-isomers of those residues. In one embodiment, the modified cupredoxin derived peptide is a retro-inverso (D-isomer) version of the cupredoxin derived peptide. In a specific embodiment, the modified cupredoxin derived peptide is

```
DDPKLYDKDLGSAMGDTVVGQMDAATSL.    (SEQ ID NO: 45)
```

Other methods to protect a cupredoxin derived peptide from biotransformative degradation are N-acetylation and C-amidation. These derivatives may protect the peptide from degradation and may make the cupredoxin derived peptide more closely mimic the charge state of the alpha amino and carboxyl groups in the native protein. Peptides with the N-acetylation and/or C-amidation can be provided by commercial suppliers. In one embodiment of the invention, the N-terminus of the cupredoxin derived peptide may be acetylated. In another embodiment of the invention, the C-terminus of the cupredoxin derived peptides may be amidated. In one specific embodiment, the modified cupredoxin derived peptide is

```
                                            (SEQ ID NO: 46)
    Acetylation-LSTAADMQGVVTDGMASGLDKDYLKPDD-
    amidation.
```

Cyclization is an additional manner of biotransformation that may be beneficial to therapeutic peptides including the cupredoxins as described herein. Cyclization may stabilize therapeutic peptides, allowing them to be stored longer, be administered at lower doses and be administered less frequently. Cyclization has been shown to protect peptides against peptidase and protease degradation. Cyclization can be done chemically or enzymatically. Enzymatic cyclization is generally less problematic than chemical cyclization, as chemical cyclization can lack in regio- and stereospecificity, can lead to multimerization in lieu of cyclization and can require complicated multistep processes. Indeed, it has been shown that thioether cyclization is more protective and stable than a disulfide bond against proteolytic enzymes.

Enzymatic cyclization has been shown in lantibiotics—(methyl)lanthionine-containing bacterial peptides. E.g., R. Rink, et al., "Lantibiotic Structures as Guidelines for the Design of Peptides That Can Be Modified by Lantibioitic Enzymes" 44 Biochem., 8873-82 (2005); R. Rink, et al., "Production of Dehydroamino Acid-Containing Peptides by Lactococcus lactis" 73:6 Applied and Environmental Microbiology, 1792-96 (2007); R. Rink, et al., "NisC, the Cylcase of the Lantibiotic Nisin, Can Catalyze Cyclization of Designed Nonlantibiotic Peptides" 46 Biochem., 13179-89 (2007) (each of which is hereby incorporated by reference in its entirety). Lantibiotics are produced by and inhibit the growth of gram-positive bacteria. In lantibiotics, dehydroalanine and dehydrobutyrine are created by enzyme mediated dehydration of serine and threonine residues. Cysteines are then enzymatically coupled to the dehydrated serine and threonine residues to form thioether cyclizations. Naturally occurring lantibiotics show such couplings via thioether bonds between residues that are up to 19 residues apart. Thioether ring formation depends upon the leader peptide. The location of the cyclization depends upon the cyclase mediated regio- and stereospecific ring closure and the positions of the dehydratable serine and threonine residues.

The best characterized of the lantibiotics is nisin—a pentacyclic peptide antibiotic produced by Lactococcus lactis. Nisin is composed of four methyllanthionines, one lanthionine, two dehydroalanines, one dehydrobutyrine, and twenty-six unmodified amino acids. Nisin's five thioether cross-links are formed by the addition of cysteine residues to dehydroalanine and dehydrobutyrine residues that originate from serine and threonine Nisin contains thioether-containing amino acids that are posttranslationally introduced by a membrane-associated enzyme complex. This enzyme complex includes: transporter NisT, serine and threonine dehydratase NisB, and cyclase NisC. NisB dehydrates serine and threonine residues, converting them into dehydroalanine and dehydrobutyrine, respectively. This is followed by NisC catalyzed enantioselective coupling of cysteines to the formed dehydroresidues. NisT facilitates the export of the modified prenisin. Another enzyme, NisP cleaves the nisin leader peptide from prenisin.

The cyclase NisC has been well characterized. Li et al, "Structure and Mechanisn of the Lantibiotic Cylclase Involved in Nisin Biosynthesis" 311 Science, 1464-67 (2006) (hereby incorporated by reference in its entirety).

An analysis of cyclization in lantibiotics has led to the identification of amino acid sequences and characteristics in peptides that favor cyclization. It has been shown that the NisB enzyme dehydrates more often where certain amino acids flank the serine and threonine nsidues. It has been shown that cyclization occurs more often in lantibiotic propeptides where hydrophobic, nonaromatic residues are in proximity to the serine and threonine nsidues. The flanking residues of the modified cysteines are typically less hydrophobic than the flanking residues of the modified threonines and serines. Exceptions have been found, including hexapeptides VSPPAR (SEQ ID NO: 47), YTPPAL (SEQ ID NO: 48) and FSFFAF (SEQ ID NO: 49). The hexapeptides suggest that the presence of a proline at position 3 or 4 or having phenylalanine flanking both sides may prohibit dehydration. The rings are typically formed by coupling a dehydrated residue to a C-terminally located cysteine. However, rings may be formed by coupling a dehydrate residue to a N-terminally located cysteine.

It has also been shown that the nisin dehydrating and transport enzymes are not specific to nisin and may, in fact, be used to modify non-nisin peptides (and non-lantibiotic peptides). NisB has been shown to dehydrate serine and threonine residues in peptides such as human peptide hormones when such peptides are N-terminally fused to the lantibiotic leader peptide. On non-lantibiotic peptides, similar ring formation characteristics apply; namely, the extent of dehydration can be controlled by the amino acid context of the flanking region of the dehydratable serine and threonine residues. The presence of hydrophobic flanking residues (e.g., alanine and valine) around the serines and threonines allowed full dehydration and therefore enhanced thioether ring formation. The presence of an N-terminal aspartate and C-terminally flanked arginine prevented dehydration. It also shown that the presence of proline residues and phenylalanine residues is disfavorable for dehydration. Generally, the presence of hydrophilic flanking residues prevented dehydration of the serine and threonine residues.

Hydrophobic flanking favors dehydration; hydrophilic flanking disfavors dehydration. Studies have shown that where dehydration does occur, the average hydrophobicity of the flanking residues of serines and threonine is positive—0.40 on the N-terminal side and 0.13 on the C-terminal side. Also, the average hydrophobicity of the residues flanking serines and threonines that are not dehydrated is negative—–0.36 on the N-terminal side and –1.03 on the C-terminal side. Dehydration is not restricted by the presence of a series of flanking threonine residues and is not restricted by the distance between the nisin leader peptide and the residue to be dehydrated.

NisC has been shown to catalyze the regiospecific formation of thioether rings in peptides unrelated to naturally occurring lantibiotics. Generally, such peptides must be fused to the nisin leader peptide. In some cases, thioether rings may form spontaneously, for example where a dehydroalanine is spaced by two amino acids from a cysteine. Unlike spontaneous cyclization, NisC catalyzed cyclization is stereospecific for dehydrated prenisin. Consequently, the methyllanthionines and lanthionine in nisin are in the DL configuration. It is thought that cyclization in nonlantibiotic peptides will also be stereospecific.

These principles can be applied to the compounds described herein, including cupredoxins and variants and truncations thereof.

Thioether Bridges

In nature, lantibiotic-enzyme-induced thioether bridges occur with up to 19 amino acids under the bridge. Thioether bridges with 2 to 4 amino acids under the bridge are abundant.

Figure 24A:
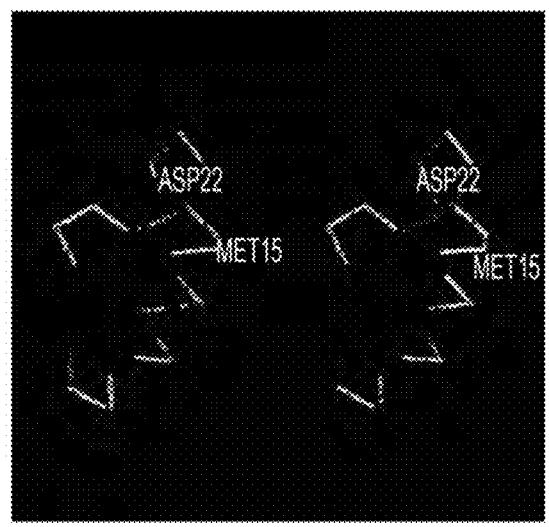
FIG. 24, A-C. Graphical representations of p28 (SEQ ID NO: 2) and modifications thereof.
Figure 24B:
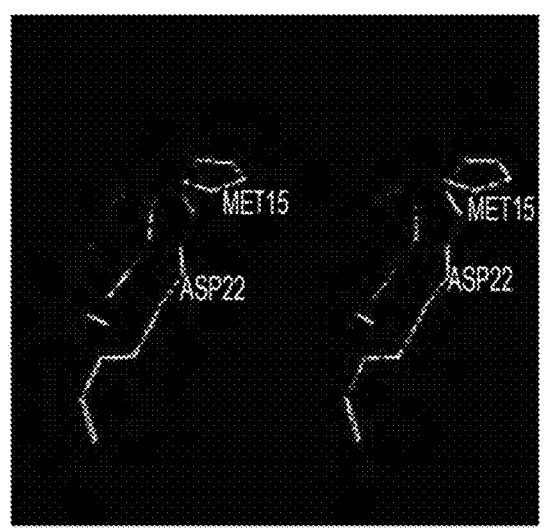

In some embodiments, the chemopreventive agents of the invention, specifically cupredoxins and derivatives, variants, truncations, or structural equivalents of cupredoxins, such as truncated azurin, may be modified by introducing thioether bridges into the structure. The azurin truncation p28 (SEQ ID NO: 2), for example, may be modified using this method. Extended molecular dynamics simulations (70 ns) using software package GROMACS (www.gromacs.org) suggest that, at 37° C., the region of the p28 (SEQ ID NO: 2) alpha helix from position 6 to 16 is unstable, and that the peptide tends to adopt a beta sheet conformation. FIGS. 24A and B. This, together with the fact that the part of the molecule presumed to be responsible for interaction with p53 remains solvent exposed, suggests that introduction of a thioether bridge in this region of the p28 (SEQ ID NO: 2) peptide may not affect its functionality.

The amino acid sequence of p28 is (LSTAADMQGVVTDGMASGLDKDYLKPDD).     SEQ ID NO: 2

The amino acid sequence known as p18 is (LSTAADMQGVVTDGMASG).     SEQ ID NO: 25

The sequence SGLDKD (SEQ ID) NO: 85) may interact with p53. Thioether bridges can be formed between Ser/Thr on the N-side to Cys on the C-side. The serine/threonine is dehydrated and subsequently coupled to the cysteine. Threonines are preferred since they are more easily dehydrated than serines. Generally, hydrophobic flanking residues (at least one) to the threonine are preferred since they enhance the extent of dehydration. Negatively charged amino acids, glutamate and aspartate, that are flanking residues have a strong negative effect on dehydration. Generally, hydrophilic flanking residues, especially glycin, do not favor dehydration. Preceding the Cys there is a slight preference for charged hydrophilic residues, especially glutamate/aspartate. Depending on the size of the thioether ring, the bulkiness of the amino acids that participate in the ring matters.

In one embodiment, the truncated azurin sequence is

LSTAADMQGVVTDGMASGLDKDYLTPGC.     (SEQ ID NO: 50)

A thioether bridge is formed between positions 25 and 28 of p28 (SEQ ID NO: 2), and will be fully protected against carboxyetidases. Positions 2, 3 and 25 will be dehydrated, but neither the import sequence, nor the sequence thought to be relevant for interaction with p53, is altered by thioether ring introduction. As such, peptide activity should not be altered. The threonine is between two hydrophobic amino acids and hence is expected to be fully dehydrated by dehydratase, NisB, according to specific guidelines. See Rink et al., Biochemistry 2005. The same guidelines also predict cyclization involving positions 25 and 28 by cyclase NisC, especially because of the aspartate located before the cysteine.

In another embodiment, the truncated azurin sequence is

LSTAADCQGVVTDGMASGLDKDYLKPDD     (SEQ ID NO: 51)

and the thioether bridge is formed between positions 3 and 7. The ring between position 3 and 7 mimics ring A of nisin and makes use of the existing threonine at position 2. The aspartate at position 6 will favor cyclization.

In another embodiment, the truncated azurin sequence is

LSTAACMQGVVTDGMASGLDKDYLKPDD,     (SEQ ID NO: 52)

and the threonine in position 2 is utilized to form a thioether bridge.

In another embodiment, two or more of the thioether rings in the truncated azurins described in the paragraphs above are combined into one peptide.

In another embodiment, many truncated azurin sequences can be created and screened for threonine rings by analyzing the peptides with a ring of one lanthionine and two to three additional amino acids under the sulfur bridge. This might involve one or combinations of the sequences below:

| | |
|---|---|
| LSTACDMQGVVTDGMASGLDKDYLKPDD | (SEQ ID NO: 53) |
| LSTAATMQCVVTDGMASGLDKDYLKPDD | (SEQ ID NO: 54) |
| LSTAATMQGCVTDGMASGLDKDYLKPDD | (SEQ ID NO: 55) |
| LSTAANTQGCVTDGMASGLDKDYLKPDD | (SEQ ID NO: 56) |
| LSTAANTQGVCTDGMASGLDKDYLKPDD | (SEQ ID NO: 57) |
| LSTAADMTAVCTDGMASGLDKDYLKPDD | (SEQ ID NO: 58) |
| LSTAADMTAVVCDGMASGLDKDYLKPDD | (SEQ ID NO: 59) |
| LSTAADMQTVVCDGMASGLDKDYLKPDD | (SEQ ID NO: 60) |
| LSTAADMQTVVTCGMASGLDKDYLKPDD | (SEQ ID NO: 61) |
| LSTAADMQATVTCGMASGLDKDYLKPDD | (SEQ ID NO: 62) |
| LSTAADMQATVTDCMASGLDKDYLKPDD | (SEQ ID NO: 63) |

```
LSTAADMQGVTADCMASGLDKDYLKPDD    (SEQ ID NO: 64)

LSTAADMQGVTADGCASGLDKDYLKPDD    (SEQ ID NO: 65)

LSTAADMQGVVTNGCASGLDKDYLKPDD    (SEQ ID NO: 66)
```

A practical approach would be to genetically make a large number of such sequences and select a group for purification on the basis of extent of modification and level of production.

Figure 24C:
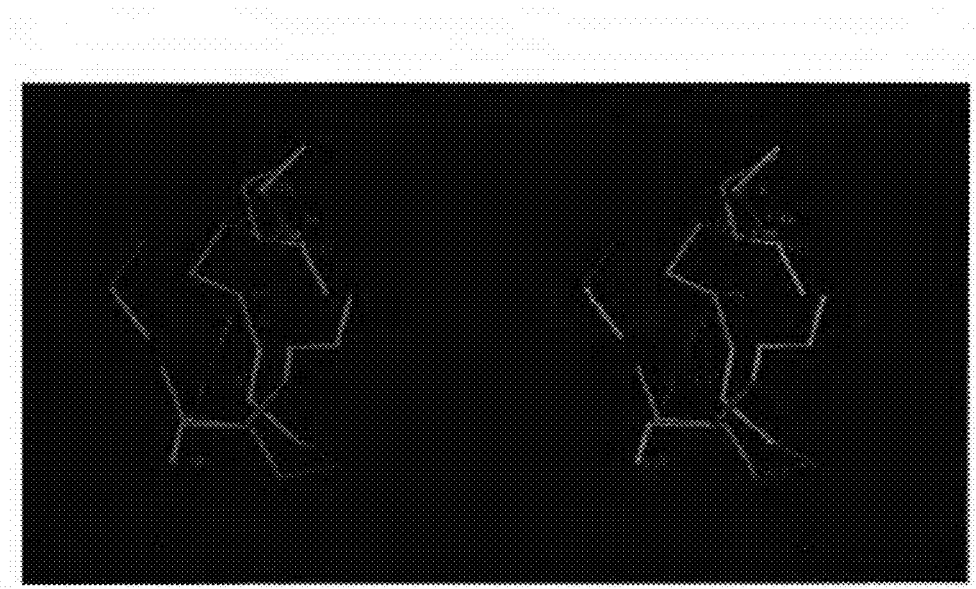

In another embodiment, a thioether bridge is formed between a threonine at position 12 in p28 (SEQ ID NO: 2) and the c-terminus of the peptide. The distance between the Cα of position 13 and the aspartate at position 28 might be 17.52 angstroms, larger than 1.5 nanometers, implying significant alteration of the structure of the peptide. FIG. 24C.

In another embodiment, the peptide sequence is

```
LSTAADMQGVVTATMGSGLCKDYLKPDD,    (SEQ ID NO: 67)
``` with a thioether bridge from position 14 to position 2 at a distance of 4.38 angstroms. The mutation of aspartate at position 13 to alanine favors dehydration of threonine at position 14. Mutation of alanine at position 16 to glycine completely prevents dehydration of serine at position 17 and enhances cyclization.

In another embodiment, the peptide sequence is

```
LSTAADMQGVVTDLTASGLCKDYLKPDD,    (SEQ ID NO: 68)
``` with the thioether bridge from position 15 to position 20 at a distance of 5.83 angstroms. In this situation, mutation of glycine at position 14 to leucine favors dehydration of threonine at position 15.

Tertiary Structure Stabilization

The stability of the tertiary structure of the cupredoxin derived peptide will affect most aspects of the pharmacokinetics, including the pharmacologic activity, plasma half-life, and/or immunogenicity among others. See Kanovsky et al., Cancer Chemother. Pharmacol. 52:202-208 (2003); Kanovsky et al., PNAS 23:12438-12443 (2001). Peptide helices often fall apart into random coils, becoming more susceptible to protease attack and may not penetrate cell membrane well. Schafmeister et Am. Chem. Soc. 122:5891-5892 (2000). Therefore, one way to stabilize the overall structure of the peptide is to stabilize the α-helix structure of the peptide. The intra-molecular hydrogen bonding associated with helix formation reduces the exposure of the polar amide backbone, thereby reducing the barrier to membrane penetration in a transport peptide, and thus increasing related pharmacologic activities and increasing the resistance of the peptide to protease cleavage. Id. *Pseudomonas aeruginosa* azurin (SEQ ID NO: 1) has α-helices at residues 53-56, 58-64 and 68-70.

One method to stabilize an α-helix is to replace in the α-helix helix breaking amino acid residues such as glycine, proline, serine and aspartic acid, or helix neutral amino acid residues such as alanine, threonine, valine, glutamine, asparagine, cysteine, histidine, lysine or arginine, with helix forming residues, such as leucine, isoleucine, phenylalanine, glutamic acid, tyrosine, tryptophan and methionine or helix favoring amino acid residue substitutions, for example α-amino-isobutyric acid (Aib). See Miranda et al., J. Med. Chem., 51, 2758-2765 (2008), the disclosure of which is incorporated by reference herein. It is contemplated that the α-helix of cupredoxin derived peptides may be stabilized by replacing one or more glycine, proline, serine and/or aspartic acid residues with other amino acids. In specific embodiments, the glycine, praline, serine, aspartic acid, alanine, threonine, valine, glutamine, asparagine, cysteine, histidine, lysine and/or arginine residues are replaced by leucine, isoleucine, phenylalanine, glutamic acid, tyrosine, tryptophan, Aib and/or methionine residues. See Lee et al., Cancer Cell Intl. 11:21 (2005). In other specific embodiments, one or more serine or glutamine residues in the α-helices of a cupredoxin derived peptide may be substituted. In still more specific embodiments, the serine and/or glutamine residues in residues 53-56, 58-64 and 68-70 of *P. aeruginosa* azurin (SEQ ID NO: 1), or equivalent residues of other cupredoxin derived peptides, may be replaced. In another specific embodiment, the glutamine residue at amino acid residue 57 of *P. aeruginosa* azurin (SEQ ID NO: 1), or an equivalent residue of another cupredoxin derived peptide, may be replaced, more specifically replaced with tryptophan. In another specific embodiment, the threonine residue at amino acid residue 52 of *P. aeruginosa* azurin (SEQ ID NO: 1), or an equivalent residue of another cupredoxin derived peptide, may be replaced, more specifically replaced with tryptophan. In another specific embodiment, the threonine residue at amino acid residue 61 of *P. aeruginosa* azurin (SEQ ID NO: 1), or an equivalent residue of another cupredoxin derived peptide, may be replaced, more specifically replaced with tryptophan. In another specific embodiment, the glycine residue at amino acid residue 63 of *P. aeruginosa* azurin (SEQ ID NO: 1), or an equivalent residue of another cupredoxin derived peptide, may be replaced, more specifically replaced with tryptophan. In another specific embodiment, one or more threonine, glutamine or glycine residues at amino acid residues 52, 57, 61 or 63 of *P. aeruginosa* azurin (SEQ ID NO: 1), or an equivalent residue of another cupredoxin derived peptide, may be replaced, more specifically replaced with tryptophan. In specific embodiments, the cupredoxin peptide comprises one of the following sequences wherein the underlined amino acid is substituted into the wildtype *Pseudomonas aeruginosa* p28 sequence:

```
LSWAADMQGVVTDGMASGLDKDYLKPDD;    (SEQ ID NO: 69)

LSTAADMWGVVTDGMASGLDKDYLKPDD;    (SEQ ID NO: 70)

LSTAADMQGVVWDGMASGLDKDYLKPDD;    (SEQ ID NO: 71)

LSTAADMQGVVTDWMASGLDKDYLKYDD;    (SEQ ID NO: 72)

LSWAADMWGVVTDGMASGLDKDYLKPDD;    (SEQ ID NO: 73)

LSWAADMQGVVWDGMASGLDKDYLKPDD;    (SEQ ID NO: 74)

LSWAADMQGVVTDWMASGLDKDYLKPDD;    (SEQ ID NO: 75)

LSTAADMWGVVWDGMASGLDKDYLKPDD;    (SEQ ID NO: 76)

LSTAADMWGVVTDWMASGLDKDYLKPDD;    (SEQ ID NO: 77)

LSTAADMQGVVWDWMASGLDKDYLKPDD;    (SEQ ID NO: 78)
or

LSWAADMWGVVWDWMASGLDKDYLKYDD.    (SEQ ID NO: 79)
```

In other embodiments, equivalent amino acids in other cupredoxin derived peptides are substituted with tryptophan.

Another method to stabilize an α-helix tertiary structure involves using unnatural amino acid residues capable of π-stacking. For example, in Andrews and Tabor (Tetrahedron 55:11711-11743 (1999)), pairs of ε-(3,5-dinitrobenzoyl)-Lys residues were substituted into the α-helix region of a peptide at different spacings. The overall results showed that the i,(i+4) spacing was the most effective stabilizing arrangement. Increasing the percentage of water, up to 90%, increased the helical content of the peptide. Pairs of ε-acyl-Lys residues in the same i,(i+4) spacing had no stabilizing effect, indicating that the majority of the stabilization arises from π-π interactions. In one embodiment, the cupredoxin derived peptide may be modified so that the lysine residues are substituted by ε-(3,5-dinitrobenzoyl)-Lys residues. In a specific embodiment, the lysine residues may be substituted by ε-(3,5-dinitrobenzoyl)-Lys in a i,(i+4) spacing.

Another method to stabilize an α-helix tertiary structure uses the electrostatic interactions between side-chains in the α-helix. When His-Cys or His-His residue pairs were substituted in into peptides in an i,(i+4) arrangement, the peptides changed from about 50% helical to about 90% helical on the addition of Cu, Zn or Cd ions. When ruthenium (Ru) salts were added to the His-His peptides, an exchange-inert complex was formed, a macrocyclic Cis-[Ru—(NH$_3$)$_4$L$_2$]$^{3+}$ complex where L$_2$ are the side chains of two histidines, which improved the helix stability. Ghadiri and Fernholz, J. Am. Chem. Soc. 112, 9633-9635 (1990). In some embodiments, the cupredoxin derived peptides may comprise macrocyclic cis-[Ru—(NH$_3$)$_4$L$_2$]$^{3+}$ complexes where L$_2$ is the side chains of two histidines. In some embodiments, one or more histidine-cysteine or histidine-histidine residue pairs may be substituted an i,(i+4) arrangement into the α-helices of the cupredoxin derived peptide. In other embodiments, one or more histidine-cysteine or histidine-histidine residue pairs may be substituted an i,(i+4) arrangement in residues 53-56, 58-64 and 68-70 of *P. aeruginosa* azurin (SEQ ID NO: 1), or equivalent residues of other cupredoxin derived peptides. In some embodiments, the cupredoxin derived peptide may further comprise Cu, Zn, Cd and/or Ru ions.

Another method to stabilize an α-helix tertiary structure involves disulfide bond formation between side-chains of the α-helix. It is also possible to stabilize helical structures by means of formal covalent bonds between residues separated in the peptide sequence. The commonly employed natural method is to use disulfide bonds. Pierret et al., Intl. J. Pept. Prot. Res., 46:471-479 (1995). In some embodiments, one or more cysteine residue pairs are substituted into the α-helices of the cupredoxin derived peptide. In other embodiments, one or more cysteine residue pairs are substituted at residues 53-56, 58-64 and 68-70 of *P. aeruginosa* azurin (SEQ ID NO: 1), or equivalent residues of other cupredoxin derived peptides.

Another method to stabilize an α-helical tertiary structure involves the use of side chain lactam bridges. A lactam is a cyclic amide which can form from the cyclisation of amino acids. Side chain to side chain bridges have been successfully used as constraints in a variety of peptides and peptide analogues, such as amphipathic or model α-helical peptides, oxytocin antagonists, melanoptropin analogues, glucagon, and SDF-1 peptide analogues. For example, the Glucagon-like Peptide-1 (GLP-1) gradually assumes a helical conformation under certain helix-favoring conditions and can be stabilized using lactam bridging. Miranda et al., J. Med. Chem., 51, 2758-2765 (2008). These lactam bridges may be varied in size, effecting stability and binding affinity. Id. Such modifications improved the stability of the compounds in plasma. Id. Depending on the space between the cyclization sites and choice of residues, lactam bridges can be used to induce and stabilize turn or helical conformations. In some embodiments, one or more cupredoxin or variant analogues are prepared with lactam bridging between nearby amino acids (such as i to i+4 glutamic acid-lysine constraints). In some embodiments, the cupredoxin derived peptide may comprise such modifications to enhance α-helix content.

Another method to stabilize an α-helix tertiary structure is the all-carbon cross-link method. The all-hydrocarbon cross-link method is proven to increase the stabilization of helical structure, protease resistant and cell-permeability. Walensky et al., Science, 305, 1466-1470 (2004). α,α-disubstituted non-natural amino acids containing olefin-bearing tethers are incorporated into peptides. Ruthenium catalyzed olefin metathesis generates an all-hydrocarbon "staple" to cross-link the helix. Schafmeister et al., J. Am. Chem. Soc., 122, 5891-5892 (2000); Walensky et al., id. Non-natural amino acids containing olefin-bearing tethers may be synthesized according to methodology provided in Schafmeister et al. (id.) and Williams and Im (J. Am. Chem. Soc., 113:9276-9286 (1991)). In some embodiments, the cupredoxin derived peptides are stabilized by all-hydrocarbon staples. In specific embodiments, one or more pairs of α,α-disubstituted non-natural amino acids containing olefin-bearing tethers corresponding to the native amino acids are substituted into the α-helices of the cupredoxin derived peptide. In other embodiments, one or more pairs of α,α-disubstituted non-natural amino acids containing olefin-bearing tethers corresponded to the native amino acids are substituted into residues 53-56, 58-64 and 68-70 of *P. aeruginosa* azurin (SEQ ID NO: 1), or equivalent residues of other cupredoxin derived peptides.

In some embodiments, the modified cupredoxin derived peptide may comprise (SEQ ID NO: 80)
X$_1$SX$_2$AADX$_3$X$_4$X$_5$VVX$_6$DX$_7$X$_8$ASGLDKDYLKPDX$_9$, where X$_1$ is L or acetylated-L, X$_2$ is T or W, X$_3$ is M, L or V, X$_4$ is Q or W, X$_5$ is G or A, X$_6$ is T or W, X$_7$ is G, T or W, X$_8$ is M, L or V, and X$_9$ is D or amidated-D. In other embodiments, the modified cupredoxin derived peptide may consist of (SEQ ID NO: 80)
X$_1$SX$_2$AADX$_3$X$_4$X$_5$VVX$_6$DX$_7$X$_8$ASGLDKDYLKPDX$_9$, where X$_1$ is L or acetylated-L, X$_2$ is T or W, X$_3$ is M, L or V, X$_4$ is Q or W, X$_5$ is G or A, X$_6$ is T or W, X$_7$ is G, T or W, X$_8$ is M, L or V, and X$_9$ is D or amidated-D. In other embodiments, the modified cupredoxin derived peptide may comprise (SEQ ID NO: 81)
X$_1$DPKLYDKDLGSAX$_2$X$_3$DAVVX$_5$X$_6$X$_7$DAAX$_8$SX$_9$, where X$_1$ is D or acetylated-D, X$_2$ is M, L or V, X$_3$ is G, T or W, X$_4$ is T or W, X$_5$ is G or A, X$_6$ is Q or W, X$_7$ is M, L or V, X$_8$ is T or W, and X$_9$ is L or amidated-L. In other embodiments, the modified cupredoxin derived peptide may consist of (SEQ ID NO: 81)
X$_1$DPKLYDKDLGSAX$_2$X$_3$DX$_4$VVX$_5$X$_6$X$_7$DAAX$_8$SX$_9$, where X$_1$ is D or acetylated-D, X$_2$ is M, L or V, X$_3$ is G, T or W, X$_4$ is T or W, X$_5$ is G or A, X$_6$ is Q or W, X$_7$ is M, L or V, $X_8$ is T or W, and $X_9$ is L or amidated-L. Specific peptides of interest are listed in Table 3.

PEGylation

Covalent attachment of PEG to drugs of therapeutic and diagnostic importance has extended the plasma half-life of the drug in vivo, and/or reduced their immunogenicity and antigenicity. Harris and Chess, Nature Reviews Drug Discovery 2:214-221 (2003). For example, PEG attachment has improved the pharmacokinetic properties of many therapeutic proteins, including interleukins (Kaufman et al., J. Biol. Chem. 263:15064 (1988); Tsutsumi et al., J. Controlled Release 33:447 (1995)), interferons (Kita et al., Drug Des. Delivery 6:157 (1990)), catalase (Abuchowski et al., J. Biol. Chem. 252:3582 (1977)), superoxide dismutase (Beauchamp et al., Anal. Biochem. 131:25 (1983)), and adenosine deanimase (Chen et al., Biochem. Biophys. Acta 660:293 (1981)), among others. The FDA has approved PEG for use as a vehicle or base in foods, cosmetics and pharmaceuticals, including injectable, topical, rectal and nasal formulations. PEG shows little toxicity, and is eliminated from the body intact by either the kidneys (for PEGs<30 kDa) or in the feces (for PEGs>20 kDa). PEG is highly soluble in water.

PEGylation of a chemopreventive agents, particularly cupredoxin-derived peptides such as truncations of azurin, may be used to increase the lifetime of the peptide in the bloodstream of the patient by reducing renal ultrafiltration, and thus reduce elimination of the drug from the body. Charge masking may affect renal permeation. Charge masking may be a consequence of the paramchemical modification of protein ionizable functional group, namely amines or carboxyls. In particular, the most common procedures for producing protein—PEG derivatives involves the conversion of protein amino groups into amides with the consequent loss of positive charges, and this can alter protein ultrafiltration. Since anionic macromolecules have been found to be cleared by renal ultrafiltration more slowly than neutral or positive ones, it could be expected that PEG conjugation to amino groups prolongs the permanence of the PEGylated peptide in the bloodstream.

Molecular size and globular ultrafiltration may also affect renal ultrafiltration of therapeutic peptides. The molecular weight cut off for kidney elimination of native globular proteins is considered to be about 70 kDa, which is close to the molecular weight of serum albumin. Thus, proteins with molecular weight exceeding 70 kDa are mainly eliminated from the body by pathways other than renal ultrafiltration, such as liver uptake, proteolytic digestion and clearance by the immune system. Therefore, increasing the size of a therapeutic peptide by PEGylation may decrease renal ultrafiltration of that peptide form the bloodstream of the patient.

Additionally, PEGylation of a peptide may decrease the immunogenicity of that peptide, as well as protect the peptide from proteolytic enzymes, phagocytic cells, and other factors that require direct contact with the therapeutic peptide. The umbrella-like structure of branched PEG in particular has been found to give better protection than linear PEG towards approaching proteolytic enzymes, antibodies, phagocytic cells, etc. Caliceti and Veronese, Adv. Drug. Deliv. Rev. 55:1261-12778 (2003).

In some embodiments, the cupredoxin derived peptides are modified to have one or more PEG molecules covalently bonded to a cysteine molecule. The covalent bonding does not necessarily need to be a covalent bond directly from the PEG molecule to the cupredoxin derived peptide, but may be covalently bonded to one or more linker molecules which in turn are covalently bonded to each other and/or the cupredoxin derived peptide. In some embodiments, the cupredoxin derived peptide have site-specific PEGylation. In specific embodiments, the PEG molecule(s) may be covalently bonded to the cysteine residues 3, 26 and/or 112 of *P. aeruginosa* azurin (SEQ ID NO: 1). In other embodiments, one or more cysteine residues may be substituted into the cupredoxin derived peptide and is PEGylated. In some embodiments, the method to PEGylate the cupredoxin derived peptide may be NHS, reductive animation, malimid or epoxid, among others. In other embodiments, the cupredoxin derived peptides may be PEGylated on one or more lysine, cysteine, histidine, arginine, aspartic acid, glutamic acid, serine, threonine, or tyrosine, or the N-terminal amino group or the C-terminal carboxylic acid. In more specific embodiments, the cupredoxin derived peptides may be PEGylated on one or more lysines or N-terminal amino groups. In other embodiments, one or more lysine, cysteine, histidine, arginine, aspartic acid, glutamic acid, serine, threonine, or tyrosine residue are substituted into the cupredoxin derived peptides and are PEGylated. In other embodiments, the cupredoxin derived peptides may be PEGylated on one or more amino groups. In other embodiments, the cupredoxin derived peptides may be PEGylated in a random, non-site specific manner. In some embodiments, the cupredoxin derived peptides may have an average molecular weight of PEG-based polymers of about 200 daltons to about 100,000 daltons, about 2,000 daltons to about 20,000 daltons, or about 2,000 daltons to about 5,000 daltons. In other embodiments, the cupredoxin derived peptides may be comprised of one or more PEG molecules that is branched, specifically a branched PEG molecule that is about 50 kDa. In other embodiments, the cupredoxin derived peptides may comprise one or more linear PEG molecules, specifically a linear PEG molecule that is about 5 kDa.

In another embodiment, the chemopreventive agent is a peptide that is a cupredoxin, or variant, structural equivalent, or derivative thereof that is a conjugate of Pep42, a cyclic 13-mer oligopeptide that specifically binds to glucose-regulated protein 78 (GRP78) and is internalized into cancer cells. The cupredoxin or variant, structural equivalent, or derivative of cupredoxin may be conjugated with Pep42 pursuant to the synthesis methods disclosed in Yoneda et al., "A cell-penetrating peptidic GRP78 ligand for tumor cell-specific prodrug therapy," Bioorganic & Medicinal Chemistry Letters 18: 1632-1636 (2008), the disclosure of which is incorporated in its entirety herein.

In another embodiment, the chemopreventive agent is a peptide that is a structural equivalent of a cupredoxin. Examples of studies that determine significant structural homology between cupredoxins and other proteins include Toth et al. (Developmental Cell 1:82-92 (2001)). Specifically, significant structural homology between a cupredoxin and the structural equivalent may be determined by using the VAST algorithm. Gibrat et al., Curr Opin Struct Biol 6:377-385 (1996); Madej et al., Proteins 23:356-3690 (1995). In specific embodiments, the VAST p value from a structural comparison of a cupredoxin to the structural equivalent may be less than about $10^{-3}$, less than about $10^{-5}$, or less than about $10^{-7}$. In other embodiments, significant structural homology between a cupredoxin and the structural equivalent may be determined by using the DALI algorithm. Holm & Sander, J. Mol. Biol. 233:123-138 (1993). In specific embodiments, the DALI Z score for a pairwise structural comparison is at least about 3.5, at least about 7.0, or at least about 10.0.

It is contemplated that the chemopreventive agents, particularly the peptides, of the composition of invention may be more than one of a variant, derivative and/or structural equivalent of a cupredoxin. For example, the peptides may be a truncation of azurin that has been PEGylated, thus making it both a variant and a derivative. In one embodiment, the peptides of the invention are synthesized with α,α-disubstituted non-natural amino acids containing olefin-bearing tethers, followed by an all-hydrocarbon "staple" by ruthenium catalyzed olefin metathesis. Scharmeister et al., J. Am. Chem. Soc. 122:5891-5892 (2000); Walensky et al., Science 305:1466-1470 (2004). Additionally, peptides that are structural equivalents of azurin may be fused to other peptides, thus making a peptide that is both a structural equivalent and a derivative. These examples are merely to illustrate and not to limit the invention. Variants, derivatives or structural equivalents of cupredoxin may or may not bind copper.

In some embodiments, the chemopreventive agent that is a cupredoxin, or variant, derivative or structural equivalent thereof has some of the pharmacologic activities of the P. aeruginosa azurin, and specifically p28. In a specific embodiment, the cupredoxins and variants, derivatives and structural equivalents of cupredoxins may inhibit or prevent the development of premalignant lesions in mammalian cells, tissues or animals, and specifically but not limited to, mammary gland cells. The invention also provides for the cupredoxins and variants, derivatives and structural equivalents of cupredoxins that may have the ability to inhibit the development of mammalian premalignant lesions, and specifically but not limited to, melanoma, breast, pancreas, glioblastoma, astrocytoma, lung, colorectal, neck and head, bladder, prostate, skin and cervical cancer cells. Inhibition of the development of cancer cells is any decrease, or lessening of the rate of increase, of the development of premalignant lesions that is statistically significant as compared to control treatments.

Because it is now known that cupredoxins can inhibit the development of premalignant lesions and ultimately cancer in mammalian cells, tissues or animals, and specifically breast cells, and more specifically, mouse mammary gland cells, it is now possible to design variants and derivatives of cupredoxins that retain this chemopreventive activity. Such variants, derivatives and structural equivalents can be made by, for example, creating a "library" of various variants, derivatives and structural equivalents of cupredoxins and cupredoxin derived peptides and then testing each for chemopreventive activity, and specifically chemopreventive activity in the mouse mammary gland organ culture using one of many methods known in the art, such the exemplary method in Example 1. It is contemplated that the resulting variants, derivatives and structural equivalents of cupredoxins with chemopreventive activity may be used in the methods of the invention, in place of or in addition to azurin or p28.

In some specific embodiments, the variant, derivative or structural equivalent of cupredoxin may inhibit the development of 7,12-dimethylbenz (a) anthracene (DMBA) induced premalignant lesions in a mouse mammary gland organ culture (MMOC) to a degree that is statistically different from a non-treated control. A peptide can be tested for this activity by using the MMOC model system is described in Example 1, or as in Mehta et al. (J Natl Cancer Inst 93:1103-1106 (2001)) and Mehta et al. (Meth Cell Sci 19:19-24 (1997)). Other methods to determine whether cancer development is inhibited another are well known in the art and may be used as well.

In some specific embodiments, the variant, derivative or structural equivalent of cupredoxin inhibits the development of mammary alveolar lesions (MAL) in the a MMOC model to a degree that is statistically different from a non-treated control. In some specific embodiments, the variant, derivative or structural equivalent of cupredoxin inhibits the development of mammary ductal lesions (MDL) in the a MMOC model to a degree that is statistically different from a non-treated control. A peptide can be tested for these activities by using the MMOC model system induced to form premalignant lesions by DMBA, as described in Example 1. Evaluation of development of premalignant lesions in a MMOC model system may be determined by morphometic analysis, or histopathological analysis, as provided in Example 1.

Cupredoxins

These small blue copper proteins (cupredoxins) are electron transfer proteins (10-20 kDa) that participate in bacterial electron transfer chains or are of unknown function. The copper ion is solely bound by the protein matrix. A special distorted trigonal planar arrangement to two histidine and one cysteine ligands around the copper gives rise to very peculiar electronic properties of the metal site and an intense blue color. A number of cupredoxins have been crystallographically characterized at medium to high resolution.

The cupredoxins in general have a low sequence homology but high structural homology. Gough & Clothia, Structure 12:917-925 (2004); De Rienzo et al., Protein Science 9:1439-1454 (2000). For example, the amino acid sequence of azurin is 31% identical to that of auracyanin B, 16.3% to that of rusticyanin, 20.3% to that of plastocyanin, and 17.3% to that of pseudoazurin. See, Table 1. However, the structural similarity of these proteins is more pronounced. The VAST p value for the comparison of the structure of azurin to auracyanin B is $10^{-7.4}$, azurin to rusticyanin is $10^{-5}$, azurin to plastocyanin is $10^{-5.6}$, and azurin to psuedoazurin is $10^{-4.1}$.

All of the cupredoxins possess an eight-stranded Greek key beta-barrel or beta-sandwich fold and have a highly conserved site architecture. De Rienzo et al., Protein Science 9:1439-1454 (2000). A prominent hydrophobic patch, due to the presence of many long chain aliphatic residues such as methionines and leucines, is present around the copper site in azurins, amicyanins, cyanobacterial plastocyanins, cucumber basic protein and to a lesser extent, pseudoazurin and eukaryotic plastocyanins. Id. Hydrophobic patches are also found to a lesser extent in stellacyanin and rusticyanin copper sites, but have different features. Id.

TABLE 1

Sequence and structure alignment of azurin (1JZG) from P. aeruginosa to other proteins using VAST algorithm.

| PDB | Alignment length[1] | % aa identity | P-value[2] | Score[3] | RMSD[4] | Description |
|---|---|---|---|---|---|---|
| 1AOZ A 2 | 82 | 18.3 | 10e−7 | 12.2 | 1.9 | Ascorbate oxidase |
| 1QHQ_A | 113 | 31 | 10e−7.4 | 12.1 | 1.9 | AuracyaninB |

TABLE 1-continued

Sequence and structure alignment of azurin (1JZG) from
*P. aeruginosa* to other proteins using VAST algorithm.

| PDB | Alignment length[1] | % aa identity | P-value[2] | Score[3] | RMSD[4] | Description |
|---|---|---|---|---|---|---|
| 1V54 B 1 | 79 | 20.3 | 10e−6.0 | 11.2 | 2.1 | Cytocrome c oxidase |
| 1GY2 A | 92 | 16.3 | 10e−5.0 | 11.1 | 1.8 | Rusticyanin |
| 3MSP A | 74 | 8.1 | 10e−6.7 | 10.9 | 2.5 | Motile Major Sperm Protein[5] |
| 1IUZ | 74 | 20.3 | 10e−5.6 | 10.3 | 2.3 | Plastocyanin |
| 1KGY E | 90 | 5.6 | 10e−4.6 | 10.1 | 3.4 | Ephrinb2 |
| 1PMY | 75 | 17.3 | 10e−4.1 | 9.8 | 2.3 | Pseudoazurin |

[1]Aligned Length: The number of equivalent pairs of C-alpha atoms superimposed between the two structures, i.e. how many residues have been used to calculate the 3D superposition.
[2]P-VAL: The VAST p value is a measure of the significance of the comparison, expressed as a probability. For example, if the p value is 0.001, then the odds are 1000 to 1 against seeing a match of this quality by pure chance. The p value from VAST is adjusted for the effects of multiple comparisons using the assumption that there are 500 independent and unrelated types of domains in the MMDB database. The p value shown thus corresponds to the p value for the pairwise comparison of each domain pair, divided by 500.
[3]Score: The VAST structure-similarity score. This number is related to the number of secondary structure elements superimposed and the quality of that superposition. Higher VAST scores correlate with higher similarity.
[4]RMSD: The root mean square superposition residual in Angstroms. This number is calculated after optimal superposition of two structures, as the square root of the mean square distances between equivalent C-alpha atoms. Note that the RMSD value scales with the extent of the structural alignments and that this size must be taken into consideration when using RMSD as a descriptor of overall structural similarity.
[5]*C. elegans* major sperm protein proved to be an ephrin antagonist in oocyte maturation. Kuwabara, Genes and Development 17: 155-161 (2003).

Azurin

The azurins are copper containing proteins of 128 amino acid residues which belong to the family of cupredoxins involved in electron transfer in certain bacteria. The azurins include those from *P. aeruginosa* (PA) (SEQ ID NO: 1), *A. xylosoxidans*, and *A. denitrificans*. Murphy et al., J. Mol. Biol. 315:859-871 (2002). The amino acid sequence identity between the azurins varies between 60-90%, these proteins showed a strong structural homology. All azurins have a characteristic β-sandwich with Greek key motif and the single copper atom is always placed at the same region of the protein. In addition, azurins possess an essentially neutral hydrophobic patch surrounding the copper site. Id.

Plastocyanins

The plastocyanins are soluble proteins of cyanobacteria, algae and plants that contain one molecule of copper per molecule and are blue in their oxidized form. They occur in the chloroplast, where they function as electron carriers. Since the determination of the structure of poplar plastocyanin in 1978, the structure of algal (*Scenedesmus, Enteromorpha, Chlamydomonas*) and plant (French bean) plastocyanins has been determined either by crystallographic or NMR methods, and the poplar structure has been refined to 1.33 Å resolution. SEQ ID NO: 3 shows the amino acid sequence of plastocyanin from *Phormidium laminosum*, a thermophilic cyanobacterium. Another plastocyanin of interest is from *Ulva pertussis*.

Despite the sequence divergence among plastocyanins of algae and vascular plants (e.g., 62% sequence identity between the Chlamydomonas and poplar proteins), the three-dimensional structures are conserved (e.g., 0.76 Å rms deviation in the C alpha positions between the *Chlamydomonas* and Poplar proteins). Structural features include a distorted tetrahedral copper binding site at one end of an eight-stranded antiparallel beta-barrel, a pronounced negative patch, and a flat hydrophobic surface. The copper site is optimized for its electron transfer function, and the negative and hydrophobic patches are proposed to be involved in recognition of physiological reaction partners. Chemical modification, cross-linking, and site-directed mutagenesis experiments have confirmed the importance of the negative and hydrophobic patches in binding interactions with cytochrome f, and validated the model of two functionally significant electron transfer paths involving plastocyanin. One putative electron transfer path is relatively short (approximately 4 Å) and involves the solvent-exposed copper ligand His-87 in the hydrophobic patch, while the other is more lengthy (approximately 12-15 Å) and involves the nearly conserved residue Tyr-83 in the negative patch. Redinbo et Bioenerg. Biomembr. 26:49-66 (1994).

Rusticyanins

Rusticyanins are blue-copper containing single-chain polypeptides obtained from a *Thiobacillus* (now called *Acidithiobacillus*). The X-ray crystal structure of the oxidized form of the extremely stable and highly oxidizing cupredoxin rusticyanin from *Thiobacillus ferrooxidans* (SEQ ID NO: 4) has been determined by multiwavelength anomalous diffraction and refined to 1.9 Å resolution. The rusticyanins are composed of a core beta-sandwich fold composed of a six- and a seven-stranded b-sheet. Like other cupredoxins, the copper ion is coordinated by a cluster of four conserved residues (His 85, Cys138, His143, Met148) arranged in a distorted tetrahedron. Walter, R. L. et al., J. Mol. Biol. 263:730-51 (1996).

Pseudoazurins

The pseudoazurins are a family of blue-copper containing single-chain polypeptide. The amino acid sequence of pseudoazurin obtained from *Achromobacter cycloclastes* is shown in SEQ ID NO: 5. The X-ray structure analysis of pseudoazurin shows that it has a similar structure to the azurins although there is low sequence homology between these proteins. Two main differences exist between the overall structure of the pseudoazurins and azurins. There is a carboxy terminus extension in the pseudoazurins, relative to the azurins, consisting of two alpha-helices. In the midpeptide region azurins contain an extended loop, shortened in the pseudoazurins, which forms a flap containing a short α-helix. The only major differences at the copper atom site are the conformation of the MET side-chain and the Met-S copper bond length, which is significantly shorter in pseudoazurin than in azurin.

Phytocyanins

The proteins identifiable as phytocyanins include, but are not limited to, cucumber basic protein, stellacyanin, mavicyanin, umecyanin, a cucumber peeling cupredoxin, a putative blue copper protein in pea pods, and a blue copper protein from *Arabidopsis thaliana*. In all except cucumber basic protein and the pea-pod protein, the axial methionine ligand normally found at blue copper sites is replaced by glutamine.

Auracyanin

Three small blue copper proteins designated auracyanin A, auracyanin B-1, and auracyanin B-2 have been isolated from the thermophilic green gliding photosynthetic bacterium *Chloroflexus aurantiacus*. The two B forms are glycoproteins and have almost identical properties to each other, but are distinct from the A form. The sodium dodecyl sulfate-polyacrylamide gel electrophoresis demonstrates apparent monomer molecular masses as 14 (A), 18 (B-2), and 22 (B-1) kDa.

The amino acid sequence of auracyanin A has been determined and showed auracyanin A to be a polypeptide of 139 residues. Van Dreissche et al., Protein Science 8:947-957 (1999). His58, Cys123, His128, and Met132 are spaced in a way to be expected if they are the evolutionary conserved metal ligands as in the known small copper proteins plastocyanin and azurin. Secondary structure prediction also indicates that auracyanin has a general beta-barrel structure similar to that of azurin from *Pseudomonas aeruginosa* and plastocyanin from poplar leaves. However, auracyanin appears to have sequence characteristics of both small copper protein sequence classes. The overall similarity with a consensus sequence of azurin is roughly the same as that with a consensus sequence of plastocyanin, namely 30.5%. The N-terminal sequence region 1-18 of auracyanin is remarkably rich in glycine and hydroxy amino acids. Id. See exemplary amino acid sequence SEQ ID NO: 15 for chain A of auracyanin from *Chloroflexus aurantiacus* (NCBI Protein Data Bank Accession No. AAM12874).

The auracyanin B molecule has a standard cupredoxin fold. The crystal structure of auracyanin B from *Chloroflexus aurantiacus* has been studied. Bond et al., J. Mol. Biol. 306:47-67 (2001). With the exception of an additional N-terminal strand, the molecule is very similar to that of the bacterial cupredoxin, azurin. As in other cupredoxins, one of the Cu ligands lies on strand 4 of the polypeptide, and the other three lie along a large loop between strands 7 and 8. The Cu site geometry is discussed with reference to the amino acid spacing between the latter three ligands. The crystallographically characterized Cu-binding domain of auracyanin B is probably tethered to the periplasmic side of the cytoplasmic membrane by an N-terminal tail that exhibits significant sequence identity with known tethers in several other membrane-associated electron-transfer proteins. The amino acid sequences of the B forms are presented in McManus et al. J. Biol. Chem. 267:6531-6540 (1992). See exemplary amino acid sequence SEQ ID NO: 16 for chain B of auracyanin from *Chloroflexus aurantiacus* (NCBI Protein Data Bank Accession No. 1QHQA).

Stellacyanin

Stellacyanins are a subclass of phytocyanins, a ubiquitous family of plant cupredoxins. An exemplary sequence of a stellacyanin is included herein as SEQ ID NO: 14. The crystal structure of umecyanin, a stellacyanin from horseradish root (Koch et al., J. Am. Chem. Soc. 127:158-166 (2005)) and cucumber stellacyanin (Hart el al., *Protein Science* 5:2175-2183 (1996)) is also known. The protein has an overall fold similar to the other phytocyanins. The ephrin B2 protein ectodomain tertiary structure bears a significant similarity to stellacyanin. Toth et al., Developmental Cell 1:83-92 (2001). An exemplary amino acid sequence of a stellacyanin is found in the National Center for Biotechnology Information Protein Data Bank as Accession No. 1JER, SEQ ID NO: 14.

Cucumber Basic Protein

An exemplary amino acid sequence from a cucumber basic protein is included herein as SEQ ID NO: 17. The crystal structure of the cucumber basic protein (CBP), a type 1 blue copper protein, has been refined at 1.8 Å resolution. The molecule resembles other blue copper proteins in having a Greek key beta-barrel structure, except that the barrel is open on one side and is better described as a "beta-sandwich" or "beta-taco". Guss et al., J. Mol. Biol. 262: 686-705 (1996). The ephrinB2 protein ectodomian tertiary structure bears a high similarity (rms deviation 1.5 Å for the 50α carbons) to the cucumber basic protein. Toth et al., Developmental Cell 1:83-92 (2001).

The Cu atom has the normal blue copper NNSS' co-ordination with bond lengths Cu—N(His39)=1.93 A, Cu—S(Cys79)=2.16 A, Cu—N(His84)=1.95 A, Cu—S(Met89)=2.61 A. A disulphide link, (Cys52)-S—S-(Cys85), appears to play an important role in stabilizing the molecular structure. The polypeptide fold is typical of a sub-family of blue copper proteins (phytocyanins) as well as a non-metalloprotein, ragweed allergen Ra3, with which CBP has a high degree of sequence identity. The proteins currently identifiable as phytocyanins are CBP, stellacyanin, mavicyanin, umecyanin, a cucumber peeling cupredoxin, a putative blue copper protein in pea pods, and a blue copper protein from *Arabidopsis thaliana*. In all except CBP and the pea-pod protein, the axial methionine ligand normally found at blue copper sites is replaced by glutamine. An exemplary sequence for cucumber basic protein is found in NCBI Protein Data Bank Accession No. 2CBP, SEQ ID NO: 17.

Antiestrogens

Antiestrogens that may be used in compositions and methods of the invention include, but are not limited to, compounds that prevent estrogen or progesterone from binding to receptors, such as Tamoxifen, toremifene, Estradiol, raloxifene, EM-652, arzoxifene, lasofoxifene, ICI-164, 384, GW7604, and Tocris (ICI-182,780). Compounds that target or block the activity of estrogens and estrogen receptors may also include fulvestrant, as well as other compounds discussed in Katzenellenbogen, B. S. and Frasor, J., *Seminars in Oncology*, Vol 31, No. 1, Suppl. 3 28-38 (2004), the disclosure of which is incorporated in its entirety herein.

Antiestrogens that may be used in compositions and methods of the invention also may include, but are not limited to, compounds that prevent production of estrogen or progesterone, such as aromatase inhibitors, which may be steroidal or non-steroidal, including but not limited to anastrazole, exemestane, and letrozole, and other compounds disclosed or discussed in Eisen, A., et al., *Cancer Treatment Reviews*, 34:157-174 (2008), the disclosure of which is incorporated in its entirety herein. The dosages disclosed in the Eisen article, such as 20 mg daily of Tamoxifen, 1 mg daily of anastrozole, 2.5 mg daily of letrozole, and 25 mg daily of exemestane, may also be used in the compositions and methods of the invention disclosed herein.

Methods of Use

Chemopreventive therapies are based on evidence that the interruption of processes involved in cancerogenesis will prevent or at least slow the development of cancer. The cupredoxin *Pseudomonas aeruginosa* azurin (SEQ ID NO: 1), the truncated azurin peptide p28, representing amino acids 50-77 of azurin (SEQ ID NO: 2), and the truncated azurin peptide p18, representing amino acids 50-57 of azurin (SEQ ID NO: 25), are now known to inhibit the development of premalignant lesions, either by inhibiting the initial formation of premalignant lesions, or killing or inhibiting the growth of premalignant lesions that are present.

It therefore contemplated that a cupredoxin, or variant, derivative, truncation, or structural equivalent thereof, as described herein, with the ability to inhibit, suppress, prevent, reverse, delay or reduce the risk of the development of premalignant lesions, may be used in chemopreventive therapies alone or in combination with one or more other chemopreventive agents in patients suffering from premalignant lesions, patients suffering from cancer, or otherwise healthy patients. Such otherwise healthy patients are, in some embodiments, patients at a higher risk to develop cancer than those in the general population. Cancers that may be treated or prevented by treatment with the compositions of the invention include, but are not limited to, melanoma, breast, pancreas, glioblastoma, astrocytoma, lung, colorectal, neck and head, bladder, prostate, skin, and cervical cancer. In some embodiments, the patient may be human. In other embodiments, the patient is not human, including a non-human mammal.

The invention provides methods to have chemopreventive effects on premalignant lesions and cancers in mammalian cells and/or patients comprising administering to the patient a pharmaceutical composition comprising a first chemopreventive agent, which may be a truncation of azurin such as p18 (SEQ ID NO: 25) or p28 (SEQ ID NO: 2), a second chemopreventive agent, such as an antiestrogen, and a pharmaceutically acceptable carrier.

The invention also provides methods to treat mammalian patients, or otherwise have chemopreventive effects in mammalian cells and/or patients, by administering at least one chemopreventive agent that is a cupredoxin, or variant, derivative, truncation, or structural equivalent thereof, as described above, alone or in combination with one or more other chemopreventive agents, such as antiestrogens. Antiestrogens used in the methods of the invention may include Tamoxifen, fenretinide, and aromatase inhibitors. As demonstrated in Examples 3 and 4, Tamoxifen and cupredoxins, such as the azurin truncation p28, have a synergistic inhibitory effect on cancerous lesions.

The invention further includes methods of increasing expression of p53 in mammalian cells and mammalian patients by administering to the cells or the patient at least one chemopreventive agent, which may be, for example, a truncation of azurin such as p18 (SEQ ID NO: 25) or p28 (SEQ ID NO: 2), and administering an antiestrogen, in any order. As demonstrated in Example 4, p28 can increase the expression of p53 in mammalian cells if Tamoxifen or another antiestrogen is present to block the activity of estrogens.

The invention further includes methods of decreasing estrogen receptor binding to p53 in mammalian cells or a mammalian patient by administering to the mammalian cells or patient at least one chemopreventive agent, which may be, for example, a truncation of azurin such as p18 (SEQ ID NO: 25) or p28 (SEQ ID NO: 2), and administering an antiestrogen, in any order. As discussed herein, the estrogen receptor ("ER")-p53 complex prevents the expression of p53. Treatment with Tamoxifen prevents ER from binding to p53. As demonstrated in Examples 3 and 4, incubation of glands with p28 in the presence of Tamoxifen enhances or increases the expression of p53 in mammalian cells.

The invention further includes methods of reducing the dose-related toxicity of Tamoxifen by administering to a mammalian patient or mammalian cells a chemopreventive agent, which may be, for example, a truncated azurin such as p18 (SEQ ID NO: 25) or p28 (SEQ ID NO: 2), in combination with a dose of Tamoxifen. As demonstrated by Example 3, inhibition of premalignant lesions and cancer can be achieved by combining a low dose of Tamoxifen with a low concentration of p28. In some embodiments, the chemopreventive agent, such as p28, and the antiestrogen, such as Tamoxifen, may be administered at or around the same time, in any order.

The invention further includes methods to study the development of cancer comprising contacting mammalian cells before or after induction with a carcinogen with a composition comprising cupredoxin, or a variant, derivative, truncation, or structural equivalent thereof, alone or in combination with one or more other chemopreventive agents, and observing the development of the cells. In some embodiments, the cells are mouse mammary gland cells, while in others they are other cells that may become malignant in mammals.

The present invention also relates to a method, comprising preventing the ubiquitination of p53 in a cell by contacting the cell with a cupredoxin-derived peptide. In further embodiments, the peptide is a truncation of a cupredoxin. In another embodiment, the cupredoxin is azurin. In a further embodiment, the azurin is from *Pseudomonas aeruginosa*. In another embodiment, the peptide comprises SEQ ID NO: 2. In a further embodiment, the peptide consists of SEQ ID NO: 2. In other embodiments, the peptide comprises an amino acid sequence selected from the group consisting of SEQ ID NO: 25, SEQ ID NO: 38, SEQ ID NO: 39, and SEQ ID NO: 86.

The present invention also relates to a method, comprising preventing ubiquitination of p53 by contacting the p53 with a compound that binds to p53 within a hydrophobic DNA-binding domain. In a further embodiment, the hydrophobic DNA-binding domain comprises amino acids 80-276. In yet another embodiment, the hydrophobic DNA-binding domain consists of amino acids 80-276. In another embodiment of this method, the compound is a cupredoxin-derived peptide. In a further embodiment, the peptide is a truncation of a cupredoxin. In another embodiment, the cupredoxin is azurin. In another embodiment, the peptide comprises SEQ ID NO: 2. In a further embodiment the peptide consists of SEQ ID NO: 2. In yet another embodiment, wherein the peptide comprises an amino acid sequence selected from the group consisting of SEQ ID NO: 25, SEQ ID NO: 38, and SEQ ID NO: 39.

The present invention also relates to a method, comprising inhibiting the development of cancer by blocking ubiquitination of p53, wherein said blocking is achieved by contacting p53 with a compound that binds to p53 within a hydrophobic DNA-binding domain. In a further embodiment, the hydrophobic DNA-binding domain comprises amino acids 80-276. In yet another embodiment, the hydrophobic DNA-binding domain consists of amino acids 80-276. In another embodiment, the compound is a cupredoxin-derived peptide. In a further embodiment, the peptide is a truncation of a cupredoxin. In another embodiment, the cupredoxin is azurin. In another embodiment, the peptide comprises SEQ ID NO: 2, and in yet another embodiment, the peptide consists of SEQ ID NO: 2. In another embodiment, the peptide comprises an amino acid sequence selected from the group consisting of SEQ ID NO: 25, SEQ ID NO: 38, and SEQ ID NO: 39.

The present invention also relates to a method, comprising preventing proteasomal degradation of p53 by contacting the p53 with a compound that binds to p53 within a hydrophobic DNA binding domain. In one embodiment, the hydrophobic DNA-binding domain comprises amino acids 80-276. In another embodiment, the hydrophobic DNA-binding domain consists of amino acids 80-276. In another embodiment, the compound is a cupredoxin-derived peptide. In a further embodiment, the peptide is a truncation of a cupredoxin. In another embodiment, the cupredoxin is azurin. In yet another embodiment, the peptide comprises SEQ ID NO: 2. In another embodiment, the peptide consists of SEQ ID NO: 2. In one embodiment, the peptide comprises an amino acid sequence selected from the group consisting of SEQ ID NO: 25, SEQ ID NO: 38, and SEQ ID NO: 39.

The present invention also relates to a method, comprising preventing proteasomal degradation of p53 through MDM2-independent and Parc-independent pathways by contacting the p53 with a compound that binds to p53 at a hydrophobic DNA-binding domain. In a further embodiment, the hydrophobic DNA-binding domain comprises amino acids 80-276. In yet another embodiment, the hydrophobic DNA-binding domain consists of amino acids 80-276. In some embodiments, the compound is a cupredoxin-derived peptide. In further embodiments, the peptide is a truncation of a cupredoxin. In another embodiment, the cupredoxin is azurin. In yet another embodiment, the peptide comprises SEQ ID NO: 2. In a further embodiment, the peptide consists of SEQ ID NO: 2. In yet another embodiment, the peptide comprises an amino acid sequence selected from the group consisting of SEQ ID NO: 25, SEQ ID NO: 38, and SEQ ID NO: 39.

The methods disclosed herein may be used to treat patients with premalignant lesions, patients with cancer, and/or patients at a higher risk of developing cancer than the general population. Patients at a higher at risk to develop cancer than the general population may be patients with high risk features, patients with premalignant lesions, and patients that have been cured of their initial cancer or definitively treated for their premalignant lesions. See generally Tsao et al., CA Cancer J Clin 54:150-180 (2004). High risk features may be behavioral, genetic, environmental or physiological factors of the patient. Behavioral factors that predispose a patient to various forms of cancer include, but are not limited to, smoking, diet, alcohol consumption, hormone replacement therapy, higher body mass index, nulliparity, betal nut use, frequent mouthwash use, exposure to human papillomavirus, childhood and chronic sun exposure, early age of first intercourse, multiple sexual partners, and oral contraceptive use. Genetic factors that predispose a patient to various forms of cancer include, but are not limited to, a family history of cancer, gene carrier status of BRCA1 and BRCA2, prior history of breast neoplasia, familial adenomatous polyposis (FAP), hereditary nonpolyposis colorectal cancer (HNPCC), red or blond hair and fair-skinned phenotype, xeroderma pigmentosum, and ethnicity. Environmental features that predispose a patient to various forms of cancer include, but are not limited to, exposure to radon, polycyclic aromatic hydrocarbons, nickel, chromate, arsenic, asbestos, chloromethyl ethers, benzo[a]pyrene, radiation, and aromatic amines from rubber or paint occupational exposure. Other miscellaneous factors that predispose a patient to various forms of cancer include, but are not limited to, chronic obstructive pulmonary disease with airflow obstruction, chronic bladder infections, schistosomiasis, older age, and immunocompromised status.

Additionally, patients at a higher risk of developing cancer may be determined by the use of various risk models that have been developed for certain kinds of cancer. For example, patients predisposed to breast cancer may be determined using the Gail risk model, or the Claus model, among others. See Gail et at, J Natl Cancer Inst 81:1879-1886 (1989); Cuzick, Breast 12:405-411 (2003); Huang et al., Am J Epidemiol 151:703-714 (2000).

Patients with premalignant lesions are at a higher risk to develop cancer than the general population. The presence of premalignant lesions in or on a patient may be determined by many methods that are well known to those in the art. Intermediate markers or biomarkers that originate from premalignant lesions may be measured in a patient to determine if the patient harbors premalignant lesions. Chromosomal abnormalities occur in tumor cells and the adjacent histologically normal tissues in the majority of cancer patients. Progression in chromosomal abnormalities parallels the phenotypic progression from premalignant lesion to invasive cancer. Thiberville et al., Cancer Res. 55:5133-5139 (1995). Therefore, chromosomal abnormalities associated with cancer may be used as intermediate markers to detect premalignant lesions in a patient. Common chromosomal abnormalities associated with cancer include, but are not limited to, allelic deletions or loss of heterozygosity (LOH) in tumor suppressor genes such as 3p (FHIT and others), 9p (9p21 for p16$^{INK4}$, p15$^{INK4B}$, and p19$^{ARF}$), 17p (17p13 for p53 gene and others) and 13q (13q14 for retinoblastoma gene Rb and others). Deletions in 3p and 9p are associated with smoking and the early stages of lung cancer. Mao et al., J. Natl. Cancer Inst. 89:857-862 (1997). Deletions affecting 3p, 5q, 8p, 17p and 18q are common change in epithelial cancers. See generally Tsao et al., CA Clin. Cancer J. Clin. 54:153 (2004). Other chromosomal mutations associated with cancer include those which activate oncogenes. Oncogenes whose presence may be used as intermediate markers include, but are not limited to, Ras, c-myc, epidermal growth factor, erb-B2 and cyclins E, D1 and B1. See generally id. at 154.

Other intermediate markers may be the products of genes up-regulated in premalignant cells and cancer cells. Genes that may be up-regulated in premalignant cells include, but are not limited to, cyclooxygenases COX-1 and COX-2, telomerase. Other biomarkers of cancer cells, and some premalignant cells, include, but are not limited to, p53, epidermal growth factor receptor (GFR), proliferating cell nuclear antigen (PCNA), RAS, COX-2, Ki-67, DNA aneuploidy, DNA polymerase-α, ER, Her2neu, E-cadherin, RARβ, hTERT, p16$^{INK4a}$, FHIT (3p14), Bcl-2, VEGF-R, HPV infection, LOH 9p21, LOH 17p, p-AKT, hnRNP A2/B1, RAF, Myc, c-KIT, cyclin D1, E and B1, IGF1, bcl-2, p16, LOH 3p21.3, LOH 3p25, LOH 9p21, LOH 17p13, LOH 13q, LOH 8p, hMSH2, APC, DCC, DPC4, JV18, BAX, PSA, GSTP1, NF-kB, AP1, D3S2, HPV infection, LOH 3p14, LOH 4q, LOH 5p, bladder tumor antigen (BTA), BTK TRAK (Alidex, Inc., Redmond Wash.), urinary tract matrix protein 22, fibrin degradation product, autodrine motility factor receptor, BCLA-4, cytokeratin 20, hyaluronic acid, CYFRA 21-1, BCA, beta-human chorionic gonadotropin, and tissue polypeptide antigen (TPA). See generally id. at 155-157.

Patients that have been cured of their initial cancers or have been definitively treated for their premalignant lesions are also at a higher risk to develop cancer than the general population. A second primary tumor refers to a new primary cancer in a person with a history of cancer. Second primary tumors are the leading cause of mortality in head and neck cancer. Id. at 150. A second primary tumor is distinct from a metastasis in that the former originates de novo while the later originates from an existing tumor. Patients that have been cured of cancer or premalignant lesions of the breast, head and neck, lung, and skin are at a particularly high risk to develop second primary tumors.

The compositions comprising a cupredoxin or variant, derivative, truncation, or structural equivalent thereof and one or more other chemopreventive agents can be administered to the patient by many routes and in many regimens that will be well known to those in the art. In specific embodiments, the cupredoxin, or variant, derivative, truncation, or structural equivalent thereof and the one or more other chemopreventive agents are administered intravenously, intramuscularly, subcutaneously, topically, orally, or by inhalation. The compositions may be administered to the patient by any means that delivers the composition to the site in the patient that is at risk of developing cancer. In specific embodiments, the cupredoxin or variant, derivative, truncation or structural equivalent thereof and the one or more other chemopreventive agents are administered intravenously.

In one embodiment, the methods may comprise co-administering to a patient with, for example, premalignant lesions or a risk of developing premalignant lesions, one unit dose of a composition comprising a cupredoxin or a variant, derivative, truncation, or structural equivalent of cupredoxin and one unit dose of a composition comprising another chemopreventive drug, in either order, administered at about the same time, or within about a given time following the administration of the other, for example, about one minute to about 60 minutes following the administration of the other drug, or about 1 hour to about 12 hours following the administration of the other drug. Chemopreventive drugs of interest include, but are not limited to, antiestrogens such as Tamoxifen and aromatase inhibitors such as letrozole, exemestane, and anastrozole (Arimidex®), retinoids such as N-[4-hydroxyphenyl]retinamide (4-HPR, fenretinide), nonsteriodal antiinflammatory agents (NSAIDs) such as aspirin and sulindac, celecoxib (COX-2 inhibitor), defluoromethylomithing (DFMO), ursodeoxycholic acid, 3-hydroxy-3-methylglutaryl coenzyme A reductase inhibitors, EKI-785 (EGFR inhibitor), bevacizumab (antibody to VEGF-receptor), cetuximab (antibody to EGFR), retinal such as vitamin A, beta-carotene, 13-cis retinoic acid, isotretinoin and retinyl palmitate, α-tocopherol, interferon, oncolytic adenovirus dl1520 (ONYX-015), gefitinib, etretinate, finasteride, indole-3-carbinol, resveratrol, chlorogenic acid, raloxifene, and oltipraz.

Pharmaceutical Compositions Comprising Cupredoxin, or a Variant, Derivative, Truncation, or Structural Equivalent Thereof and One or More Other Chemopreventive Agents Pharmaceutical compositions comprising cupredoxin or variant, derivative, truncation, or structural equivalents thereof and one or more other chemopreventive agents can be manufactured in any conventional manner, e.g., by conventional mixing, dissolving, granulating, dragee-making, emulsifying, encapsulating, entrapping, or lyophilizing processes. The substantially pure or pharmaceutical grade cupredoxin or variants, derivatives, truncations, and structural equivalents thereof and one or more other chemopreventive agents can be readily combined with a pharmaceutically acceptable carrier well-known in the art. Such carriers enable the preparation to be formulated as a tablet, pill, dragee, capsule, liquid, gel, syrup, slurry, suspension, and the like. Suitable carriers or excipients can also include, for example, fillers and cellulose preparations. Other excipients can include, for example, flavoring agents, coloring agents, detackifiers, thickeners, and other acceptable additives, adjuvants, or binders. In some embodiments, the pharmaceutical preparation is substantially free of preservatives. In other embodiments, the pharmaceutical preparation may contain at least one preservative. General methodology on pharmaceutical dosage forms is found in Ansel et al., *Pharmaceutical Dosage Forms and Drug Delivery Systems* (Lippencott Williams & Wilkins, Baltimore Md. (1999)).

The composition comprising a cupredoxin or variant, derivative, truncation, or structural equivalent thereof and one or more other chemopreventive agents used in the invention may be administered in a variety of ways, including by injection (e.g., intradermal, subcutaneous, intramuscular, intraperitoneal and the like), by inhalation, by topical administration, by suppository, by using a transdermal patch or by mouth. General information on drug delivery systems can be found in Ansel et al., id. In some embodiments, the composition comprising a cupredoxin or variant, derivative, truncation, or structural equivalent thereof and one or more other chemopreventive agents can be formulated and used directly as injectables, for subcutaneous and intravenous injection, among others. The injectable formulation, in particular, can advantageously be used to treat patients that are appropriate for chemopreventive therapy. The composition comprising a cupredoxin or variant, derivative, truncation, or structural equivalent thereof and one or more other chemopreventive agents can also be taken orally after mixing with protective agents such as polypropylene glycols or similar coating agents.

When administration is by injection, the cupredoxin or variant, derivative, truncation, or structural equivalent thereof and one or more other chemopreventive agents may be formulated in aqueous solutions, specifically in physiologically compatible buffers such as Hanks solution, Ringer's solution, or physiological saline buffer. The solution may contain formulatory agents such as suspending, stabilizing and/or dispersing agents. Alternatively, the cupredoxin or variant, derivative, truncation, or structural equivalent thereof and one or more other chemopreventive agents may be in powder form for constitution with a suitable vehicle, e.g., sterile pyrogen-free water, before use. In some embodiments, the pharmaceutical composition does not comprise an adjuvant or any other substance added to enhance the immune response stimulated by the peptide. In some embodiments, the pharmaceutical composition comprises a substance that inhibits an immune response to the peptide.

When administration is by intravenous fluids, the intravenous fluids for use administering the cupredoxin or variant, derivative, truncation, or structural equivalent thereof and one or more other chemopreventive agents may be composed of crystalloids or colloids. Crystalloids as used herein are aqueous solutions of mineral salts or other water-soluble molecules. Colloids as used herein contain larger insoluble molecules, such as gelatin. Intravenous fluids may be sterile.

Crystalloid fluids that may be used for intravenous administration include but are not limited to, normal saline (a solution of sodium chloride at 0.9% concentration), Ringer's lactate or Ringer's solution, and a solution of 5% dextrose in water sometimes called D5W, as described in Table 2.

TABLE 2

Composition of Common Crystalloid Solutions

| Solution | Other Name | [Na$^+$] | [Cl$^-$] | [Glucose] |
|---|---|---|---|---|
| D5W | 5% Dextrose | 0 | 0 | 252 |
| ⅔ & ⅓ | 3.3% Dextrose/ 0.3% saline | 51 | 51 | 168 |

TABLE 2-continued

Composition of Common Crystalloid Solutions

| Solution | Other Name | [Na$^+$] | [Cl$^-$] | [Glucose] |
|---|---|---|---|---|
| Half-normal saline | 0.45% NaCl | 77 | 77 | 0 |
| Normal saline | 0.9% NaCl | 154 | 154 | 0 |
| Ringer's lactate* | Ringer's solution | 130 | 109 | 0 |

*Ringer's lactate also has 28 mmol/L lactate, 4 mmol/L K$^+$ and 3 mmol/L Ca$^{2+}$.

When administration is by inhalation, the cupredoxin or variant, derivative, truncation, or structural equivalent thereof and one or more other chemopreventive agents may be delivered in the form of an aerosol spray from pressurized packs or a nebulizer with the use of a suitable propellant, e.g., dichlorodifluoromethane, trichlorofluoromethane, carbon dioxide or other suitable gas. In the case of a pressurized aerosol, the dosage unit may be determined by providing a valve to deliver a metered amount. Capsules and cartridges of, e.g., gelatin, for use in an inhaler or insufflator may be formulated containing a powder mix of the proteins and a suitable powder base such as lactose or starch.

When administration is by topical administration, the cupredoxin or variant, derivative, truncation, or structural equivalent thereof and one or more other chemopreventive agents may be formulated as solutions, gels, ointments, creams, jellies, suspensions, and the like, as are well known in the art. In some embodiments, administration is by means of a transdermal patch. When administration is by suppository (e.g., rectal or vaginal), cupredoxin or variants, truncations, and derivatives thereof and one or more other chemopreventive agents compositions may also be formulated in compositions containing conventional suppository bases.

When administration is oral, a cupredoxin or variant, derivative, truncation, or structural equivalent thereof and one or more other chemopreventive agents can be readily formulated by combining the cupredoxin or variant, derivative, truncation or structural equivalent thereof and one or more other chemopreventive agents with pharmaceutically acceptable carriers well known in the art. A solid carrier, such as mannitol, lactose, magnesium stearate, and the like may be employed; such carriers enable the cupredoxin and variants, derivatives or structural equivalent thereof to be formulated as tablets, pills, dragees, capsules, liquids, gels, syrups, slurries, suspensions and the like, for oral ingestion by a subject to be treated. For oral solid formulations such as, for example, powders, capsules and tablets, suitable excipients include fillers such as sugars, cellulose preparation, granulating agents, and binding agents.

Other convenient carriers, as well-known in the art, also include multivalent carriers, such as bacterial capsular polysaccharide, a dextran or a genetically engineered vector. In addition, sustained-release formulations that include a cupredoxin or variant, derivative, truncation, or structural equivalent thereof and one or more other chemopreventive agents allow for the release of cupredoxin or variant, derivative, truncation, or structural equivalent thereof and one or more other chemopreventive agents over extended periods of time, such that without the sustained release formulation, the cupredoxin or variant, derivative, truncation, or structural equivalent thereof and one or more other chemopreventive agents would be cleared from a subject's system, and/or degraded by, for example, proteases and simple hydrolysis before eliciting or enhancing a therapeutic effect.

The half-life in the bloodstream of the peptides and one or more other chemopreventive agents of the invention can be extended or optimized by several methods well known to those in the art. The peptide variants and one or more other chemopreventive agents of the invention may include, but are not limited to, various variants that may increase their stability, specific activity, longevity in the bloodstream, and/or decrease immunogenicity of the cupredoxin, while retaining the ability of the peptide and one or more other chemopreventive agents to inhibit the development of premalignant lesions in mammalian cells, tissues and animals. Such variants include, but are not limited to, those which decrease the hydrolysis of the peptide and one or more other chemopreventive agents, decrease the deamidation of the peptide and one or more other chemopreventive agents, decrease the oxidation, decrease the immunogenicity, increase the structural stability of the peptide or increase the size of the peptide and one or more other chemopreventive agents. Such peptides also include circularized peptides (see Monk et al., BioDrugs 19(4):261-78, (2005); DeFreest et al., J. Pept. Res. 63(5):409-19 (2004)), D,L-peptides (diastereomer), Futaki et al., J. Biol. Chem. February 23; 276(8): 5836-40 (2001); Papo et al., Cancer Res. 64(16):5779-86 (2004); Miller et al., Biochem. Pharmacol. 36(1):169-76, (1987)); peptides containing unusual amino acids (see Lee et al., J. Pept. Res. 63(2):69-84 (2004)), N- and C-terminal modifications (see Labrie et al., Clin. Invest. Med. 13(5): 275-8, (1990)), hydrocarbon stapling (see Schafmeister et al., J. Am. Chem. Soc. 122:5891-5892 (2000); Walenski et al., Science 305:1466-1470 (2004)) and PEGylation.

In various embodiments, the pharmaceutical composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils, saline solutions, aqueous dextrose and glycerol solutions, other pharmaceutically acceptable auxiliary substances as required to approximate physiological conditions, such as buffering agents, tonicity adjusting agents, wetting agents and the like. It will be recognized that, while any suitable carrier known to those of ordinary skill in the art may be employed to administer the compositions of this invention, the type of carrier will vary depending on the mode of administration. Compounds may also be encapsulated within liposomes using well-known technology. Biodegradable microspheres may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The pharmaceutical compositions may be sterilized by conventional, well-known sterilization techniques, or may be sterile filtered. The resulting aqueous solutions may be packaged for use as is, or lyophilized, the lyophilized preparation being combined with a sterile solution prior to administration.

Administration of Cupredoxin or Variant, Derivative, Truncation, or Structural Equivalent Thereof and One or More Chemopreventive Agents The cupredoxin or variant, derivative, truncation, or structural equivalent thereof and one or more other chemopreventive agents can be administered formulated as pharmaceutical compositions and administered by any suitable route, for example, by oral, buccal, inhalation, sublingual, rectal, vaginal, transurethral, nasal, topical, percutaneous, i.e., transdermal or parenteral (including intravenous, intramuscular, subcutaneous and intracoronary) or vitreous administration. The pharmaceutical formulations thereof can be administered in any amount effective to achieve its intended purpose. More specifically, the composition is administered in a therapeutically effective amount. In specific embodiments, the therapeutically effective amount is generally from about 0.01-20 mg/day/kg of body weight.

The compounds comprising cupredoxin or variant, derivative, truncation, or structural equivalent thereof are useful for the prevention of cancer, alone or in combination with other chemopreventive agents. The appropriate dosage will, of course, vary depending upon, for example, the compound of cupredoxin or variant, derivative or structural equivalent thereof employed, the type of other chemopreventive agent selected for co-administration, if any, the host, the mode of administration and the nature and severity of the potential cancer. However, in general, satisfactory results in humans are indicated to be obtained at daily dosages from about 0.01-20 mg/kg of body weight. An indicated daily dosage in humans is in the range from about 0.7 mg to about 1400 mg of a compound of cupredoxin or variant, derivative or structural equivalent thereof conveniently administered, for example, in daily doses, weekly doses, monthly doses, and/or continuous dosing. Daily doses can be in discrete dosages from 1 to 12 times per day. Alternatively, doses can be administered every other day, every third day, every fourth day, every fifth day, every sixth day, every week, and similarly in day increments up to 31 days or over. Alternatively, dosing can be continuous using patches, i.v. administration and the like.

The exact formulation, route of administration, and dosage is determined by the attending physician in view of the patient's condition. Dosage amount and interval can be adjusted individually to provide plasma levels of the active cupredoxin or variant, derivative or structural equivalent thereof and one or more other chemopreventive agents which are sufficient to maintain therapeutic effect. Generally, the desired cupredoxin or variant, derivative, truncation, or structural equivalent thereof and one or more other chemopreventive agents is administered in an admixture with a pharmaceutical carrier selected with regard to the intended route of administration and standard pharmaceutical practice.

In one aspect, the cupredoxin or variant, derivative, truncation, or structural equivalent thereof and, if possible, one or more other chemopreventive agents, is delivered as DNA such that the polypeptide is generated in situ. In one embodiment, the DNA is "naked," as described, for example, in Ulmer et al., (Science 259:1745-1749 (1993)) and reviewed by Cohen (Science 259:1691-1692 (1993)). The uptake of naked DNA may be increased by coating the DNA onto a carrier, e.g., biodegradable beads, which are then efficiently transported into the cells. In such methods, the DNA may be present within any of a variety of delivery systems known to those of ordinary skill in the art, including nucleic acid expression systems, bacterial and viral expression systems. Techniques for incorporating DNA into such expression systems are well known to those of ordinary skill in the art. See, e.g., WO90/11092, WO93/24640, WO 93/17706, and U.S. Pat. No. 5,736,524.

Vectors, used to shuttle genetic material from organism to organism, can be divided into two general classes: Cloning vectors are replicating plasmid or phage with regions that are essential for propagation in an appropriate host cell and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA, such as the DNA of a cupredoxin.

In expression vectors, the introduced DNA is operably-linked to elements such as promoters that signal to the host cell to highly transcribe the inserted DNA. Some promoters are exceptionally useful, such as inducible promoters that control gene transcription in response to specific factors. Operably-linking a cupredoxin and variants and derivatives thereof and one or more other chemopreventive agents to an inducible promoter can control the expression of the cupredoxin and variants, truncations, and derivatives thereof and one or more other chemopreventive agents in response to specific factors. Examples of classic inducible promoters include those that are responsive to α-interferon, heat shock, heavy metal ions, and steroids such as glucocorticoids (Kaufman, Methods Enzymol. 185:487-511 (1990)) and tetracycline. Other desirable inducible promoters include those that are not endogenous to the cells in which the construct is being introduced, but, are responsive in those cells when the induction agent is exogenously supplied. In general, useful expression vectors are often plasmids. However, other forms of expression vectors, such as viral vectors (e.g., replication defective retroviruses, adenoviruses and adeno-associated viruses) are contemplated.

Vector choice is dictated by the organism or cells being used and the desired fate of the vector. In general, vectors comprise signal sequences, origins of replication, marker genes, polylinker sites, enhancer elements, promoters, and transcription termination sequences.

Kits Comprising Cupredoxin, or Variant, Derivative, Truncation, or Structural Equivalent Thereof and One or More Chemopreventive Agents In one aspect, the invention provides regimens or kits comprising one or more of the following in a package or container: (1) a pharmacologically active composition comprising at least one cupredoxin or variant, derivative, truncation, or structural equivalent thereof; (2) one or more other chemopreventive agents, and (3) apparatus to administer the biologically active composition to the patient, such as a syringe, nebulizer etc.

When a kit is supplied, the different components of the composition may be packaged in separate containers, if appropriate, and admixed immediately before use. Such packaging of the components separately may permit long-term storage without losing the active components' functions.

The reagents included in the kits can be supplied in containers of any sort such that the life of the different components are preserved and are not adsorbed or altered by the materials of the container. For example, sealed glass ampoules may contain lyophilized cupredoxin and variants, derivatives and structural equivalents thereof, or buffers that have been packaged under a neutral, non-reacting gas, such as nitrogen. Ampoules may consist of any suitable material, such as glass, organic polymers, such as polycarbonate, polystyrene, etc., ceramic, metal or any other material typically employed to hold similar reagents. Other examples of suitable containers include simple bottles that may be fabricated from similar substances as ampoules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, flash memory device etc. Detailed instructions may not be physically associated with the kit; instead, a user may be directed to an internet web site specified by the manufacturer or distributor of the kit, or supplied as electronic mail.

Modification of Cupredoxin and Variants, Derivatives, Truncations, and Structural Equivalents Thereof Cupredoxin or variants, derivatives, truncations, or structural equivalents thereof may be chemically modified or genetically altered to produce variants and derivatives as explained above. Such variants, truncations, and derivatives may be synthesized by standard techniques.

In addition to naturally-occurring allelic variants of cupredoxin, changes can be introduced by mutation into cupredoxin coding sequence that incur alterations in the amino acid sequences of the encoded cupredoxin that do not significantly alter the ability of cupredoxin to inhibit the development of premalignant lesions. A "non-essential" amino acid residue is a residue that can be altered from the wild-type sequences of the cupredoxin without altering pharmacologic activity, whereas an "essential" amino acid residue is required for such pharmacologic activity. For example, amino acid residues that are conserved among the cupredoxins are predicted to be particularly non-amenable to alteration, and thus "essential."

Amino acids for which conservative substitutions that do not change the pharmacologic activity of the polypeptide can be made are well known in the art. Useful conservative substitutions are shown in Table 3, "Preferred substitutions." Conservative substitutions whereby an amino acid of one class is replaced with another amino acid of the same type fall within the scope of the invention so long as the substitution does not materially alter the pharmacologic activity of the compound.

TABLE 3

Preferred substitutions

| Original residue | Exemplary substitutions | Preferred substitutions |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Non-conservative substitutions that affect (1) the structure of the polypeptide backbone, such as a β-sheet or α-helical conformation, (2) the charge, (3) hydrophobicity, or (4) the bulk of the side chain of the target site can modify the pharmacologic activity. Residues are divided into groups based on common side-chain properties as denoted in Table 4. Non-conservative substitutions entail exchanging a member of one of these classes for another class. Substitutions may be introduced into conservative substitution sites or more specifically into non-conserved sites.

TABLE 4

Amino acid classes

| Class | Amino acids |
|---|---|
| hydrophobic | Norleucine, Met, Ala, Val, Leu, Ile |
| neutral hydrophilic | Cys, Ser, Thr |
| acidic | Asp, Glu |
| basic | Asn, Gln, His, Lys, Arg |
| disrupt chain conformation | Gly, Pro |
| aromatic | Trp, Tyr, Phe |

The variant polypeptides can be made using methods known in the art such as oligonucleotide-mediated (site-directed) mutagenesis, alanine scanning, and PCR mutagenesis. Site-directed mutagenesis (Carter, Biochem J. 237:1-7 (1986); Zoller and Smith, Methods Enzymol. 154:329-350 (1987)), cassette mutagenesis, restriction selection mutagenesis (Wells et al., Gene 34:315-323 (1985)) or other known techniques can be performed on the cloned DNA to produce the cupredoxin variant DNA.

Known mutations of cupredoxins can also be used to create variant cupredoxin to be used in the methods of the invention. For example, the C112D and M44KM64E mutants of azurin are known to have cytotoxic and growth arresting activity that is different from the native azurin, and such altered activity can be useful in the treatment methods of the present invention.

A more complete understanding of the present invention can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Modifications and variations of the invention as hereinbefore set forth can be made without departing from the spirit and scope thereof.

EXAMPLES

Example 1

Effect of Peptide p28 (SEQ ID NO: 2) on DMBA-Induced Mammary Lesions in the MMOC Model The mouse mammary gland organ (MMOC) culture model has been successfully used to identify potential chemopreventive agents for mammary carcinogenesis. There is a 75% positive correlation observed between the efficacy in vitro in MMOC and in vivo in experimental carcinogenesis models. Mehta and Pezzuto, Curr. Oncol. Rep 4: 478-486 (2002).

The MMOC model allows evaluating efficacy of potentially chemopreventive agents against development of mammary alveolar lesions (MAL) or mammary ductal lesions (MDL) in response to DMBA. DMBA under appropriate incubation conditions forms either MAL or MDL based on the hormonal milieu in the medium. Hawthorne et al., Pharmaceutical Biology 40: 70-74 (2002); Mehta et al., J. Natl. Cancer Inst. 93: 1103-1106 (2001). Estrogen and progesterone-treated glands in culture develop ductal lesions whereas aldosterone and hydrocortisone-treated glands form estrogen and progesterone-independent alveolar lesions. Mammary glands not exposed to a carcinogen or chemopreventive agent, undergo structural regression in the absence of growth-promoting hormones, whereas treatment with DMBA for the 24-hr period between days 3 and 4 prevents the regression of structures caused by deprivation of hormones. It is assumed that this is because the glands have lost normal hormonal responsiveness and now have altered their course of development. Generating mammary adenocarcinoma by transplanting transformed cells into syngeneic mice has proved the premalignant preneoplastic nature of these unrepressed areas.

The thoracic pair of mammary glands was excised aseptically from each Balb/c mouse, and the glands were divided into several groups. The effects of p28 were evaluated at 4 different dilutions in the medium. Carcinogen treated glands without the test agent served as a measure to determine percent incidence in the absence of a chemopreventive agent. An additional control was included to serve as a positive control for chemoprevention. Azurin was included in the medium at 50 µg/ml concentration. For alveolar lesions (MAL) stained glands were evaluated for the incidence of lesions (glands containing any lesions as compared to total number of glands in a given treatment group). For the ductal lesions (MDL) similar protocol was adapted, however, as indicated below in the methods section the hormonal combination is different for alveolar and ductal lesions. The glands were fixed in formalin and then processed for histopathology. The sections are stained with eosin and hematoxelene and evaluated under microscope. Here the multiplicity of ductal lesions between the control and the treatment groups are compared.

Organ Culture Procedure.

The experimental animals used for the studies were young, virgin BALB/c female mice 3 to 4 weeks of age obtained from Charles River, Wilmington, Mass. The mice were treated daily by subcutaneous injections with 1 µg estradiol-17β+1 mg progesterone for 9 days. This treatment is a prerequisite inasmuch as animals not pretreated with steroids fail to respond to hormones in vitro. The entire culture procedure is described in detail. Jang et al., Science 275:218-220 (1997); Mehta, Eu. J. Cancer 36:1275-1282 (2000); Mehta et al., J. Natl. Cancer Inst. 89:212-219 (1997); Mehta et al., J. Natl. Cancer Inst. 93:1103-1106 (2001).

Briefly, the animals were killed by cervical dislocation, and the thoracic pair of mammary glands were dissected out on silk rafts and incubated for 10 days in serum free Waymouth MB752/1 medium (5-glands/5 ml/dish). The medium was supplemented with glutamine, antibiotics (penicillin and streptomycin 100 units/ml medium) and growth-promoting hormones, 5 µg insulin (I), 5 µg prolactin (P), 1 µg aldosterone (A) and 1 µg hydrocortisone (H) per ml of medium for the protocol to induce mammary alveolar lesions (MAL). For induction of ductal lesions (MDL), the medium contained 5 µg/ml, 5 µg/ml P, 0.001 µg/ml estradiol 17β and 1 µg/ml progesterone (Pg). Mehta et al., J. Natl. Cancer Inst. 93:1103-1106 (2001). The carcinogen, DMBA (2 µg/ml) was added to the medium between days 3 and 4. For the present study, DMBA was dissolved in DMSO at a final concentration of 4 mg/ml, and 50 µg I was added to 100 ml medium resulting in 2 µg/ml final concentrations. The control dishes contained DMSO as vehicle.

On day 4, DMBA is removed from the medium by rinsing the glands in fresh medium and transferring them to new dishes containing fresh medium without DMBA. After 10 days of incubation, the glands were maintained for another 14 days in the medium containing only I (5 µg/ml). During the entire culture period, the glands were maintained at 37° C. under 95% $O_2$ and 5% $CO_2$ environment. The chemopreventive agent was included in the medium during the first ten days of growth-promoting phase. The test peptide p28 was evaluated at 4 concentrations ranging from 12.5 µg/ml to 100 µg/ml. Azurin was evaluated at 50 µg/ml in the medium. The peptide was dissolved in sterile water and filtered prior to use. The medium was changed three times per week (Monday, Wednesday and Friday). At the end of the exposure, the glands were fixed in formalin.

Results were analyzed by Chi-square analysis and Fisher's Exact Test.

Morphometic Analysis of MAL.

For examination of MAL, the glands were stained in alum carmine, and evaluated for the presence of the lesions. The glands were scored for the presence or absence of mammary lesions, severity of lesions per gland, and toxicity of the agent. The glands stored in xylene were evaluated for the presence or absence, incidence, and severity of mammary lesions for each gland under a dissecting microscope. Mammary glands were scored as positive or negative for mammary lesions, and the percent incidence was determined as a ratio of glands exhibiting lesions and the total number of glands in that group. Dilation of ducts or disintegration of mammary structure because of treatment with chemopreventive agent was considered a toxic effect. The data were subjected to statistical analysis for the incidence to determine the effectiveness of the potential chemopreventive agents.

Figure 2:
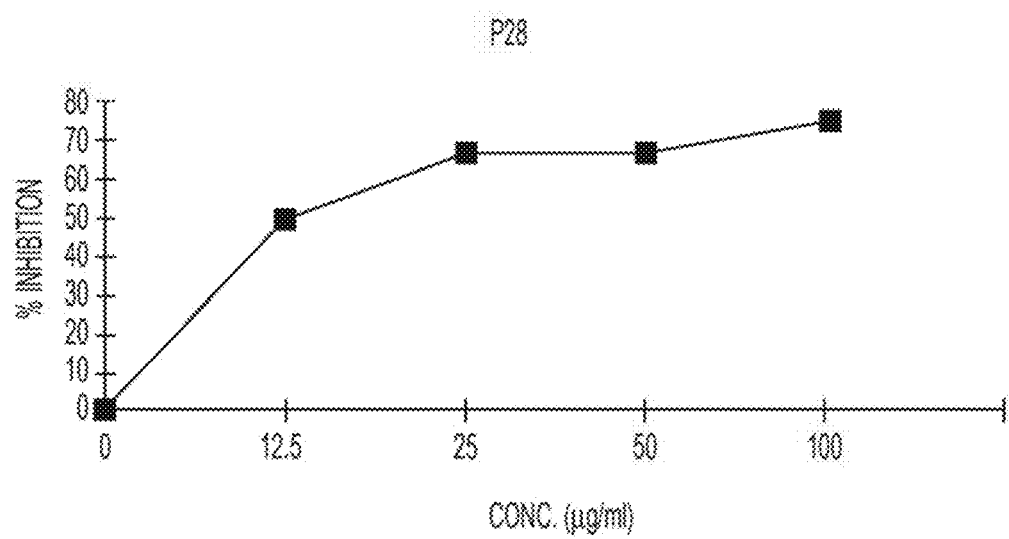
FIG. 2 depicts a graph showing the efficacy of p28 (SEQ ID NO: 2) against DMBA-induced mammary alveolar lesions.

FIG. 1A shows a representative photograph of alveolar lesions in a DMBA treated gland and its comparison with a gland that was treated with DMBA along with a chemopreventive agent. The effects of p28 (SEQ ID NO: 2) on the development of alveolar lesion are shown in FIGS. 1B-1G and summarized in FIG. 2. The peptide p28 (SEQ ID NO: 2) inhibited MAL formation by 67% at 25 µg/ml concentration. Increasing concentration further up to 100 µg/ml did not enhance the efficacy of the peptide. The comparison of the peptide with azurin indicated that p28 (SEQ ID NO: 2) was as effective as azurin for MAL development. Azurin at 50 µg/ml concentration resulted in a 67% inhibition. Statistical analyses indicated that the effect of p28 (SEQ ID NO: 2) was statistically significant compared to DMBA control at concentrations greater than 12.5 µg/ml ($p<0.01$, Fisher's Exact Test; Chi Square analysis).

Histopathological Evaluation of MDL.

For MDL, the glands were processed for histopathological evaluations. The glands were sectioned longitudinally into 5-micron sections and stained with eosin hematoxeline. The longitudinal section of each gland was divided into several fields and each field was evaluated for ductal lesions. Mehta et al., J. Natl. Cancer Inst. 93:1103-1106 (2001). Briefly, the entire gland is evaluated under the scope; smaller glands will have fewer total fields as compared to larger glands. Thus, each gland will have variable number of fields. Often the number of sections through the ducts also varies greatly from gland to gland. This results in the variable number from group to group. Fields containing ductal hyperplasia or atypia were determined and were compared with total number of field evaluated for each gland. No discrimination is made between the hyperplasia or atypia and severely occluded glands. Any field containing any of these histological patterns was considered positive for the lesion. The treatment groups were compared with the controls for the severity and percent inhibition was calculated.

Figure 3:
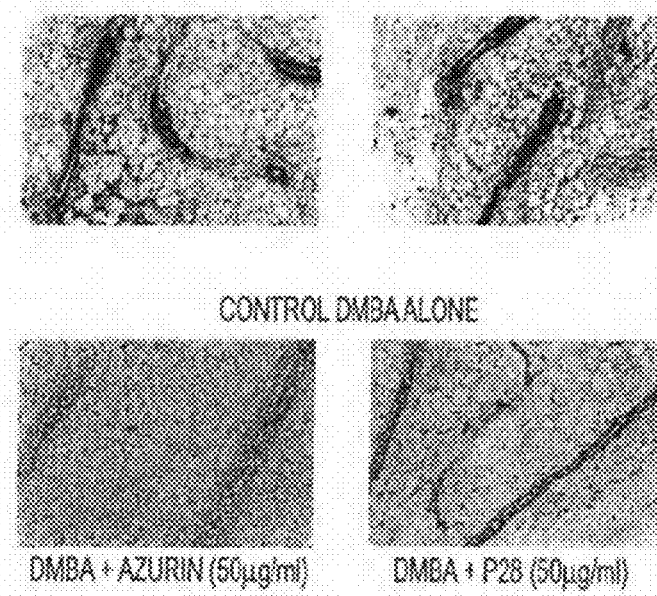
FIG. 3 depicts photographs of representative sections of ductal lesions and effect of p28 (SEQ ID NO: 2).
Figure 4:
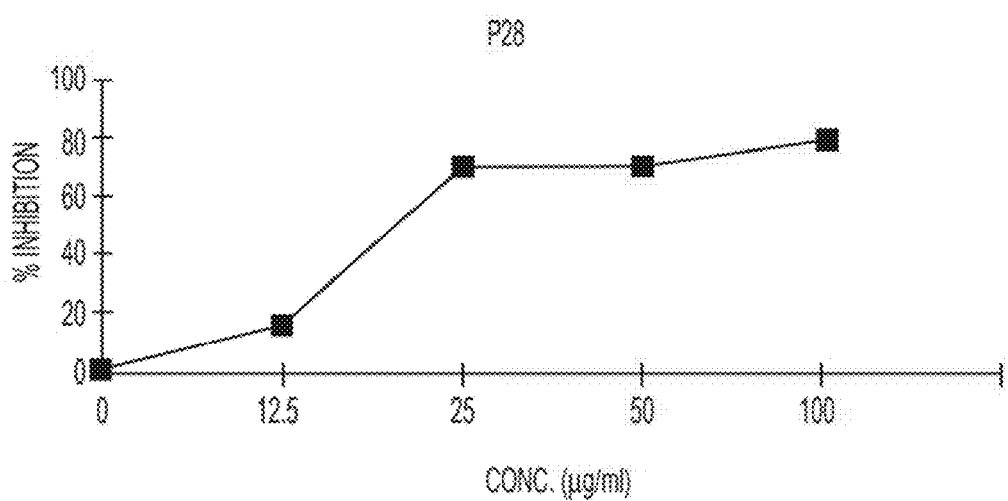
FIG. 4 depicts a graph showing the efficacy of p28 (SEQ ID NO: 2) against DMBA-induced ductal lesions.

FIG. 3 shows a representative ductal lesion. DMBA induces ductal lesions varying from hyperplasia, atypia to complete occlusion of the ducts. A ratio of ductal lesions/total number of ductal sections was determined. Again, 12.5 μg/ml concentration of p28 suppressed only 15% of the MDL formation. However, at 25 μg/ml there was a significant inhibition of the lesions comparable to that observed with 50 μg/ml azurin. The efficacy of p28 (SEQ ID NO: 2) at concentrations greater than 12.5 μg/ml was statistically significant (p<0.01, Fishers Exact Test). These results are summarized in FIG. 4. Often effects of chemopreventive agents can be differentiated between the MAL and MDL. For example Tamoxifen inhibited the development of MDL but not MAL. It is interesting to note that azurin and p28 (SEQ ID NO: 2) inhibited both estrogen and progesterone-dependent ductal lesions as well as independent alveolar lesions.

This example indicates that both p28(SEQ ID NO: 2) and azurin can prevent the development of precancerous lesions in breast tissue. Thus, p28 (SEQ ID NO: 2) and azurin may be used as chemopreventive agents in mammalian patients.

Example 2

Effects of Azurin and Peptide p28 (SEQ ID NO: 2) on the Induction of Mammary Alveolar Lesions in the MMOC Model Chemicals: Azurin and other synthetic peptides: *Escherichia coli* JM109 was used as a host strain for expression of the azurin-encoding gene (azuA) of *P. aeruginosa* strain PA01. The recombinant *E. coli* strain was cultivated in 2YT medium containing 50 μg of ampicillin/ml, 0.1 mM IPTG, and 0.5 mM $CUSO^4$ for 16 h at 37° C. (31). Azurin (SEQ ID NO 1) was purified from periplasmic fraction of the recombinant *E. coli* JM109 strain to a single band as described previously in Wang et al., Biochem Biophys Res Commun. 349:1117-1124 (2006), and determined to be endotoxin free. The sequence of p28 is (SEQ ID NO 2)
LSTAADMQGVVTDGMASG LDKDYLKPDD, and has been chemically synthesized to >95% purity by C S Bio Inc. (Menlo Park, Calif.). Azurin and p28 (SEQ ID NO: 2) were aliquoted, dried and stored in clean sterile vials at −20° C. in a desiccator. All compounds were dissolved in culture media and filter (0.22 μpm) sterilized immediately prior to use.

Mammary Gland Organ Culture (MMOC):

The procedure of MMOC has been described in detail previously. Mehta et al., J. Natl. Cancer Inst. 92: 418-423 (2000). Briefly, thoracic mammary glands are aseptically dissected from the estrogen and progesterone pretreated 4 weeks old female Balb/c mice and explanted into chemically defined Weymouth 752/MB culture medium containing growth promoting hormones. For ovarian hormone independent growth the glands were incubated with insulin (5 μg/ml), prolactin (5 μg/ml) aldosterone (1 μg/ml) and hydrocortisone (1 μg/ml). For hormone dependent lesions the glands were incubated with insulin, prolactin and estradiol 17β (0.001 μg/ml) and progesterone (1 μg/ml) for 10 days. The carcinogen, 7,12 dimethylbenz(a)anthracene (DBMA) (2 μg/ml) was introduced for 24 hours on day 3. The glands were incubated for 10 days and then were regressed in the presence of only insulin for additional 14 days. Thus, typically for the development of mammary lesions the culture period is 24 days. The glands are stained with alum carmine for alveolar lesions (estrogen independent) and histopathologically identified ductal lesions (estrogen dependent lesions). Glands were treated with azurin, p28 (SEQ ID NO: 2) or Tamoxifen only during the first 10 days of culture. For determining the p28 (SEQ ID NO: 2) and p53 interactions, the glands were incubated for four days with the hormones and p28 (SEQ ID NO: 2). The expressions both by PCR and immunohistochemistry were measured after 48 hours.

Immunohistochemistry:

Mammary glands were incubated with growth promoting hormones for 4 days in the presence or absence of azurin or p28 (SEQ ID NO: 2). DMBA was included in the medium for 24 hours on day 3. Formalin fixed paraffin embedded tissue sections were deparaffinized, hydrated. For p53 antigen retrieval was performed by placing slides in 10 mM citrate buffer prewarmed (95° C.) and microwave for 3 min. Slides were then placed in oven at 95-1000 for 1 h in citrate buffer. For ER/PgR and Ki-67 immunostaining antigen retrieval was achieved using pressure chambers, in 10 mM citrate buffer for 6 min. After PBS rinse, nonspecific staining was blocked by incubating slides in 5% gelatin followed by avidin and biotin (Zymed Laboratories, South California, CA). Sections were incubated with primary antibody (p53, Vector/novacastra-VP-P956, PGR,ER and Ki-67 from Labvision, Freemont Calif., Ki-67 Santa Cruz Biotechnology (Santa Cruz, Calif.), preabsorbed with mouse serum,) for 90 min at RT. Following PBS washes (3×) sections were incubated with appropriate biotinylated goat anti-rabbit/anti-mouse antibody, then with ABC reagent (Vectashield Elite ABC kit) DAB (Diaminobenzidine, Sigma, St Louis, Mo.) was used as chromogen to visualize immunoreactivity. Sections were counterstained using Gill's #1 Hematoxylin.

RNA Extraction and Real-Time PCR:

Individual mammary glands were homogenized by using Tissue Tearor (Biospec Products, Inc., Racine, Wis.). RNA was extracted using the phenol: chloroform extraction procedure, which separates out the nucleic acids in the aqueous phase and the proteins being eluted out in the lower organic phase. The aqueous phase is further purified by isopropanol and RNA precipitated by ice cold 70% ethanol prepared in DEPC water. RNA was dissolved in DEPC and analyzed by Spectrophotometry. RNA was converted to cDNA by using the Bio-Rad thermal cycler PCR machine.

Real-time PCR was performed as previously described using 1 μL reverse transcription product in a MyiQ real-time PCR detection system (Bio-Rad, Hercules, Calif.) by using iQ SYBR Green PCR Supermix (Bio-Rad) according to the manufacturer's guidelines. The expression of p53 was determined. Expression of two housekeeping genes 18S mitochondrial DNA and CAPM were used for data analyses. For p53 the Primers used for real time PCR were (forward: 5-GATGACTGCCATGGAGGAG-3' reverse: '-GTCCATG-CAAGGTGATG-3') (SEQ ID NOS: 36 and 83), Ribosomal 18S (forwards 5'-CATGCCCGTTCTTAGTTGGT-3' reverse: 5'-GAACGCCACTTGTCCCTCTA-3') (SEQ ID NOS: 37 and 84).

Statistical Analyses:

Chi-square analyses were carried out to evaluate statistical significance between the incidence of MAL and MDL in control and chemopreventive agent treatment groups.

Figure 5:
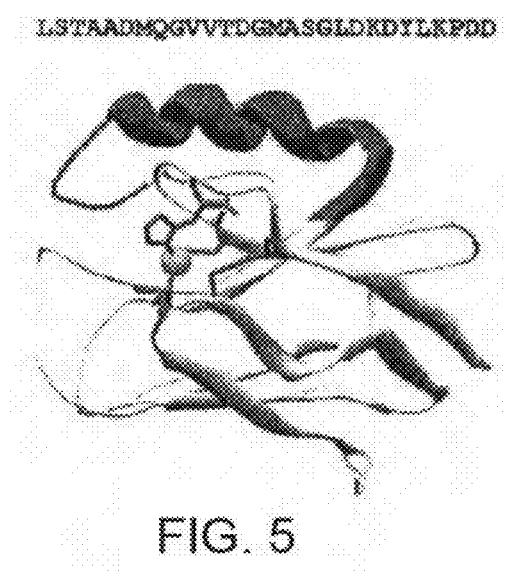
FIG. 5 depicts the overall 3D structure of azurin, with the p28 peptide region bolded (SEQ ID NO: 2).

Azurin and p28 (SEQ ID NO: 2):

As shown in FIG. 5, Azurin is a 128 amino acid, 14 kD copper containing protein produced by aerobic bacteria. p28 (SEQ ID NO: 2) was generated and evaluated for entry into the cells. The results indicated that a 28 amino acid peptide, azu 55-77 (SEQ ID NO: 2) (FIG. 5) fused to GST could transport GST into the J774 cells; however, GST by itself could not be internalized. These results provided a sound rationale for selecting a 28 amino acid (aa 50-77, SEQ ID NO 2) construct of azurin as an active peptide for possible azurin action and was designated as p28 (SEQ ID NO: 2). Therefore initial experiments were carried out using azurin and subsequent studies used p28 (SEQ ID NO: 2), keeping azurin as a positive control.

Effects of Azurin and p28 on the Induction of Mammary Alveolar Lesions (MAL):

Effects of azurin at 3 different concentrations (10, 20 and 50 µg/ml) was evaluated, 15 glands were included in each group. The results showed that there was 71.4% incidence of MAL in the DMBA control group of glands and there was a 16, 20 and 63% inhibition of incidence was observed with azurin at three concentrations respectively. At 50 µg/ml concentration, azurin mediated inhibition of the MAL development was statistically significant (p<0.05). Efficacy of p28 (SEQ ID NO: 2) on MAL development was also determined by evaluating p28 (SEQ ID NO: 2) at concentration range of 10 to 100 µg/ml. The peptide was added in the medium during the initial 10 days of growth phase of the mammary gland development.

Figure 6A:
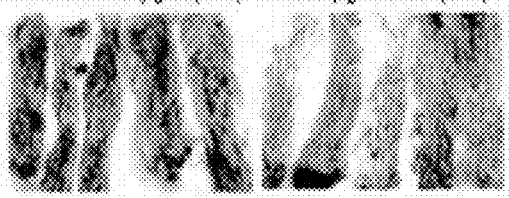
FIG. 6A depicts a photograph of representative sections of mammary alveolar lesions and effects of p28 (SEQ ID NO: 2) on the development of mammary alveolar lesions.
Figure 6B:
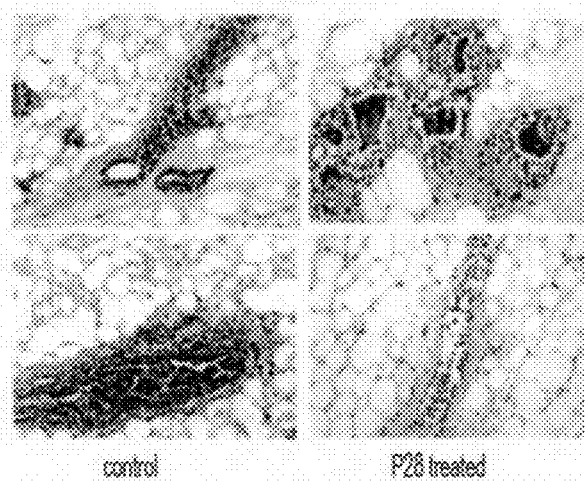
FIG. 6B depicts photographs of representative sections of mammary lesions and effects of p28 (SEQ ID NO: 2) on said lesions.

FIGS. 6A and 6B show representative whole mounts of glands with MAL in control and p28 (SEQ ID NO: 2) (50 µg/ml) treatment groups. With regard to FIG. 6A, Mammary glands were either incubated with DMBA or DMBA and p28 (SEQ ID NO: 2) for 10 days during the growth promoting phase of MAL development. Glands were stained after 24 days of culture period with alumn carmine. A reduced number of MAL is observed in p28 (SEQ ID NO: 2) treated glands. Specifically, FIG. 6A shows histopathology of mammary alveolar lesions either in the absence or the presence of 50 µg p28 (SEQ ID NO: 2). p28 (SEQ ID NO: 2) at 25 µg resulted in >60% inhibition of MAL development (p<0.05), which is comparable to the inhibition obtained with azurin. There was no toxicity associated with any concentration of p28 (SEQ ID NO: 2) as no dilation of ducts was observed in any of the treatment groups.

With regard to FIG. 6B, ductal lesions were identified in hematoxelene and eosin stained histopathological sections. Representative sections show mammary ducts are occluded in DMBA treated glands, whereas p28 (SEQ ID NO: 2) treatment exhibits normal histology of the mammary ducts.

This example further indicates that both p28 (SEQ ID NO: 2) and azurin can prevent the development of precancerous lesions in breast tissue. Thus, p28 (SEQ ID NO: 2) and azurin may be used as chemopreventive agents in mammalian patients.

Example 3

Effect of Combination of Peptide p28 (SEQ ID NO: 2) and Tamoxifen on DMBA-Induced Mammary Lesions in the MMOC Model The MMOC system can discriminate between the lesions induced by DMBA that are estrogen and progesterone dependent and hormone independent. The lesions developed in the presence of estrogen and progesterone are MDL and they can be compared to human DCIS/ductal carcinoma. Unlike distinct alveolar lesions developed in the absence of estrogen, the alveolar structures formed in the presence of estrogen and absence of aldosterone are very small, which makes it difficult to measure the effects of chemopreventive agents on the alveolar structure of estrogen dependent lesions. Tamoxifen, an antiestrogen, which can selectively inhibit MDL, fails to inhibit MAL in this model.

Figure 6C:
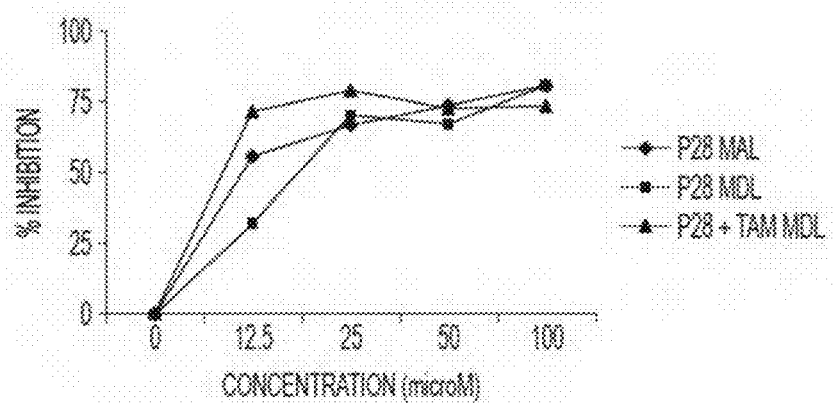
FIG. 6C depicts a graph showing the effects of p28 (SEQ ID NO: 2) and Tamoxifen on mammary lesions.

The effects of p28 (SEQ ID NO: 2) and Tamoxifen on MDL development were evaluated based on the experimental procedures discussed in Example 2 above. FIG. 6C shows the effects of either p28 (SEQ ID NO: 2) on MAL and MDL or p28 (SEQ ID NO: 2) with 1 µg/ml Tamoxifen on MDL. Ten glands per group were incubated with various treatments either with IPAF for MAL or with IPEPg for MDL. The glands were stained with alumn carmine for MAL or histologically processed for MDL. The effects of experimental agents were evaluated either on the incidence of MAL (number of glands with MAL in treatment group as compared to experimental group) or multiplicity (number of ducts with MDL per field in controls as compared to experimental groups) for MDL Results showed that p28 (SEQ ID NO: 2) inhibited the development of MDL at 50 µg/ml (FIG. 6C). At 12.5 µg/ml there was only 30% inhibition as compared to 70% inhibition of MDL at 25 µg/ml. Increasing concentrations to 100 µg/ml did not further enhance prevention of the MDL. Tamoxifen (1 µM) treatment alone inhibited MDL formation by about 50%. However the combination of ineffective concentration of p28 (12.5 µg/ml) with 1 µM Tamoxifen increased the effectiveness to 70% (FIG. 6C). These dramatic effects of combination can have clinical translational value because the dose-related toxicity of Tamoxifen can be significantly curtailed by combining the treatment of Tamoxifen with lower concentration of p28 (SEQ ID NO: 2). Suppression of both MAL and MDL formation by p28 (SEQ ID NO: 2) was due to inhibition of cell proliferation as reduced expression of Ki67 was observed in p28 treated mammary gland sections compared to control (FIG. 3).

These results provide a translational benefit of combining Tamoxifen and p28 (SEQ ID NO: 2) at low concentrations for enhanced protection against the development of estrogen dependent precancerous mammary ductal lesions.

Example 4

Effects of Peptide p28 (SEQ ID NO: 2) and Tamoxifen on Induction of p53 in the MMOC Model Earlier studies provided some evidence for possible interactions between azurin and p53; however the functional significance of these interactions or stabilization of p53 by azurin have not been reported. Since the design of MMOC experiments can identify interactive role of estrogen and progesterone with p53 by comparing the p53 expression under two separate hormonal conditions, a set of studies were carried out to determine if the steroid hormones have a selective role on p53 expression. Aldosterone/hydrocortisone and estrogen/progesterone independently induce development of alveolar structures in mammary glands and yet the DMSA-induced lesions formed under these two hormonal environments are different. Moreover, the development of preneoplastic lesions is a late event. The lesions are formed after 24 days even though the glands are exposed to carcinogen much earlier during the culture period. Thus, the earlier cell signaling events, which may play a major role in development of premalignant lesions, can be monitored within the first few days of culture.

Figure 7A:
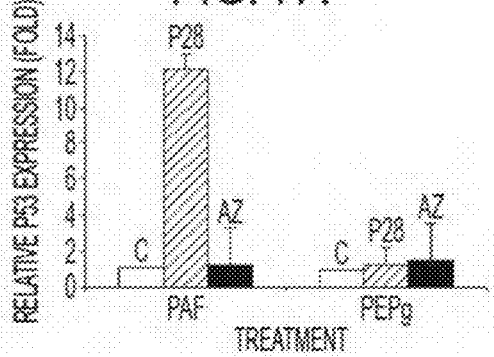
FIG. 7A depicts a graph comparing the expression of p53 in mammary glands incubated in the presence or absence of estrogen and progesterone.

FIG. 7A depicts a comparison of p53 mRNA expression in mammary glands incubated in the presence or absence of estrogen and progesterone. After culturing the glands for four days with aldosterone plus progesterone or estradiol plus progesterone in chemically defined medium, total RNA was isolated from four glands individually in each group. RNA was converted to cDNA and real-time PCR was performed using 1 μL reverse transcription product in a MyiQ real-time PCR detection system by using iQ SYBR Green PCR Supermix. The expression of p53 was determined. Expression of two housekeeping genes 18S mitochondrial DNA and GAPDH were used for data analyses. The p53 expression was normalized to a control.

As demonstrated in FIG. 7A, mammary glands incubated with either IPAF (absence) or IPEPg (presence) did not have significant mRNA expression of p53. These control glands were normalized to 1 and relative increase or decrease caused by p28 (SEQ ID NO: 2) was determined. Results showed that the glands incubated with p28 (SEQ ID NO: 2) in the absence of estrogen plus progesterone exhibited 12 fold increase of p53 mRNA expression whereas there was no enhanced expression of p53 observed when the glands were incubated with p28 (SEQ ID NO: 2) in the presence of estrogen and progesterone.

Figure 7B:
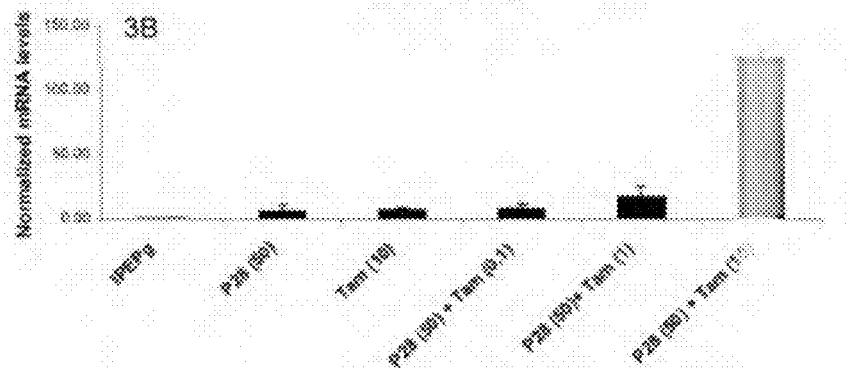
FIG. 7B depicts a graph showing the effects of p28 (SEQ ID NO: 2), Tamoxifen, and a combination of the two on p53 expression.
Figure 7C:
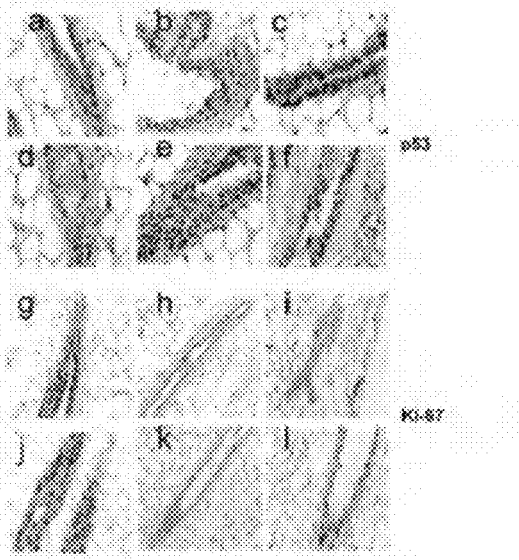
FIG. 7C depicts photographs of immunohistochemical staining of p53 and Ki67 in representative sections of mammary glands of MMOC.

However, enhanced p53 expression was observed in p28 (SEQ ID NO: 2) treated glands irrespective of culture conditions (presence/absence of estrogen) as determined by immunohistochemistry. FIG. 7C depicts immunohistochemical staining of p53 (photos a-f) and Ki67 (photos g-l) in mammary glands in MMOC. Mouse mammary glands were incubated with either DMBA alone (a, d, g, j) or in the presence of p28 (SEQ ID NO: 2) (b, e, h, k) or Azurin (c, f, i, l) for 4 days. Paraffin embedded sections were processed for immunohistochemical staining of p53 (a-f) and Ki67 (g-l). Certain of these glands were incubated in the absence of estrogen/IPAF (a, b, c, g, h, i) and others were incubated in the presence of estrogen/IPEPg (d, e, f, j, k, l).

The cell proliferative activity determined by determining Ki67 staining by immunohistochemistry further suggested that both p28 and azurin inhibited cell proliferation. The growth promoting effect of hormone treatment resulted in intense Ki67 staining in the epithelial cells (FIG. 7C), whereas there was significant decrease in the Ki67 expression when the glands were treated with azurin. It is therefore thought that p28 (SEQ ID NO: 2) stabilizes p53 protein rebuilding in the antiproliferative effects of azurin and p28 (SEQ ID NO: 2).

Figure 7D:
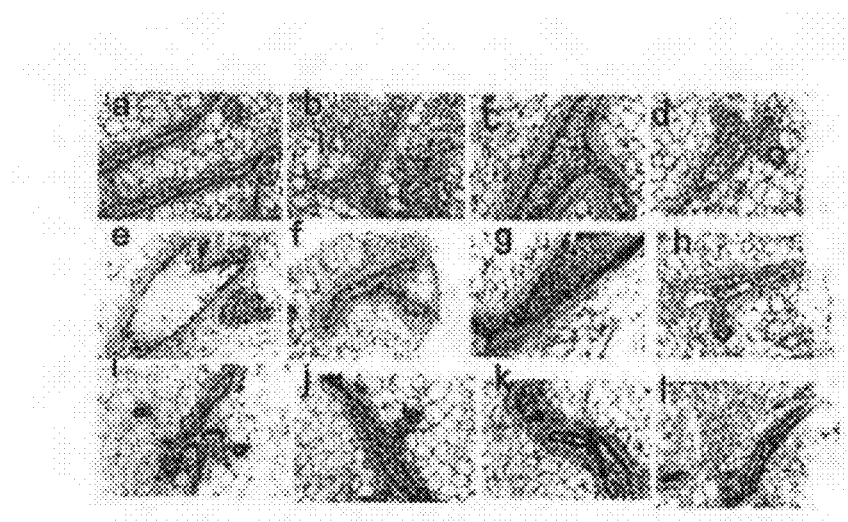
FIG. 7D depicts photographs of representative sections of mouse mammary glands and effects of azurin, p28 (SEQ ID NO: 2), and Tamoxifen on p53 and Ki-67 in said mammary glands.

Since recent literature indicates that estrogen interferes with p53 action in breast cancer cells, the expression of p53 in the mammary glands treated with estrogen and progesterone was examined. FIG. 7D shows the effects of azurin and p28 (SEQ ID NO: 2) on the p53 and Ki67 protein expression by immunohistochemistry. Paraffin embedded sections of mouse mammary glands were incubated with IPEPg containing media, control (a,e, i); IPEPg+50 μg of p28 (SEQ ID NO: 2) (b, f, j); IPEPg+10 μM Tamoxifen (c, g, k); and IPEPg+Tamoxifen+50 μg/ml p28 (SEQ ID NO: 2) (d, h, l) for 4 days as indicated in the methods described in Example 2 above. After 4 days glands were fixed in buffered formalin and processed for paraffin sectioning. Immunohistochemical staining of p53 (a-d) and Ki-67 (e-h) was performed after antigen retrieval procedure. Nuclear p53 expression (i-l) in mammary epithelial cells was observed in glands incubated in the presence of Tamoxifen and Tamoxifen+p28 (SEQ ID NO: 2). Similarly decreased Ki-67 was observed in Tamoxifen and Tamoxifen+p28 (SEQ ID NO: 2) treated glands. H and E sections are shown.

The results showed repressed p53 expression in glands treated with estrogen and progesterone. p53 expression in glands treated with Tamoxifen, an antiestrogen, was measured to determine if estrogen mediated suppression of p53 expression can be overcome by Tamoxifen. As shown in FIG. 7B, while p28 (SEQ ID NO: 2) or Tamoxifen individually did not affect the expression of p53 in mammary glands, in the presence of a combination of low concentrations of p28 (SEQ ID NO: 2) and Tamoxifen there was an unexpected 125 fold increases in the p53 mRNA expression. These studies clearly showed that p28 (SEQ ID NO: 2) mediated induction of p53 in mammary gland is not selective for glands incubated with glucocorticoids, however p28 (SEQ ID NO: 2) can equally induce p53 in the estrogen and progesterone treated glands if the estrogen function is blocked. Immunohistochemical studies further confirmed these findings. Results showed that the estrogen and progesterone treated glands or the glands treated with the hormones and p28 or Tamoxifen individually did not express nuclear p53 protein. However when the glands are incubated with a combination of p28 (SEQ ID NO: 2) and Tamoxifen, a surprising increase in nuclear expression of the p53 protein was observed (FIG. 7,1). The immunohistochemical analyses also showed that mammary glands incubated with estradiol induces upregulation of ER and PR in the glands.

There are thus significant, and previously unexpected, benefits to combining Tamoxifen and p28 (SEQ ID NO: 2) at low concentrations to enhance p53 induction and thus inhibit premalignant lesion and tumor development.

Example 5

Effect of Peptide p28 (SEQ ID NO: 2) in Combination With Fenretinide and Tamoxifen on DMBA-Induced Mammary Lesions The mouse mammary gland organ culture (MMOC) assay was used to evaluate the inhibitory effects of potential chemopreventive agents on both hormone-induced structural differentiation of mammary glands and on the development of DMBA-induced preneoplastic hyperplastic alveolar nodule-like lesions in the gland. Mammary glands from young, virgin animals, when incubated for 6 days in the presence of insulin (I)+prolactin (P)+aldosterone (A), can differentiate into fully-grown glands. These glands morphologically resemble the glands obtained from pregnant mice. Aldosterone can be replaced by estrogen (E)+progesterone (Pg). Inclusion of hydrocortisone (H) to the medium stimulates the glands for functional differentiation. Mehta, R. G., and Banerjee, M. R, Acta Endocrinol., 80: 501 (1975); Mehta, R. G., and Moon, R C., Can Maturation Be Induced in Breast Cancer, In: Breast Cancer: Treatment and Prognosis, Basil A. Stoll (ed.), Blackwell Press, 300, 1986. Thus, the hormone-induced structural and functional differentiation, observed in this culture system, mimics the responses to hormones observed during various physiological stages of the animal.

Two known chemopreventive compounds were selected. For MAL development fenretinide (4-HPR, N-4-Hydroxyphenyl retinamide) was selected. Fenretinide inhibits MAL development by >60% and showed clinical efficacy against breast cancer development in high-risk premenopausal women. Veronesi, U., et al, Ann. Oncol. 17: 1065-1071 (2006). The second chemopreventive agent selected for the current project was Tamoxifen for MDL. Tamoxifen has been used clinically for prevention and treatment of breast cancer patients. Since it mediates its action as an antiestrogen and is effective against MDL development in MMOC, it was evaluated in combination with p28 (SEQ ID NO: 2) for prevention of MDL development in MMOC. Four experiments were conducted: two for MAL and two for MDL. For MAL, 4-HPR was used at an effective concentration either alone or in combination with increasing concentrations of p28 (SEQ ID NO: 2). Similarly, for MDL experiments Tamoxifen was used at a single concentration either alone or in the presence of increasing concentrations of p28 (SEQ ID NO: 2). A sample protocol is shown in Table 5.

TABLE 5

Protocol to evaluate the efficacy of peptide p28 (SEQ ID NO: 2) in combination with Fenretinide (4-HPR) on the development of DMBA-induced mammary alveolar lesions in mouse mammary gland organ culture (MMOC)

| Group | Number of Glands | Carcinogen | Agent (Conc.) |
|---|---|---|---|
| 1 | 15 | DMBA (2 µg/ml) | None |
| 2 | 15 | DMBA (2 µg/ml) | 4-HPR (1 µM) |
| 3 | 15 | DMBA (2 µg/ml) | P28 (12.5 µg/ml) |
| 4 | 15 | DMBA (2 µg/ml) | P28 (12.5 µg/ml) + 4-HPR (1 µM) |
| 5 | 15 | DMBA (2 µg/ml) | P28 (25 µg/ml) |
| 6 | 15 | DMBA (2 µg/ml) | P28 (25 µg/ml) + 4-HPR (1 µM) |
| Expt 3 B | | | |
| 7 | 15 | DMBA (2 µg/ml) | None |
| 8 | 15 | DMBA (2 µg/ml) | P28 (50 µg/ml) |
| 9 | 15 | DMBA (2 µg/ml) | P28 (50 µg/ml) + 4-HPR (1 µM) |
| 10 | 15 | DMBA (2 µg/ml) | P28 (100 µg/ml) |
| 11 | 15 | DMBA (2 µg/ml) | P28 (100 µg/ml) + 4-HPR (1 µM) |
| 12 | 15 | DMBA (2 µg/ml) | Azurin (50 µg/ml) |

Preparation of peptide solution: Weigh out 5 vials of 3 mg P28 and save them at −70 C. Dissolve 1 mg/2 ml, filter and then add 1 ml to 4 ml medium (500 µg/5 ml to reach final conc. of 100 µg/ml). Similarly add P28 to achieve final concentrations as shown in the protocol.
4-HPR:
Culture Protocol: Standard for MAL.

The effects of p28 (SEQ ID NO: 2) were evaluated at 4 different concentrations (12.5, 25, 50 and 100 µg/ml) either alone or in combination with either 4-HPR or Tamoxifen. Carcinogen treated glands without the test agent served as a measure to determine percent incidence in the absence of a chemopreventive agent. An additional control of Azurin (50 µg/ml) was included to serve as a positive control for chemoprevention. For alveolar lesions, stained glands were evaluated for the incidence of lesions (glands containing any lesions as compared to total number of glands in a given treatment group). For the ductal lesions, similar protocol was adapted; however, hormonal combination is different for alveolar and ductal lesions. A protocol for determining the effects of p28 (SEQ ID NO: 2) and Tamoxifen on MDL is shown in Table 6.

TABLE 6

Protocol to evaluate the efficacy of peptide p28 (SEQ ID NO: 2) in combination with Tamoxifen on the development of DMBA-induced mammary Ductal lesions in mouse mammary gland organ culture (MMOC)

| Group | Number of Glands | Carcinogen | Agent (Conc.) |
|---|---|---|---|
| 1 | 15 | DMBA (2 µg/ml) | None |
| 2 | 15 | DMBA (2 µg/ml) | Tamoxifen (1 µM) |

TABLE 6-continued

Protocol to evaluate the efficacy of peptide p28 (SEQ ID NO: 2) in combination with Tamoxifen on the development of DMBA-induced mammary Ductal lesions in mouse mammary gland organ culture (MMOC)

| Group | Number of Glands | Carcinogen | Agent (Conc.) |
|---|---|---|---|
| 3 | 15 | DMBA (2 µg/ml) | P28 (12.5 µg/ml) |
| 4 | 15 | DMBA (2 µg/ml) | P28 (12.5 µg/ml) + Tamoxifen (1 µM) |
| 5 | 15 | DMBA (2 µg/ml) | P28 (25 µg/ml) |
| 6 | 15 | DMBA (2 µg/ml) | P28 (25 µg/ml) + Tamoxifen (1 µM) |
| Ext. 4 B | | | |
| 7 | 15 | DMBA (2 µg/ml) | None |
| 8 | 15 | DMBA (2 µg/ml) | P28 (50 µg/ml) |
| 9 | 15 | DMBA (2 µg/ml) | P28 (50 µg/ml) + Tamoxifen (1 µM) |
| 10 | 15 | DMBA (2 µg/ml) | P28 (100 µg/ml) |
| 11 | 15 | DMBA (2 µg/ml) | P28 (100 µg/ml) + Tamoxifen (1 µM) |
| 12 | 15 | DMBA (2 µg/ml) | Azurin (50 µg/ml) |

Preparation of peptide solution: Weigh out 5 vials of 3 mg p28 (SEQ ID NO: 2) and save them at −70 C. Dissolve 1 mg/2 ml, filter and then add 1 ml to 4 ml medium (500 µg/5 ml to reach final conc. of 100 µg/ml) Similarly add p28 (SEQ ID NO: 2) to achieve final concentrations as shown in the protocol.
Tamoxifen
Culture protocol: Standard for MDL.

The glands were fixed in formalin and then processed for histopathology. The sections are stained with eosin and hematoxelene and evaluated under microscope.

Organ Culture Procedure:

The experimental animals used for the studies were young, virgin BALB/c female mice 3 to 4 weeks of age obtained from Charles River, Wilmington, Mass. These mice are readily available, and most of the past studies have used the BALB/c mice. The mice were treated daily by subcutaneous injections with 1 µg estradiol-17β+1 mg progesterone for 9 days. This treatment is a prerequisite inasmuch as animals not pretreated with steroids fail to respond to hormones in vitro. The entire culture procedure is described in detail in Mehta, R. G. and Banerjhee, M., Acta Endocrinol. 80: 501 (1975) and Mehta, R. G. et al., JNCI 93: 1103-1106 (2001).

Briefly, the animals were killed by cervical dislocation, and the thoracic pair of mammary glands were dissected out on silk rafts and incubated for 10 days in serum free Waymouth MB752/1 medium (5-glands/5 ml/dish). The medium was supplemented with glutamine, antibiotics (penicillin and streptomycin 100 units/ml medium) and growth-promoting hormones, 5 µg I, 5 µg P, 1 µg A and 1 µg H per ml of medium for the protocol to induce mammary alveolar lesions (MAL). For induction of ductal lesions (MDL), the medium contains 5 µg/ml I, 5 µg/ml P, 0.001 µg/ml estradiol-17β, and 1 µg/ml progesterone (Pg) (14). The carcinogen, DMBA (2 µg/ml) was added to the medium between days 3 and 4. For the present study, DMBA was dissolved in DMSO at a final concentration of 4 mg/ml, and 50 µg I was added to 100 ml medium resulting in 2 µg/ml final concentrations. The control dishes contained OMSO as vehicle. On day 4, OMBA is removed from the medium by rinsing the glands in fresh medium and transferring them to new dishes containing fresh medium without OMBA. After 10 days of incubation, the glands were maintained for another 14 days in the medium containing only I (5 µg/ml). During the entire culture period, the glands were maintained at 3° C. under 95% $O_2$ and 5% $CO_2$ environment. The chemopreventive agents were included in the medium during the first ten days of growth promoting phase. The test peptide p28 (SEQ ID NO: 2) was evaluated at 4 concentrations ranging from 12.5 µg/ml to 100 µg/ml. Fenretinide (for MAL studies) and Tamoxifen (for MDL studies) were included (dissolved in ethanol) at 1 µM concentrations. Azurin was evaluated at 50 µg/ml in the medium. The p28 (SEQ ID NO: 2) peptide was dissolved in sterile water and filtered prior to use. The medium was changed three times per week (Monday, Wednesday and Friday). At the end of the exposure, the glands were fixed in formalin. For examination of MAL, the glands were stained in alum carmine, and evaluated for the presence of the lesions. The glands were scored for the presence or absence of mammary lesions, severity of lesions per gland, and toxicity of the agent. For MDL, the glands were processed for histopathological evaluations, The glands were sectioned longitudinally into 5-micron sections and stained with eosin hematoxeline.

Chemopreventive Agents:

The agents azurin and p28 (SEQ ID NO: 2) were supplied by CDG Therapeutics Inc. The agents were assumed to be stable and pure.

Morphometric Analysis:

The glands stored in xylene were evaluated for the presence or absence, incidence, and severity of mammary lesions for each gland under a dissecting microscope. Mammary glands were scored as positive or negative for mammary lesions, and the percent incidence was determined as a ratio of glands exhibiting lesions and the total number of glands in that group. Dilation of ducts or disintegration of mammary structure because of treatment with chemopreventive agent was considered a toxic effect. The data were subjected to statistical analysis for the incidence to determine the effectiveness of the potential chemopreventive agents.

Histopathological Evaluation of MDL:

The longitudinal section of each gland was divided into several fields and each field was evaluated for ductal lesions. Briefly, the entire gland is evaluated under the scope; smaller glands will have fewer total fields as compared to larger glands. Thus, each gland will have variable number of fields. Often the number of sections through the ducts also varies greatly from gland to gland. This results in the variable number from group to group. Fields containing ductal hyperplasia or atypia were determined and were compared with total number of field evaluated for each gland. No discrimination is made between the hyperplasia or atypia and severely occluded glands. Any field containing any of these histological patterns was considered positive for the lesion. The treatment groups were compared with the controls for the severity and percent inhibition was calculated.

Statistical Analysis:

If the chemopreventive agent shows 60% or greater inhibition when using 15 glands per group, this assures that the results will be statistically significant (p<0.05). Results were analyzed by Fisher's Exact Test.

Results and Discussion:

The MMOC model allows evaluation of efficacy of potentially efficacious chemicals against development of mammary alveolar or ductal lesions in response to DMBA. DMBA, under appropriate incubation conditions, forms either MAL or MDL based on the hormonal milieu in the medium. Mehta, R. G. et al., JNCI 93: 1103-1106 (2001). Estrogen and progesterone treated glands in culture develop ductal lesions whereas aldosterone and hydrocortisone treated glands form estrogen progesterone independent alveolar lesions. The mammary glands not exposed to carcinogen or chemopreventive agent undergo structural regression in the absence of growth-promoting hormones, whereas treatment with DMBA for the 24-hr period between days 3 and 4 prevents the regression of structures caused by deprivation of hormones. It is assumed that this is because the glands have lost normal hormonal responsiveness and now have altered their course of development. As indicated previously, generating mammary adenocarcinoma by transplanting transformed cells into syngeneic mice has proved the preneoplastic nature of these unrepressed areas.

Figure 8:
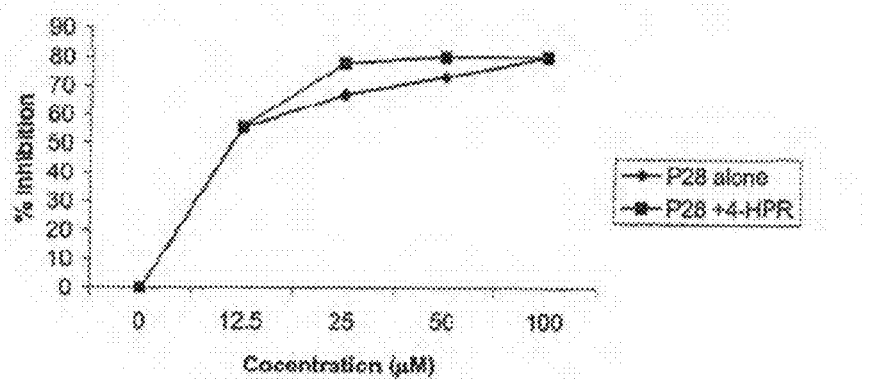
FIG. 8 depicts a graph showing the effects of combinations of fenretinide and p28 (SEQ ID NO: 2) on MAL development in the MMOC model.

Effects of p28 (SEQ ID NO: 2) and 4-HPR:

The effects of p28 (SEQ ID NO: 2) and 4-HPR alone as well as in combination on the development of alveolar lesion are summarized in Table 7 and FIG. 8.

TABLE 7

Effects of combination of p28 (SEQ ID NO: 2) and 4-HPR on DMBA Induced Mammary Alveolar Lesions in MMOC

| Gp. No. | Treatment DMBA + X | No. Glands per group | Glands with Lesions | Percent Incidence | Percent Inhibition |
|---|---|---|---|---|---|
| Exp. 1 | | | | | |
| 1 | None | 15 | 9 | 60.0 | |
| 2 | 4-HPR (1 µM) | 15 | 3 | 20.0 | 67% |
| 3 | P28 (12.5 µg/ml) | 15 | 4 | 26.7 | *56% |
| 4 | P28 (12.5 µg/ml( + 4-HPR (1 µM) | 15 | 3 | 20.0 | 67% |
| 5 | P28 (25 µg/ml) | 15 | 3 | 20.0 | 67% |
| 6 | P28 (25 µg/ml) + 4-HPR (1 µM) | 15 | 2 | 13.3 | 78% |
| Exp. 2 | | | | | |
| 7 | None | 15 | 10 | 66.7 | |
| 8 | P28 (50 µg/ml) | 15 | 3 | 20 | 70% |
| 9 | P28 (50 µg/ml) + 4-HPR (1 µM) | 15 | 2 | 13.3 | 80% |
| 10 | P28 (100 µg/ml) | 15 | 2 | 13.3 | 80% |
| 11 | P28 (100 µg/ml) + 4HPR (1 µM) | 15 | 3 | 20 | 70% |
| 12 | Azurin (50 µg/ml) | 15 | 3 | 20 | 70 |

Fisher's Exact Test
*1 Gp1 vs 3 + NS p + 0.1394
All Others VS gp 1: p < 0.05

All glands were photographed and the pictures are shown in FIG. 10. The peptide p28 (SEQ ID NO: 2) inhibited MAL formation by 67% at 25 µg/ml concentration. Increasing the concentration of p28 (SEQ ID NO: 2) further up to 100 µg/ml resulted in inhibition to 80%. Combination chemoprevention studies indicated that 4-HPR inhibited MAL development as expected by 67%. Azurin suppressed the MAL development by about 70%. Statistical analyses indicated that the effects of p28 (SEQ ID NO: 2) (>25 µg/ml), 4-HPR and all combinations were statistically significant compared to DMBA control (p<0.01, Fisher's ExactTest).

Effects of p28 (SEQ ID NO: 2) and Tamoxifen—

Figure 9:
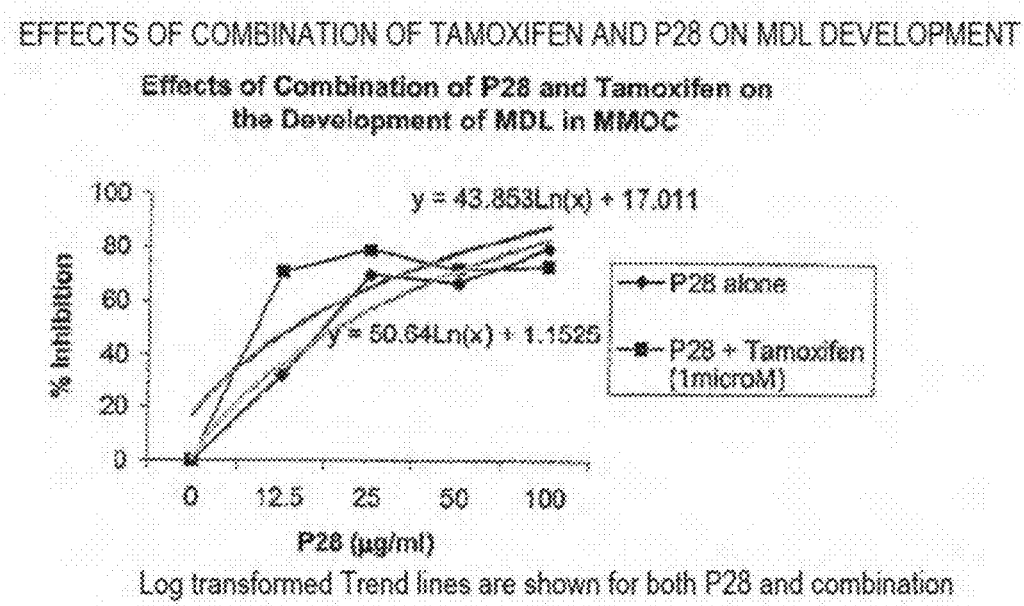
FIG. 9 depicts a graph showing the effects of combinations of Tamoxifen and p28 (SEQ ID NO: 2) on MDL development in the MMOC model FIGS. 10A-L. Depict photographs of representative sections of mouse mammary glands and the effects of fenretinide and p28 (SEQ ID NO: 2), alone and in combination, in these mammary glands.
Figure 10A:
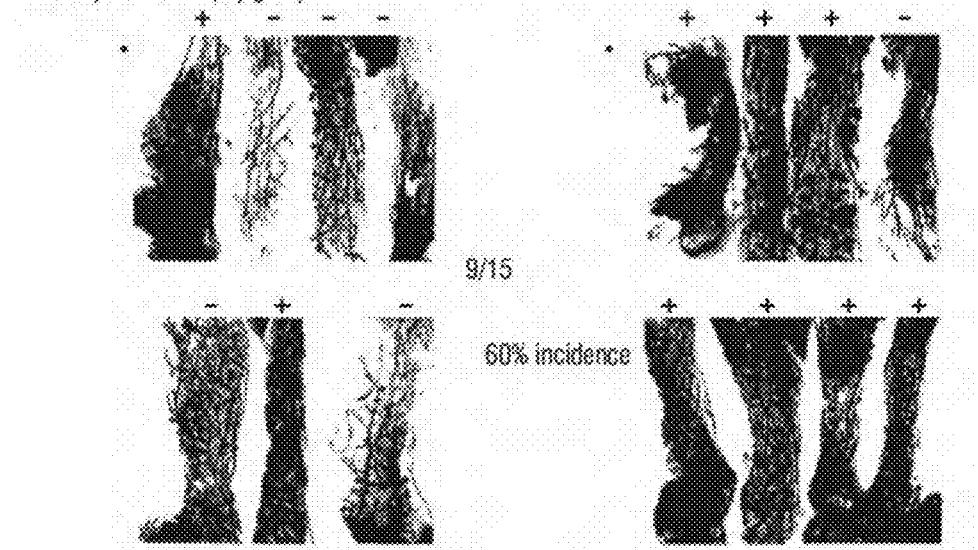
Figure 10B:
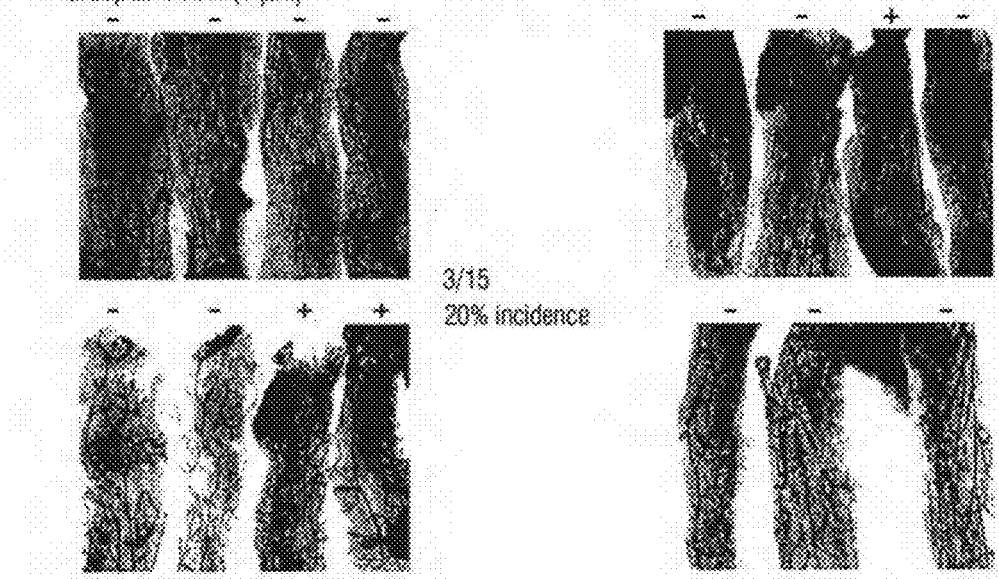
Figure 10C:
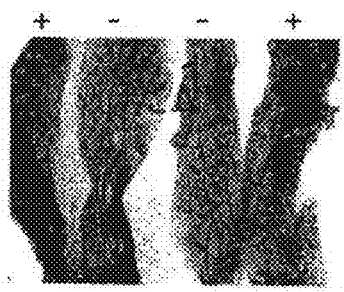
Figure 10C:
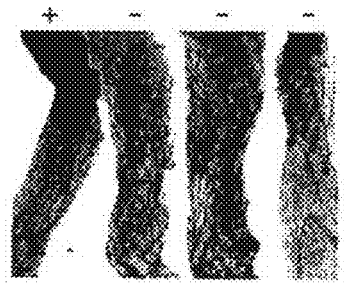
Figure 10C:
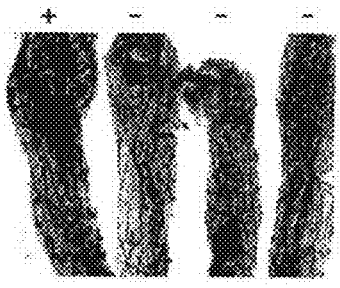
Figure 10C:
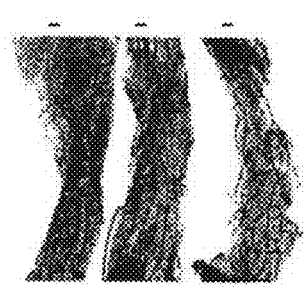
Figure 10D:
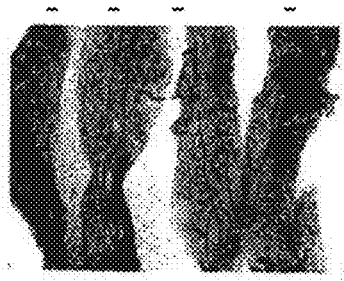
Figure 10D:
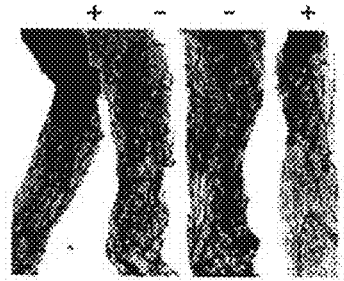
Figure 10D:
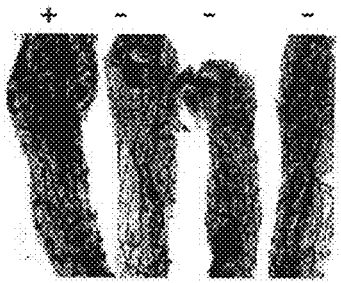
Figure 10D:
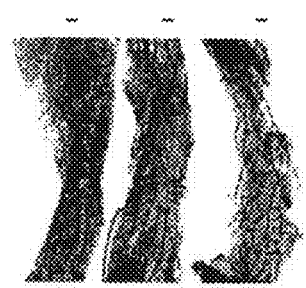
Figure 10E:
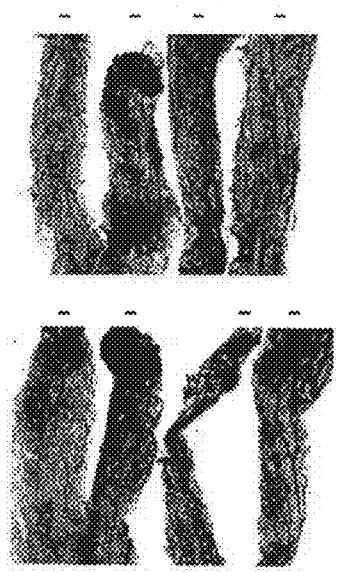
Figure 10E:
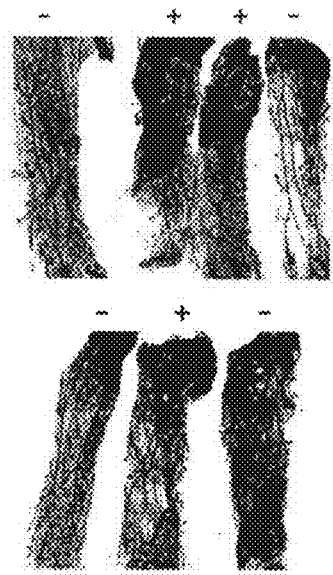
Figure 10F:
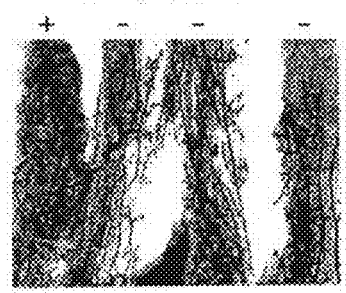
Figure 10F:
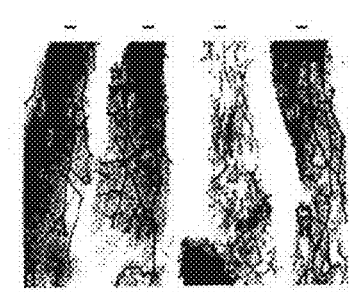
Figure 10F:
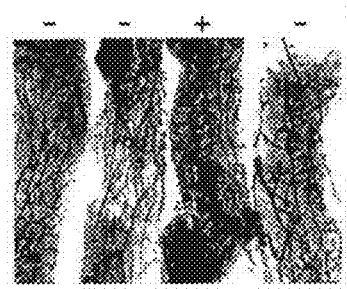
Figure 10F:
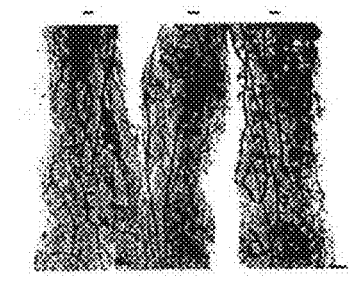
Figure 10G:
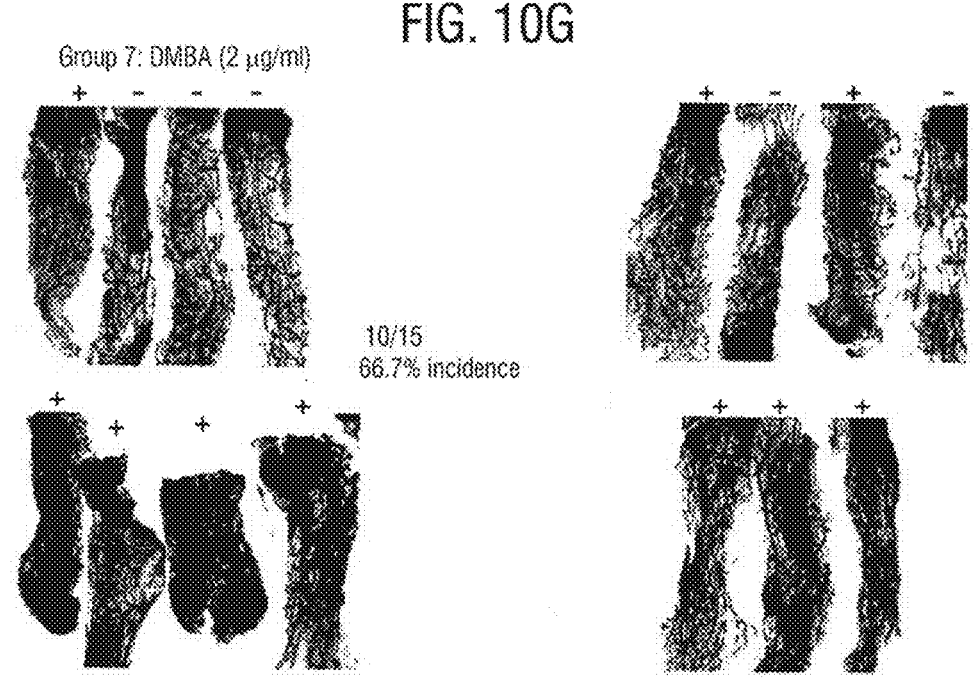
Figure 10H:
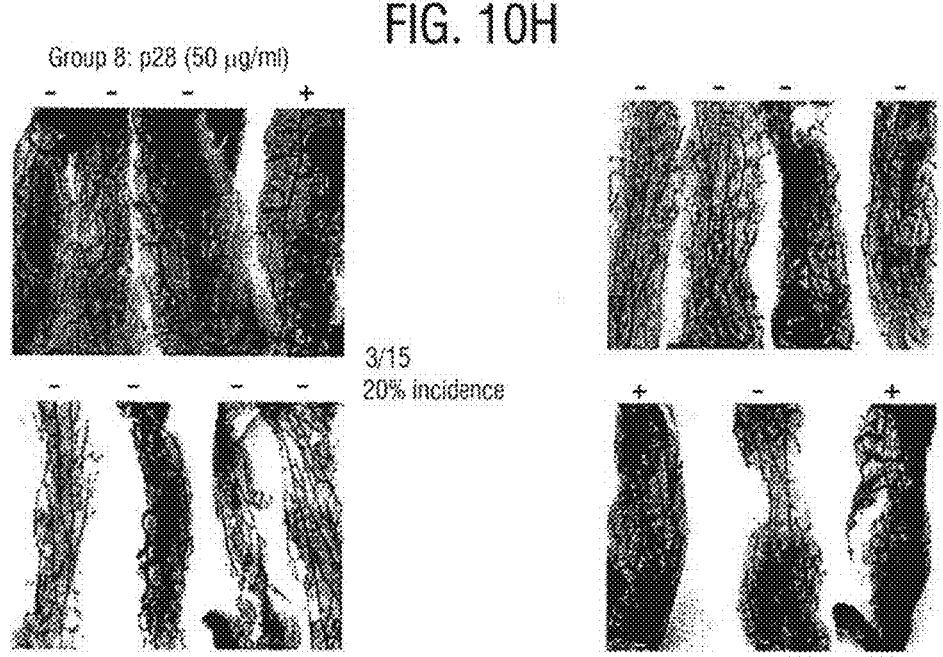
Figure 10I:
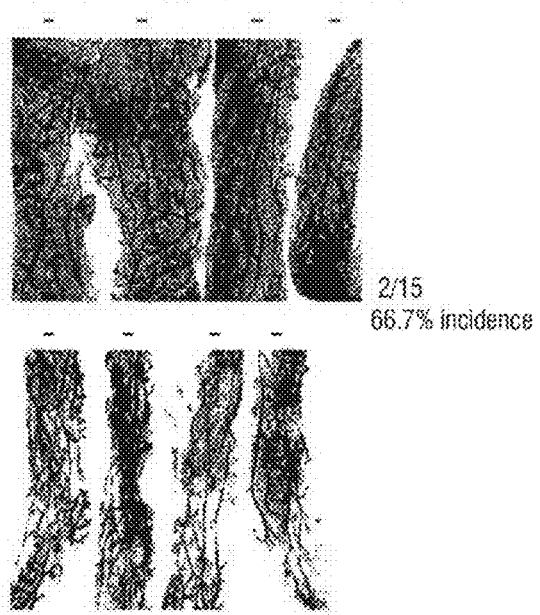
Figure 10I:
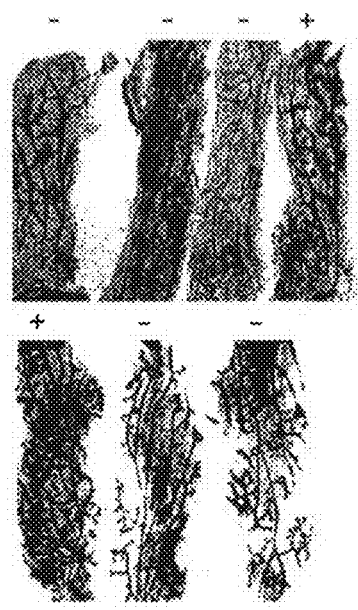
Figure 10J:
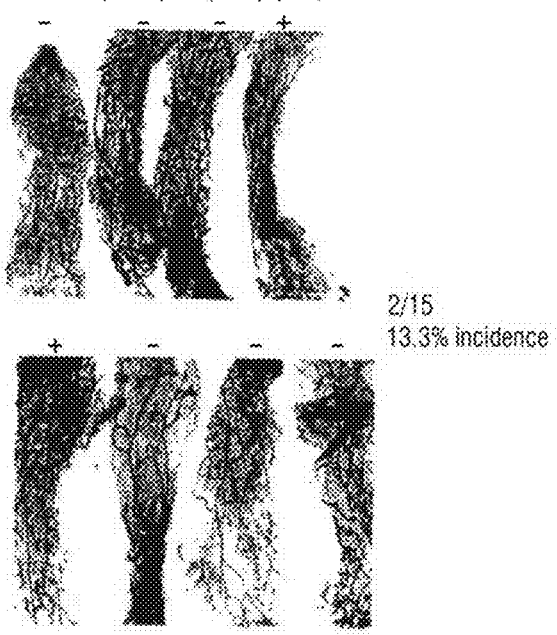
Figure 10J:
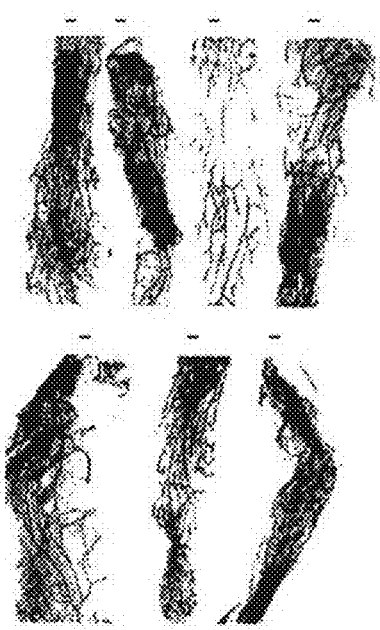
Figure 10K:
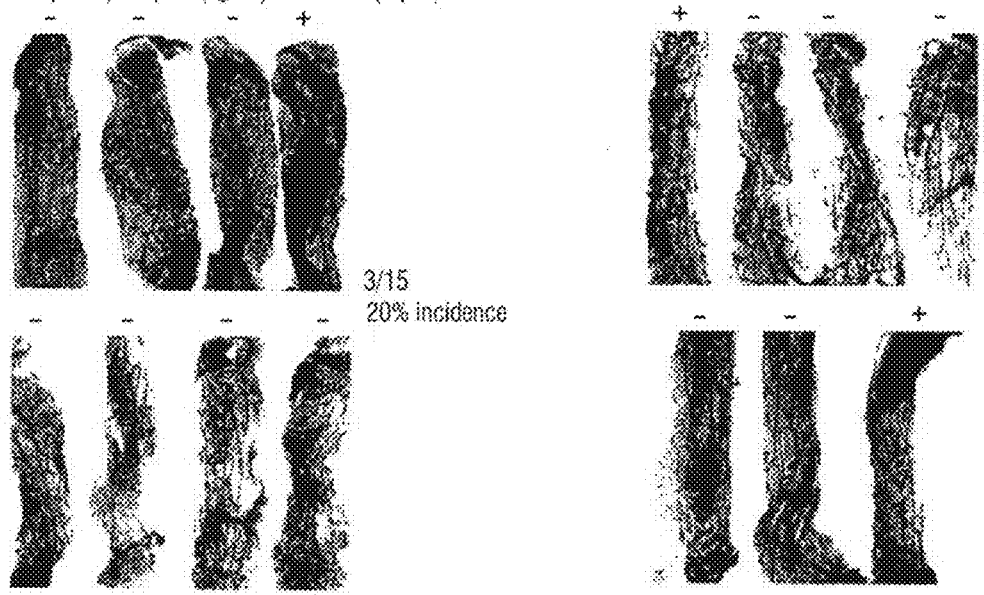
Figure 10L:
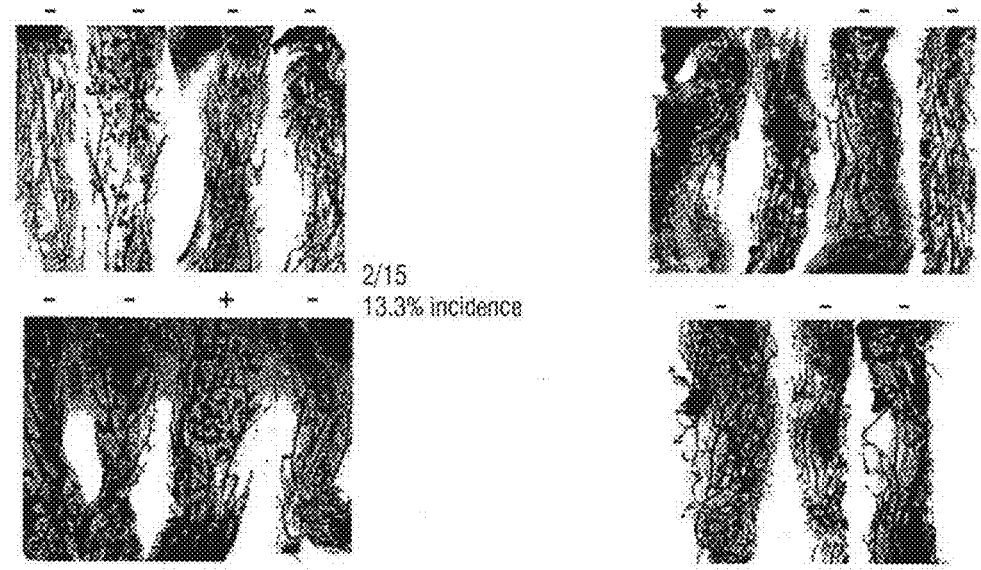

Table 8 and FIG. 9 summarize results for the chemoprevention of MDL by p28 (SEQ ID NO: 2) and in combination with Tamoxifen.

TABLE 8

EFFECT OF POTENTIAL CHEMOPREVENTIVE AGENT ON DMBA-INDUCED MAMMARY DUCTAL LESIONS IN ORGAN CULTURE: BALB/C SCREENING

| Group No. | Treatment | No. of Fields Examined | Fields with ductal lesions | Multiplicity % | Percent Inhibition |
|---|---|---|---|---|---|
| 1 | DMBA | 84 | 69 | 82.1 | |
| 2 | DMBA + Tamoxifen (1 µM) | 71 | 30 | 42.3 | 49% |
| 3 | DMBA + P28 (12.5 µg/ml) | 79 | 44 | 55.7 | 32% |
| 4 | DMBA + P28 (12.5 µg/ml) + Tamoxifen (1 µM) | 88 | 21 | 23.9 | 71% |
| 5 | DMBA + P28 (25 µg/ml) | 73 | 18 | 24.7 | 70% |
| 6 | DMBA + P28 (25 µg/ml) + Tamoxifen (1 µM) | 68 | 12 | 17.6 | 79% |
| Expt. 4 B | | | | | |
| 7 | DMBA | 87 | 62 | 71.3 | |
| 8 | DMBA + P28 (50 µg/ml) | 63 | 15 | 23.8 | 67% |
| 9 | DMBA + P28 (50 µg/ml) + Tamoxifen (1 µM) | 76 | 15 | 20 | 72% |
| 10 | DMBA + P28 (100 µg/ml) | 82 | 12 | 14.6 | 80% |
| 11 | DMBA + P28 (100 µg/ml) + Tamoxifen (1 µM) | 73 | 14 | 19.2 | 73% | p28 (SEQ ID NO: 2) (12.5 µg/ml) suppressed 32% of the MDL formation, whereas Tamoxifen alone inhibited nearly 50% of the lesions. The combination of low p28 (SEQ ID NO: 2) and Tamoxifen increased inhibition to 71%. All chemopreventive agents at all concentrations were statistically significant compared to DMBA alone. At the same time, p28 (SEQ ID NO: 2) (12.5 µg/ml) or Tamoxifen alone were also significantly different as compared to combination treatment. Results show that p28 (SEQ ID NO: 2) can suppress both MAL and MDL development. p28 (SEQ ID NO: 2) (12.5 µg/ml) in combination with Tamoxifen results in significantly enhanced chemopreventive activity compared to either agent alone. Azurin and p28 (SEQ ID NO: 2) inhibited both estrogen progesterone dependent ductal lesions as well as independent alveolar lesions.

Mechanism of Preferential Entry into Cells

Example 6

Entry of p18 (SEQ ID NO: 25) and p28 (SEQ ID NO: 2) Into Human Cell Lines

Cell Culture and Cell Lines:

Human cancer and non-cancer (immortalized and non-immortalized) cell lines were obtained from ATCC [lung cancer (A549 and NCI-H23 adenocarcinoma), normal lung (CCD-13Lu), prostate cancers (DU145 and LN-CAP), normal prostate (CRL11611), breast cancer (MCF-7), normal breast (MCF-10A), colon cancer (HCT116), normal colon (CCD33Co), fibrosarcoma (HT1080), and ovarian cancer (SK-OV3 adenocarcinoma)]. Normal fibroblasts isolated from skin were established. Normal ovarian cells (HOSE6-3) were donated by Dr. S. W. Tsao (University of Hong Kong). Melanoma lines (UISO-Mel-2, 23, 29) were established and characterized. All cells except UISO-Mel-2 were cultured in MEM-E (Invitrogen, Carlsbad, Calif.) supplemented with 10% heat-inactivated fetal bovine serum (Atlanta Biological Inc., Lawrenceville, Ga.), 100 units/ml penicillin and 100 µg/ml streptomycin at 37 C in 5% CO2 or air.

Proliferation Assays/Cell Growth:

Melanoma cells were seeded (four replicates) in flat bottom 24 well plates (Becton Dickinson, Franklin Lakes, N.J.) at a density of 12×103 cells/well. After 24 hrs media was changed and fresh p18 (SEQ ID NO: 25), p28 (SEQ ID NO: 2), azurin or a similar volume of media without peptide (eight replicates) added daily for 72 hr. Cells were then counted in a Beckman Coulter (Z1 coulter particle counter). Values represent the mean±SD of 4 replicates.

MTT Assay:

Melanoma cells were seeded at a density of 2000 cells/well in flat-bottomed 96 well plates (Becton Dickinson, Franklin Lakes, N.J.) and allowed to attach for 24 hrs. Freshly prepared peptide (10 µl) or culture medium was then added to each well. After 24 hrs, medium was changed and p18 (SEQ ID NO: 25), p28 (SEQ ID NO: 2) or azurin added daily. After 72 hr incubation, 10 µl of MTT reagent (Trevigen, Gaithersburg, Md.) was added to each well, the samples incubated for 3 hr, RT/sig 100 µl of detergent added to each well, and the samples incubated for an additional 3 hr at 37° C. Absorbance was measured with a SpectraMax 340 plate reader (Molecular Devices Corporation, Sunnyvale, Calif.) and percent change in the absorbance at 570 nm in treated cells relative to untreated controls determined. Values represent the mean±−SD. Significance between control and treated groups was determined by Student's t-test.

Peptide Synthesis:

All azurin derived peptides including p18, $Leu^{50}$-$Gly^{67}$ LSTAADMQGVVTDGMASG (SEQ ID NO: 25), p28 $Leu^{50}$-$Asp^{77}$ LSTAADMQGVVTDGMASGLDKDYLKPDD (SEQ ID NO: 2), p18b $Val^{60}$-$Asp^{77}$ VTDGMASGLDKDYLKPDD (SEQ ID NO: 38), MAP, Mastoparan-7, and poly arginine ($Arg_8$, SEQ ID NO: 82) were synthesized by C S Bio, Inc. (Melo Park, Calif.). Peptides were received as lyophilized powder aliquoted and stored at −20° C. in air-tight desiccators. All peptides were subsequently analyzed by mass spectrometry and reverse phase HPLC as >95% purity and mass balance.

Predictive Modeling for Azurin Peptides:

GENETYX software (ver. 6.1) was used to generate Robson structure models for azurin derived peptides. Gamier, J., Osguthorpe, D. J., and Robson, B., J Mol Biol, 120: 97-120 (1978). The MAPAS Software was used to predict a given protein structure for strong membrane contacts and define regions of the protein surface that most likely form such contacts. Sharikov, Y. et al, Nat Methods, 5: 119 (2008). If a protein, i.e., azurin, has a membranephilic residue score (MRS)>3, membranephilic area score (MAS) >60%, and coefficient of membranephilic asymmetry ($K_{mpha}$)>2.5, there is a high probability that the protein has a true membrane-contacting region.

Peptide/Protein Labeling:

Peptides were dissolved in 1 ml PBS mixed with Alexafluor 568 dye (Molecular Probes, Eugene, Oreg.) at a 1:2 protein:dye ratio, 100 µl sodium bicarbonate added, and the mixture incubated overnight at 4° C. with continuous stirring. Labeled peptide was separated from free dye by dialyzing against cold-PBS using Slide-A-Lyzerg Dialysis Cassettes 1000 MWCO for p12 and 2000 MWCO for others (Pierce Biotechnology, Rockford, Ill.).

Cell Penetration/Confocal Analysis:

Cells were seeded on glass coverslips and allowed to attach overnight at 37° C. under 5% $CO_2$. Cells were rinsed with fresh media and incubated at 37° C. for 2 hrs in pre-warmed media containing Alexafluor 568 labeled azurin peptides (20 µM) or $Arg_8$ (SEQ ID NO: 82) (5 µM), or media alone. Following incubation, coverslips were rinsed 3× with PBS, cells fixed in 2.5% formalin for 5 min, and washed 2× in PBS, once in d.i. $H_2O$, and coverslips mounted in media containing 1.5 µg/ml DAPI for nuclear counter staining (VECTASHIELD® Vector Laboratories, Burlingame Calif.). Cellular uptake and distribution were photographed under an inverted confocal laser scanning microscope ('Model LC510, Carl Zeiss Inc., Gottingen, Germany).

Peptide co-localization with lysosomes or mitochondria was determined by incubating cells growing on a glass coverslip for 2 hrs at 37° with Alexafluor 568 labeled azurin or peptides. Mitrotracker (MitroTracker® Green FM Invitrogen Corporation, Carlsbad, Calif.) or lysotracker (LysoTracker® Green DND-26 Invitrogen Corporation, Carlsbad, Calif.) was added (final concentration 1 µM) for the last 30 mins of incubation. Cells were rinsed 3× with PBS, fixed in 2.5% formalin for 5 mins, washed 2× with PBS and incubated in 0.1% Triton-X100 in PBS for 15 min. Cells were then incubated with 1 µg/ml rabbit anti-human golgin 97 or anti-human caveolin I (Abeam, Cambridge, Mass.) in PBS with 1% BSA. After 1 hr incubation at 4° C., coverslips were washed once with PBS, incubated 10 min in PBS containing Alexafluor 468 conjugated goat anti-rabbit antibody, washed 2× in PBS and once in d.i. H20. Coverslips were then mounted in media containing 1.5 µg/mlDAPI for nuclear counter staining. Colocalization (yellow) of Alexafluor 568 (red) and Alexafluor 468 (green) was analyzed and photographed.

UISO-Mel-2 cells on coverslips were preincubated in MEM-E containing 100 µg/ml heparin sulfate (Sigma-Aldrich, St. Louis, Mo.) for 30 min and p18 (SEQ ID NO: 25), p28 (SEQ ID NO: 2) or $Arg_8$ (SEQ ID NO: 82) added to bring the final concentration to 20 µM. After 1 hr, coverslips were washed, fixed, and analyzed as described above.

Cell Penetration by FACS:

Cells ($1.0\times10^6$/500 µl PBS) were incubated for 2 hrs at 37° C. with Alexafluor 568 labeled p18 (SEQ ID NO: 25) or p28 (SEQ ID NO: 2) (20 µM), $Arg_8$ (SEQ ID NO: 82) (5 µM), or media alone, washed 3× in PBS, fixed in 2.5% formalin for 5 min, washed twice in PBS, resuspended in 200 µl PBS, and passed through a screen to obtain a single cell suspension. Samples were analyzed with a MoFlo Cell Sorter (Dako, Glostrup, Denmark) $\lambda_{ex}$ 568 nm and $\lambda_{em}$ 603 nm and the fold increase of the mean fluorescence intensity over background levels calculated. Results represent mean fluorescence of three separate experiments.

Entry Inhibitors:

UISO-Mel-2 cells ($3\times10^5$ per 300 µl), maintained in phenol red-, serum-free MEM-E at 37° C., were pretreated with inhibitors, including: Chlorpromazine (inhibitor of clathrin-mediated endocytosis, 10 µg/ml, 60 min); Amiloride (macropinocytosis inhibitor, 50 µM, 30 min); Nystatin (50 µg/ml, 30 min); Methyl-β-cyclodextrin (MβCD, 5 mM, 60 min); Filipin (inhibitor of caveolae-mediated endocytosis, 3 µg/ml, 60 min); Taxol (microtubule stabilizer, 20 µM, 30 min); Staurosporine (cell cycle inhibitor, 250 nM, 10 min); Sodium azide (metabolic inhibitor, 1 mM, 60 min); Oauabain (ATPase-dependent Na+/K+ pump inhibitor, 50 mM, 60 min); Brefeldin A (BFA; Golgi apparatus disrupter, 100 µM, 60 min); Wortmannin (early endosome inhibitor, 100 nM, 30 min); Monensin (inhibits at late endosome/lysosome, 10 µM, 60 min); Nocodazole (inhibits caveosome formation, 10 µM, 60 min); Cytochalasin D (actin filament and microtubule disrupter, 5 µM, 30 min); Benzyl 2-acetamido-2-deoxy-α-D-galactopyranoside (BnGalNac; O-linked glycosylation inhibitor, 3 mM, 48 hrs); Tunicamycin (N-linked glycosylation inhibitor, 20 µg/ml, 48 hrs); and Neuraminidase (cleave sialic acid residues from proteins, IU/ml, 30 min). Final concentrations were derived from the dose response curves of individual inhibitors. Alexafluor 568 labeled p18 (SEQ ID NO: 25) or p28 (SEQ ID NO: 2 (20 µM) were then added, incubated for 1 hr, and the cells washed, fixed and prepared for flow cytometric analysis as described above.

Cell Membrane Toxicity Assays/LDH Leakage Assay:

An LDH leakage assay was performed according to the manufacturer's instructions (CytoTox-One, Promega, WI) with 100 µl of UISO-Mel-2 cells ($5\times10^3$). Cells without peptides/proteins were used as a negative control. Experiments were carried out in triplicate (data represent mean±SEM).

Hemolysis Assay:

Human whole blood samples (2-3 ml) were centrifuged for 10 min at 1000×g, and the pellets washed once with PBS and once with HKR buffer pH7.4 (18). Cell pellets were then resuspended in HKR buffer to 4% erythrocytes, 50 µl transferred to a 1.5 ml tube with 950 µl of peptides, azurin (5, 50 and 100 µM) or 0.1% Triton X-100 in HRK buffer to completely disrupt the RBC membrane. MAP and Mastoparan7 (Bachem California, Inc., Torrance, Calif.) were used as positive controls. After 30 min incubation at 37° C. with rotation, tubes were centrifuged for 2 min at 1000×g, 300 µl of supernatants transferred to a 96-well plate and absorbance recorded at 540 nm.

Kinetics of Entry:

UISO-Mel-2 cells ($5\times10^5$ cells) in 1.5 ml tubes were suspended in MEME media without phenol red. Reactions were started by adding either Alexa fluor 568-conjugated p18 (SEQ ID NO: 25) at 0, 10, 20, 50, 100, 150 and 200 µM for 5, 10, 15 and 20 sec., or Alexafluor 568-conjugated p28 (SEQ ID NO: 2) at 1, 10, 25, 50, 100, 150 and 200 µM for 30, 60, 90 and 120 sec on ice. After incubation, 1 ml of cold-PBS was added to the 250 µl reaction in mixture. Cells were centrifuged twice at 600×g for 2 min at 4° C. At least 10,000 fixed cells were analyzed by flow cytometry in each reaction and their background and relative fluorescence calculated.

$I^{125}$ Labeling of Azurin and Competition Assays:

Peptide binding and entry was determined using a whole cell assay with UISO-Mel-2 cells in HEPES solution (50, 000 cells/ml), were incubated for 30 min at 37° C. with increasing concentrations (0-175 nM) of radiolabeled azurin in the presence/absence of 1000 fold excess of unlabeled p18 (SEQ ID NO: 25), p28 (SEQ ID NO: 2), or azurin, then washed 3 times with ice cold PBS, and radioactively remaining in the cell pellet counted using a gamma counter. Radioactivity in cells incubated with $I^{125}$ azurin alone was considered total binding; radioactivity in the presence of unlabeled azurin, p18 (SEQ ID NO: 25), or p28 (SEQ ID NO: 2) was considered nonspecific binding. Specific binding was determined by subtracting nonspecific binding from total binding and Scatchard plots generated.

Example 7

Figure 11A:
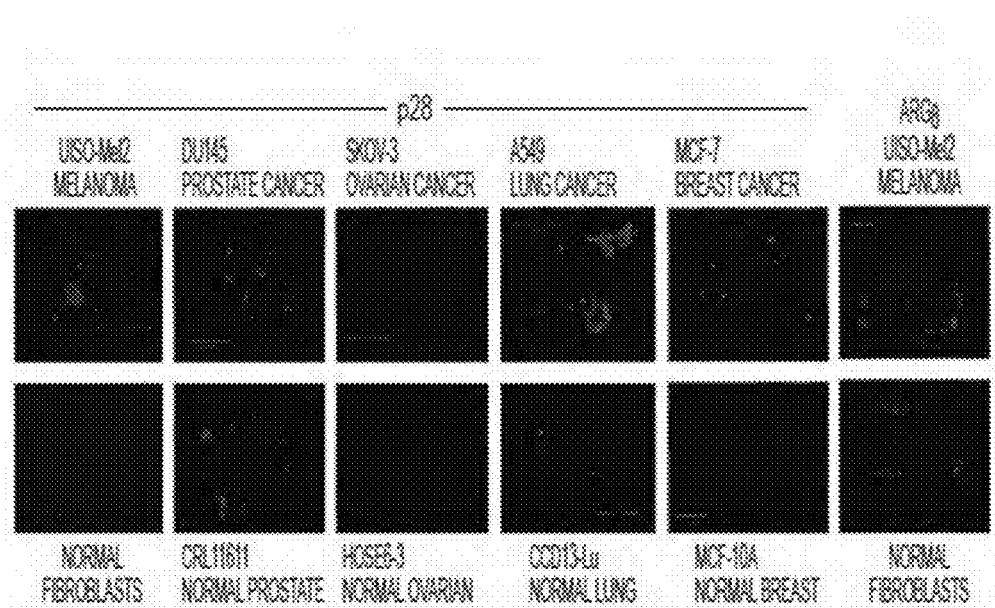
FIGS. 11A-D.
Figure 11B:
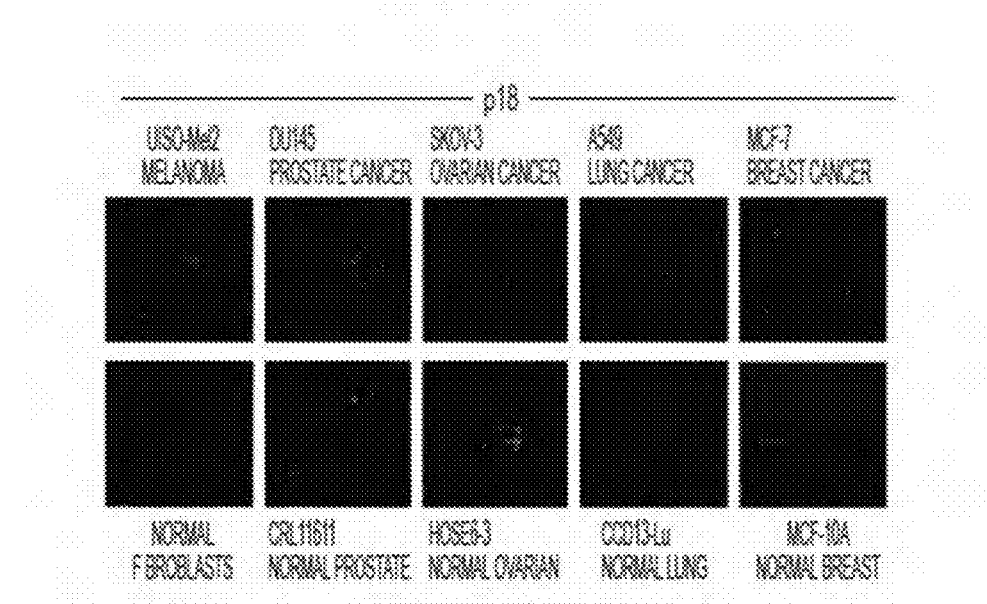

Domain of p28 (SEQ ID NO: 2) Responsible for Preferential Entry into Cancer Cells Initial data from peptide-GST constructs defined aa 50-77 of azurin as a putative PTD for cell penetration, which fits well with structural evidence for an α-helical region encompassing residues 54-67 of azurin stabilizing the azurin molecule. Confocal analyses initially suggested that p28 (SEQ ID NO: 2) and p18 (SEQ ID NO: 25) of p28/azurin (FIGS. 11A and 11B) penetrated human melanoma, prostate, lung, breast and ovarian cancer cells with relatively similar efficiency, but did not penetrate histologically matched normal cell lines to the same degree (FIGS. 11A and 11B). A singular exception was CCD13-Lu, a cell line derived from lung fibroblasts. The cationic $Arg_8$ (SEQ ID NO: 82) was rapidly and efficiently taken up into fibroblasts (FIGS. 11A and 11B) and all other normal cell lines tested (data not shown).

Figure 11C:
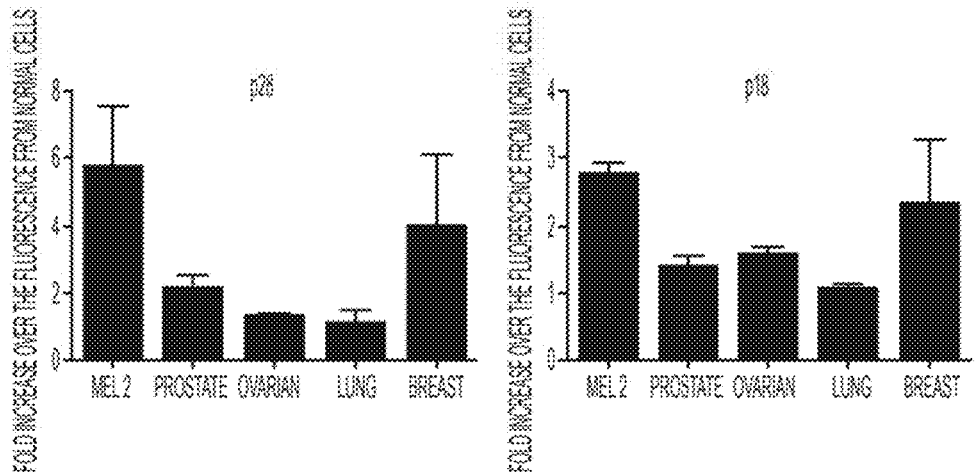
Figure 11D:
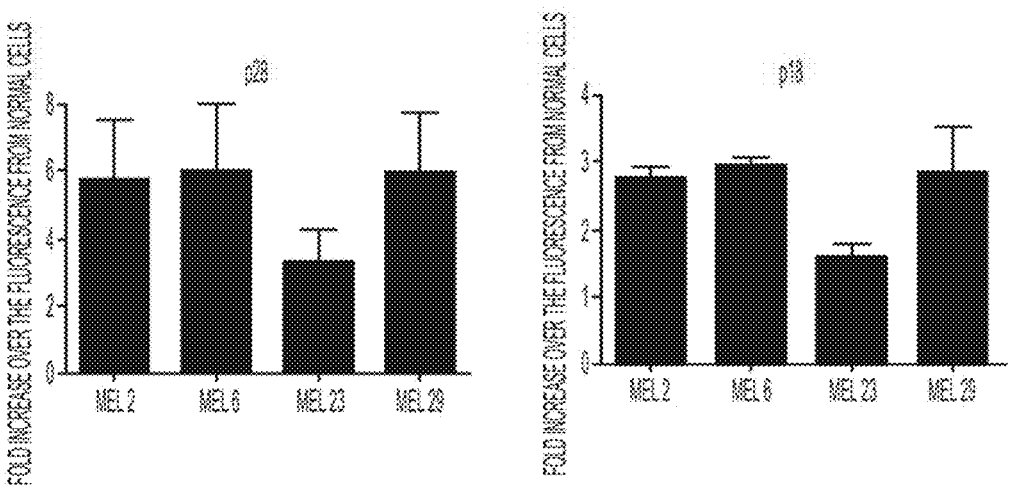

These observations were essentially confirmed by a more sensitive FACs analyses (FIG. 11C) where p28 (SEQ ID NO: 2) fluorescence was about 0.5-6 and p18 (SEQ ID NO: 25) about 0.5-3 fold higher than the corresponding normal cell line, with the exception of lung cancer. A similar pattern in intracellular fluorescence intensity was observed within a histopathologic subtype, melanoma, where the relative intensity of p18 (SEQ ID NO: 25) was about 50% of that observed with p28 (FIG. 11D). Fluorescence intensity over background was also consistently lower in normal and cancer cell pairs exposed to p18 (SEQ ID NO: 25) than p28 (SEQ ID NO: 2) (data not shown), again suggesting less p18 (SEQ ID NO: 25) entered individual cells. In all cases, the degree of entry of p18 (SEQ ID NO: 25) and p28 (SEQ ID NO: 2) into either cancer or normal cells was significantly less than that observed with $Arg_8$ (SEQ ID NO: 82), where no preference for entry was observed (FIGS. 11A and 11B). The predicted Robson structure (data not shown) of p18 (SEQ ID NO: 25) suggests that the C-terminal amino acids form a partial β-sheet. This and the shorter length of p18 (SEQ ID NO: 25), which lacks the hydrophilic C-terminal 10 amino acids (aa 68-77) (SEQ ID NO: 40) of p28 (SEQ ID NO: 2), suggests that p18(SEQ ID NO: 25), as a putative PTD for azurin, may have a more rapid entry into cancer and normal cells via a non-endocytotic over an endocytotic or membrane receptor mediated process. MAPAS data (MRS 3.74, MAS 87.1, $K_{mpha}$ 2.37) predict that aa's 69, 70, 75, 76, 85 of azurin provide the best opportunity for membrane contact, suggesting the C-terminal region of p28 (SEQ ID NO: 2), not present on p18 (SEQ ID NO: 25) (aa 50-67) is most likely to contact specific residues on the cell membrane, irrespective of a cell's status.

Figure 12A:
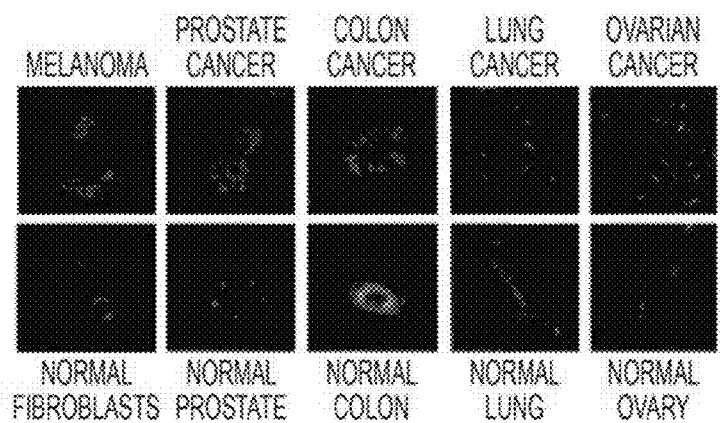
FIGS. 12A and B. Depict photographs showing entry of azu 60-77 (p18b, SEQ ID NO: 38) and azu 66-77 (p12, SEQ ID NO: 39) into cancer and normal cells. Cells were incubated with alexafluor 568 labeled p18b (SEQ ID NO: 38) (A) or p12 (SEQ ID NO: 39) (B) at 37° C. for 2 hrs and images recorded by confocal microscopy.
Figure 12B:
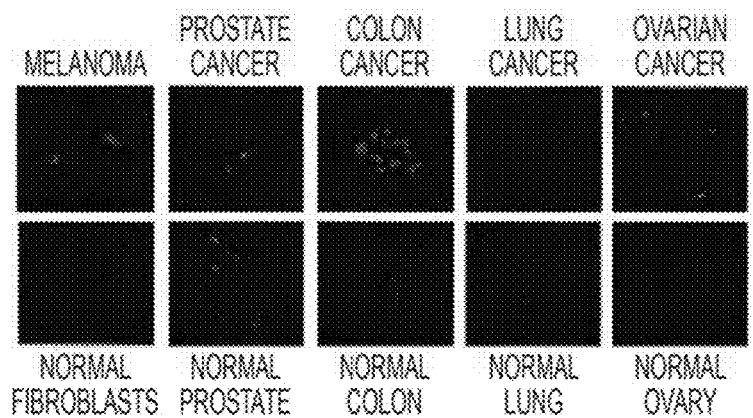

The preferential penetration of p18 (SEQ ID NO: 25) and p28 (SEQ ID NO: 2) was confirmed by exposing the same cell lines to azurin 60-77 (p 18b, SEQ ID NO: 38), or aa 66-77 (p12, SEQ ID NO: 39), the C-terminal 12 aa of p28 (FIGS. 12A, B). Here, the preferential penetration observed with p18 and p28 was completely abolished. p18b (SEQ ID NO: 38) (theoretical pI 4.13) has a short α-helix and partial β-sheet, and is extremely hydrophilic which together may negate preferential entry. p12 (theoretical pI 4.33) lacks a secondary α-helical structure, but is also hydrophilic suggesting overall hydrophilicity may be a major contributor to the decrease in selectivity of cell penetration.

Example 8

Cell Penetration is not a Result of Membrane Disruption

Figure 13A:
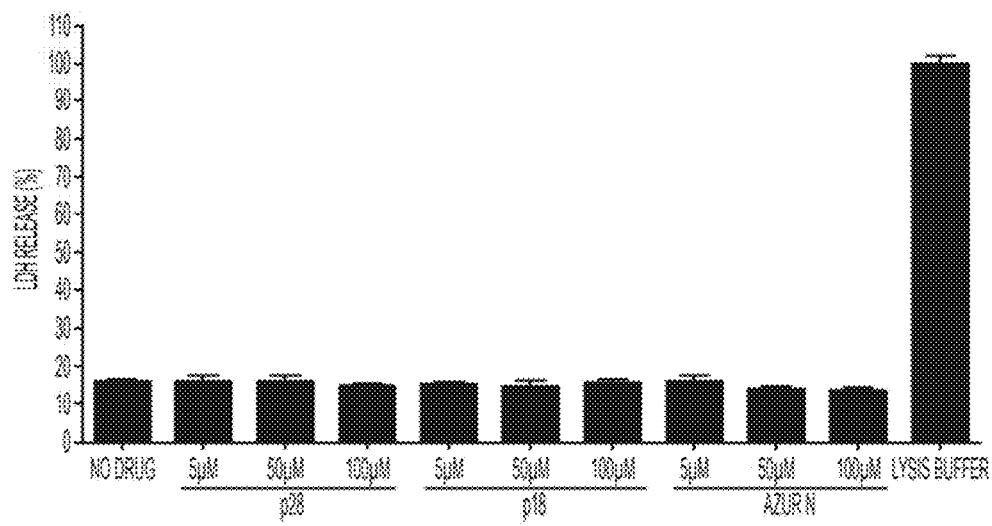
FIGS. 13A and B. Graphs depicting cellular membrane toxicity of azurin and its peptides. (A) LDH leakage assay of UISOMel-2 cells exposure for 10 min to different concentrations of p28 (SEQ ID NO: 2), p18 (SEQ ID NO: 25) and azurin at 37° C. A standard lysis buffer (cytotox-one reagent) was included as a positive control. Changes in fluorescence following exposure were measured at k,x 560 nm and kern 590 nm. Lysis buffer was defined as 100% LDH release. Data represent % of positive fluorescence of control. Data are shown as mean±SEM. (B) Hemoglobin leakage from human erythrocytes incubated with p28 (SEQ ID NO: 2), p18 (SEQ ID NO: 25) and azurin. Human erythrocytes were incubated with peptide for 30 min at 37° C. and absorbance at 540 nm determined. Hemoglobin release following 0.1% Triton X-100 was defined as 100% hemoglobin release. Data represent mean±SEM of triplicate determinations.
Figure 13B:
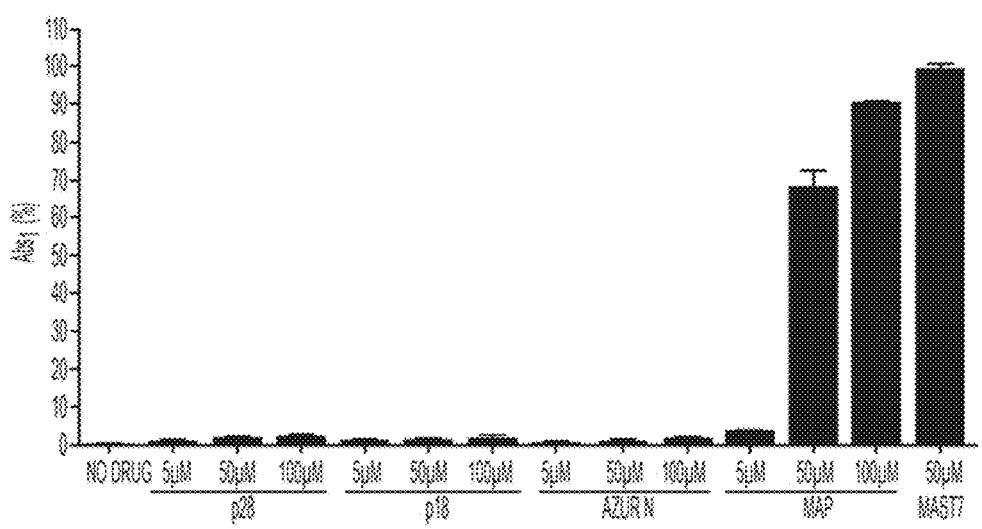

Cell penetration by azurin, p28 (SEQ ID NO: 2), and p18 (SEQ ID NO: 25) does not result from membrane disruption. An LDH leakage assay using UISO-Mel-2 cells in the presence of 5-100 μM p28 (SEQ ID NO: 2), p18 (SEQ ID NO: 25) or azurin (FIG. 13A) suggested that neither peptide nor azurin entered cells by altering plasma membrane integrity. The lack of membrane disruption was confirmed by determining the hemolytic activity of azurin, p28 (SEQ ID NO: 2), and p18 (SEQ ID NO: 25) on human erythrocytes against the receptor mimetic MAP and mast cell degranulating peptide mastoparan 7, which translocates cell membranes as an amphipathic alpha-helix, and activates heterotrimeric G proteins. Mastoparan 7 caused complete cell lysis at 25 μM, while azurin, p28 (SEQ ID NO: 2), and p18 (SEQ ID NO: 25) had no hemolytic effect when compared to control (no peptide) (FIG. 13B).

Figure 14A:
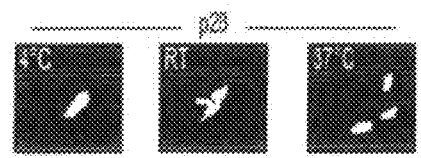
FIGS. 14A-D. Depict photographs showing temperature dependent and competitive internalization of p28 (SEQ ID NO: 2) and p18 (SEQ ID NO: 25) into UISO-Mel-2 cells. Penetration of Alexafluor 568 labeled p28 (SEQ ID NO: 2) (A) or p18 (SEQ ID NO: 25) (B) at 2011M was evaluated by confocal microscopy at different temperatures. (C) and (D) Confocal analysis of entry of Alexafluor 568 labeled p28 (SEQ ID NO: 2) (C) or p18 (SEQ ID NO: 25) (D) at 5 µM into UISO-Mel-2 cells after 30 min at 37° C. in the presence/absence of unlabeled peptide (200 fold excess).
Figure 14B:
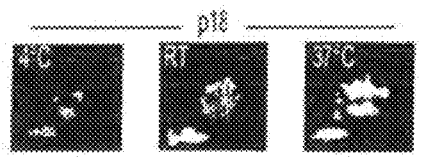
Figure 14C:
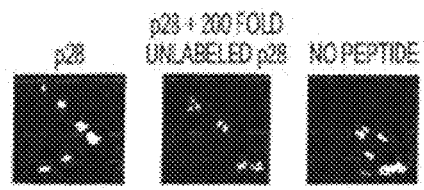
Figure 14D:
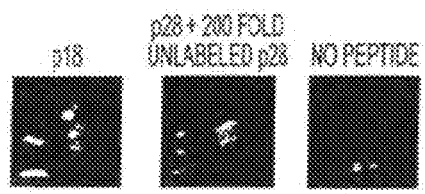

Example 9 p18 (SEQ ID NO: 25)/p28 (SEQ ID NO: 2) Penetration is Energy Dependent and Saturable The penetration of p28 (SEQ ID NO: 2) (FIG. 14A) and p18 (SEQ ID NO: 25) (FIG. 14 B) into UISO-Mel-2 cells is temperature dependent. Cell penetration and intracellular transport occurs relatively slowly over 3 hr at 4° C., while entry and intracellular transport through various compartments is rapid at 22 and 37° C. as p18 (SEQ ID NO: 25) and p28 (SEQ ID NO: 2) were present in the nucleus of UISO-Mel-2 cells within 2 hrs post exposure. The penetration of 5 μM p28 (SEQ ID NO: 2) (FIG. 14C) or p18 (SEQ ID NO: 25) (FIG. 14D) into UISO-Mel-2 cells after 30 min in the presence of a 200 fold excess of unlabeled peptide was severely curtailed, suggesting that entry was a saturable process and specific receptors or cell surface proteins or specific residues were, at least in part, responsible for initial entry.

Example 10

Kinetics of p28 (SEQ ID NO: 2) and p18 (SEQ ID NO: 25)

The kinetics of p28 (SEQ ID NO: 2) and p18 (SEQ ID NO: 25) entry into UISO-Mel-2 cells relative to human fibroblasts was calculated after incubation, when cells were fixed and mean fluorescence intensity (MFI) determined. The Km and Vmax of each peptide were calculated by plotting peptide concentration (μM) vs velocity (MFI/sec) or by Scatchard analysis. Although the penetration of azurin fragments 50-67 (p18 (SEQ ID NO: 25): Vmax 2.46, Km 101.6) and 50-77 (p28 (SEQ ID NO: 2): Vmax 1.87, Km 159.1) into cancer and normal cells (Vmax 2.88, Km 102.1 and Vmax 1.89, Km 166.0, respectively) differs significantly from each other, with p18 (SEQ ID NO: 25) entering −42% faster, the rate of the entry of each peptide into normal and cancer cells is virtually identical. The increase in amount of fluorescence following exposure of cancer cells to p28 (SEQ ID NO: 2) relative to p18 (SEQ ID NO: 25) is likely due to the increase in the amount of p28 (SEQ ID NO: 2) entering malignant cells. $^{125}$I azurin and p18 (SEQ ID NO: 25) bound to UISO-Mel-2 cells with a similar affinity. In contrast, significantly more p28 (SEQ ID NO: 2) ($K_d$ 2.5 µm, Bmax 3.0 pm) bound to UISO-Mel-2 cells with a higher affinity when exposed for a longer period of time (20 min vs 2 min) at a higher temperature (37° C. vs 4° C.) than either p18 (SEQ ID NO: 25) ($K_d$ 18 min, Bmax 0.51 pm) or azurin ($K_d$ 10 nm and 0.48 pm). These results show that azurin, p28 (SEQ ID NO: 2), and p18 (SEQ ID NO: 25) all bind with relatively high affinity and capacity to a site on the cancer and normal cell surface prior to entry, but may enter via more than one mechanism.

Example 11 p18 (SEQ ID NO: 25)/p28 (SEQ ID NO: 2) Penetration Involves Caveolae and the Golgi Complex Peptides called cell-penetrating peptides (CPPs) or cell-delivery vectors (CDVs), such as penetratin, transportan, Tat (amino acids 47-57 or 48-60), and the model amphipathic peptide MAP, are short, amphipathic and cationic peptides and peptide derivatives, usually containing multiple lysine and arginine residues. Fischer, P. M., Med Res Rev, 27: 755-795 (2007). They form a class of small molecules receiving significant attention as potential transport agents or delivery vehicles for a variety of cargoes, including cytotoxic drugs, anti-sense oligo-nucleotides, proteins, and peptides, in gene therapy, and as decoy peptides. Hallbrink, M. et al. Biochim. Biophys. Acta 1515: 101-109 (2001); Lindgren, M., et al. Trends Pharmacol. Sci. 21: 99-103 (2000); Gusarova, et al, J Clin Invest, 117: 99-111 (2007); Melnick, A., Biochem Soc Trans, 35: 802-806 (2007); Astriab-Fisher et al., Pharm Res, 19: 744-754 (2002); El-Andaloussi et al., J Gene Med, 8: 1262-1273 (2006); Cashman et al., Mol Ther, 6: 813-823 (2002).

As a class, cationic CPPs such as pTat and Arg$_8$ (SEQ ID NO: 82) enter cells by initially binding to anionic, sulfated proteoglycans prior to endocytosis. Incubation of p28 (SEQ ID NO: 2) and p18 (SEQ ID NO: 25) and Arg$_8$ (SEQ ID NO: 82) with UISO-Mel-2 cells under serum free conditions in the presence/absence of 100 µml heparin sulfite (HS) significantly reduced the amount of intracellular Arg$_8$ (SEQ ID NO: 82), but did not alter the entry of either p28 (SEQ ID NO: 2) or p18 (SEQ ID NO: 25) (FIG. 15A). The penetration of p18 (SEQ ID NO: 25) and p28 (SEQ ID NO: 2) into UISO-Mel-2 cells in the presence or absence of a specific inhibitor of O-linked glycosylation, BnGalNac, and neruaminidase, which cleaves sialic acid residues, was further characterized (FIG. 15B), and no inhibition of penetration was observed. However, tunicamycin, an inhibitor of N-linked glycosylation, significantly reduced the penetration of p18 (SEQ ID NO: 25) and p28 (SEQ ID NO: 2) across the cell membrane.

The entry of p18 (SEQ ID NO: 25) and p28 (SEQ ID NO: 2) into UISO-Mel-2 cells was also analyzed using inhibitors of energy dependent transport mechanisms, i.e., ATP. Sodium azide (FIG. 15B) and ouabain (Na$^+$K$^+$ ATPase pump) did not significantly inhibit the penetration of either peptide suggesting non endocytotic pathways might also be involved in the penetration of these peptides. Chlorpromazine (CPZ), a specific inhibitor of clathrin mediated endocytosis, also had no effect on penetration, nor did the macropinocytosis inhibitor amiloride. (FIG. 15B). Stabilization of microtubules with taxol had no effect on penetration, but disruption of actin filaments and macropinocytosis with Cytochalasin D produced a small (−20%), reproducible inhibition of the penetration of p18 and p28. The lack of effect of amiloride shows that the inhibitory activity of Cytochalasin D is probably through its effect on actin filaments.

Inhibition of the cell cycle with staurosporine did not block penetration, showing that penetration was not cell cycle specific. The lack of effect of staurosporine on p18 (SEQ ID NO: 25) and p28 (SEQ ID NO: 2) penetration of the cancer cell plasma membrane also shows that a Src kinase/tyrosine kinase dependent pathway was not involved in penetration, was dynamin independent, and hence independent of caveolae budding. Neither p18 nor p28 co-localized with flotillin-1 (data not shown) a protein that resides within the plasma membrane and in a specific population of endocytic intermediates, again arguing against a role for flotillin and dynamin in internalization. In contrast, nocodazole, which disrupts caveolae transport and inhibitors of cholesterol mobilization and hence, caveolae-mediated endocytosis, inhibited penetration 50-65%.

The intracellular disposition of p18 (SEQ ID NO: 25) and p28 (SEQ ID NO: 2) was then analyzed using wortmannin, an inhibitor of early endosome formation, monensin, which inhibits late endosome/lysosome, and brefeldin A (BFA), a disrupter of the Golgi apparatus. Wortmannin did not block the intracellular accumulation of either p18 (SEQ ID NO: 25) or p28 (SEQ ID NO: 2) showing that, unlike cholera toxin, a caveolae to early endosome pathway is not involved in the intracellular trafficking of p18 (SEQ ID NO: 25) and p28 (SEQ ID NO: 2). The lack of early endosome involvement in the intracellular trafficking of p18 (SEQ ID NO: 25) and p28 (SEQ ID NO: 2) also shows that clathrin mediated endocytosis is not involved in internalization of these peptides.

Figure 15C:
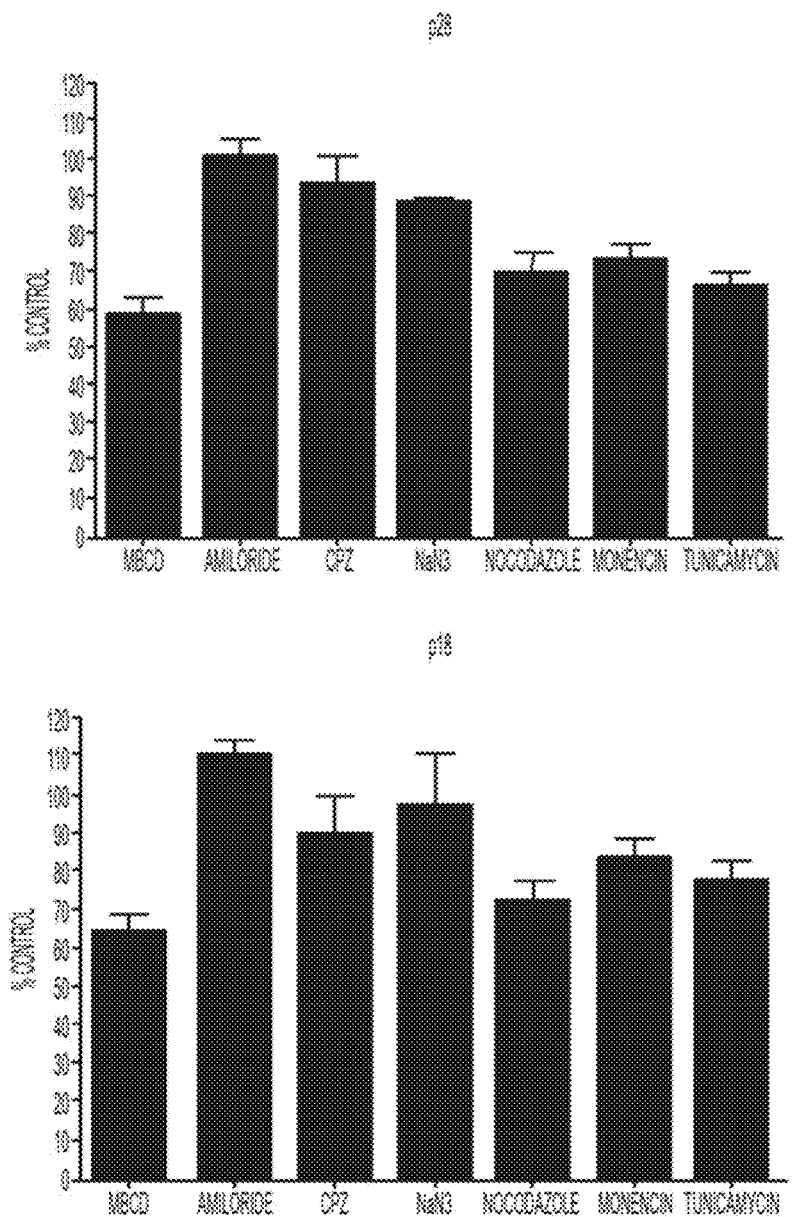
Figure 15D:
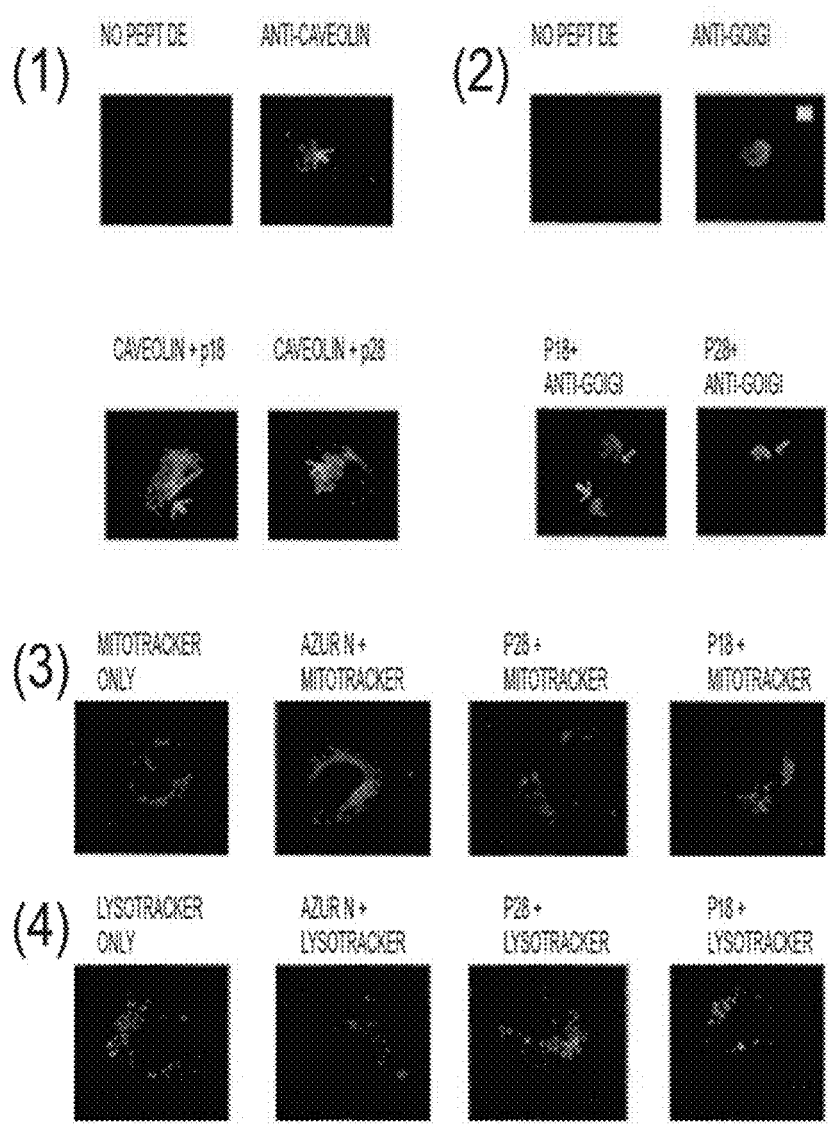

However, monensin (FIG. 15B) and BFA reduced the intracellular accumulation of both peptides with a greater inhibitory effect on p28 (SEQ ID NO: 2) (~30%) than p18 (SEQ ID NO: 25) (~10%) (FIG. 15B). The penetration of p28 (SEQ ID NO: 2) and p18 (SEQ ID NO: 25) into fibroblasts was also inhibited by MβCD, nocodazole, monensin and tunicamycin, but not by amiloride, sodium azide, and CPZ (FIG. 15C). This shows that at least one mechanism of entry into cancer and normal cells may be similar, but additional preferential accumulation into cancer cells may be a function of the number of common membrane receptors or structures, ie., caveolae (FIG. 15D, panels 1, 2). Alexafluor 568 labeled p18 (SEQ ID NO: 25) and p28 (SEQ ID NO: 2) co-localized with caveolin-1 and golgin 97 antibodies (FIG. 15D panels 1,2). This confirms that these organelles are involved in the intracellular trafficking of p18 (SEQ ID NO: 25) and p28 (SEQ ID NO: 2). Interestingly, azurin, but neither p18 (SEQ ID NO: 25) nor p28 (SEQ ID NO: 2) colocalized with mitochondrial specific fluorescence (FIG. 15D panel 3). In contrast, p28 (SEQ ID NO: 2) and azurin, but not p18 (SEQ ID NO: 25), co-localized with lysosomes (FIG. 15D panel 4).

Example 12

Functional Analysis of p28 (SEQ ID NO: 2) and p18 (SEQ ID NO: 25)

Figure 16A:
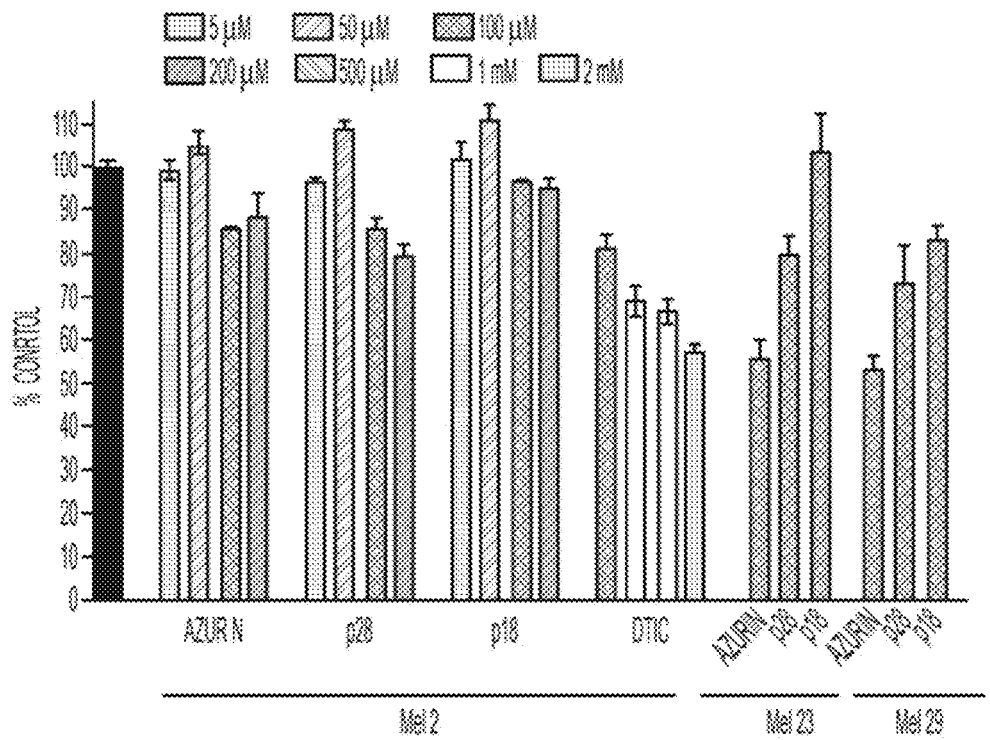
FIGS. 16A and B. Graphs depicting UISO-Mel-2 cells that were incubated with increasing concentrations of azurin, p28 (SEQ ID NO: 2), or p18 (SEQ ID NO: 25) at 37° C. for 72 hrs. MTT (A); Direct cell count (B). Cell viability (MTT) or cell number in control wells were considered as 100%. Data represent mean±SEM.
Figure 16B:
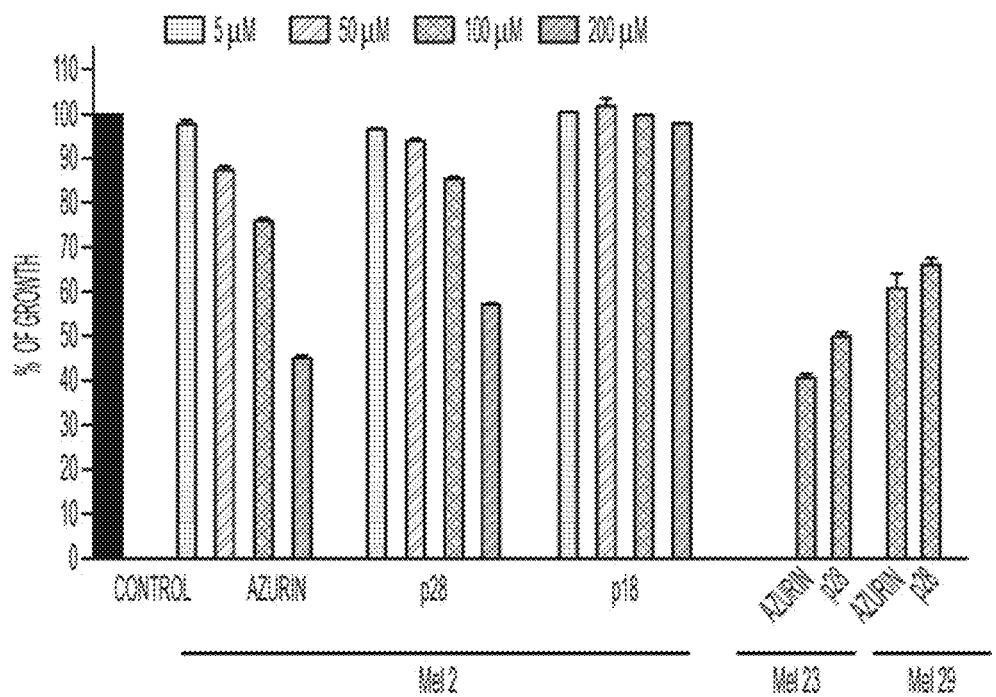

Azurin inhibits the growth of several human cancer cell lines in vitro and in vivo. FIGS. 16A and B illustrate the effect of p18 (SEQ ID NO: 25) and p28 (SEQ ID NO: 2) relative to azurin and dacarbazine (DTIC) on UISO-Mel-2 cells as determined by MTT and cell count. After 72 hrs exposure, azurin decreased (p<0.05) cell survival at 100 and 200 µM ~15% (FIG. 15A). p28 (SEQ ID NO: 2) had inhibited cell survival 14 and 22% (p<0.05) at 100 and 200 µM, respectively. In contrast, p18 (SEQ ID NO: 25) had no effect, while dacarbazine (DTIC) produced a significant dose-related decrease on UISO-Mel-2 survival. Azurin and p28 (SEQ ID NO: 2) (200 µM) also significantly decreased the survival of UISO-Mel-23 and 29 cells. p18 (SEQ ID NO: 25) had no effect on UISO-Mel-2 cell proliferation.

The apparent increase (~30-35%; UISO-Mel-2) in p28 (SEQ ID NO: 2) and azurin inhibition of melanoma cell proliferation, as measured by direct cell counting, shows that the inhibitory effect may reside primarily at the level of cell cycle with apoptosis subsequent to any delay. Although p18 (SEQ ID NO: 25) penetrated cancer cells preferentially, unlike p28 (SEQ ID NO: 2), it had virtually no inhibitory activity on cell proliferation. This result shows that the cytostatic and cytotoxic activity of p28 (SEQ ID NO: 2) lies in the C-terminal 10-12 aa of the sequence.

p53 Experiments

Example 13

Inhibition of Cancer Growth Through p53 Using Azurin-Derived Peptides: Materials and Methods Cell Culture:

Human breast cancer cell lines, MCF-7 (p53 wt), T47D (p53 mut) ZR-75-1 (ATCC; Manassas, Va.) and MDD2 (p53 dominant negative; courtesy of Dr. Andrei V. Gudkov, Rosewell Park Cancer Institute, Buffalo, N.Y.) cells were cultured in MEM-E (Invitrogen, Carlsbad, Calif.) containing 2 mmol/L L-glutamine, 0.1 mmol/L essential amino acids supplemented with 10% heat inactivated fetal bovine serum.

Bacterial Culture and Isolation of Azurin:

*Escherichia coli* JM109 culture and wt azurin purification steps were as described in Yamada, et al., Infect Immun, 70:7054-7062 (2002) and Goto, et al., Mol Microbiol, 47:549-449 (2003).

Peptide Synthesis:

All azurin-derived peptides including p18 (Leu$^{50}$-Gly$^{67}$ LSTAADMQGVVTDGMASG (SEQ ID NO: 25)), p28 (Leu$^{50}$-Asp$^{77}$ LSTAADMQGVVTDGMASGLDKDYLK-PDD (SEQ ID NO: 2)), p18b (Val$^{60}$-Asp$^{77}$ VTDGMAS-GLDKDYLKPDD (SEQ ID NO: 38)), p12 (Ser$^{66}$-Asp$^{77}$ SGLDKDYLKPDD (SEQ ID NO: 39)), and poly arginine (Arg$_8$, SEQ ID NO: 82) were synthesized by C S Bio, Inc. (Menlo Park, Calif.) at >95% purity and mass balance.

Proliferation Assays:

Cells were seeded in MEM-E in quadruplicate into 24-well plates (Becton Dickinson, Franklin Lakes, N.J.) at a density of 12×10$^3$ cells/well and incubated in the presence of 5, 50, 100 and 200 µM p28 (SEQ ID NO: 2) for 24, 48 and 72 hr. Media was changed daily. Control wells received MEM-E without p28 (SEQ ID NO: 2) (8 replicates). Doxorubicin (10 µM) was used as positive control (Z1 coulter; Beckman Coulter Inc., Fullerton, Calif.). Values represent (%) of control. Significance between control and treated groups was determined by Student's t-test.

MTT Assay:

MCF-7 cells were seeded at a density of 2000 cells/well (quadruplicate) allowed to attach for 24 hrs, and freshly prepared peptide (10 µl) or MEM-E added to each well. After 24 hrs, medium and p18 (SEQ ID NO: 25), p28 (SEQ ID NO: 2), azurin or doxorubicin were added daily. After incubation, 10 µl of MTT reagent (Trevigen, Gaithersburg, Md.) was added to each well, the samples incubated for 3 hr at RT, 100 µl of detergent added to each well, and incubated for an additional 3 hr at 37° C. Absorbance (570 nm) was measured (SpectraMax 340 plate reader, Molecular Devices Corporation, Sunnyvale, Calif.) and percent change in treated cells determined. Significance (p<0.05) between control and treated groups was determined by Student's t-test.

Xenograft Model:

Estradiol pre-treated (0.72 mg/pellet, 60-day release; Innovative Research, Sarasota, Fla.) female athymic mice (Harlan; 4-5 weeks old) received 3×10$^6$ MCF-7 cells s.c. in the right flank and were randomized into control and experimental groups prior to treatment. Control animals received PBS (phosphate-buffered saline)/castor oil i.p. Paclitaxel, 15 µmol/kg in PBS/castor oil was injected i.p. on days 10, 14, 21 and 25 post-tumor cell inoculation, p28 (SEQ ID NO: 2), 5 or 10 mg/kg in sterile PBS i.p. daily was injected for 30 days. Tumor volume was determined 3×/week. Body weights were measured twice weekly. Mice were necropsied on day 31 and all tumors collected for histopathology and immunocytochemistry. Significance (p<0.05) between control and treated groups was determined by Student's t-test.

Immunocytochemistry:

BrdU, 50 mg/kg body weight, was injected i.p., 2 hrs prior to necropsy. Tumor cell nuclei labeled with BrdU were identified with an anti-BrdU monoclonal antibody (Beckon Dickinson, Franklin Lakes, N.J.). p53 expression was quantified in formalin fixed, 5µ paraffin sections treated with 10 mM citrate buffer in a pressure cooker for 6 min. Cooled slides were treated with 3% $H_2O_2$ for 10 min to block endogenous peroxidase, covered with blocking serum for 10 min, and exposed to p53 antibody (DO-1, Santa Cruz Biotechnology, Santa Cruz, Calif.) for 2 hrs at room temperature. Rat anti-mouse IgG2a was used as the second antibody. Cells expressing p53 were identified using a Vectastain Elite ABC kit (Vector Laboratories, Burlingame, Calif.) and 3,3'-diaminobenzidine tetrahydrochloride (Sigma Aldrich, St. Louis, Mo.). Slides were counterstained with hematoxylin. Ten non-overlapping fields (250 cells/field) from each tumor periphery were screened (40×) for p53 labeled cells.

Cell Penetration Studies by Confocal Microscopy and FACS:

Cells were seeded overnight on glass cover slips at 37° C. under 5% $CO_2$, rinsed with fresh media, and incubated at 37° C. for 2 hr in pre-warmed media containing Alexa Fluor 568 labeled peptides (20 µM), Arg$_8$ (SEQ ID NO: 82) (5 µM), or media alone. After incubation, cover slips were rinsed 3× with PBS, fixed in 2.5% formalin for 5 min, washed 2× in PBS, once in d.i.$H_2O$, and mounted in media containing 1.5 µg/ml DAPI to counter stain nuclei (VECTASHIELD®, Vector Laboratories). Cyclin B1 and p21 staining were performed in fixed cells, permeabilized by methanol and acetone, washed with PBS and incubated with anti-p21 or cyclin B at a 1:200 dilution (Santa Cruz Biotechnology). Secondary antibody conjugated Alexa Fluor 568 was used at 1:100 dilution. Images were taken and cellular uptake and intracellular distribution were determined using an inverted confocal laser scanning microscope (Model LC510, Carl Zeiss Inc., Gottingen, Germany).

Kinetics of p28 Entry:

MCF-7, MCF-10A, and MDD2 cells ($3\times10^5$ cells) were suspended in MEM-E without phenol red. Reactions were started by adding Alexa Fluor 568-conjugated p28 at 1-300 200 μmol/L for 30, 60, 90 and 120 sec on ice. After incubation, 1 ml of cold-PBS was added to the reaction mixture and cells centrifuged 2× at 600×g for 2 min at 4° C. At least 10,000 fixed cells were analyzed for each time point and concentration by flow cytometry and their background and relative fluorescence calculated.

Cell Cycle Analysis.

MCF-7 and MDD2 cells were incubated with 50 μmol/L of p28 for 48 and 72 hr at 37° C., washed twice with phosphate-buffered saline (PBS) and fixed with 70% ethanol at −20° C. Fixed cells were washed twice with PBS and stained by 50 μg/mL of propidium iodide (PI) in PBS containing 20 μg/mL of RNase A. Flow cytometry (EPICS Elite ESP, Beckman Coulter, Fullerton, Calif.) was used to determine DNA content. A minimum of ten thousand cells were collected in each experiment.

Immunoblotting and Immunoprecipitation Analyses:

MCF-7 and MDD2 cells were cultured with 50 μmol/L p28 (SEQ ID NO: 2) for 0, 24, 48 and 72 hours and whole cell lysates prepared as described in Yamada et al., Infect Immun, 70:7054-7062 (2002). Phosphorylated cdc2 (p-cdc2) was analyzed in cell lysates prepared in 10 mmol/L NaF, 137 mmol/l NaCl, 1 mmol/L $NaVO_4$, 10 mmol/L EDTA, 1% NP-40, 1 mmol/L DTT and proteinase inhibitors (Sigma Aldrich). Ubiquitinated p53 was detected as described in Tsukamoto, et al., Biol Pharm Bull, 27:699-701 (2004) and Kitagaki, et al., Mol Cancer Ther, 7:2445-54 (2008). MCF-7 cells were cultured with p28 at 50 μmol/L for 24, 48 and 72 hr in the absence or presence of the proteasome inhibitor MG132 (Sigma-Aldrich) for 7 hr before harvesting. Equal amounts of protein were immunoprecipitated with anti-p53 antibody. Whole cell lysates (Input) were also subjected to Western analysis with anti-actin antibody as a loading control. Immunocomplexes were washed twice and separated by 4-12% gel and transferred to PVDF membrane. Antibodies against p53 (DO-1 and FL393), p27, CDKs, cyclins (Santa Cruz Biotechnology), p21 (Invitrogen) were used for immunoblotting according to the suppliers' instructions. Actin expression was determined with a monoclonal actin antibody (Santa Cruz Biotechnology) and protein bands visualized using ECL reagent (Santa Cruz Biotechnology).

Anti-p28 Antibody:

A cysteine was introduced at the N-terminus of p28 (SEQ ID NO: 2) (CS Bio Inc., Menlo Park, Calif.), and then the peptide was conjugated with Keyhole limpet hemocyanin (KLH) through the thiol groups of the cysteine residue, the complex was inoculated intradermally and subcutaneously, and a polyclonal antibody specific for 11-28aa of p28 (SEQ ID NO: 2, 60-77 aa of azurin) in rabbits (New Zealand White, Covance, Mich.) was generated. Antibody titer was determined by direct ELISA using p28 (0-3 μg/well). An antibody dilution of 1:140,000 was sufficient to give a reproducible change in absorbance of 0.5 at 450 nm after 15 min incubation with substrate (1-Step PNPP, Pierce, Rockford, Ill.) at 25° C., when 96 well-plates (Nunc, Rochester, N.Y.) were coated with 1 μg/well p28 (SEQ ID NO: 2).

GST Pull-Down and Competition Assay:

p28 (SEQ ID NO: 2) binding to p53 was assayed using a GST pull down assay essentially as described in Punj, et al, Oncogene 23:2367-2378 (2004). Purified GST-p28 (10 and 20 μg/reaction), GST-MDM2 (Murine double minute 2 20 μg/reaction) and GST alone (20 μg/reaction) were bound to Glutathione Sepharose 4B beads (GE Healthcare, NJ) and unbound peptide removed by washing 2× with PBS. Whole cell lysates of MCF-7 cells were generated with PBS/0.1% Triton X-100 containing proteinase inhibitor cocktail (Sigma-Aldrich) on ice for 15 min, and centrifuged at 14000 r.p.m. for 30 min at 4° C. Resultant supernatants were mixed with beads, incubated for 2 hr at 4° C., membranes washed 2× with PBS to remove unbound cell lysate and then boiled in SDS-sample buffer prior to loading on 10% SDS-PAGE. Membranes were then incubated with skim milk (5%) in TBST (Tris/0.05% Tween20) and polyclonal p53 antibody (FL-393, Santa Cruz Biotechnology) in 5% skim milk at 4° C., washed 3× with TBST, secondary rabbit IgG-HRP antibody (Sigma-Aldrich) added, and incubated for 1 hr at room temperature (r/t), and washed 3× with TBST.

Figure 21A:
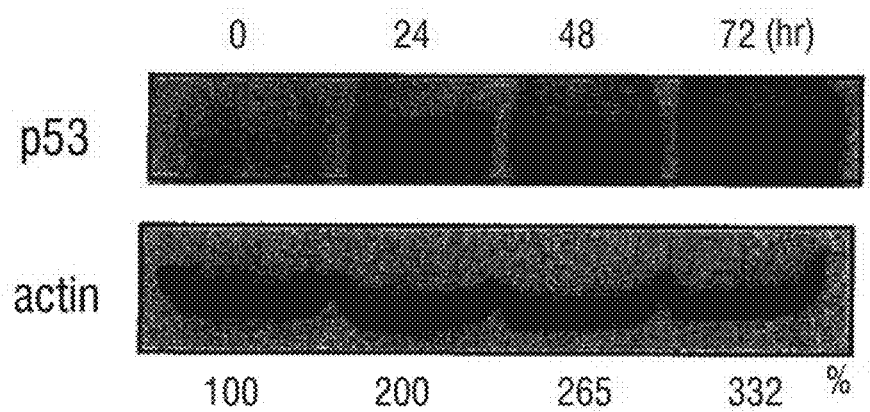
FIGS. 21 (A) and (B) are photographs depicting p53 levels in cells. (A) p53 levels in MCF-7 cells with time after incubation with p28 (SEQ ID NO: 2). (%) change relative to p53 level immediately prior to treatment (0 hr as 100%). (B) GST pull-down assay demonstrating complex formation between GST-p28 and p53. Left to right GST-p28 (10 and 20 µg/reaction), GST-MDM2 (20 µg/reaction) and GST alone (20 µg/reaction). p53 was detected by immunoblotting (IB) using anti-p53 antibody. (C) A photograph depicting competition for p28 binding to GST-p53 by a molar excess of p28 fragments p12 (SEQ ID NO: 39), p18 (SEQ ID NO: 25) and p18b (SEQ ID NO: 38). Relative amount of binding (p28, SEQ ID NO: 2, alone expressed as 100%). M: p28 marker. (D) is a graph depicting a p53 DNA-binding activity assay in MCF-7 nuclear extracts after exposure to p28 (SEQ ID NO: 2) or azurin. Nuclear extracts of $H_2O_2$-treated MCF-7 cells served as an internal control. The p53-oligonucleotide complex was quantified with a monoclonal antibody to p53. Data are expressed as Mean±SEM of triplicates.
Figure 21B:
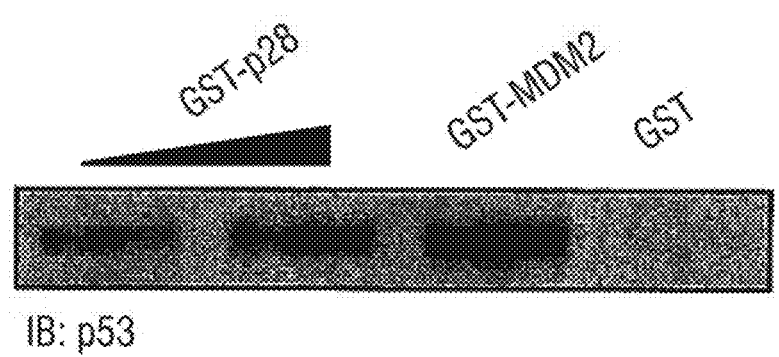
Figure 21C:
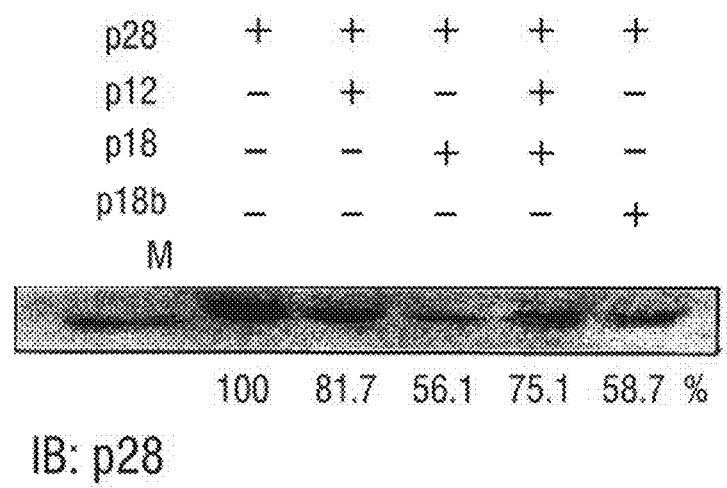

Potential binding sites on p53 were identified as follows. Interaction at the MDM2 binding site (19-26 aa) of p53 was analyzed using a GST-pull down assay in the presence of p28 (SEQ ID NO: 2) (10-50 molar excess) and p53 bands detected by immunoblotting (IB). Three different anti-p53 antibodies, Pab 1801 (32-79 aa; Santa Cruz Biotechnology), ab 2433 (277-296aa; Abcam Inc., Cambridge, Mass.) and Pab1802 (306-393aa; Santa Cruz Biotechnology), representing the broadest coverage of the native p53 protein commercially available, were each reacted with GST-p53 immobilized beads in the presence of p28 (SEQ ID NO: 2). After incubation, samples were washed 2× with PBS to remove unbound p28 (SEQ ID NO: 2), boiled in native PAGE sample buffer (Tri/glycerol/BPB) and loaded on 5% Native-PAGE. Samples were transferred to PVDF membrane by electroblotting (0.2 Amp for 1 hr), membranes blocked with skim milk (5%) in TBST and incubated with a polyclonal antibody to p28 (SEQ ID NO: 2) (1:5000 dilution) in 5% skim milk at 4° C. After washing with TBST, HRP-conjugated rabbit anti-IgG antibody (1:7000 dilution, Santa Cruz Biotechnology) was applied. p28 (SEQ ID NO: 2) bands were visualized using ECL reagent.

p28 (SEQ ID NO: 2) regions binding to p53 were identified using a competition assay between p28 (SEQ ID NO: 2) and the p28 fragments p12 (SEQ ID NO: 39), p18 (SEQ ID NO: 25) and p18b (SEQ ID NO: 38) for GST-p53 (20 μg/reaction) immobilized on Glutathione Sepharose 4B beads. Reactions were incubated for 2 hr at 4° C., washed 2× with PBS to remove unbound p28, then boiled in native PAGE sample buffer (Tri/glycerol/BPB) and loaded on 5% Native-PAGE. Proteins were transferred to a PVDF membrane by electroblotting (0.2 Amp for 1 hr), blocked, and incubated with the polyclonal antibody to p28 at 4° C. for 16 hr. p28 (SEQ ID NO: 2) bands were visualized with ECL reagent. Band intensity was determined using Gel & Graph Digitizing Software, UN-SCAN-IT™ (Silk Scientific Inc., Orem, Utah) and the ratio of specific protein/actin calculated. Numbers displayed below each protein band are relative percentage of the protein band intensity immediately prior to treatment (0 hr expressed as 100%). FIG. 21C.

p53 DNA-Binding Activity:

Nuclear fractions (Nuclear Extraction Kit, Active Motif, Carlsbad, Calif.) were isolated from MCF-7 cells after incubation with either 50 μmol/L p28 (SEQ ID NO: 2) or azurin for 24 hr according to the manufacturers' instructions. Nuclear extract supernatants were collected by centrifugation at 14,000 rpm for 10 min at 4° C. Protein concentrations were determined using the Bradford method. DNA-binding activity of p53 was analyzed using a TransAM p53 kit (Active Motif). Briefly, 40 µl of binding buffer containing DTT and poly[d(I-C)] was introduced to each well to prevent non-specific binding to the p53 consensus oligonucleotide. Nuclear extracts were applied to each well, with $H_2O_2$-treated or buffer only as positive and negative controls, respectively, and incubated 1 hr r/t. Wells were washed 3× and 100 µl of p53 antibody (1:1000 dilution) applied and incubated at r/t for 1 hr. After washing, secondary antibody conjugated with HRP was added, samples incubated for 1 hr and developed for 3 min in the dark. p53 binding to DNA was determined by absorbance at 450 and 655 nm.

RT-PCR: MCF-7 cells were exposed to 50 µmol/L of p28 (SEQ ID NO: 2) for 16, 24, 48 and 72 hr. RNA was extracted using QIAshredder and RNeasy kit (QIAGEN, Valencia, Calf.) and 1 µg of RNA used for reverse transcription with 500 ng of oligo $(dT)_{12-18}$ and SuperScript™ III Reverse Transcriptase (Invitrogen, CA) at 50° C. for 50 min. The annealing temperature was 57° C. (25 cycles) and the primers used were as follows: p53, 5'-CAG CCA AGT CTG TGA CTT GCA CGT AC-3' and 5'-CTA TGT CGA AAA GTG TTT CTG TCA TC (SEQ ID NOS: 87 and 88); GAPDH, 5'-ACC TGA CCT GCC GTC TAG AA-3' and 5'-TCC ACC ACC CTG TTG CTG TA-3' (SEQ ID NOS: 89 and 90). PCR products underwent electrophoresis on a 2% agarose gel and were visualized with ethidium bromide.

Example 14

Figure 17A:
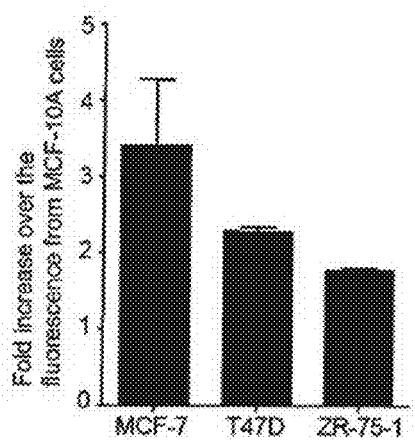
FIG. 17. Graphs depicting preferential penetration of p28 (SEQ ID NO: 2) into human breast cancer cells. (A) Entry of p28 (SEQ ID NO: 2) into human breast cancer cells (MCF-7, T47D, and ZR-75-1) and normal breast cells (MCF-10A) was examined by flow cytometry. Values represent calculated fold increase over fluorescence from normal breast cells. (B) The kinetics of p28 (SEQ ID NO: 2) entry into MCF-7 cells (triangle) relative to MCF-10A cells (circle) was determined by flow cytometric analysis and calculated mean fluorescence intensity (MFI). The $K_m$ and $V_{max}$ were determined by plotting p28 (SEQ ID NO: 2) concentration (µmol/L) vs velocity (MFI/sec). (C and D) Flow cytometric analysis of p28 (SEQ ID NO: 2) entry into MCF-7 and MCF-10A cells in the absence or presence of inhibitors. MCF-7 (C) and MCF-10A (D) cells were pretreated with inhibitor and incubated with 20 µmol/L of Alexa Fluor 568 labeled p28 (SEQ ID NO: 2) for 1 hr. MFI in the absence of inhibitor (control) was considered as 100%. Bars represent Mean±SEM.
Figure 17B:
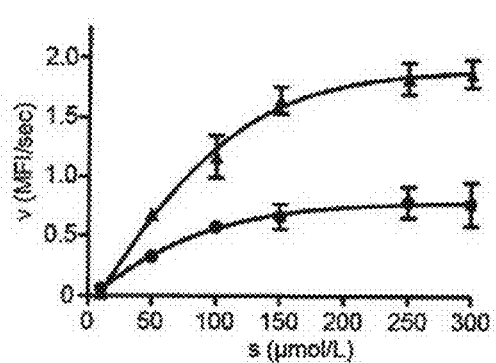
Figure 17C:
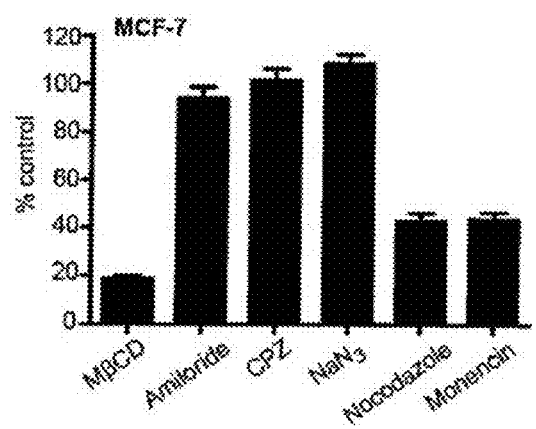
Figure 17D:
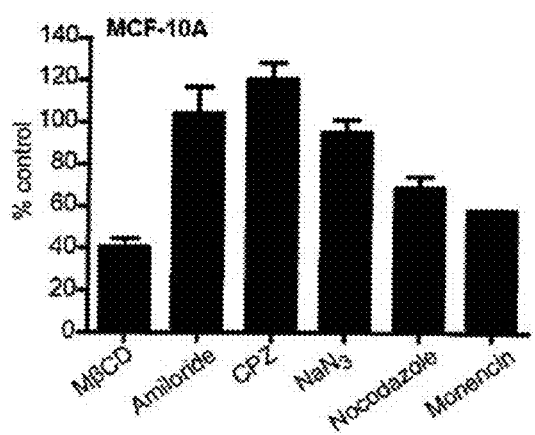

Peptide Entry into Human Breast Cancer Cells p28 (SEQ ID NO: 2) entry into the human breast cancer cell lines MCF-7, T47D, and ZR-75-1, was ~2-3 fold higher than the normal breast cell line, MCF-10A (FIG. 17A). p28 (SEQ ID NO: 2) entry into MCF-7 cells relative to MCF-10A, determined by FACs, showed p28 penetration of MCF-7 breast cancer ($V_{max}$ 1.89 MFI/sec, $K_m$ 144.3 µmol/L) and normal MCF-10A cells ($V_{max}$ 0.79 MFI/sec, $K_m$ 99.4 µmol/L) was saturable and ~2.4 faster in MCF-7 cells (FIG. 17B). Exposure of MCF-7 cells to methyl-β-cyclodextrin (MβCD), a specific inhibitor of caveolae mediated endocytosis, significantly inhibited the penetration of p28 (FIG. 17C). The microtubule-disrupting agent, nocodazole, which inhibits caveosome formation and transport, confirmed p28 (SEQ ID NO: 2) penetration involves caveolae mediated endocytosis (FIG. 17C). In contrast, chlorpromazine (CPZ), amiloride, and sodium azide ($NaN_3$), inhibitors of clathrin mediated endocytosis, macropinocytosis, and energy dependent transport, respectively, had no effect on the penetration of p28 (SEQ ID NO: 2) (FIG. 17C). Monensin, an inhibitor of late endosome/lysosome processing, also reduced the intracellular accumulation of p28 (FIG. 17C). The penetration of p28 (SEQ ID NO: 2) into MCF-10A cells was also inhibited by MβCD, nocodazole, and monensin, but not by amiloride, CPZ, and sodium azide (FIG. 17D). MCF-7 cells were also more sensitive to the effects of MβCD (~2.1 fold higher), nocodazole (~1.6 fold higher), and possibly monensin than MCF-10A (FIGS. 17C and D), showing that although MCF-7 and MCF-10A may share a similar route of entry, the number of entry sites may be greater on (breast) cancer cells.

Example 15

Figure 18A:
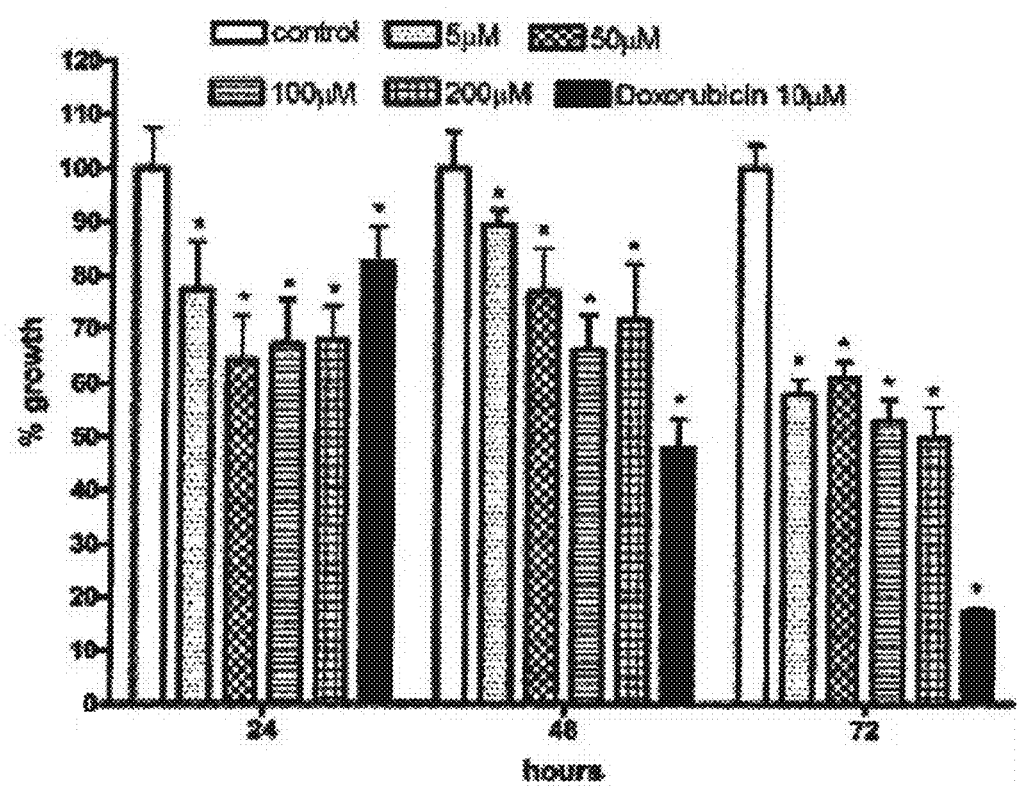
FIG. 18. Graphs depicting growth inhibition of human breast cancer cells by p28 (SEQ ID NO: 2). MCF-7 cells were incubated with p28 (SEQ ID NO: 2) (0-200 µM) at 37° C. for 24, 48 and 72 h. Cell count (A) and MTT assays (B). Doxorubicin (10 µM) was used as a positive control. Cell number or viability of control wells were considered as 100%. Data represent mean % of control±SEM. *, p<0.05. (C) Inhibition of MCF-7 xenograft growth by p28 (SEQ ID NO: 2). A minimum of 10 mice per group were treated with Paclitaxel 15 µmol/kg i.p. on days 10, 14, 21 and 25 or 5 or 10 mg/kg p28 (SEQ ID NO: 2) i.p. daily for 30 days. Bars represent Mean±SEM. *, p<0.05.
Figure 18B:
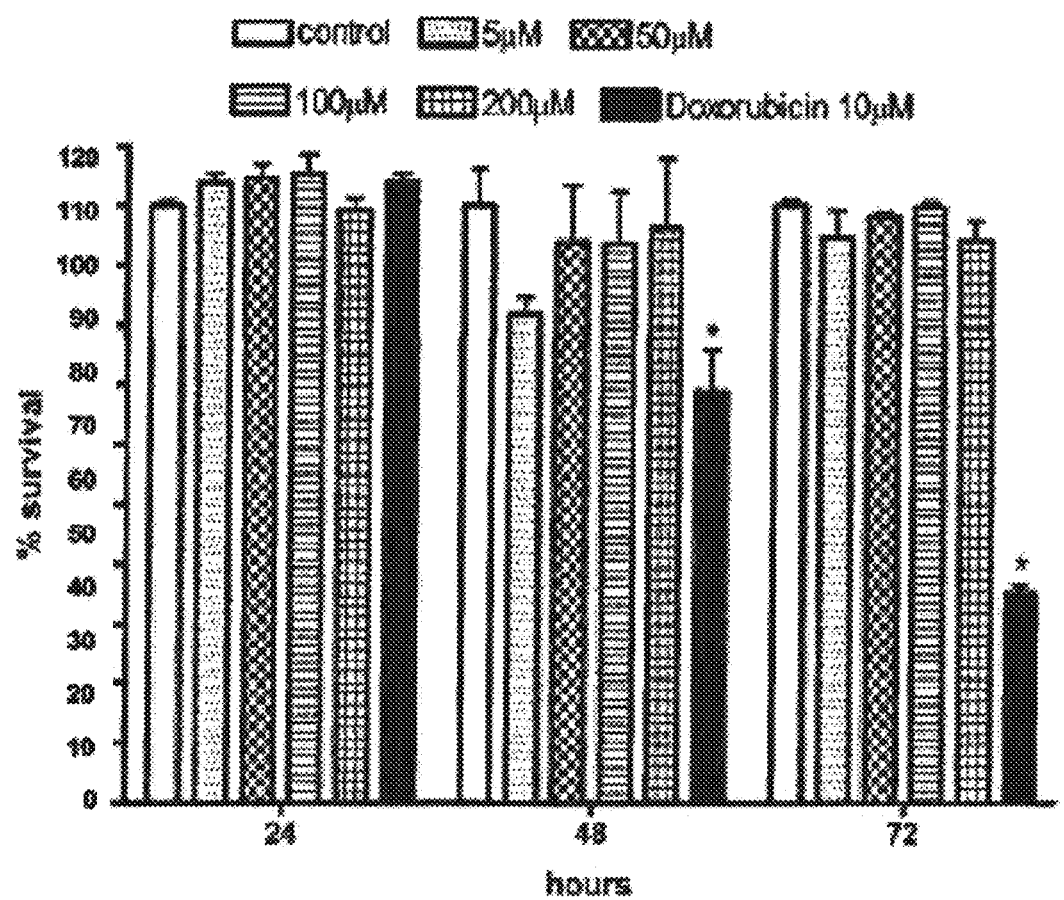
Figure 19A:
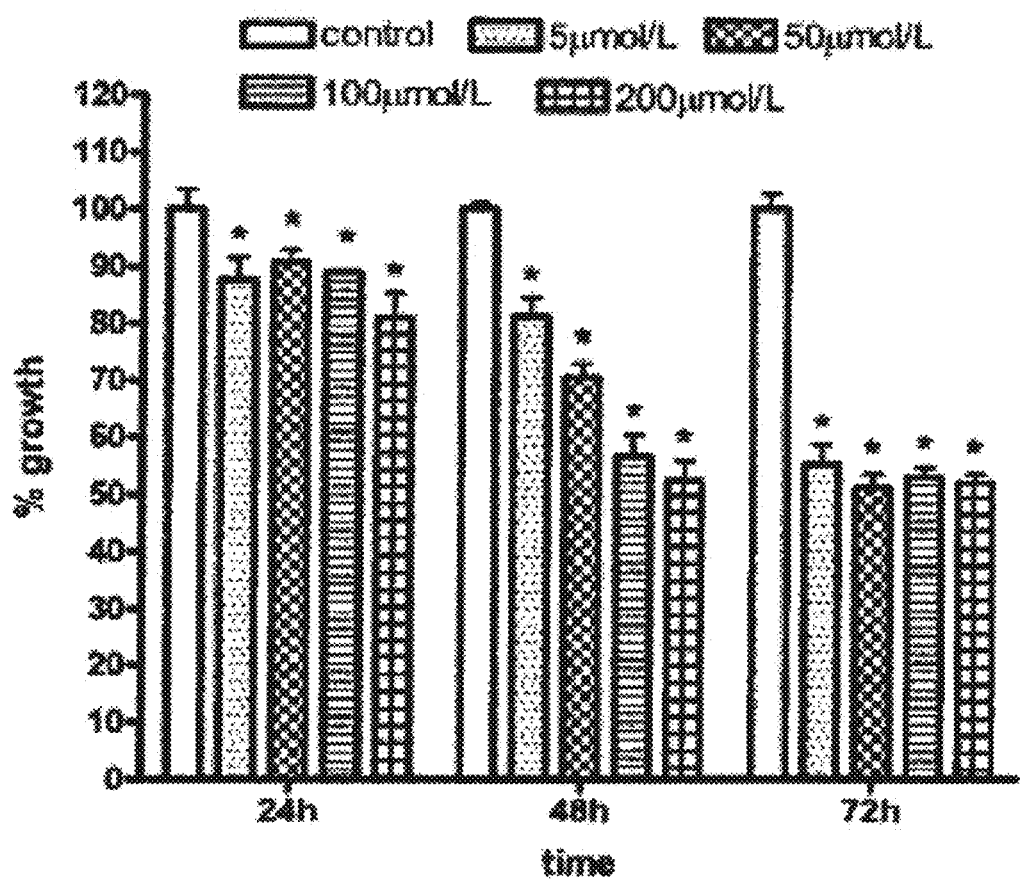
FIG. 19. Graphs depicting growth inhibition of human breast cancer cells by p28. (A) MCF-7 cells were incubated with p28 (SEQ ID NO: 2) (0-200 µmol/L) at 37° C. for 24, 48 and 72 hr and the number of cells counted. (B) ZR-75-1 cells were treated with p28 (SEQ ID NO: 2) for 72 hr in triplicates. Doxorubicin (Doxo) 5-10 µmol/L was used as an internal control. Cell number in untreated (control) wells was considered as 100%. Data represent mean % of control±SEM. *, p<0.05.
Figure 19B:
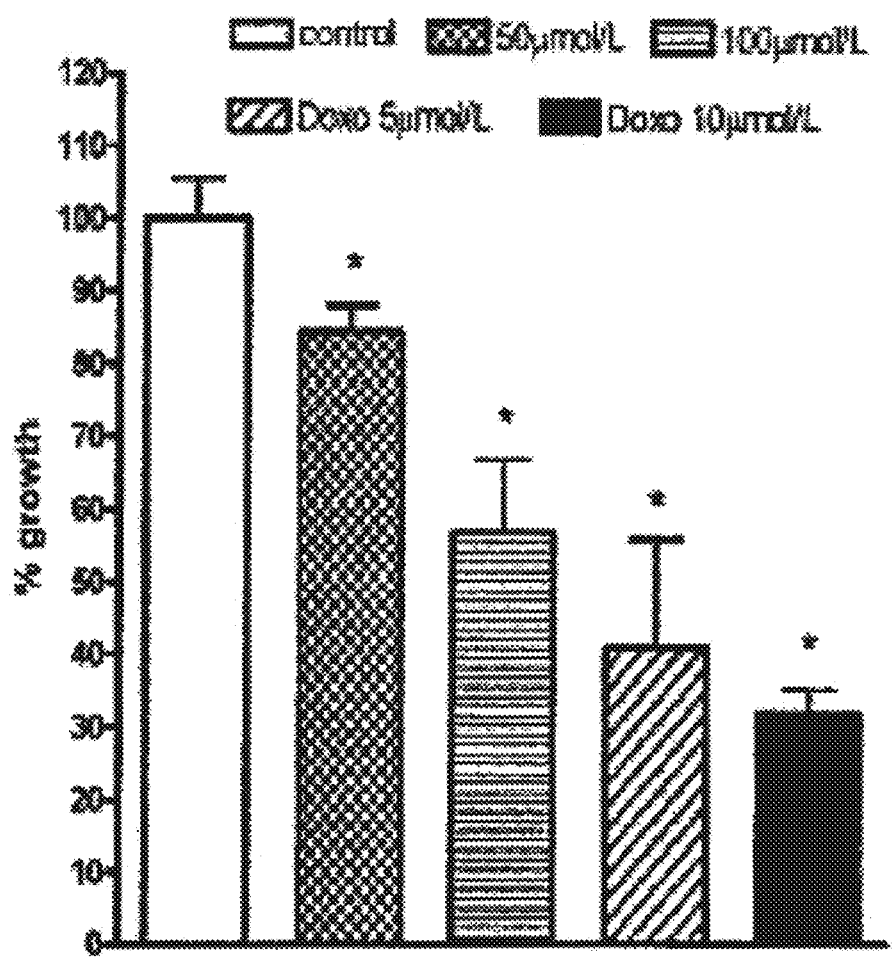

Effect of p28 (SEQ ID NO: 2) Treatment on the Growth of Human Cancer Cells In Vitro and In Vivo Azurin exerts its anti-cancer activity through induction of p53-mediated apoptosis. FIGS. 18A-B and FIG. 19 illustrate the effect of p28 (SEQ ID NO: 2) and doxorubicin on wt p53 (positive) MCF-7 and p53mut ZR-75-1 cells as determined by direct cell count and MTT assay. p28 (SEQ ID NO: 2) inhibited the proliferation of MCF-7 cells (FIGS. 18A and 19A) and ZR-75-1 cells (FIG. 19B) in vitro in a dose and time related manner. In an initial experiment (FIG. 18A), this inhibition produced an initial significant decrease (p<0.05) in cell number of ~23% at 5 µM and ~36% at 50-200 µM after 24 hr exposure. Doxorubicin (a DNA intercalating agent) also significantly inhibited cell growth in a time-dependent manner. Cell survival determined by MTT assay was not significantly altered by p28 (SEQ ID NO: 2), while doxorubicin exhibited a significant time related decrease in MCF-7 cell survival (FIG. 18B). The anti-proliferative effect of p28 (SEQ ID NO: 2) on MCF-7 cells in a second experiment (FIG. 19A) was dose- and time-dependent decreasing (p<0.05) cell number ~9.3%, ~29% and ~50% at 50 µmol/L for 24, 48 and 72 hr, respectively (FIG. 19A). p28 also inhibited (p<0.05) the growth of ZR-75-1 cells, 16% at 50 µmol/L and 44% at 100 µmol/L after 72 hr exposure, similar to the effect of doxorubicin (FIG. 19B).

Figure 18C:
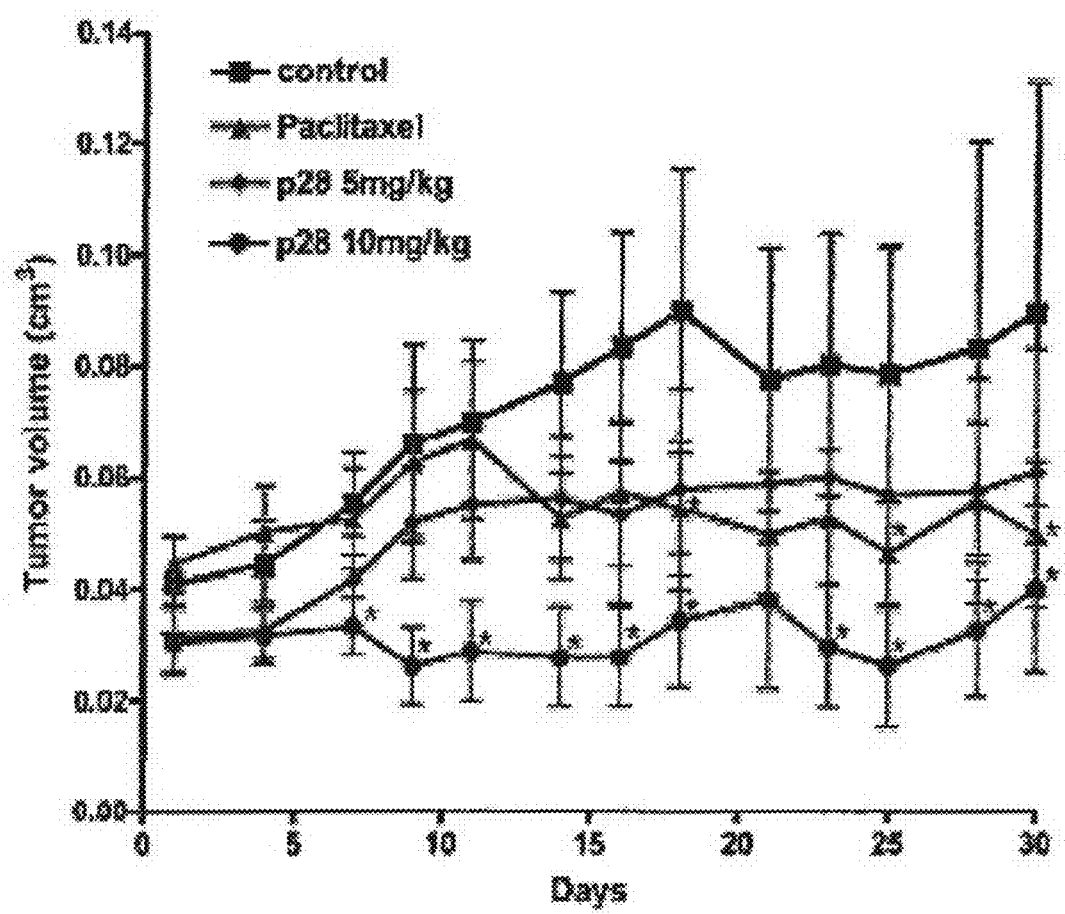

Moreover, p28 (SEQ ID NO: 2) produced a significant dose related decrease in the volume of xenografted MCF-7 cells in athymic mice over a daily, 30-day i.p. exposure (FIG. 18C), decreasing tumor volume (p<0.05) to that observed with Paclitaxel®, without inducing either a loss in body weight or behavioral change. By day 30, 10 mg/kg p28 daily i.p. inhibited MCF-7 growth to a greater extent (~20%) than 15 µmol/kg Paclitaxel® on days 10, 14, 21 and 25 post-tumor cell inoculation, reducing tumor volume below that of Paclitaxel® over almost the entire course of the study. A reduction in BrdU labeling associated with the p28-induced decrease in tumor volume confirmed the reduction in cell proliferation (Table 9). The reduction in BrdU labeling and tumor volume was accompanied by a slight increase in nuclear p53-staining in p28 (SEQ ID NO: 2) and a significant increase in the Paclitaxel® treated groups compared to control (Table 9).

TABLE 9

BrdU and p53 in MCF-7 xenograft tumors

| | N | BrdU (%) | p53 (%) |
|---|---|---|---|
| Control | 7 | 21.0 ± 2.7 | 15.6 ± 0.82 |
| p28 (5 mg/kg) | 4 | 17.6 ± 0.75* | 15.8 ± 0.51 |
| p28 (10 mg/kg) | 3 | 16.1 ± 1.4* | 17.7 ± 0.92 |
| Paclitaxel | 6 | 9.0 ± 1.8** | 25.4 ± 0.65** |

All tumors were collected on day 31 post treatment. Values represent Mean ± SEM.
*p < 0.025;
**p < 0.01 from respective control; student's T-test.

Example 16

Inhibition of Cell Cycle Progression by p28 (SEQ ID NO: 2)

p28 (SEQ ID NO: 2) entered the two isogenic human breast cancer cell lines, MCF-7 and MDD2 (FIG. 20A) with similar kinetics: $V_{max}$ (MCF-7: 1.89 MFI/sec; MDD2: 2.21

Figure 20B:
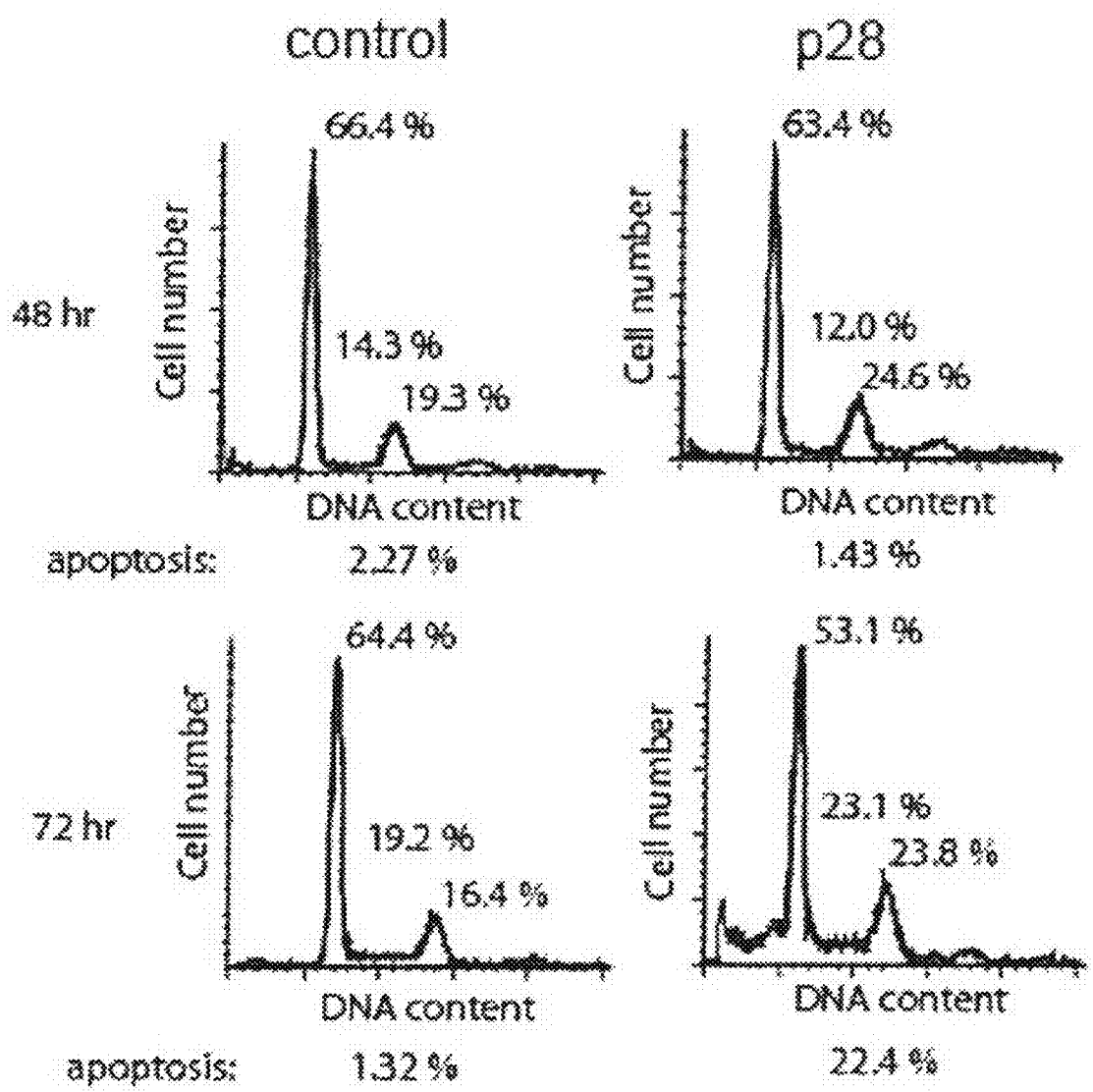
Figure 20C:
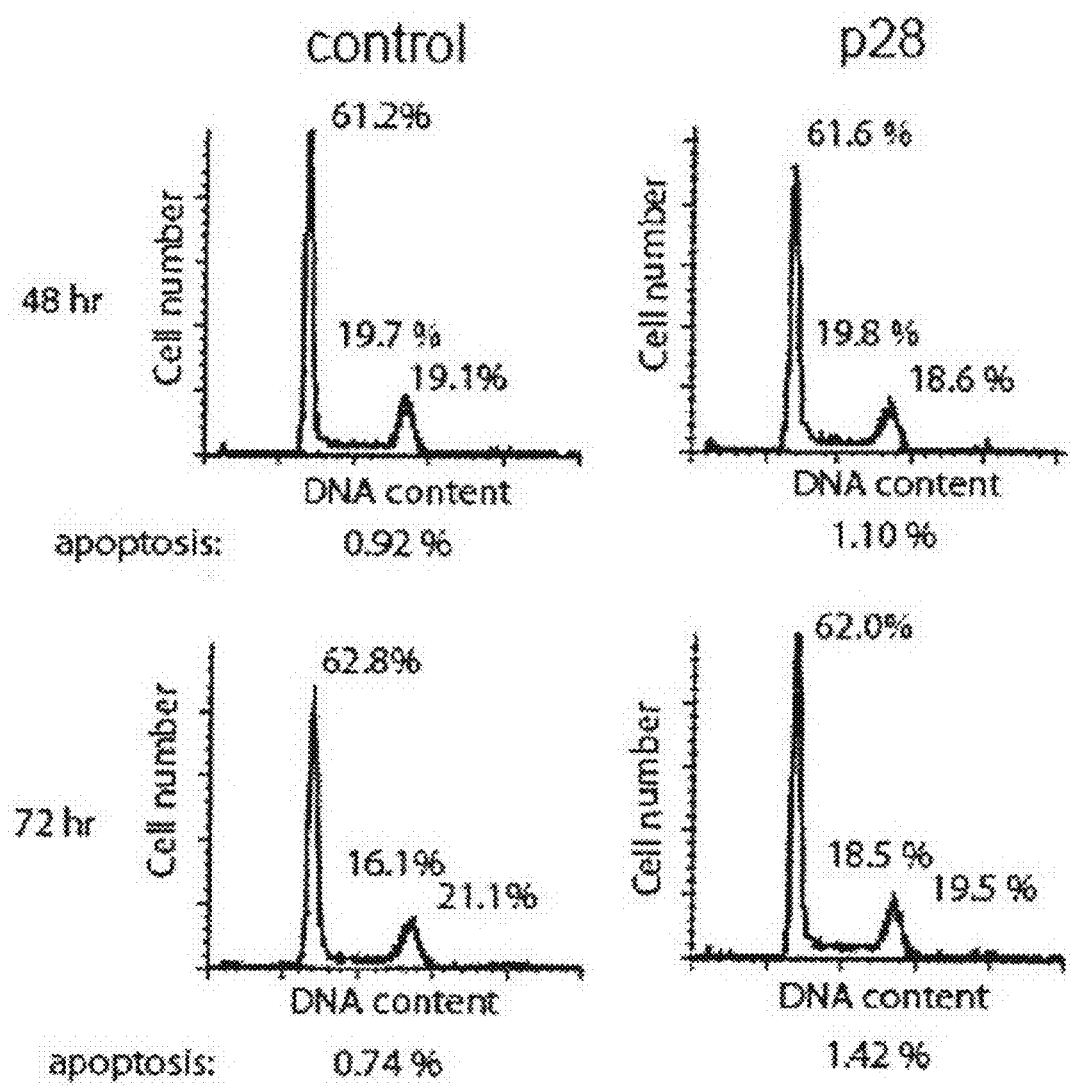

MFI/sec), $K_m$ (MCF-7: 144.2 µmol/L; MDD2: 147.9 µmol/L). Cell cycle analysis of the two isogenic breast cancer cell lines, MCF-7 (p53 wt) and MDD2 (p53 dominant negative), revealed an increased cell population at the $G_2$/M phase after exposure to p28 (SEQ ID NO: 2) for 48-72 hrs and subsequent induction of apoptosis (~22%) at 72 hrs in MCF-7 cells (FIG. 20B). In contrast, there was essentially no inhibition of cell cycle progression or apoptosis in p28-treated MDD2 cells (FIG. 20C). The lack of cell cycle inhibition and apoptosis in p28-treated MDD2 cells was not due to a difference in p28 (SEQ ID NO: 2) entry into MDD2 cells (FIG. 20A) or a difference in the kinetics of entry.

Example 17 p53 Levels are Elevated by p28 (SEQ ID NO: 2)

Azurin forms a complex with p53 and elevates intracellular p53 levels in MCF-7 cells. Exposure of MCF-7 cells to p28 (SEQ ID NO: 2) followed by immunoblotting of cell lysates revealed that the intracellular level of p53 in MCF-7 cells also markedly increased with time post exposure to p28 (FIG. 21A). A GST pull-down assay showed p28 (SEQ ID NO: 2) binds to p53 (FIG. 21B). Here, GST-p28 and GST-MDM2 (Murine double minute 2) successfully pulled down p53 from MCF-7 cell lysates, but GST alone did not.

The p53-interacting region of p28 (SEQ ID NO: 2) was mapped using a similar assay and fragments of p28 (SEQ ID NO: 2). When GST-p53 protein immobilized on Sepharose 4B-glutathione beads were incubated with p28 (SEQ ID NO: 2) and either p18 (aa 50-67, SEQ ID NO: 25), p18b (aa 60-77, SEQ ID NO: 38), or p12 (aa 66-77, SEQ ID NO: 39) of azurin, a significant amount of p28 (SEQ ID NO: 2) was displaced by p18 (SEQ ID NO: 25) and p18b (SEQ ID NO: 38), but only weakly when p12 (SEQ ID NO: 39) was used as the competitor (FIG. 21C). These results show that maximal binding to p53 occurs within aa 11-18 of p28 (SEQ ID NO: 2) (aa 60-67 of azurin), with the C-terminal 12 aa less efficient in binding p53.

Figure 21D:
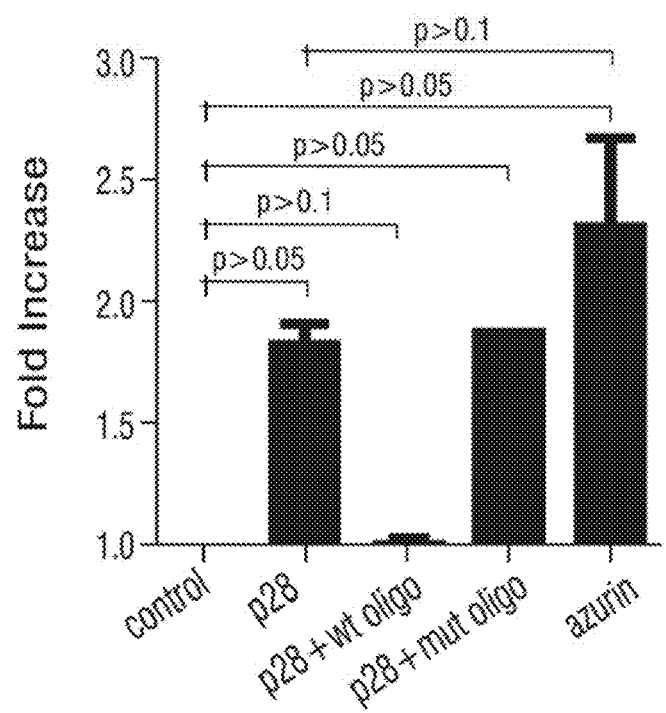

The DNA-binding activity of p53 obtained from MCF-7 cell nuclear extracts treated with p28 (SEQ ID NO: 2) or azurin was also ~1.8 and ~2.3 fold higher than control (p>0.1, p28 (SEQ ID NO: 2) vs azurin). The p53 wt consensus, but not the mutated oligonucleotide sequence, completely blocked the p28 (SEQ ID NO: 2) induced increase in p53, confirming that the p53 in nuclear extracts of MCF-7 cells remains active, binding specifically to the consensus oligonucleotide sequence for wt p53 (FIG. 21D).

Example 18

Stabilization of p53 by Prevention of Proteasomal Degradation

Figure 22A:
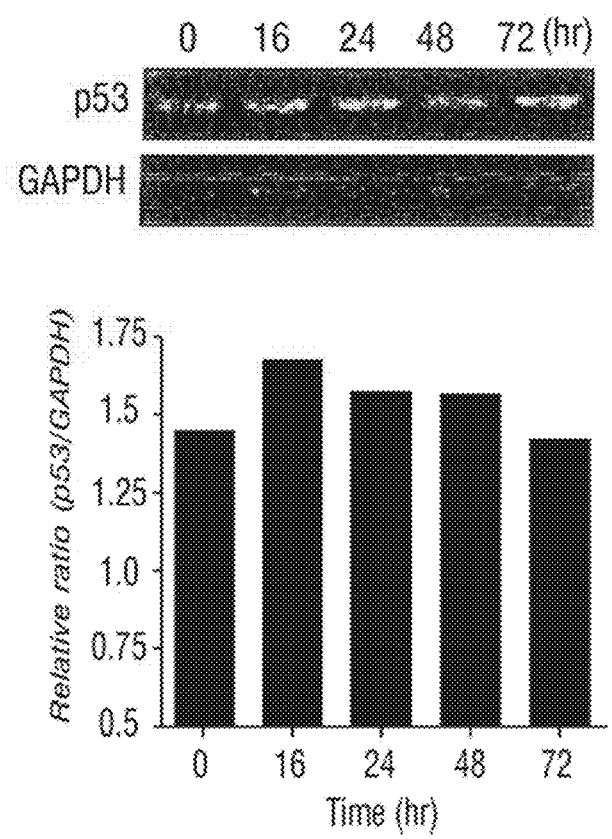
FIG. 22. (A) A photograph depicting RNA extracted from MCF-7 cells exposed to p28 (SEQ ID NO: 2) for 16, 24, 48 and 72 hr. The mRNA levels of p53 and GAPDH as an internal control gene were determined by RT-PCR analysis. p53 bands were quantified and normalized against GAPDH, as depicted in the graph on the right. (B) A photograph depicting p53 protein levels pulled down by GST-MDM2 in the presence of a molar excess of p28 (SEQ ID NO: 2). Protein samples were loaded on SDS-PAGE and p53 detected by IB using anti-p53 antibody. (C) A photograph depicting ubiquitination of p53 in MCF-7 cells that were exposed to p28 (SEQ ID NO: 2) at 50 µmol/L for 24, 48 and 72 hr in absence or presence of proteasome inhibitor MG132. The position of the p53-ubiquitin conjugates (p53-$Ub_n$) is indicated. The histogram on the right shows relative amounts of p53-$Ub_n$ (untreated control samples at each time point expressed as 100%). (D) Three different anti-p53 antibodies, Pab 1801 (32-79 aa), ab 2433 (277-296aa) and Pab1802 (306-393aa) reacted with GST-p53 immobilized beads in the presence of p28 (SEQ ID NO: 2). p28 (SEQ ID NO: 2) detected by IB using an anti-p28 antibody.
Figure 22B:
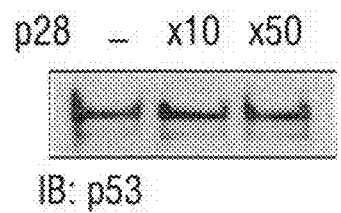
Figure 22C:
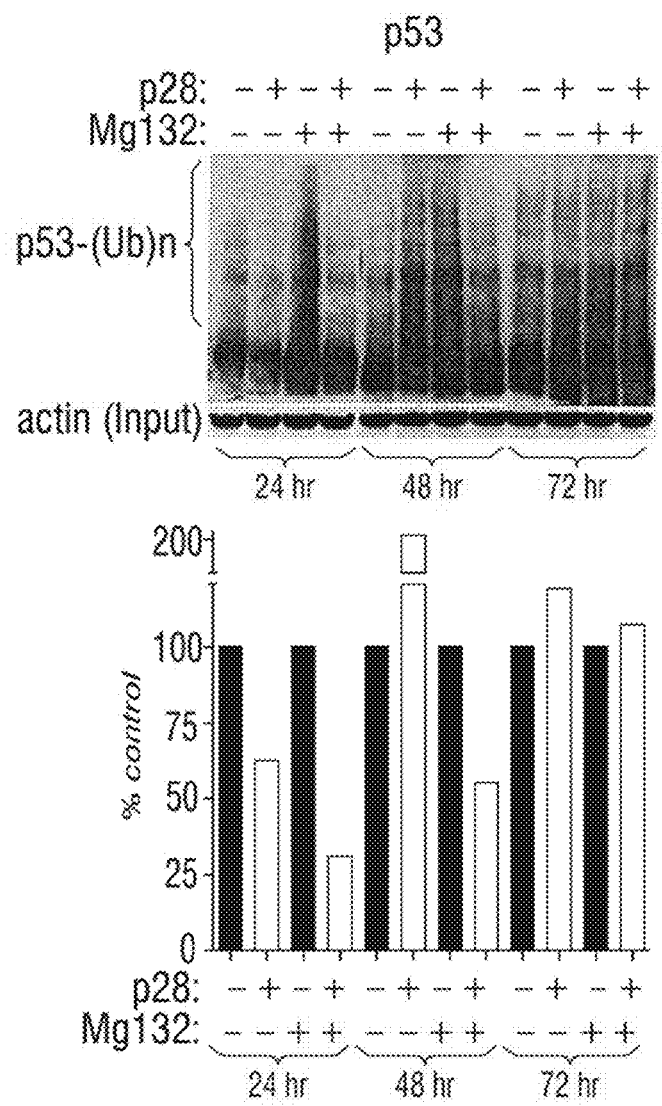
Figure 22D:
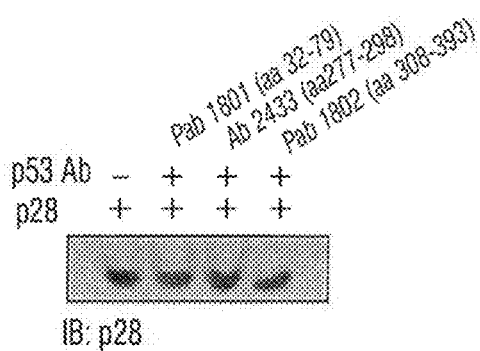

As the elevation in p53 in response to p28 (SEQ ID NO: 2) exposure could result from either transcriptional activation of p53 or protein stabilization, the level and time course of p53 expression in MCF-7 cells during exposure to p28 (SEQ ID NO: 2) was determined. RT-PCR showed that p53 mRNA was only slightly and transiently up-regulated ~16 hr post-p28 (SEQ ID NO: 2) exposure, showing that p28 (SEQ ID NO: 2) stabilized p53 post-translationally (FIG. 22A). Molar increases of p28 (SEQ ID NO: 2) did not compete for binding with GST-MDM2 (FIG. 22B), showing that any p28 (SEQ ID NO: 2) induced decrease in the ubiquitination of p53 was not via an MDM2 mediated pathway (FIG. 22C) and that aa 19-26 of p53, the MDM2 binding site, were not a preferred binding site for p28 (SEQ ID NO: 2). The ladder of p53-specific high molecular weight and smear bands that result from ubiquitination of p53 ($p53-Ub_n$), the main p53 degradation pathway, in the presence of the proteasome inhibitor MG132 was markedly reduced compared to untreated control when MCF-7 cells were exposed to p28 at 50 µmol/L for 24 hr (FIG. 22C). The inhibitory effect was increased and extended 48 hr post exposure to p28 when the proteasome inhibitor MG132 was incorporated into the reaction. At 72 hrs, the level of $p53-Ub_n$ was slightly higher than control. Since p28 continued to accumulate p53 after 72 hr exposure (~332%, FIG. 21A), the slightly higher level of p53 may provide substrate for several additional known E3 ubiquitin ligases promoting degradation by the proteasome pathway. In sum, the results shows that the p28 induced increase in p53 levels resulted from stabilizing p53 through decreased ubiquitination and proteasomal degradation rather than transcriptional activation.

This shows that p28 (SEQ ID NO: 2) binds to a region of p53 outside these recognition sites (FIG. 22D), but within a region bounded by either aa 1-18, 27-31, 80-276 or 297-305.

Example 19

Modulation of Cell Cycle Related Proteins by p28 (SEQ ID NO: 2)

Figure 23C:
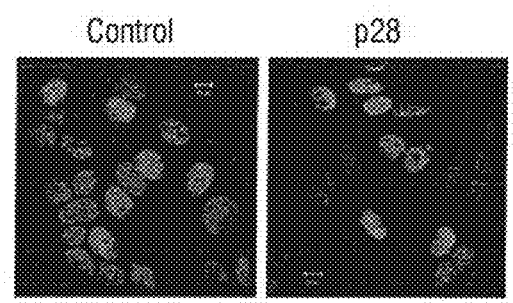
Figure 23D:
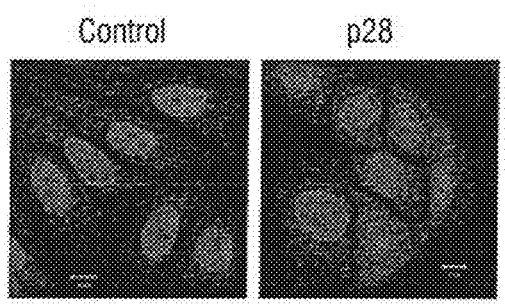
Figure 23E:
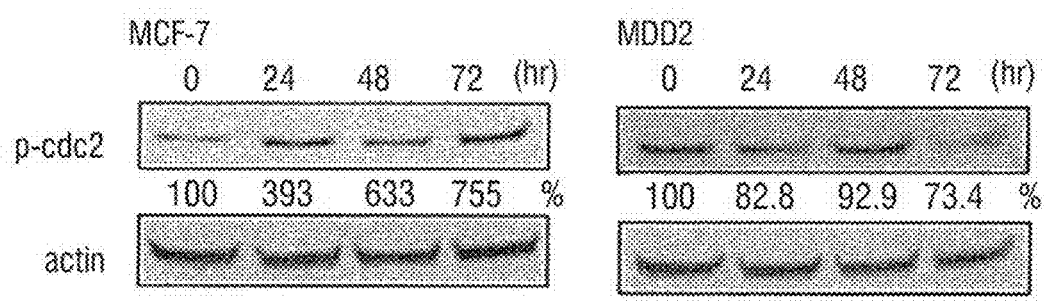

Upregulation of the CDK inhibitors (CDKIs), p21 and p27, blocks cell cycle progression. p28 (SEQ ID NO: 2) increased intracellular levels of p21, p27, CDK6 and cyclin B1 over control in MCF-7 cells with time post-exposure (FIG. 23A). The levels of CDK2 and cyclin A, essential proteins in the mitotic process, subsequently decreased with time post-exposure of MCF-7 cells to p28 (FIG. 23A). In contrast, p53, cdc2, CDK2, CDK4 and CDK6 essentially remained constant in MDD2 cells (FIG. 23B), while cyclin A and cyclin B1 (48 hrs) increased slightly. Since p21 can be expressed by a p53-independent pathway in MDD2 cells, p21 remained detectable. However, p28 (SEQ ID NO: 2) did not alter the level of p21 (FIG. 23B). In contrast, p27 was not detectable in untreated or p28 (SEQ ID NO: 2) exposed MDD2 cells. The increased levels of p21 and cyclin B1 in MCF-7 cells detected by immunoblotting in response to p28 (SEQ ID NO: 2) are reflected by their increase in nuclear and cytosolic compartments, respectively (FIGS. 23C and D). Exposure of MCF-7 cells to p28 (SEQ ID NO: 2) also induced the accumulation of phosphorylated cdc2 (p-cdc2), the inactive form of cdc2, which did not increase following exposure of MDD2 cells to p28 (SEQ ID NO: 2) (FIG. 23E).

What is claimed is:

1. A method comprising: stabilizing p53 in a cell and enhancing its intracellular concentration in a cell by contacting the cell with a composition comprising a cupredoxin-derived peptide, wherein the peptide consists of the amino acid sequence selected from the group consisting of: SEQ ID NO: 38 and SEQ ID NO: 86.

2. A method comprising: inhibiting the development of cancer by stabilizing p53 and enhancing its intracellular concentration in a cancerous cell by contacting the cancerous cell with a composition comprising a cupredoxin-derived peptide, wherein the peptide consists of the amino acid sequence selected from the group consisting of: SEQ ID NO: 38 and SEQ ID NO: 86.

3. A method comprising: inducing apoptosis of cancer cells by stabilizing p53 by forming a complex of a cupredoxin-derived peptide and p53, wherein the peptide consists of the amino acid sequence selected from the group consisting of SEQ ID NO: 38 and SEQ ID NO: 86.

* * * * *